United States Patent
Ono et al.

(10) Patent No.: US 7,994,204 B2
(45) Date of Patent: Aug. 9, 2011

(54) BINDING INHIBITOR OF SPHINGOSINE-1-PHOSPHATE

(75) Inventors: Naoya Ono, Toshima-ku (JP); Tetsuo Takayama, Toshima-ku (JP); Fumiyasu Shiozawa, Toshima-ku (JP); Hironori Katakai, Toshima-ku (JP); Tetsuya Yabuuchi, Toshima-ku (JP); Tomomi Ota, Toshima-ku (JP); Takeshi Koami, Toshima-ku (JP); Rie Nishikawa, Toshima-ku (JP)

(73) Assignee: Taisho Pharmaceutical Co., Ltd, Tokyo (JP)

( * ) Notice: Subject to any disclaimer, the term of this patent is extended or adjusted under 35 U.S.C. 154(b) by 346 days.

(21) Appl. No.: 12/278,477

(22) PCT Filed: Feb. 6, 2007

(86) PCT No.: PCT/JP2007/052052
§ 371 (c)(1),
(2), (4) Date: Aug. 6, 2008

(87) PCT Pub. No.: WO2007/091570
PCT Pub. Date: Aug. 16, 2007

(65) Prior Publication Data
US 2009/0182144 A1 Jul. 16, 2009

(30) Foreign Application Priority Data
Feb. 6, 2006 (JP) ................. 2006-028973

(51) Int. Cl.
| | |
|---|---|
| A61K 31/4152 | (2006.01) |
| A61K 31/4166 | (2006.01) |
| A61K 31/4168 | (2006.01) |
| A61K 31/4155 | (2006.01) |
| A61K 31/4178 | (2006.01) |
| A61K 31/4439 | (2006.01) |
| A61K 31/4709 | (2006.01) |
| A61K 31/5377 | (2006.01) |
| C07D 233/70 | (2006.01) |
| C07D 413/12 | (2006.01) |
| C07D 403/12 | (2006.01) |
| C07D 413/14 | (2006.01) |
| C07D 215/36 | (2006.01) |
| C07D 401/12 | (2006.01) |

(52) U.S. Cl. .............. 514/392; 514/235.8; 514/236.5; 514/398; 514/404; 548/324.5; 548/323.5; 548/370.1; 544/139; 544/370; 544/124; 546/153; 546/274.4

(58) Field of Classification Search .............. 548/323.5, 548/370.4; 514/398, 404, 407
See application file for complete search history.

(56) References Cited

U.S. PATENT DOCUMENTS
| | | | |
|---|---|---|---|
| 5,516,783 A | | 5/1996 | Whittaker et al. |
| 5,910,506 A | * | 6/1999 | Sugimoto et al. ............. 514/397 |
| 6,147,097 A | * | 11/2000 | Sugimoto et al. ............. 514/341 |

| | | | |
|---|---|---|---|
| 2003/0229125 A1 | 12/2003 | Haaf et al. |
| 2005/0124654 A1 | 6/2005 | Groneberg et al. |
| 2007/0232682 A1 | 10/2007 | Beard et al. |
| 2009/0131438 A1 | 5/2009 | Ono et al. |
| 2010/0041655 A1 | 2/2010 | Ono et al. |

FOREIGN PATENT DOCUMENTS
| | | |
|---|---|---|
| EP | 0786455 A1 | 7/1997 |
| EP | 786455 A1 | 7/1997 |
| EP | 1 798 226 A1 | 6/2007 |
| JP | 5-194412 A | 8/1993 |
| JP | 2002-212070 A | 7/2002 |
| JP | 2002-332278 A | 11/2002 |
| JP | 2003-137894 A | 5/2003 |
| JP | 2003137894 A | 5/2003 |
| JP | 2003/530388 A | 10/2003 |
| JP | 2004/532276 A | 10/2004 |
| WO | 96/10019 A1 | 4/1996 |
| WO | 01/77089 A1 | 10/2001 |
| WO | 02/18395 A1 | 3/2002 |

(Continued)

OTHER PUBLICATIONS

Schafer et al. Drug Discovery Today 2008, 13 (21/22), 913-916.*
Horig et al. Journal of Translational Medicine 2004, 2(44).*
J. G. Cannon Chapter Nineteen in Burger's Medicinal Chemistry and Drug Discovery, Fifth Edition, vol. I: Principles and Practice, Wiley-Interscience 1995, pp. 783-802.*
Y. Igarashi, J. Biochem. 1997, 122, 1080-1087.*
Baumruker et al., Expert Opin. Investig. Drugs 2007, 16(3) 283-289.*
Pyne et al. Nature Reviews Cancer 2010, 10, 489-503.*
International Search Report dated Sep. 22, 2008, as issued in International Application No. PCT/JP2008/063851.

(Continued)

*Primary Examiner* — Jason M Nolan
(74) *Attorney, Agent, or Firm* — Sughrue Mion, PLLC

(57) ABSTRACT

The present invention aims to provide compounds which have an inhibitory effect on the binding between S1P and its receptor Edg-1($S1P_1$) and which are useful for pharmaceutical purposes.
A compound represented by formula (I) or a pharmaceutically acceptable salt thereof:

[Formula 1]

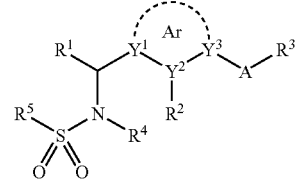

[wherein Ar represents a monocyclic heterocyclic ring containing one or two nitrogen atoms, A represents an oxygen atom or the like, $Y^1$, $Y^2$ and $Y^3$ each represent a carbon atom or a nitrogen atom, $R^1$ represents a hydrogen atom, a $C_1$-$C_6$ alkyl group or the like, $R^2$ represents a $C_1$-$C_6$ alkyl group, a $C_3$-$C_8$ cycloalkyl group or the like, $R^3$ represents a $C_1$-$C_{18}$ alkyl group or the like, $R^4$ represents a hydrogen atom or a $C_1$-$C_6$ alkyl group, and $R^5$ represents a $C_1$-$C_{10}$ alkyl group or the like].

34 Claims, No Drawings

FOREIGN PATENT DOCUMENTS

| | | |
|---|---|---|
| WO | 0218395 A1 | 3/2002 |
| WO | 02/100853 A1 | 12/2002 |
| WO | 03/000679 A2 | 1/2003 |
| WO | 03/073986 A2 | 9/2003 |
| WO | 03/074008 A2 | 9/2003 |
| WO | 03073986 A2 | 9/2003 |
| WO | 03074008 A2 | 9/2003 |
| WO | 03/097028 A1 | 11/2003 |
| WO | 03097028 A1 | 11/2003 |
| WO | 03/105771 A2 | 12/2003 |
| WO | 2004/024673 A1 | 3/2004 |
| WO | 2004/074257 A1 | 9/2004 |
| WO | 2004/089367 A1 | 10/2004 |
| WO | 2004/103279 A2 | 12/2004 |
| WO | 2005/123677 A1 | 12/2005 |
| WO | 2006/0136948 A1 | 2/2006 |
| WO | 2006013948 A1 | 2/2006 |
| WO | 2006/097489 A1 | 9/2006 |
| WO | 2007/083089 A1 | 7/2007 |
| WO | 2007/091570 A1 | 8/2007 |
| WO | 2007/112322 A2 | 10/2007 |
| WO | 2007/122401 A1 | 11/2007 |
| WO | 2007/129019 A1 | 11/2007 |

OTHER PUBLICATIONS

H. Gehlen, et al., "2-Amino-1, 3,4-oxidiazoles. VII. Formation of 2-amino-5-aminoalkyl-1, 3,4-oxidiazoles and their conversion into 1,2,4-triazoles and triazolones", Justus Liebigs Annalen der Chemi. vol. 651, pp. 128-132, Sep. 23, 1962 with Full English language translation.

James R. Van Brocklyn et al., Sphingosine-1-phosphate stimulates motility and invasiveness of human glioblastoma multiforme cells, Cancer Letters, Elsevier, 2003, pp. 53-60, vol. 199.

Zdzislaw Brzozowski, 2-Mercapto-N-(Azolyl) Benzenesulphonamides I. Synthesis of N-(1,1-Dioxo-7,4,2-Benzodithianzin-3-YL)Guanidines and Their Transformations Into 2-Mercapto-N-(5-Amino-1,2,4-Triazol-3-YL) Benzenesulphonamide Dervatives with Potential Anti-HIV or Anti-cancer Activity, Department of Drug Technology, Faculty of Pharmacy, School of Medicine, Acta Poloniae Pharmaceutica-Drug Research, Polish Pharmaceutical Society, 1995, pp. 91-101, vol. 52, No. 2.

Guofeng Jia, et al., "Syntheses of Some New 4-Amino-5-(N-methyl-arylsulfonamido)methyl-1,2,4-triazole-3-thiones and Their Derivatives", Heteroatom Chemistry, vol. 7, No. 4, pp. 263-267, 1996.

Gehlen, H., et al., 2-Amino-1,3,4-oxadiazoles. IX. Oxidation of Aldehyde Semicarbazones to 2-amino-1, 3,4-oxadiazoles and Their Conversion Into 1-acylsemicarbazides, Justus Liebigs Annalen Der Chemi, vol. 651, pp. 133-136, 1962.

Von Heinz Gehlen, et al; Zur Kenntnis der 2-Amino-1,3,4-oxdiazole, X 3-Xlkoxy-1,2,4-Triazole Durch Alkoholyse von 2-Amino-1,3,4-Oxdiazolen; Liebigs Ann. Chem. 651, 137 (1962); pp. 137-141 (with an English translation).

M. Germana Sanna et al., "Sphingosine 1-Phosphate (SIP) Receptor Subtypes $SIP_1$ and $SIP_3$, Respectively, Regulate Lymphocyte Recirculation and Heart Rate", The Journal of Biological Chemistry, vol. 279, No. 14, Issue of Apr. 2, pp. 13839-13848, 2004.

Jeremy J. Clemens et al., "Synthesis of *Para*-Alkyl Aryl Amide Analogues of Sphingosine-I-phosphate: Discovery of Potent SIP Receptor Agonists", Bioorganic & Medicinal Chemistry Letters, 13 (2003) 3401-3404.

H. Gehlen, et al., "2-Amino-1, 3,4-oxidiazoles. VIII. Formation of 2-amino-5-aminoalkyl-1,3,4-oxidiazoles and their conversion into 1,2,4-triazoles and triazolones", Chemical Abstracts, Database Accession No. 57:16892, Justus Liebigs Annalen der Chemie, vol. 651, pp. 128-132, 1962.

Supplemental European Search Report dated Oct. 13, 2009, issued in European Application No. 07708069.5.

Extended European Search Report issued Nov. 23, 2010 from the European Patent Office in a counterpart European Application No. 07713881.6.

Hla, Timothy, "Physiological and Pathological Actions of Sphingosine 1-Phosphate", 15 Sem. Cell & Dev. Bio. 513 (2004).

* cited by examiner

BINDING INHIBITOR OF SPHINGOSINE-1-PHOSPHATE

CROSS REFERENCE TO RELATED APPLICATION

This application is a National Stage of International Application No. PCT/JP2007/052052 filed Feb. 6, 2007, claiming priority based on Japanese Patent Application No. 2006-028973, filed Feb. 6, 2006, the contents of all of which are incorporated herein by reference in their entirety.

TECHNICAL FIELD

The present invention relates to novel compounds which have an inhibitory effect on the binding between sphingosine-1-phosphate having various physiological actions and its receptor Edg-1 (Endothelial differentiation gene receptor type-1, $S1P_1$). The present invention also relates to pharmaceutical preparations comprising these compounds as active ingredients, and synthetic intermediates for these compounds.

BACKGROUND ART

Sphingosine-1-phosphate (hereinafter referred to as "S1P") is a physiologically active lipid which is generated when sphingolipids (typified by sphingomyelin) are metabolized in cells. S1P is known to have a wide variety of actions such as cell differentiation induction, cell growth stimulation, cell motility inhibition and apoptosis inhibition, and is also known to show physiological actions such as angiogenesis, bradycardia induction, inflammatory cell activation and platelet activation (Non-patent Document 1).

As S1P receptors, the following 5 subtypes have been reported: Edg-1($S1P_1$), Edg-3($S1P_3$), Edg-5($S1P_2$), Edg-6 ($S1P_4$) and Edg-8($S1P_5$) (Non-patent Document 2).

Among these subtypes, Edg-1($S1P_1$) is highly expressed in immunocytes (e.g., T cells, dendritic cells) and vascular endothelial cells, suggesting that Edg-1($S1P_1$) contributes deeply to S1P-stimulated T cell migration (Non-patent Document 3), mast cell migration (Non-patent Document 4), T and B cell egress from lymphoid organs (Non-patent Document 5) and angiogenesis (Non-patent Document 6), and is involved in autoimmune diseases such as Crohn's disease, irritable colitis, Sjogren's syndrome, multiple sclerosis and systemic lupus erythematosus, as well as other diseases such as rheumatoid arthritis, asthma, atopic dermatitis, rejection after organ transplantation, cancer, retinopathy, psoriasis, osteoarthritis, age-related macular degeneration, etc.

Thus, ligands for Edg-1($S1P_1$) would be effective for treatment or prevention of these diseases.

Edg-1($S1P_1$) ligands previously known include certain types of thiophene derivatives (Non-patent Document 7), phosphoric acid derivatives (Patent Documents 1 and 2, Non-patent Documents 8 and 9) and thiazolidine derivatives (Patent Document 3), carboxylic acid derivatives (Patent Documents 4, 5, 6 and 8, Non-patent Documents 10 and 11), amino group-containing derivatives (Patent Document 7), and pyrrole derivatives (Patent Document 9).
Patent Document 1: WO2002-18395
Patent Document 2: JP 2003-137894 A
Patent Document 3: JP 2002-332278 A
Patent Document 4: WO2002-092068
Patent Document 5: WO2003-105771
Patent Document 6: WO2004-058149
Patent Document 7: WO2004-103279
Patent Document 8: WO2005-058848
Patent Document 9: WO2005-123677
Non-patent Document 1: J Biol. Chem. 2004, 279: 20555, FASEB J 2002, 16: 625, Proceedings of the Japanese Society for Immunology 2003, 33: 2-J-W30-20-P
Non-patent Document 2: Pharmacol Res 2003, 47: 401
Non-patent Document 3: FASEB J 2002, 16:1874
Non-patent Document 4: J Exp Med 2004, 199: 959
Non-patent Document 5: Nature 2004, 427: 355
Non-patent Document 6: J Clin Invest 2000, 106: 951, Biochim Biophys Acta 2002, 1582: 222
Non-patent Document 7: J Biol Chem 2004, 279: 13839
Non-patent Document 8: Bioorg Med Chem Lett 2003, 13: 3401
Non-patent Document 9: J Biol. Chem. 2005; 280: 9833
Non-patent Document 10: J Med. Chem. 2004, 47: 6662
Non-patent Document 11: J Med. Chem. 2005, 48: 6169

DISCLOSURE OF THE INVENTION

Problems to be Solved by the Invention

The object of the present invention is to provide compounds having a novel skeleton, which have an inhibitory effect on the binding between S1P and its receptor Edg-1 ($S1P_1$) and which are useful for pharmaceutical purposes.

Means for Solving the Problems

As a result of extensive and intensive efforts made to find ligand compounds for Edg-1($S1P_1$), the inventors of the present invention have found that this object is achieved by a compound of the following formula (I) or a pharmaceutically acceptable salt thereof. This finding led to the completion of the present invention.

Embodiments will be given below for a compound of formula (I) and its intermediate compound of formula (II) (hereinafter each referred to as "the compound of the present invention").

1. A compound represented by formula (I) or a pharmaceutically acceptable salt thereof:

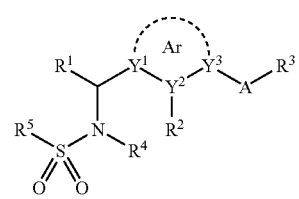

[Formula 1]

{wherein Ar represents a monocyclic heterocyclic ring containing one or two nitrogen atoms,
wherein said Ar may be substituted with a substituent(s) selected from the group consisting of a $C_1$-$C_6$ alkyl group, a phenyl group and a halogen atom,
$Y^1$, $Y^2$ and $Y^3$ each represent a carbon atom or a nitrogen atom,
A represents an oxygen atom, a sulfur atom, a group represented by the formula —$SO_2$—, or a group represented by the formula —$NR^6$— (wherein $R^6$ represents a hydrogen atom or a $C_1$-$C_6$ alkyl group),
$R^1$ represents a hydrogen atom, a $C_1$-$C_6$ alkyl group which may be substituted with a substituent(s) selected from the following group [wherein said group consists of a hydroxyl group, a halogen atom, a $C_1$-$C_6$ alkoxy group (wherein said alkoxy group may be substituted with a phenyl group) and a phenyl group (wherein said phenyl group may be substituted with a substituent(s) selected from the group consisting of a halogen atom and a $C_1$-$C_6$ alkyl group)], a $C_3$-$C_8$ cycloalkyl group, a $C_2$-$C_8$ alkenyl group, a $C_2$-$C_8$ alkynyl group, or a phenyl group, $R^2$ represents a hydrogen atom, a $C_1$-$C_6$ alkyl group, or a $C_3$-$C_8$ cycloalkyl group, $R^3$ represents (i) a hydrogen atom, (ii) a $C_1$-$C_{18}$ alkyl group, (iii) a $C_2$-$C_8$ alkenyl group which may be substituted with a phenyl group or a benzyloxy group, (iv) a $C_2$-$C_8$ alkynyl group which may be substituted with a phenyl group, (v) a $C_3$-$C_8$ cycloalkyl group which may be condensed with a benzene ring, (vi) a $C_1$-$C_6$ alkyl group substituted with a substituent(s) selected from the following group [wherein said group consists of a halogen atom, a phenyl group (wherein said phenyl group may be substituted with 1 to 5 substituents selected from the group consisting of a phenyl group, a cyano group, a halogen atom, a $C_1$-$C_6$ alkyl group, a $C_1$-$C_6$ alkoxy group, a trifluoromethyl group, a methoxycarbonyl group, a $C_1$-$C_6$ alkylthio group, a dimethylamino group, a nitro group and an acetamido group), a $C_3$-$C_8$ cycloalkyl group, a hydroxyl group, a $C_1$-$C_6$ alkylthio group, a $C_1$-$C_6$ alkoxy group, a benzyloxy group, a phenoxy group, a trifluoromethyl group, a difluoromethyl group, a benzenesulfonyl group, a naphthyl group, a $C_7$-$C_{10}$ tricycloalkyl group, a carbomethoxy(phenyl)methyl group, a diphenylmethyl group, a 1-phenylethyl group, an imidazolyl group, an indolyl group, a pyridyl group, an oxetanyl group, an oxolanyl group, a methylpiperidinyl group, a piperazino group which may be substituted with a $C_1$-$C_6$ alkyl group(s), a benzylpiperidinyl group, a morpholino group, a 2-oxopyrrolidin-1-yl group, a 2-oxoimidazolidin-1-yl group, a group represented by the formula:

—$CO_2R^{11}$ (wherein $R^{11}$ represents a hydrogen atom or a $C_1$-$C_6$ alkyl group), a group represented by the formula:

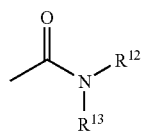
[Formula 2]

(wherein $R^{12}$ and $R^{13}$ each represent a hydrogen atom or a $C_1$-$C_6$ alkyl group), a group represented by the formula:

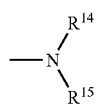
[Formula 3]

(wherein $R^{14}$ and $R^{15}$ each represent a hydrogen atom, a $C_1$-$C_6$ alkyl group, a phenyl group or a 4-pyridylcarbonyl group), and the formula:

—$COR^{16}$ (wherein $R^{16}$ represents a $C_1$-$C_6$ alkyl group or a phenyl group)], (vii) an oxolanyl group, a methylpiperidinyl group, or a group represented by the formula:

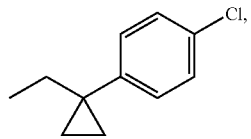
[Formula 4]

or (viii) an optionally substituted aryl group, $R^4$ represents a hydrogen atom, or a $C_1$-$C_6$ alkyl group which may be substituted with a carboxyl group, and $R^5$ represents (i) a $C_1$-$C_{10}$ alkyl group, (ii) a $C_1$-$C_{10}$ alkyl group which is substituted with one or two substituents selected from the following group (wherein said group consists of a $C_3$-$C_8$ cycloalkyl group, a pyridyl group, and a phenyl, phenoxy or naphthyl group which may be substituted with one or two substituents selected from the group consisting of a halogen atom and a $C_1$-$C_6$ alkoxy group) (iii) a $C_3$-$C_8$ cycloalkyl group, (iv) a $C_2$-$C_8$ alkenyl group, (v) a $C_2$-$C_8$ alkenyl group substituted with a phenyl group, (vi) a $C_2$-$C_8$ alkynyl group, (vii) a $C_2$-$C_8$ alkynyl group substituted with a phenyl group, or (viii) an optionally substituted aryl group, provided that when Ar is a group represented by the following formula:

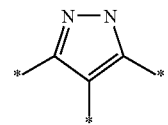
[Formula 5]

which may be substituted with a $C_1$-$C_6$ alkyl group, $R^5$ is not a $C_1$-$C_{10}$ alkyl group}.

2.

The compound or pharmaceutically acceptable salt thereof according to embodiment 1, wherein in formula (I), Ar represents a monocyclic heterocyclic ring containing one or two nitrogen atoms, A represents an oxygen atom, a sulfur atom, or a group represented by the formula —$NR^6$— (wherein $R^6$ represents a hydrogen atom or a $C_1$-$C_6$ alkyl group), $R^1$ represents a hydrogen atom, a $C_1$-$C_6$ alkyl group, or a $C_1$-$C_6$ alkyl group substituted with a phenyl group, $R^2$ represents a $C_1$-$C_6$ alkyl group, or a $C_3$-$C_8$ cycloalkyl group, $R^3$ represents a $C_1$-$C_6$ alkyl group, or an optionally substituted aryl group, $R^4$ represents a hydrogen atom, or a $C_1$-$C_6$ alkyl group, and $R^5$ represents (i) a $C_1$-$C_{10}$ alkyl group, (ii) a $C_1$-$C_{10}$ alkyl group which is substituted with one or two substituents selected from the following group (wherein said group consists of a $C_3$-$C_8$ cycloalkyl group, a phenyl group, a naphthyl group, a pyridyl group, and a phenyl group substituted with one or two substituents selected from the group consisting of a halogen atom and a $C_1$-$C_6$ alkoxy group) (iii) a $C_3$-$C_8$ cycloalkyl group, (iv) a $C_2$-$C_8$ alkenyl group, (v) a $C_2$-$C_8$ alkenyl group substituted with a phenyl group, (vi) a $C_2$-$C_8$ alkynyl group, (vii) a $C_2$-$C_8$ alkynyl group substituted with a phenyl group, or (viii) an optionally substituted aryl group.

3.

The compound or pharmaceutically acceptable salt thereof according to embodiment 1, wherein Ar is a substituent represented by the following formula:

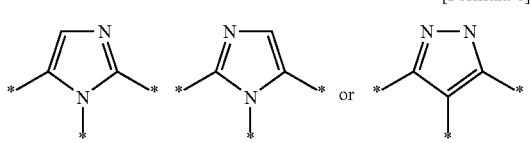

[Formula 6]

which may be substituted with a substituent selected from the group consisting of a $C_1$-$C_6$ alkyl group, a phenyl group and a halogen atom.

4. The compound or pharmaceutically acceptable salt thereof according to embodiment 1, wherein Ar is a substituent represented by the following formula:

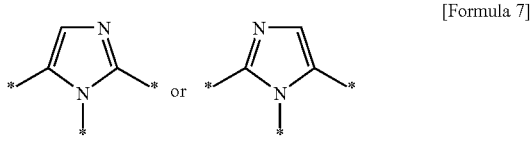

[Formula 7]

which may be substituted with a substituent selected from the group consisting of a $C_1$-$C_6$ alkyl group, a phenyl group and a halogen atom.

5. The compound or pharmaceutically acceptable salt thereof according to embodiment 1, wherein Ar is a substituent represented by the following formula:

[Formula 8]

which may be substituted with a substituent selected from the group consisting of a $C_1$-$C_6$ alkyl group, a phenyl group and a halogen atom.

6. The compound or pharmaceutically acceptable salt thereof according to any one of embodiments 1 to 5, wherein A is an oxygen atom.

7. The compound or pharmaceutically acceptable salt thereof according to any one of embodiments 1 and 3 to 6, wherein $R^1$ is a $C_1$-$C_6$ alkyl group which may be substituted with a halogen atom(s), or a benzyl group which may be substituted with a substituent(s) selected from the group consisting of a halogen atom and a $C_1$-$C_6$ alkyl group.

8. The compound or pharmaceutically acceptable salt thereof according to any one of embodiments 1 and 3 to 6, wherein $R^1$ is a methyl group, an ethyl group or a benzyl group which may be substituted with a halogen atom(s).

9. The compound or pharmaceutically acceptable salt thereof according to any one of embodiments 1 to 6, wherein $R^1$ is a methyl group or an ethyl group.

10. The compound or pharmaceutically acceptable salt thereof according to any one of embodiments 1 to 9, wherein $R^4$ is a hydrogen atom.

11. The compound or pharmaceutically acceptable salt thereof according to any one of embodiments 1 to 10, wherein $R^2$ is a $C_1$-$C_6$ alkyl group or a $C_3$-$C_6$ cycloalkyl group.

12. The compound or pharmaceutically acceptable salt thereof according to any one of embodiments 1 to 10, wherein $R^2$ is an ethyl group or a cyclopropyl group.

13. The compound or pharmaceutically acceptable salt thereof according to any one of embodiments 1 and 3 to 12, wherein $R^5$ is (i) a $C_1$-$C_{10}$ alkyl group, (ii) a $C_1$-$C_{10}$ alkyl group which is substituted with one or two substituents selected from the following group (wherein said group consists of a $C_3$-$C_8$ cycloalkyl group, a pyridyl group, and a phenyl, phenoxy or naphthyl group which may be substituted with one or two substituents selected from the group consisting of a halogen atom and a $C_1$-$C_6$ alkoxy group), (iii) a $C_2$-$C_8$ alkenyl group which may be substituted with a phenyl group, or (iv) a phenyl group, a naphthyl group, a thienyl group, a pyrrolyl group, a pyrazolyl group, a pyridyl group, a furanyl group, a benzothienyl group, an isoquinolinyl group, an isoxazolyl group, a thiazolyl group, a benzothiadiazolyl group, a benzoxadiazolyl group, a phenyl group condensed with a 5- to 7-membered saturated hydrocarbon ring which may contain one or two oxygen atoms as ring members, a uracil group, a coumaryl group, a dihydroindolyl group, or a tetrahydroisoquinolinyl group, wherein these groups may each be substituted with 1 to 5 substituents selected from the following group [wherein said group consists of a $C_1$-$C_6$ alkyl group which may be substituted with a fluorine atom(s), a $C_2$-$C_8$ alkenyl group, a halogen atom, a $C_1$-$C_6$ alkoxy group which may be substituted with a fluorine atom(s), a pyrazolyl, oxazolyl, isoxazolyl, thiadiazolyl or pyrimidinyl group, which may be substituted with a substituent(s) selected from the group Y (wherein the group Y consists of a methyl group, a trifluoromethyl group, a halogen atom and a methylsulfanyl group), a $C_1$-$C_6$ alkylthio group, a $C_1$-$C_6$ alkylsulfonyl group, a benzenesulfonyl group, a morpholinosulfonyl group, a morpholinocarbonylamino group, an aminosulfonyl group, a $C_2$-$C_{10}$ alkoxycarbonyl group, a morpholino group which may be substituted with a $C_1$-$C_6$ alkyl group(s), a phenyl group which may be substituted with a $C_1$-$C_6$ alkoxy group(s), a phenoxy group, a pyridinecarbonyl group, a pyridineoxy group, a cyano group, a $C_2$-$C_7$ alkanoyl group which may be substituted with a fluorine atom(s) and a $C_2$-$C_7$ alkanoylamino group].

14. The compound or pharmaceutically acceptable salt thereof according to any one of embodiments 1 to 12, wherein $R^5$ is a $C_1$-$C_{10}$ alkyl group substituted with a $C_3$-$C_8$ cycloalkyl group, a $C_1$-$C_{10}$ alkyl group substituted with a naphthyl group, a $C_2$-$C_8$ alkenyl group substituted with a phenyl group, a phenyl or naphthyl group which may be substituted with 1 to 5 substituents selected from the following group (wherein said group consists of a $C_1$-$C_6$ alkyl group, a halogen atom, a $C_1$-$C_6$ alkoxy group, a trifluoromethoxy group, a difluoromethoxy group, a trifluoromethyl group, a $C_1$-$C_6$ alkenyl group, a $C_1$-$C_6$ alkylsulfonyl group, a $C_2$-$C_7$ alkanoyl group, a $C_2$-$C_7$ alkoxycarbonyl group and a cyano group), a pyrrolyl group which may be substituted with a substituent(s) selected from the group consisting of a $C_1$-$C_6$ alkyl group and a methoxycarbonyl group, a furanyl group which may be substituted with a substituent(s) selected from the following group (wherein said group consists of a $C_1$-$C_6$ alkyl group, a trifluoromethyl group and a halogen atom), a thienyl group which may be substituted with a substituent(s) selected from the following group (wherein said group consists of a $C_1$-$C_6$ alkyl group, a trifluoromethyl group, a thiadiazolyl group, an oxazolyl group and a halogen atom), or a benzothienyl, dihydrobenzodioxepinyl, benzodioxolyl, dihydrobenzodioxinyl, dihydrobenzofuranyl, tetrahydronaphthyl, indanyl, thiadiazolyl, benzoxadiazolyl or benzothiadiazolyl group which may be substituted with a substituent(s) selected from the group consisting of a $C_1$-$C_6$ alkyl group and a halogen atom.

15.

The compound or pharmaceutically acceptable salt thereof according to any one of embodiments 1 to 12, wherein $R^5$ is a $C_1$-$C_6$ alkyl group substituted with a naphthyl group, a $C_2$-$C_6$ alkenyl group substituted with a phenyl group, an unsubstituted phenyl group, a phenyl group substituted with 1 to 5 substituents selected from the following group (wherein said group consists of a methyl group, a methoxy group and a halogen atom), a phenyl group which is substituted with 1 to 3 substituents selected from the following group and at least one of whose 3- and 4-positions is substituted (wherein said group consists of a $C_1$-$C_6$ alkyl group, a halogen atom, a methoxy group, a trifluoromethoxy group, a difluoromethoxy group, a trifluoromethyl group, a $C_1$-$C_6$ alkenyl group, a methylsulfonyl group, an acetyl group, a methoxycarbonyl group and a cyano group), a naphthyl group which may be substituted with a substituent(s) selected from the following group (wherein said group consists of a halogen atom, a $C_1$-$C_6$ alkyl group, a cyano group and a $C_1$-$C_6$ alkylsulfonyl group), a furanyl group which may be substituted with a substituent(s) selected from the group consisting of a trifluoromethyl group and a halogen atom, or a benzothienyl, benzoxadiazolyl, benzodioxolyl, dihydrobenzodioxinyl, dihydrobenzofuranyl, indanyl or benzothiadiazolyl group which may be substituted with a substituent(s) selected from the group consisting of a $C_1$-$C_6$ alkyl group and a halogen atom.

16.

The compound or pharmaceutically acceptable salt thereof according to any one of embodiments 1 to 12, wherein $R^5$ is a phenyl group whose 3- and 4-positions are each substituted with a halogen atom, or a naphthyl group which may be substituted with a substituent(s) selected from the group consisting of a halogen atom, a $C_1$-$C_6$ alkyl group and a cyano group.

17.

The compound or pharmaceutically acceptable salt thereof according to any one of embodiments 1 to 16, wherein $R^3$ is a phenyl group, a naphthyl group, a pyrazolyl group, a pyridyl group, an indolyl group, a benzothiazolyl group, a benzothiadiazolyl group, a pyrazolopyrimidinyl group, a quinolinyl group, an isoquinolinyl group, a benzothienyl group or a dihydroquinolinonyl group, wherein these groups may each be substituted with 1 to 3 substituents selected from the following group [wherein said group consists of substituents listed below: a $C_1$-$C_6$ alkyl group which may be substituted with a fluorine atom(s), a $C_3$-$C_8$ cycloalkyl group, a halogen atom, a $C_1$-$C_6$ alkoxy group (wherein said alkoxy group may be substituted with a substituent(s) selected from the group consisting of a fluorine atom, a phenyl group, an amino group substituted with two $C_1$-$C_4$ alkyl groups and a morpholino group), a phenoxy group, a phenyl group, a carboxyl group, a $C_2$-$C_{10}$ alkoxycarbonyl group, a hydroxyl group, a $C_2$-$C_7$ monocyclic saturated hydrocarbon group containing a nitrogen atom(s) as a ring member(s) (wherein said saturated hydrocarbon group may be substituted with a $C_1$-$C_6$ alkyl group(s)), a nitrogen-containing monocyclic unsaturated hydrocarbon group, a morpholinyl group which may be substituted with a $C_1$-$C_6$ alkyl group(s), a piperazino group which may be substituted with a substituent(s) selected from the following group (wherein said group consists of a $C_1$-$C_6$ alkyl group (wherein said alkyl group may be substituted with an amino group which may be substituted with one or two $C_1$-$C_6$ alkyl groups, a morpholino group, a hydroxyl group, or a $C_1$-$C_6$ alkoxy group), a formyl group, a $C_2$-$C_7$ alkanoyl group, a carbamoyl group which may be substituted with one or two $C_1$-$C_4$ alkyl groups, an aminosulfonyl group which may be substituted with one or two $C_1$-$C_6$ alkyl groups, and a $C_1$-$C_6$ alkylsulfonyl group), and the formula:

—NR$^7$R$^8$ wherein $R^7$ and $R^8$ each represent a hydrogen atom, a $C_1$-$C_6$ alkyl group (wherein said alkyl group may be substituted with an amino group which may be substituted with one or two $C_1$-$C_6$ alkyl groups, a hydroxyl group, or a $C_1$-$C_6$ alkoxy group), a $C_1$-$C_6$ alkanoyl group, a carbamoyl group which may be substituted with one or two $C_1$-$C_4$ alkyl groups, a morpholinocarbonyl group, an aminosulfonyl group which may be substituted with one or two $C_1$-$C_6$ alkyl groups, or a $C_1$-$C_6$ alkylsulfonyl group, or alternatively, $R^7$ and $R^8$ optionally form, together with the nitrogen atom to which $R^7$ and $R^8$ are attached, a 3- to 8-membered saturated hydrocarbon ring, wherein said ring may be substituted with a substituent(s) selected from the group consisting of a dimethylenedioxy group, an oxo group and a hydroxyl group].

18.

The compound or pharmaceutically acceptable salt thereof according to any one of embodiments 1 to 16, wherein $R^3$ is a 2-naphthyl group (wherein said naphthyl group may be substituted with a substituent(s) selected from the group consisting of a halogen atom and a $C_1$-$C_6$ alkyl group), a 3-pyrazolyl group (wherein said pyrazolyl group may be substituted with a substituent(s) selected from the group consisting of a $C_1$-$C_6$ alkyl group, a trifluoromethyl group and a halogen atom), or a 5-benzothiazolyl, 5-benzothiadiazolyl, 7-dihydroquinolinonyl, 7-isoquinolinyl, 7-quinolinyl, 3-pyridyl or indolyl group which may be substituted with a $C_1$-$C_6$ alkyl group(s), an unsubstituted phenyl group, or a substituted phenyl group shown in (A) to (C) below:

(A) a phenyl group whose 4-position is substituted with a substituent selected from the group consisting of a $C_1$-$C_6$ alkyl group, a $C_3$-$C_8$ cycloalkyl group, a $C_1$-$C_6$ alkoxy group (wherein said alkoxy group may be substituted with a substituent(s) selected from the group consisting of an amino group substituted with two $C_1$-$C_4$ alkyl groups, a morpholino group and a phenyl group), a halogen atom, a trifluoromethoxy group, a phenoxy group, a phenyl group, a 1-pyrrolyl group, and —NR$^A$R$^B$ (wherein R$^A$ and R$^B$ are each a $C_1$-$C_6$ alkyl group, or R$^A$ and R$^B$ optionally form, together with the nitrogen atom to which R$^A$ and R$^B$ are attached, a 3- to 5-membered saturated hydrocarbon ring), and further whose 3-position may be substituted with a substituent selected from the group consisting of a $C_1$-$C_6$ alkyl group, a halogen atom and a $C_1$-$C_6$ alkoxy group, (B) a phenyl group whose 3-position is substituted with a substituent selected from the group consisting of a hydroxyl group, a $C_1$-$C_6$ alkyl group and a $C_1$-$C_6$ alkoxy group (wherein said alkoxy group may be substituted with a substituent(s) selected from the group consisting of an amino group substituted with two $C_1$-$C_4$ alkyl groups, a morpholino group and a phenyl group), and further which may be substituted with one or two $C_1$-$C_6$ alkyl groups or whose 4-position may be substituted with a halogen atom, and (C) a phenyl group whose 3-position is substituted with a substituent selected from the group consisting of nitrogen-containing groups shown in (i) to (v) below, and further whose 4-position may be substituted with a halogen atom:

(i) a $C_2$-$C_7$ monocyclic saturated hydrocarbon group containing a nitrogen atom(s) as a ring member(s) (wherein said saturated hydrocarbon group may be substituted with a $C_1$-$C_6$ alkyl group(s)), (ii) a nitrogen-containing monocyclic unsaturated hydrocarbon group, (iii) a morpholinyl group which may be substituted with a $C_1$-$C_6$ alkyl group(s), (iv) a piperazino group [wherein said piperazino group may be substituted with a $C_1$-$C_6$ alkyl group which may be substituted with a substituent(s) selected from the following group (wherein said group consists of an amino group substituted with two $C_1$-$C_4$ alkyl groups and a morpholino group) or a $C_2$-$C_7$ alkanoyl group], and (v) the formula —$NR^7R^8$ wherein $R^7$ and $R^8$ each represent a hydrogen atom, a $C_1$-$C_6$ alkyl group (wherein said alkyl group may be substituted with an amino group which may be substituted with one or two $C_1$-$C_6$ alkyl groups, a hydroxyl group, or a $C_1$-$C_6$ alkoxy group), a $C_1$-$C_6$ alkanoyl group, a carbamoyl group which may be substituted with one or two $C_1$-$C_4$ alkyl groups, a morpholinocarbonyl group, an aminosulfonyl group which may be substituted with one or two $C_1$-$C_6$ alkyl groups, or a $C_1$-$C_6$ alkylsulfonyl group, or alternatively, $R^7$ and $R^8$ optionally form, together with the nitrogen atom to which $R^7$ and $R^8$ are attached, a 3- to 8-membered saturated hydrocarbon ring, wherein said ring may be substituted with a substituent(s) selected from the group consisting of a dimethylenedioxy group, an oxo group and a hydroxyl group.

19.

The compound or pharmaceutically acceptable salt thereof according to any one of embodiments 1 to 16, wherein $R^3$ is a phenyl group whose 3-position is substituted with a substituent selected from the group consisting of nitrogen-containing groups shown in (i) to (v) below, and further whose 4-position may be substituted with a halogen atom:

(i) a $C_2$-$C_7$ monocyclic saturated hydrocarbon group containing a nitrogen atom(s) as a ring member(s) (wherein said saturated hydrocarbon group may be substituted with a $C_1$-$C_6$ alkyl group(s)), (ii) a nitrogen-containing monocyclic unsaturated hydrocarbon group, (iii) a morpholinyl group which may be substituted with a $C_1$-$C_6$ alkyl group(s), (iv) a piperazino group [wherein said piperazino group may be substituted with a $C_1$-$C_6$ alkyl group which may be substituted with a substituent(s) selected from the following group (wherein said group consists of an amino group substituted with two $C_1$-$C_4$ alkyl groups and a morpholino group) or a $C_2$-$C_7$ alkanoyl group], and (v) the formula —$NR^7R^8$ wherein $R^7$ and $R^8$ each represent a hydrogen atom, a $C_1$-$C_6$ alkyl group (wherein said alkyl group may be substituted with an amino group which may be substituted with one or two $C_1$-$C_6$ alkyl groups, a hydroxyl group, or a $C_1$-$C_6$ alkoxy group), a $C_1$-$C_6$ alkanoyl group, a carbamoyl group which may be substituted with one or two $C_1$-$C_4$ alkyl groups, a morpholinocarbonyl group, an aminosulfonyl group which may be substituted with one or two $C_1$-$C_6$ alkyl groups, or a $C_1$-$C_6$ alkylsulfonyl group, or alternatively, $R^7$ and $R^8$ optionally form, together with the nitrogen atom to which $R^7$ and $R^8$ are attached, a 3- to 8-membered saturated hydrocarbon ring, wherein said ring may be substituted with a substituent(s) selected from the group consisting of a dimethylenedioxy group, an oxo group and a hydroxyl group.

20.

The compound or pharmaceutically acceptable salt thereof according to any one of embodiments 1 to 16, wherein $R^3$ is a phenyl group whose 4-position is substituted with a fluorine atom or a chlorine atom.

21.

The compound or pharmaceutically acceptable salt thereof according to any one of embodiments 1 to 16, wherein $R^3$ is a 6-indolyl group.

22.

The compound or pharmaceutically acceptable salt thereof according to any one of embodiments 1 and 3 to 16, wherein $R^3$ is a $C_1$-$C_{18}$ alkyl group which may be substituted with a substituent(s) selected from the following group (wherein said group consists of a halogen atom, an amino group which may be substituted with one or two $C_1$-$C_6$ alkyl groups, a $C_1$-$C_6$ alkoxy group, a piperazino group which may be substituted with a $C_1$-$C_6$ alkyl group(s), a phenyl group and a morpholino group), a $C_2$-$C_8$ alkenyl group, a $C_2$-$C_8$ alkynyl group, or a $C_3$-$C_8$ cycloalkyl group.

23.

The compound or pharmaceutically acceptable salt thereof according to any one of embodiments 1 and 3 to 16, wherein $R^3$ is a $C_1$-$C_6$ alkyl group substituted with a substituent(s) selected from the following group (wherein said group consists of an amino group which may be substituted with one or two $C_1$-$C_6$ alkyl groups, and a $C_1$-$C_6$ alkoxy group), or a $C_3$-$C_5$ cycloalkyl group.

24.

A pharmaceutical preparation comprising the compound or pharmaceutically acceptable salt thereof according to any one of embodiments 1 to 23.

25.

The pharmaceutical preparation according to embodiment 24, which is a therapeutic agent for an autoimmune disease such as Crohn's disease, irritable colitis, Sjogren's syndrome, multiple sclerosis or systemic lupus erythematosus, rheumatoid arthritis, asthma, atopic dermatitis, rejection after organ transplantation, cancer, retinopathy, psoriasis, osteoarthritis or age-related macular degeneration.

26.

A compound represented by formula (II) or a salt thereof:

[Formula 9]

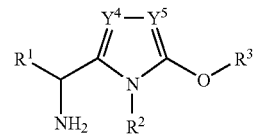

(wherein $R^1$, $R^2$ and $R^3$ are as defined above in embodiment 1, and $Y^4$ and $Y^5$ each represent a nitrogen atom or the formula $CR^{17}$ (wherein $R^{17}$ represents a hydrogen atom, a $C_1$-$C_6$ alkyl group, a phenyl group, or a halogen atom), provided that either of $Y^4$ and $Y^5$ is a nitrogen atom).

27.

The compound or salt thereof according to embodiment 26, wherein in formula (II), $Y^4$ is CH, and $Y^5$ is a nitrogen atom.

28.

The compound or salt thereof according to embodiment 26 or 27, wherein $R^1$ is a $C_1$-$C_6$ alkyl group which may be substituted with a halogen atom(s), or a benzyl group which may be substituted with a substituent(s) selected from the group consisting of a halogen atom and a $C_1$-$C_6$ alkyl group.

29.

29.
The compound or salt thereof according to embodiment 26 or 27, wherein $R^1$ is a methyl group, an ethyl group or a benzyl group which may be substituted with a halogen atom(s).
30.
The compound or salt thereof according to embodiment 26 or 27, wherein $R^1$ is a methyl group or an ethyl group.
31.
The compound or salt thereof according to any one of embodiments 26 to 30, wherein $R^2$ is a $C_1$-$C_6$ alkyl group or a $C_3$-$C_8$ cycloalkyl group.
32.
The compound or salt thereof according to any one of embodiments 26 to 30, wherein $R^2$ is an ethyl group or a cyclopropyl group.
33.
The compound or salt thereof according to any one of embodiments 26 to 32, wherein $R^3$ is a phenyl group, a naphthyl group, a pyrazolyl group, a pyridyl group, an indolyl group, a benzothiazolyl group, a benzothiadiazolyl group, a pyrazolopyrimidinyl group, a quinolinyl group, an isoquinolinyl group, a benzothienyl group or a dihydroquinolinonyl group, wherein these groups may each be substituted with 1 to 3 substituents selected from the following group [wherein said group consists of substituents listed below: a $C_1$-$C_6$ alkyl group which may be substituted with a fluorine atom(s), a $C_3$-$C_8$ cycloalkyl group, a halogen atom, a $C_1$-$C_6$ alkoxy group (wherein said alkoxy group may be substituted with a substituent(s) selected from the group consisting of a fluorine atom, a phenyl group, an amino group substituted with two $C_1$-$C_4$ alkyl groups and a morpholino group), a phenoxy group, a phenyl group, a carboxyl group, a $C_2$-$C_{10}$ alkoxycarbonyl group, a hydroxyl group, a $C_2$-$C_7$ monocyclic saturated hydrocarbon group containing a nitrogen atom(s) as a ring member(s) (wherein said saturated hydrocarbon group may be substituted with a $C_1$-$C_6$ alkyl group(s)), a nitrogen-containing monocyclic unsaturated hydrocarbon group, a morpholinyl group which may be substituted with a $C_1$-$C_6$ alkyl group(s), a piperazino group which may be substituted with a substituent(s) selected from the following group [wherein said group consists of a $C_1$-$C_6$ alkyl group (wherein said alkyl group may be substituted with an amino group which may be substituted with one or two $C_1$-$C_6$ alkyl groups, a morpholino group, a hydroxyl group, or a $C_1$-$C_6$ alkoxy group), a formyl group, a $C_2$-$C_7$ alkanoyl group, a carbamoyl group which may be substituted with one or two $C_1$-$C_4$ alkyl groups, an aminosulfonyl group which may be substituted with one or two $C_1$-$C_6$ alkyl groups, and a $C_1$-$C_6$ alkylsulfonyl group], and the formula:

—$NR^7R^8$ wherein $R^7$ and $R^8$ each represent a hydrogen atom, a $C_1$-$C_6$ alkyl group (wherein said alkyl group may be substituted with an amino group which may be substituted with one or two $C_1$-$C_6$ alkyl groups, a hydroxyl group, or a $C_1$-$C_6$ alkoxy group), a $C_1$-$C_6$ alkanoyl group, a carbamoyl group which may be substituted with one or two $C_1$-$C_4$ alkyl groups, a morpholinocarbonyl group, an aminosulfonyl group which may be substituted with one or two $C_1$-$C_6$ alkyl groups, or a $C_1$-$C_6$ alkylsulfonyl group, or alternatively, $R^7$ and $R^8$ optionally form, together with the nitrogen atom to which $R^7$ and $R^8$ are attached, a 3- to 8-membered saturated hydrocarbon ring, wherein said ring may be substituted with a substituent(s) selected from the group consisting of a dimethylenedioxy group, an oxo group and a hydroxyl group].
34.
The compound or salt thereof according to any one of embodiments 26 to 32, wherein $R^3$ is a 2-naphthyl group (wherein said naphthyl group may be substituted with a substituent(s) selected from the group consisting of a halogen atom and a $C_1$-$C_6$ alkyl group), a 3-pyrazolyl group (wherein said pyrazolyl group may be substituted with a substituent(s) selected from the group consisting of a $C_1$-$C_6$ alkyl group, a trifluoromethyl group and a halogen atom), or a 5-benzothiazolyl, 5-benzothiadiazolyl, 7-dihydroquinolinonyl, 7-isoquinolinyl, 7-quinolinyl, 3-pyridyl or indolyl group which may be substituted with a $C_1$-$C_6$ alkyl group(s), an unsubstituted phenyl group, or a substituted phenyl group shown in (A) to (C) below:
(A) a phenyl group whose 4-position is substituted with a substituent selected from the group consisting of a $C_1$-$C_6$ alkyl group, a $C_3$-$C_8$ cycloalkyl group, a $C_1$-$C_6$ alkoxy group (wherein said alkoxy group may be substituted with a substituent(s) selected from the group consisting of an amino group substituted with two $C_1$-$C_4$ alkyl groups, a morpholino group and a phenyl group), a halogen atom, a trifluoromethoxy group, a phenoxy group, a phenyl group, a 1-pyrrolyl group, and —$NR^AR^B$ (wherein $R^A$ and $R^B$ are each a $C_1$-$C_6$ alkyl group, or $R^A$ and $R^B$ optionally form, together with the nitrogen atom to which $R^A$ and $R^B$ are attached, a 3- to 5-membered saturated hydrocarbon ring), and further whose 3-position may be substituted with a substituent selected from the group consisting of a $C_1$-$C_6$ alkyl group, a halogen atom and a $C_1$-$C_6$ alkoxy group,
(B) a phenyl group whose 3-position is substituted with a substituent selected from the group consisting of a hydroxyl group, a $C_1$-$C_6$ alkyl group and a $C_1$-$C_6$ alkoxy group (wherein said alkoxy group may be substituted with a substituent(s) selected from the group consisting of an amino group substituted with two $C_1$-$C_4$ alkyl groups, a morpholino group and a phenyl group), and further which may be substituted with one or two $C_1$-$C_6$ alkyl groups or whose 4-position may be substituted with a halogen atom,
and
(C) a phenyl group whose 3-position is substituted with a substituent selected from the group consisting of nitrogen-containing groups shown in (i) to (v) below, and further whose 4-position may be substituted with a halogen atom:
(i) a $C_2$-$C_7$ monocyclic saturated hydrocarbon group containing a nitrogen atom(s) as a ring member(s) (wherein said saturated hydrocarbon group may be substituted with a $C_1$-$C_6$ alkyl group(s)),
(ii) a nitrogen-containing monocyclic unsaturated hydrocarbon group,
(iii) a morpholinyl group which may be substituted with a $C_1$-$C_6$ alkyl group(s),
(iv) a piperazino group [wherein said piperazino group may be substituted with a $C_1$-$C_6$ alkyl group which may be substituted with a substituent(s) selected from the following group (wherein said group consists of an amino group substituted with two $C_1$-$C_4$ alkyl groups and a morpholino group) or a $C_2$-$C_7$ alkanoyl group], and
(v) the formula —$NR^7R^8$
wherein $R^7$ and $R^8$ each represent a hydrogen atom, a $C_1$-$C_6$ alkyl group (wherein said alkyl group may be substituted with an amino group which may be substituted with one or two $C_1$-$C_6$ alkyl groups, a morpholino group, a hydroxyl group, or a $C_1$-$C_6$ alkoxy group), a $C_1$-$C_6$ alkanoyl group, a carbamoyl group which may be substituted with one or two $C_1$-$C_4$ alkyl groups, a morpholinocarbonyl group, an aminosulfonyl group which may be substituted with one or two $C_1$-$C_6$ alkyl groups, or a $C_1$-$C_6$ alkylsulfonyl group, or alternatively, $R^7$ and $R^8$ optionally form, together with the nitrogen atom to which $R^7$ and $R^8$ are attached, a 3- to 8-membered saturated hydrocarbon ring, wherein said ring may be substituted with a substituent(s) selected from the group consisting of a dimethylenedioxy group, an oxo group and a hydroxyl group.

35. The compound or salt thereof according to any one of embodiments 26 to 32, wherein $R^3$ is a $C_1$-$C_{18}$ alkyl group which may be substituted with a substituent(s) selected from the following group (wherein said group consists of a halogen atom, an amino group which may be substituted with one or two $C_1$-$C_6$ alkyl groups, a $C_1$-$C_6$ alkoxy group, a piperazino group which may be substituted with a $C_1$-$C_6$ alkyl group(s), a phenyl group and a morpholino group), a $C_2$-$C_8$ alkenyl group, a $C_2$-$C_8$ alkynyl group, or a $C_3$-$C_8$ cycloalkyl group.

The present invention will be illustrated in detail below.

The monocyclic heterocyclic ring containing one or two nitrogen atoms represented herein by Ar is intended to include pyrrole, imidazole and pyrazole shown below.

[Formula 10]

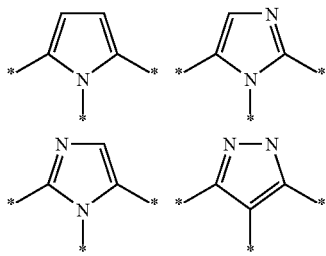

The term "halogen atom" refers to a fluorine atom, a chlorine atom, a bromine atom or an iodine atom.

The term "$C_1$-$C_6$ alkyl group" refers to a linear or branched alkyl group containing 1 to 6 carbon atoms. Examples include a methyl group, an ethyl group, a n-propyl group, an isopropyl group, a n-butyl group, an isobutyl group, a tert-butyl group, a sec-butyl group, a n-pentyl group, an isopentyl group, a neopentyl group, a tert-pentyl group, and a n-hexyl group.

The term "$C_3$-$C_8$ cycloalkyl group" refers to a cycloalkyl group containing 3 to 8 carbon atoms. Examples include a cyclopropyl group, a cyclobutyl group, a cyclopentyl group, and a cyclohexyl group.

The term "$C_2$-$C_8$ alkenyl group" refers to a linear or branched alkenyl group containing 2 to 8 carbon atoms. Examples include a vinyl group, an allyl group, a 1-propenyl group, an isopropenyl group, a 1-butenyl group, a 2-butenyl group, a 3-butenyl group, a 1,3-butadienyl group, a 2-methylallyl group, a 2-methyl-propenyl group, a 2-pentenyl group, and a 3-methyl-but-2-enyl group.

The term "$C_2$-$C_8$ alkynyl group" refers to a linear or branched alkynyl group containing 2 to 8 carbon atoms. Examples include an ethynyl group, a 2-propynyl group, a 2-butynyl group, a 1-methyl-prop-2-ynyl group, a 2-pentynyl group, and a 4-pentynyl group.

The term "$C_1$-$C_6$ alkoxy group" refers to a linear or branched alkoxy group containing 1 to 6 carbon atoms. Examples include a methoxy group, an ethoxy group, a propoxy group, an isopropoxy group, a butoxy group, an isobutoxy group, a sec-butoxy group, a tert-butoxy group, a pentyloxy group, and a hexyloxy group.

The term "$C_1$-$C_{10}$ alkyl group" refers to a linear or branched alkyl group containing 1 to 10 carbon atoms. Examples include a methyl group, an ethyl group, a n-propyl group, an isopropyl group, a n-butyl group, an isobutyl group, a tert-butyl group, a sec-butyl group, a n-pentyl group, an isopentyl group, a neopentyl group, a tert-pentyl group, a n-hexyl group, a n-heptyl group, a n-octyl group, and a n-hexadecyl group.

The term "$C_1$-$C_6$ alkylthio group" refers to a linear or branched alkylthio group containing 1 to 6 carbon atoms. Examples include a methylthio group, an ethylthio group, a propylthio group, an isopropylthio group, a butylthio group, an isobutylthio group, a pentylthio group, and a hexylthio group.

The term "$C_1$-$C_6$ alkylsulfonyl group" refers to a linear or branched alkylsulfonyl group containing 1 to 6 carbon atoms. Examples include a methanesulfonyl group, an ethanesulfonyl group, a propane-2-sulfonyl group, and a hexanesulfonyl group.

The term "$C_2$-$C_{10}$ alkoxycarbonyl group" refers to a linear or branched alkoxycarbonyl group containing 2 to 10 carbon atoms. Examples include $C_2$-$C_7$ alkoxycarbonyl groups such as a methoxycarbonyl group, an ethoxycarbonyl group and a t-butoxycarbonyl group, as well as an octyloxycarbonyl group.

The term "$C_2$-$C_7$ alkanoyl group" refers to a linear or branched alkanoyl group containing 2 to 7 carbon atoms. Examples include an acetyl group, a propanoyl group, a butanoyl group, and a hexanoyl group.

The term "$C_1$-$C_6$ alkanoyl group" refers to a linear or branched alkanoyl group containing 1 to 6 carbon atoms. Examples include a formyl group, an acetyl group, a propanoyl group, and a butanoyl group.

The phrase "amino group which may be substituted with one or two $C_1$-$C_6$ alkyl groups" is intended to include, for example, an amino group, a methylamino group, an ethylamino group, an isopropylamino group, a hexylamino group, a dimethylamino group, a diethylamino group, a diisopropylamino group, and a dihexylamino group.

The phrase "aminosulfonyl group which may be substituted with one or two $C_1$-$C_6$ alkyl groups" is intended to include, for example, a sulfamoyl group, a dimethylaminosulfonyl group, and a diethylaminosulfonyl group.

The phrase "carbamoyl group which may be substituted with $C_1$-$C_4$ alkyl group(s)" is intended to include a carbamoyl group, a methylcarbamoyl group, an ethylcarbamoyl group, and a propylcarbamoyl group.

The phrase "piperazino group which may be substituted" or "optionally substituted piperazino group" refers to a piperazino group which may be substituted (preferably on its nitrogen atom) with a substituent(s) selected from the group consisting of a $C_1$-$C_6$ alkyl group (wherein said alkyl group may be substituted with an amino group which may be substituted with one or two $C_1$-$C_6$ alkyl groups, a morpholino group, a hydroxyl group, or a $C_1$-$C_6$ alkoxy group), a formyl group, a $C_2$-$C_7$ alkanoyl group, a carbamoyl group which may be substituted with one or two $C_1$-$C_4$ alkyl groups, an aminosulfonyl group which may be substituted with one or two $C_1$-$C_6$ alkyl groups, and a $C_1$-$C_6$ alkylsulfonyl group. Specific examples include a piperazino group, a methylpiperazino group, an isopropylpiperazino group, a dimethylaminoethylpiperazino group, and an acetylpiperazino group.

The phrase "$C_2$-$C_7$ monocyclic saturated hydrocarbon group containing a nitrogen atom(s) as a ring member(s)" refers to a 3- to 9-membered monocyclic saturated hydrocarbon group which contains one or two nitrogen atoms as its ring members and is substituted via its ring carbon atom. Examples include an azetidinyl group, a pyrrolidinyl group, and a piperidinyl group (e.g., a 4-piperidinyl group).

The term "nitrogen-containing monocyclic unsaturated hydrocarbon group" refers to a 5- or 6-membered unsaturated ring containing 1 to 3 nitrogen atoms as its ring members.

Examples include a pyrrolyl group (e.g., a pyrrol-1-yl group), an imidazol-1-yl group (e.g., an imidazolyl group), a pyrazolyl group, a triazol-4-yl group (e.g., a [1,2,4]triazol-4-yl group), and a pyridyl group.

The 3- to 5-membered saturated hydrocarbon ring formed by $R^A$ and $R^B$ together with the nitrogen atom to which $R^A$ and $R^B$ are attached is intended to include an aziridinyl group, an azetidinyl group, and a pyrrolidinyl group.

The 3- to 8-membered saturated hydrocarbon ring formed by $R^7$ and $R^8$ (or $R^C$ and $R^D$) together with the nitrogen atom to which $R^7$ and $R^8$ (or $R^C$ and $R^D$) are attached is intended to include an aziridinyl group, an azetidinyl group, a pyrrolidinyl group, and a piperidinyl group.

The phrase "phenyl group condensed with a 5- to 7-membered saturated hydrocarbon ring which may contain one or two oxygen atoms as ring members" is intended to include a benzodioxepinyl group, a benzodioxolyl group, a dihydrobenzodioxinyl group, a dihydrobenzofuranyl group, a tetrahydronaphthyl group, and an indanyl group.

The term "aryl group" as used herein refers to an aromatic hydrocarbon group, a partially saturated aromatic hydrocarbon group, an aromatic heterocyclic group, or a partially saturated aromatic heterocyclic ring. The aromatic hydrocarbon group refers to, for example, a $C_6$-$C_{14}$ aromatic hydrocarbon group, including a phenyl group, a naphthyl group, and an anthryl group.

The partially saturated aromatic hydrocarbon group refers to a group obtained by partial saturation of a $C_6$-$C_{14}$ polycyclic aromatic hydrocarbon group. Examples include a tetrahydronaphthyl group and an indanyl group.

The aromatic heterocyclic group refers to a $C_2$-$C_{13}$ monocyclic or polycyclic aromatic heterocyclic group containing 1 to 6 heteroatoms (e.g., oxygen, sulfur and/or nitrogen atoms). Examples include a thienyl group, a furanyl group, a pyrrolyl group, an isothiazolyl group, an isoxazolyl group, a pyrazolyl group, a thiazolyl group, an oxazolyl group, an imidazolyl group, a pyridyl group, a pyridazinyl group, a pyrimidinyl group, a pyrazinyl group, a benzothienyl group, a benzofuranyl group, an indolyl group, a benzothiazolyl group, a benzoxazolyl group, a benzimidazolyl group, a quinolinyl group, an isoquinolinyl group, a benzoxadiazolyl group, a benzothiadiazolyl group, and a pyrazolopyrimidinyl group (e.g., a 5,7-dimethyl-pyrazolo[1,5-a]pyrimidin-2-yl group).

The partially saturated aromatic heterocyclic ring refers to a heterocyclic ring obtained by partial saturation of a polycyclic aromatic heterocyclic group. Such a heterocyclic ring may be substituted with an oxo group. Examples include a dihydroquinolinonyl group:

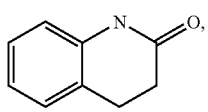

[Formula 11]

a dihydrobenzofuranyl group, a dihydrobenzodioxinyl group, a dihydrobenzodioxepinyl group, a benzodioxolyl group, a dihydrobenzoxazolyl group, and a dihydrobenzoxazinyl group.

In a case where such an aryl group is substituted, substituents for the aryl group include those listed below and the aryl group can be substituted with 1 to 5 of these substituents:

a halogen atom, a cyano group, a nitro group, a sulfamoyl group, a hydroxyl group, a carboxyl group, a $C_1$-$C_6$ alkyl group, a trifluoromethyl group, a methoxycarbonylethyl group, a $C_1$-$C_6$ alkoxy group (wherein said alkoxy group may be substituted with a phenyl group, a $C_1$-$C_6$ alkylamino group, a $C_2$-$C_{12}$ dialkylamino group, or a morpholino group), a trifluoromethoxy group, a difluoromethoxy group, a cyanoethoxy group, a $C_2$-$C_8$ alkenyl group, a $C_2$-$C_8$ alkynyl group, a $C_3$-$C_8$ cycloalkyl group, a $C_2$-$C_7$ alkanoyl group, a trifluoroacetyl group, a $C_2$-$C_{10}$ alkoxycarbonyl group, a phenyl group (wherein said phenyl group may be substituted with a $C_2$-$C_7$ alkanoyl group or a $C_1$-$C_6$ alkoxy group), a phenoxy group which may be substituted with a $C_1$-$C_6$ alkoxy group, a pyrazolyl group, a 1-methyl-5-trifluoromethyl-1H-pyrazol-3-yl group, a methylpyrimidinyl group, a 2-methylsulfanyl-pyrimidin-4-yl group, an oxazolyl group (e.g., an oxazol-5-yl group), an isoxazol-5-yl group, a 5-trifluoromethyl-isoxazol-3-yl group, a pyridyloxy group (e.g., a 4-pyridyloxy group), a pyridinecarbonyl group, a benzoyl group, a pyrrolyl group (e.g., a pyrrol-1-yl group), an imidazolyl group (e.g., an imidazol-1-yl group), a thiazolyl group, a [1,2,3]thiadiazol-4-yl group, a triazolyl group (e.g., a [1,2,4]triazol-4-yl group), a $C_1$-$C_6$ alkylthio group (e.g., methylthio group), a $C_1$-$C_6$ alkylsulfonyl group (e.g., a methanesulfonyl group), a benzenesulfonyl group, a pyrrolidinesulfonyl group, a morpholinylsulfonyl group, a 4-piperidinyl group which may be substituted with a $C_1$-$C_6$ alkyl group(s), a morpholino group which may be substituted with a $C_1$-$C_6$ alkyl group(s), a piperazino group which is substituted with a $C_1$-$C_6$ alkyl group(s) or with a $C_1$-$C_6$ alkyl group(s) substituted with a dimethylamino group, or a group represented by the formula —$NR^7R^8$

[wherein $R^7$ and $R^8$ each represent a hydrogen atom, a $C_1$-$C_6$ alkyl group (wherein said alkyl group may be substituted with a $C_1$-$C_6$ alkoxy group or a dimethylamino group), a $C_1$-$C_6$ alkanoyl group, a carbamoyl group, a carbamoyl group substituted with a $C_1$-$C_4$ alkyl group(s), a morpholinocarbonyl group, a dimethylaminosulfonyl group, or a $C_1$-$C_6$ alkylsulfonyl group, or alternatively, $R^7$ and $R^8$ may optionally form, together with the nitrogen atom to which $R^7$ and $R^8$ are attached, a 3- to 8-membered saturated hydrocarbon ring, wherein said ring may be substituted with a dimethylenedioxy group, an oxo group or a hydroxyl group]

(e.g., an acetamido group, a dimethylamino group, a methylureido group, a butylureido group, a trimethylureido group, a morpholinylcarbonylamino group), a methoxyethylureido group, and a pyridylethoxycarbonylamino group.

The term "pharmaceutically acceptable salt" refers to a salt with an alkali metal, an alkaline earth metal, ammonium or an alkylammonium, or a salt with a mineral acid or an organic acid. Examples include a sodium salt, a potassium salt, a calcium salt, an ammonium salt, an aluminum salt, a triethylammonium salt, an acetate salt, a propionate salt, a butyrate salt, a formate salt, a trifluoroacetate salt, a maleate salt, a tartrate salt, a citrate salt, a stearate salt, a succinate salt, an ethylsuccinate salt, a lactobionate salt, a gluconate salt, a glucoheptate salt, a benzoate salt, a methanesulfonate salt, an ethanesulfonate salt, a 2-hydroxyethanesulfonate salt, a benzenesulfonate salt, a paratoluenesulfonate salt, a lauryl sulfate salt, a malate salt, an aspartate salt, a glutamate salt, an adipate salt, a salt with cysteine, a salt with N-acetylcysteine, a hydrochloride salt, a hydrobromide salt, a phosphate salt, a sulfate salt, a hydroiodide salt, a nicotinate salt, an oxalate salt, a picrate salt, a thiocyanate salt, an undecanoate salt, a salt with an acrylate polymer, and a salt with a carboxyvinyl polymer.

The compounds of the present invention may have stereoisomers including optical isomers, diastereoisomers and geometrical isomers. All of these stereoisomers and mixtures thereof also fall within the scope of the present invention. Some of the compounds and intermediates of the present invention may also exist, e.g., as keto-enol tautomers.

As shown in the test example described later, the compounds of the present invention exert a strong inhibitory effect on the binding between S1P and its receptor Edg-1 (S1P$_1$), and are therefore expected to produce a prophylactic or therapeutic effect on autoimmune diseases such as Crohn's disease, irritable colitis, Sjogren's syndrome, multiple sclerosis and systemic lupus erythematosus, as well as other diseases such as rheumatoid arthritis, asthma, atopic dermatitis, rejection after organ transplantation, cancer, retinopathy, psoriasis, osteoarthritis, age-related macular degeneration, etc.

Preferred embodiments of the compound of the present invention will be given below.

A preferred example of Ar is a 5-membered unsaturated ring containing one or two nitrogen atoms. More preferred is an imidazole group represented by the following formula:

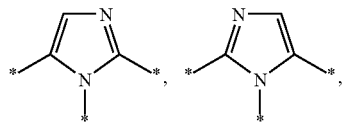

[Formula 12]

and even more preferred is

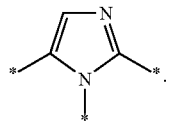

These rings may be substituted with a substituent selected from the group consisting of a $C_1$-$C_6$ alkyl group, a phenyl group and a halogen atom. More preferably, Ar is unsubstituted.

A preferred example of A is an oxygen atom.

A preferred example of $R^1$ is a $C_1$-$C_6$ alkyl group which may be substituted with a halogen atom(s), or a benzyl group which may be substituted with a substituent(s) selected from the group consisting of a halogen atom and a $C_1$-$C_6$ alkyl group. More preferred is a methyl group, an ethyl group, or a benzyl group which may be substituted with a halogen atom(s) (more preferably with a fluorine atom(s)), and even more preferred is a methyl group.

A preferred example of $R^2$ is an ethyl group or a cyclopropyl group.

A preferred example of $R^4$ is a hydrogen atom.

A preferred embodiment of $R^3$ is a $C_1$-$C_6$ alkyl group substituted with a substituent(s) selected from the following group (wherein said group consists of an amino group which may be substituted with one or two $C_1$-$C_6$ alkyl groups, and a $C_1$-$C_6$ alkoxy group), a $C_3$-$C_3$ cycloalkyl group, or an optionally substituted phenyl group, a 2-naphthyl group which may be substituted with a substituent(s) selected from the group consisting of a halogen atom and a $C_1$-$C_6$ alkyl group, a 3-pyrazolyl group which may be substituted with a substituent(s) selected from the following group [wherein said group consists of a $C_1$-$C_6$ alkyl group (preferably a methyl group), a trifluoromethyl group and a halogen atom], or a 5-benzothiazolyl, 5-benzothiadiazolyl, 7-dihydroquinolinonyl, 7-isoquinolinyl, 7-quinolinyl, 3-pyridyl or indolyl (preferably 6-indolyl) group which may be substituted with a $C_1$-$C_6$ alkyl group(s) (preferably a methyl group).

The "optionally substituted phenyl group" among preferred embodiments of $R^3$ is intended to include an unsubstituted phenyl group and a substituted phenyl group shown in (A) to (C) below:

(A) a phenyl group whose 4-position is substituted with a substituent selected from the group consisting of a $C_1$-$C_6$ alkyl group, a $C_3$-$C_8$ cycloalkyl group, a $C_1$-$C_6$ alkoxy group (wherein said alkoxy group may be substituted with a substituent(s) selected from the group consisting of an amino group substituted with two $C_1$-$C_4$ alkyl groups, a morpholino group and a phenyl group), a halogen atom, a trifluoromethoxy group, a phenoxy group, a phenyl group, a 1-pyrrolyl group, and —NR$^A$R$^B$ (wherein R$^A$ and R$^B$ are each a $C_1$-$C_6$ alkyl group, or R$^A$ and R$^B$ optionally form, together with the nitrogen atom to which R$^A$ and R$^B$ are attached, a 3- to 5-membered saturated hydrocarbon ring), and further whose 3-position may be substituted with a substituent selected from the group consisting of a $C_1$-$C_6$ alkyl group, a halogen atom and a $C_1$-$C_6$ alkoxy group, (B) a phenyl group whose 3-position is substituted with a substituent selected from the group consisting of a hydroxyl group, a $C_1$-$C_6$ alkyl group and a $C_1$-$C_6$ alkoxy group (wherein said alkoxy group may be substituted with a substituent(s) selected from the group consisting of an amino group substituted with two $C_1$-$C_4$ alkyl groups, a morpholino group and a phenyl group), and further which may be substituted with one or two $C_1$-$C_6$ alkyl groups or whose 4-position may be substituted with a halogen atom, and (C) a phenyl group whose 3-position is substituted with a substituent selected from the group consisting of nitrogen-containing groups shown in (i) to (v) below, and further whose 4-position may optionally be substituted with a halogen atom, wherein the nitrogen in said nitrogen-containing group is preferably tertiary and is preferably used for attachment to the phenyl group:

(i) a $C_2$-$C_7$ monocyclic saturated hydrocarbon group containing a nitrogen atom(s) as a ring member(s), which is substituted on the phenyl group via a carbon atom (wherein said saturated hydrocarbon group may be substituted with a $C_1$-$C_6$ alkyl group(s)) (e.g., a piperidinyl group which may be substituted with a $C_1$-$C_6$ alkyl group(s), as exemplified by a 4-piperidinyl group), (ii) a nitrogen-containing monocyclic unsaturated hydrocarbon group (e.g., a pyrrolyl group, an imidazolyl group), (iii) a morpholinyl group which may be substituted with a $C_1$-$C_6$ alkyl group(s) (e.g., a morpholino group), (iv) an optionally substituted piperazino group [e.g., a piperazino group which may be substituted (preferably on its ring member nitrogen atom) with a substituent(s) selected from the following group [wherein said group consists of a $C_1$-$C_6$ alkyl group (wherein said alkyl group may be substituted with a substituent(s) selected from the group consisting of an amino group substituted with two $C_1$-$C_4$ alkyl groups and a morpholino group), and a $C_2$-$C_7$ alkanoyl group]], and (v) the formula —NR$^7$R$^8$ wherein R$^7$ and R$^8$ each represent a hydrogen atom, a $C_1$-$C_6$ alkyl group (wherein said alkyl group may be substituted with an amino group which may be substituted with one or two $C_1$-$C_6$ alkyl groups, a morpholino group, a hydroxyl group, or a $C_1$-$C_6$ alkoxy group), a $C_1$-$C_6$ alkanoyl group, a carbamoyl group which may be substituted with one or two $C_1$-$C_4$ alkyl groups, a morpholinocarbonyl group, an aminosulfonyl group which may be substituted with one or two $C_1$-$C_6$ alkyl groups, or a $C_1$-$C_6$ alkylsulfonyl group, or alternatively, $R^7$ and $R^8$ optionally form, together with the nitrogen atom to which $R^7$ and $R^8$ are attached, a 3- to 8-membered saturated hydrocarbon ring, wherein said ring may be substituted with a substituent(s) selected from the group consisting of a dimethylenedioxy group, an oxo group and a hydroxyl group].

The formula —$NR^7R^8$ in (v) is more preferably —$NR^CR^D$ as defined below:

$R^C$ and $R^D$ each represent a hydrogen atom, a $C_1$-$C_6$ alkyl group (wherein said alkyl group may be substituted with an amino group which may be substituted with one or two $C_1$-$C_4$ alkyl groups, a hydroxyl group, or a $C_1$-$C_4$ alkoxy group), a formyl group, an acetyl group, an aminocarbonyl group, a dimethylaminosulfonyl group or a methylsulfonyl group, or alternatively, $R^C$ and $R^D$ optionally form, together with the nitrogen atom to which $R^C$ and $R^D$ are attached, a 3- to 8-membered saturated hydrocarbon ring, wherein said ring may be substituted with a substituent(s) selected from the group consisting of a dimethylenedioxy group, an oxo group and a hydroxyl group.

A particularly preferred embodiment of $R^3$ is a phenyl group whose 4-position is substituted with a fluorine atom or a chlorine atom, a 6-indolyl group, or a phenyl group which is substituted with a substituent selected from the group consisting of the nitrogen-containing groups shown in embodiments (i), (iv) and (v) in (C) above, and further whose 4-position may be substituted with a halogen atom.

A preferred embodiment of $R^5$ is a $C_1$-$C_{10}$ (preferably $C_1$-$C_6$) alkyl group substituted with a $C_3$-$C_8$ cycloalkyl group, a $C_1$-$C_{10}$ (preferably $C_1$-$C_6$) alkyl group substituted with a naphthyl group, a $C_2$-$C_8$ (preferably $C_2$-$C_6$) alkenyl group substituted with a phenyl group, a phenyl or naphthyl group (preferably a 2-naphthyl group) which may be substituted with 1 to 5 substituents selected from the following group (wherein said group consists of a $C_1$-$C_6$ alkyl group, a halogen atom, a $C_1$-$C_6$ alkoxy group, a trifluoromethoxy group, a difluoromethoxy group, a trifluoromethyl group, a $C_1$-$C_6$ alkenyl group, a $C_1$-$C_6$ alkylsulfonyl group, a $C_2$-$C_7$ alkanoyl group, a $C_2$-$C_7$ alkoxycarbonyl group and a cyano group), a pyrrolyl group which may be substituted with a substituent(s) selected from the following group [wherein said group consists of a $C_1$-$C_6$ alkyl group (preferably a methyl group) and a methoxycarbonyl group], a furanyl group which may be substituted with a substituent(s) selected from the following group [wherein said group consists of a $C_1$-$C_6$ alkyl group (preferably a methyl group), a trifluoromethyl group and a halogen atom], a thienyl group which may be substituted with a substituent(s) selected from the following group [wherein said group consists of a $C_1$-$C_6$ alkyl group (preferably a methyl group), a trifluoromethyl group, a thiadiazolyl group, an oxazolyl group and a halogen atom], or alternatively, a benzothienyl group (preferably a 2-benzothienyl group), a phenyl group condensed with a 5- to 7-membered saturated hydrocarbon ring which may contain one or two oxygen atoms as ring members (e.g., a benzodioxepinyl group, a benzodioxolyl group, a dihydrobenzodioxinyl group, a dihydrobenzofuranyl group, a tetrahydronaphthyl group, an indanyl group), a thiadiazolyl group, a benzoxadiazolyl group or a benzothiadiazolyl group (preferably a 5-benzothiadiazolyl group), each of which may be substituted with a substituent(s) selected from the group consisting of a $C_1$-$C_6$ alkyl group (preferably a methyl group) and a halogen atom.

The "phenyl group which may be substituted" among preferred embodiments of $R^5$ is intended to include an unsubstituted phenyl group, a phenyl group which is substituted with 1 to 5 substituents selected from the group consisting of a $C_1$-$C_6$ alkyl group (preferably a methyl group), a $C_1$-$C_6$ alkoxy group (preferably a methoxy group) and a halogen atom, and a phenyl group which is substituted with 1 to 3 substituents selected from the following group and at least one of whose 3- and 4-positions is substituted, wherein said group consists of a $C_1$-$C_6$ alkyl group, a halogen atom, a $C_1$-$C_6$ alkoxy group (preferably a methoxy group), a trifluoromethoxy group, a difluoromethoxy group, a trifluoromethyl group, a $C_1$-$C_6$ alkenyl group, a $C_1$-$C_6$ alkylsulfonyl group (preferably a methylsulfonyl group), a methoxycarbonyl group, an acetyl group and a cyano group, more preferably a halogen atom, a methyl group and a methoxy group, and even more preferably a halogen atom.

The "naphthyl group which may be substituted" among preferred embodiments of $R^5$ is intended to include a naphthyl group which may be substituted with a substituent(s) (preferably with 1 to 3 substituents) selected from the group consisting of a halogen atom, a $C_1$-$C_6$ alkyl group (preferably a methyl group), a cyano group and a $C_1$-$C_6$ alkylsulfonyl group (preferably a methylsulfonyl group). More preferred is a naphthyl group which may be substituted with a substituent(s) selected from the group consisting of a halogen atom, a $C_1$-$C_6$ alkyl group (preferably a methyl group) and a cyano group. In the case of a 2-naphthyl group, examples include an unsubstituted 2-naphthyl group, and a 2-naphthyl group which is substituted with a substituent(s) selected from the group consisting of a $C_1$-$C_6$ alkyl group (substituted at any position, more preferably at the 5-, 7- and/or 8-position(s)) and other substituents (substituted at the 5-, 7- and/or 8-position(s)). Likewise, in the case of a 1-naphthyl group, examples include an unsubstituted 1-naphthyl group, and a 1-naphthyl group which is substituted with a substituent(s) selected from the group consisting of a $C_1$-$C_6$ alkyl group (substituted at any position) and other substituents, preferably a halogen atom (substituted preferably at the 4-position).

A particularly preferred embodiment of $R^5$ is a phenyl group whose 3- and 4-positions are each substituted with a halogen atom, an unsubstituted 2-naphthyl group, or a 2-naphthyl group whose 5-, 7- and/or 8-position(s) is/are substituted with a substituent(s) selected from the group consisting of a halogen atom, a $C_1$-$C_6$ alkyl group (preferably a methyl group) and a cyano group.

Particularly preferred combinations of $R^3$ and $R^5$ are as follows.

In a case where $R^3$ is a phenyl group whose 4-position is substituted with a fluorine atom or a chlorine atom, $R^5$ is a $C_1$-$C_{10}$ (preferably $C_1$-$C_6$) alkyl group substituted with a naphthyl group, a $C_2$-$C_8$ (preferably $C_2$-$C_6$) alkenyl group substituted with a phenyl group, a substituted phenyl group [e.g., a phenyl group which is substituted with 1 to 5 methyl groups, a phenyl group which is substituted with 1 to 3 substituents selected from the following group and at least one of whose 3- and 4-positions is substituted, wherein said group consists of a $C_1$-$C_6$ alkyl group (preferably a methyl group, an ethyl group, a propyl group), a halogen atom, a methoxy group, a trifluoromethoxy group, a difluoromethoxy group, a trifluoromethyl group, a $C_1$-$C_6$ alkenyl group (preferably a vinyl group), a methoxycarbonyl group, an acetyl group and a cyano group], a benzothienyl group, a naphthyl group which may be substituted with a substituent(s) selected from the following group [wherein said group consists of a halogen atom, a $C_1$-$C_6$ alkyl group (preferably a methyl group), a cyano group and a $C_1$-$C_6$ alkylsulfonyl group (preferably a methylsulfonyl group)], a pyrrolyl group which may be substituted with a substituent(s) selected from the group consisting of a methyl group and a methoxycarbonyl group, a thienyl group substituted with a $C_1$-$C_6$ alkyl group(s) (preferably a methyl group), or a benzodioxolyl group, a dihydrobenzodioxinyl group, a dihydrobenzofuranyl group, a tetrahydronaphthyl group, an indanyl group or a benzothiadiazolyl group (preferably a 5-benzothiadiazolyl group).

In a case where $R^3$ is a 6-indolyl group:

$R^5$ is a $C_1$-$C_{10}$ (preferably $C_1$-$C_6$) alkyl group substituted with a naphthyl group, a $C_2$-$C_8$ (preferably $C_2$-$C_6$) alkenyl group substituted with a phenyl group, an optionally substituted phenyl group [e.g., an unsubstituted phenyl group, a phenyl group which is substituted with 1 to 5 methyl groups, a phenyl group which is substituted with 1 to 3 substituents selected from the following group and at least one of whose 3- and 4-positions is substituted, wherein said group consists of a $C_1$-$C_6$ alkyl group (preferably a methyl group, an ethyl group, a propyl group), a halogen atom, a methoxy group, a trifluoromethoxy group, a difluoromethoxy group, a trifluoromethyl group, a $C_1$-$C_6$ alkenyl group (preferably a vinyl group), a methoxycarbonyl group, an acetyl group and a cyano group], a benzothienyl group, a naphthyl group which may be substituted with a substituent(s) selected from the following group [wherein said group consists of a halogen atom, a $C_1$-$C_6$ alkyl group (preferably a methyl group), a cyano group and a $C_1$-$C_6$ alkylsulfonyl group (preferably a methylsulfonyl group)], a pyrrolyl group which may be substituted with a substituent(s) selected from the group consisting of a $C_1$-$C_6$ alkyl group (preferably a methyl group) and a methoxycarbonyl group, or a benzodioxolyl, dihydrobenzodioxinyl, dihydrobenzofuranyl, tetrahydronaphthyl, indanyl or benzothiadiazolyl (preferably 5-benzothiadiazolyl) group which may be substituted with a substituent(s) selected from the group consisting of a $C_1$-$C_6$ alkyl group (preferably a methyl group) and a halogen atom.

In a case where $R^3$ is the embodiment shown in (C) above:

$R^5$ is a $C_1$-$C_6$ alkyl group substituted with a $C_3$-$C_8$ cycloalkyl group, a $C_1$-$C_{10}$ (preferably $C_1$-$C_6$) alkyl group substituted with a naphthyl group, a $C_2$-$C_8$ (preferably $C_2$-$C_6$) alkenyl group substituted with a phenyl group, an optionally substituted phenyl group [e.g., an unsubstituted phenyl group, a phenyl group which is substituted with 1 to 5 substituents selected from a $C_1$-$C_6$ alkyl group (preferably a methyl group) and a halogen atom, a phenyl group which is substituted with 1 to 3 substituents selected from the following group and at least one of whose 3- and 4-positions is substituted, wherein said group consists of a $C_1$-$C_6$ alkyl group, a halogen atom, a methoxy group, a trifluoromethoxy group, a difluoromethoxy group, a trifluoromethyl group, a $C_1$-$C_6$ alkenyl group, a $C_1$-$C_6$ alkylsulfonyl group (preferably a methylsulfonyl group), a methoxycarbonyl group, an acetyl group and a cyano group], a naphthyl group which may be substituted with a substituent(s) selected from the following group [wherein said group consists of a halogen atom, a $C_1$-$C_6$ alkyl group (preferably a methyl group), a cyano group and a $C_1$-$C_6$ alkylsulfonyl group (preferably a methylsulfonyl group)], a pyrrolyl group which may be substituted with a substituent(s) selected from the group consisting of a $C_1$-$C_6$ alkyl group (preferably a methyl group) and a methoxycarbonyl group, a thienyl group which may be substituted with a substituent(s) selected from the following group [wherein said group consists of a $C_1$-$C_6$ alkyl group (preferably a methyl group), a trifluoromethyl group, a thiadiazolyl group, an oxazolyl group and a halogen atom], a furanyl group which may be substituted with a substituent(s) selected from the following group [wherein said group consists of a $C_1$-$C_6$ alkyl group (preferably a methyl group), a trifluoromethyl group and a halogen atom], or a benzothienyl, benzodioxolyl, dihydrobenzodioxinyl, dihydrobenzofuranyl, tetrahydronaphthyl, indanyl, thiadiazolyl (preferably 5-thiadiazolyl), benzoxadiazolyl or benzothiadiazolyl (preferably 5-benzothiadiazolyl) group which may be substituted with a substituent(s) selected from the group consisting of a $C_1$-$C_6$ alkyl group (preferably a methyl group) and a halogen atom.

Preferred optically active forms of the compounds of the present invention are those having the following structure.

[Formula 13]

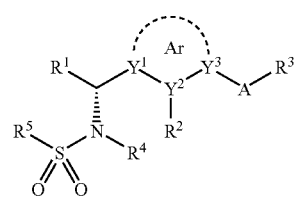

The compounds of the present invention can be synthesized by the procedures shown below, by way of example.

(Scheme 1)

Procedure A

[Formula 14]

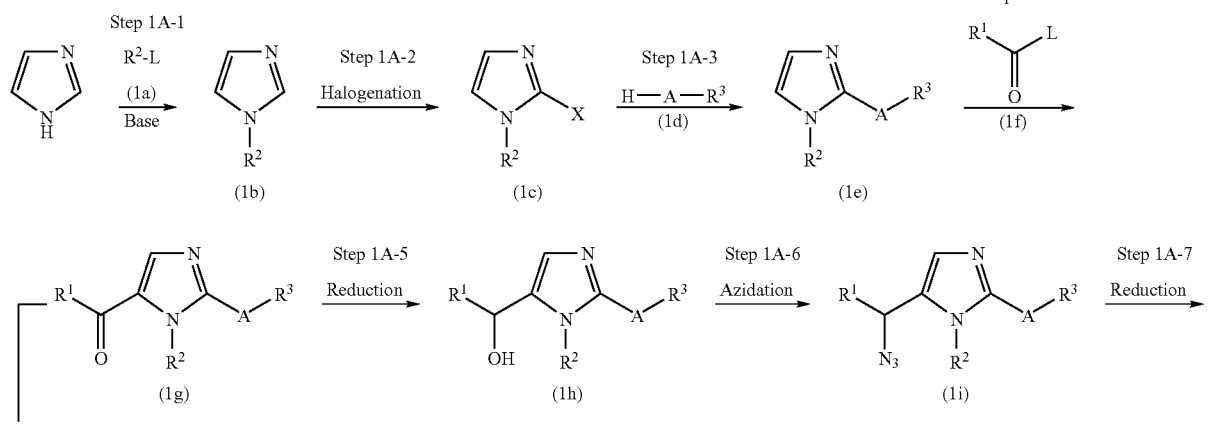

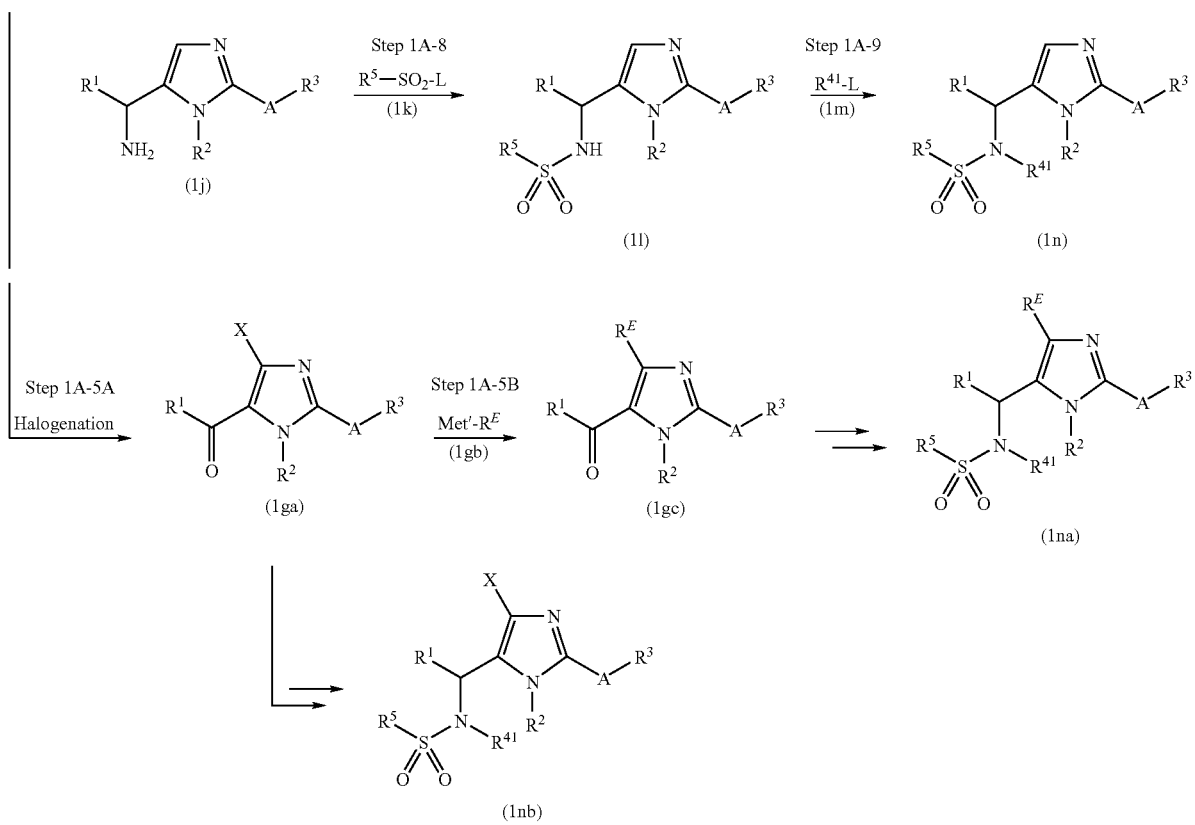
(Scheme 1)
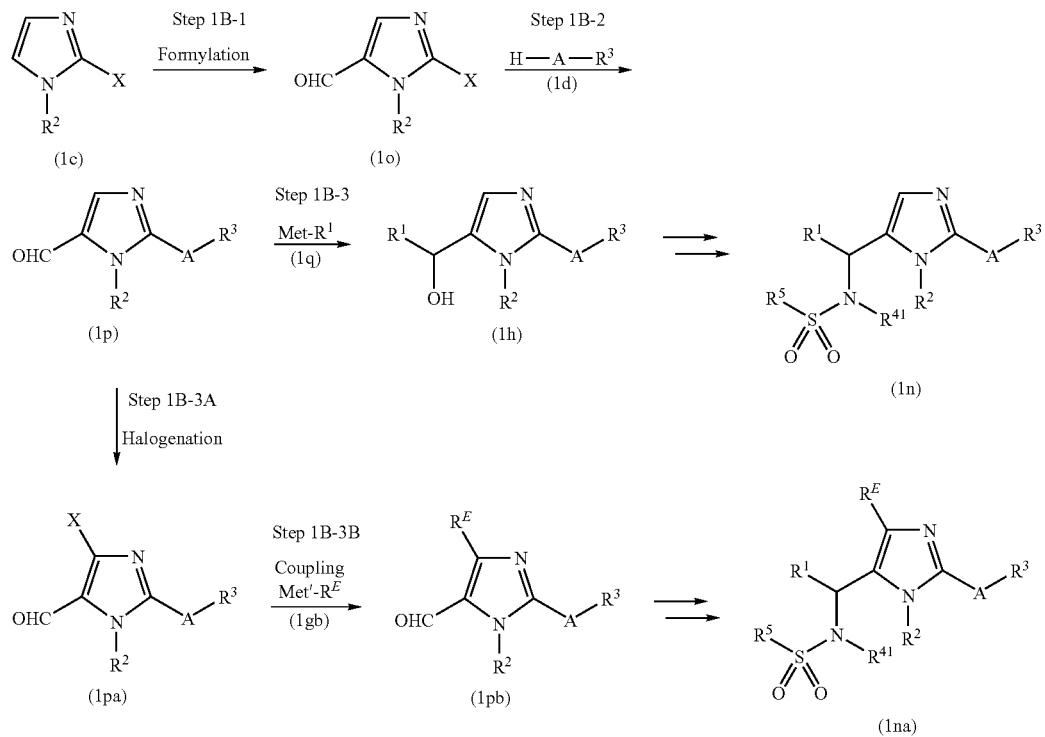

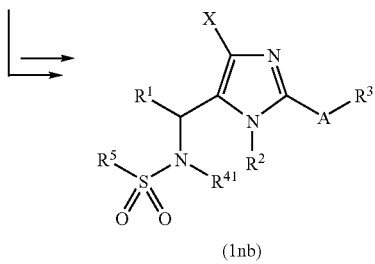

(1nb)

(Scheme 1)

Procedure C

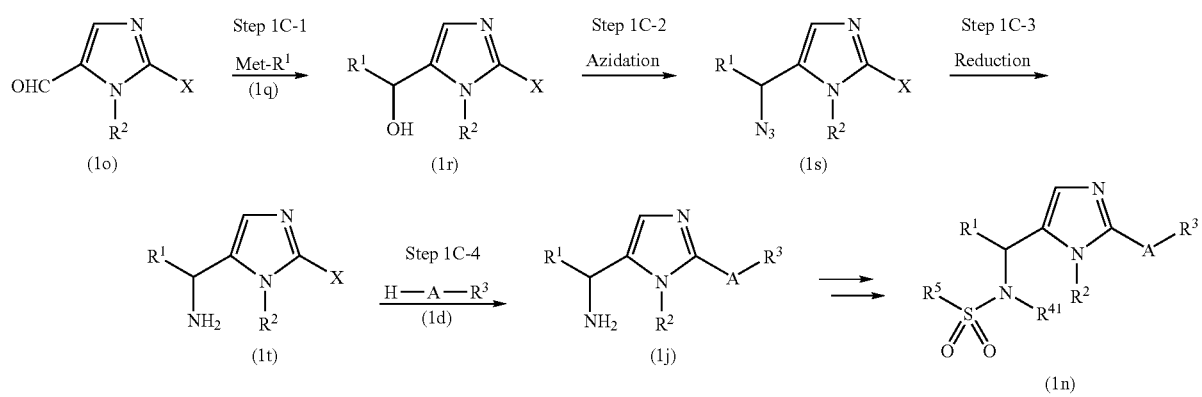

In the above steps, $R^1$, $R^2$, $R^3$, $R^5$ and A are as defined above, $R^{41}$ is the same as $R^4$ except for a hydrogen atom, $R^E$ represents a $C_1$-$C_6$ alkyl group or a phenyl group, Met represents a typical metal such as Li, Na, MgCl or MgBr, Met' represents a typical metal (e.g., Li, Na, B, Mg, Al, Zn, Sn) or a group represented by a complex between such a typical metal and its ligand (wherein the ligand may be a hydroxyl group, a halogen atom, a methoxy group, or a bidentate ligand represented by the formula —O(CH$_2$)$_3$O—), L represents a leaving group (wherein the leaving group may be, for example, a halogen atom such as a chlorine atom, a bromine atom or an iodine atom, an acetyloxy group, a methanesulfonyloxy group, or a p-toluenesulfonyloxy group), and X represents a halogen atom such as a chlorine atom, a bromine atom or an iodine atom.

(Scheme 2)

[Formula 16]

Procedure A

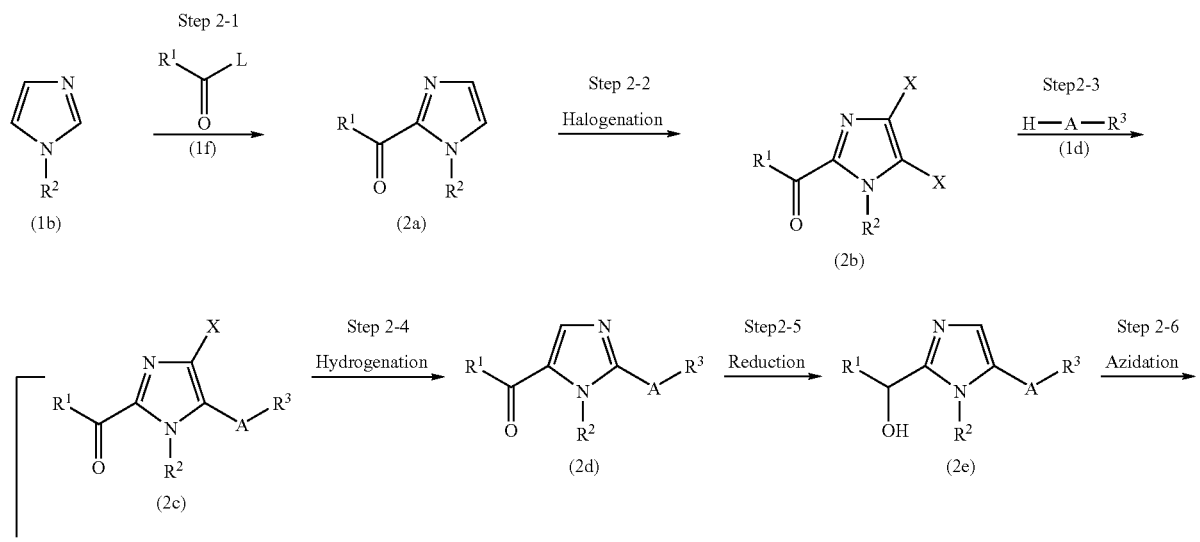

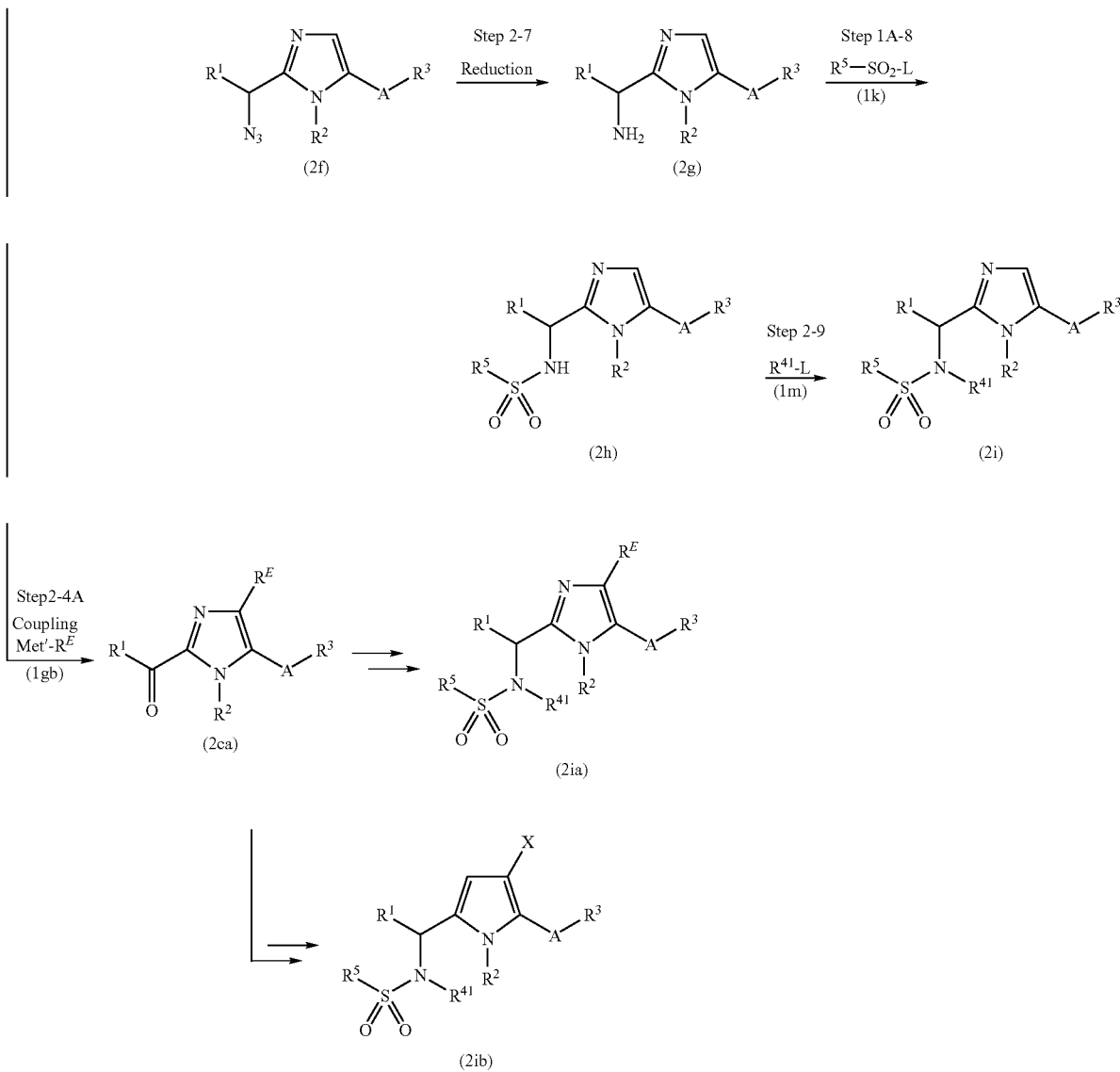

In the above steps, $R^1$, $R^2$, $R^3$, $R^5$ and A are as defined above, $R^{41}$ is the same as $R^4$ except for a hydrogen atom, $R^E$ represents a $C_1$-$C_6$ alkyl group or a phenyl group, Met represents a typical metal such as Li, Na, MgCl or MgBr, Met' represents a typical metal (e.g., Li, Na, B, Mg, Al, Zn, Sn) or a group represented by a complex between such a typical metal and its ligand (wherein the ligand may be a hydroxyl group, a halogen atom, a methoxy group, or a bidentate ligand represented by the formula —O(CH$_2$)$_3$O—), L represents a leaving group (wherein the leaving group may be, for example, a halogen atom such as a chlorine atom, a bromine atom or an iodine atom, an acetyloxy group, a methanesulfonyloxy group, or a p-toluenesulfonyloxy group), and X represents a halogen atom such as a chlorine atom, a bromine atom or an iodine atom.

(Scheme 3)

[Formula 17]

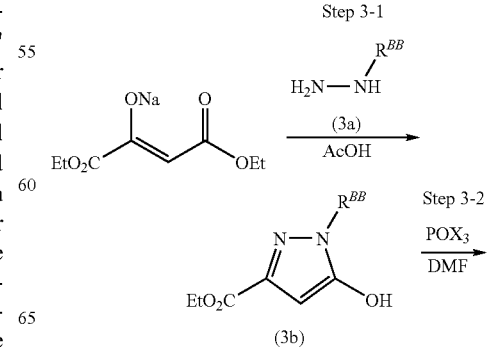

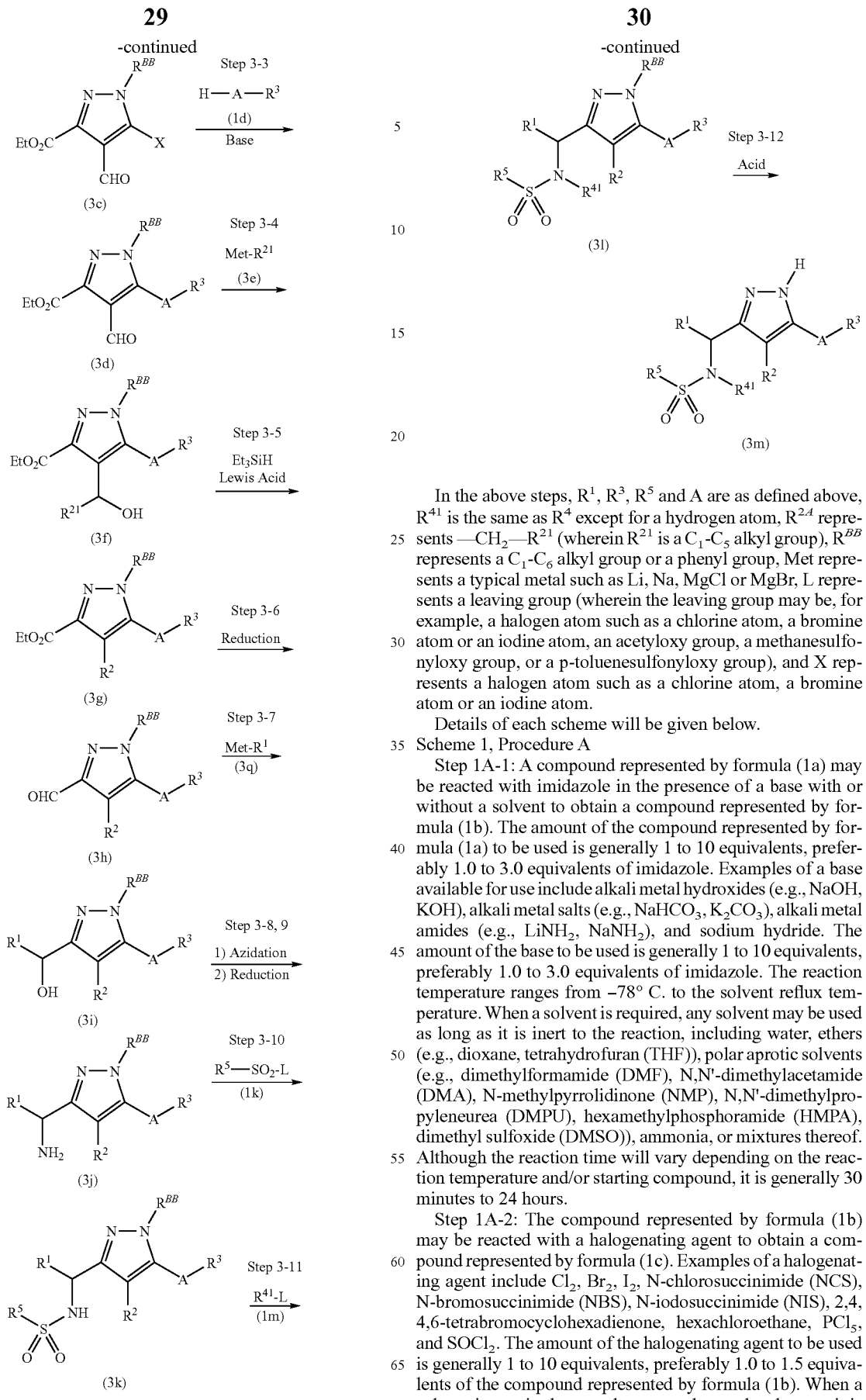

In the above steps, $R^1$, $R^3$, $R^5$ and A are as defined above, $R^{41}$ is the same as $R^4$ except for a hydrogen atom, $R^{2A}$ represents —$CH_2$—$R^{21}$ (wherein $R^{21}$ is a $C_1$-$C_5$ alkyl group), $R^{BB}$ represents a $C_1$-$C_6$ alkyl group or a phenyl group, Met represents a typical metal such as Li, Na, MgCl or MgBr, L represents a leaving group (wherein the leaving group may be, for example, a halogen atom such as a chlorine atom, a bromine atom or an iodine atom, an acetyloxy group, a methanesulfonyloxy group, or a p-toluenesulfonyloxy group), and X represents a halogen atom such as a chlorine atom, a bromine atom or an iodine atom.

Details of each scheme will be given below.

Scheme 1, Procedure A

Step 1A-1: A compound represented by formula (1a) may be reacted with imidazole in the presence of a base with or without a solvent to obtain a compound represented by formula (1b). The amount of the compound represented by formula (1a) to be used is generally 1 to 10 equivalents, preferably 1.0 to 3.0 equivalents of imidazole. Examples of a base available for use include alkali metal hydroxides (e.g., NaOH, KOH), alkali metal salts (e.g., $NaHCO_3$, $K_2CO_3$), alkali metal amides (e.g., $LiNH_2$, $NaNH_2$), and sodium hydride. The amount of the base to be used is generally 1 to 10 equivalents, preferably 1.0 to 3.0 equivalents of imidazole. The reaction temperature ranges from −78° C. to the solvent reflux temperature. When a solvent is required, any solvent may be used as long as it is inert to the reaction, including water, ethers (e.g., dioxane, tetrahydrofuran (THF)), polar aprotic solvents (e.g., dimethylformamide (DMF), N,N'-dimethylacetamide (DMA), N-methylpyrrolidinone (NMP), N,N'-dimethylpropyleneurea (DMPU), hexamethylphosphoramide (HMPA), dimethyl sulfoxide (DMSO)), ammonia, or mixtures thereof. Although the reaction time will vary depending on the reaction temperature and/or starting compound, it is generally 30 minutes to 24 hours.

Step 1A-2: The compound represented by formula (1b) may be reacted with a halogenating agent to obtain a compound represented by formula (1c). Examples of a halogenating agent include $Cl_2$, $Br_2$, $I_2$, N-chlorosuccinimide (NCS), N-bromosuccinimide (NBS), N-iodosuccinimide (NIS), 2,4,4,6-tetrabromocyclohexadienone, hexachloroethane, $PCl_5$, and $SOCl_2$. The amount of the halogenating agent to be used is generally 1 to 10 equivalents, preferably 1.0 to 1.5 equivalents of the compound represented by formula (1b). When a solvent is required, any solvent may be used as long as it is inert to the reaction, including water, ethers (e.g., dioxane, THF, Et$_2$O), polar aprotic solvents (e.g., DMF, DMA, NMP, DMPU, HMPA), alcohols (e.g., MeOH, EtOH), halogenated solvents (e.g., CCl$_4$, CHCl$_3$, CH$_2$Cl$_2$), CH$_3$CN, acetic acid, or mixtures thereof. If necessary, a base is added. Examples of a base include alkali metal hydroxides (e.g., NaOH, KOH), alkali metal salts (e.g., NaHCO$_3$, K$_2$CO$_3$, AcONa), amines (e.g., Et$_3$N, iPr$_2$NEt, iPr$_2$NH), n-BuLi, lithium diisopropylamide (LDA), and NaH. The amount of the base is generally 1 to 10 equivalents, preferably 1.0 to 1.2 equivalents of the compound represented by formula (1b). The reaction temperature ranges from −78° C. to the solvent reflux temperature, preferably −78° C. to room temperature. Although the reaction time will vary depending on the reaction temperature and/or starting compound, it is generally 30 minutes to 24 hours.

Step 1A-3: The compound represented by formula (1c) may be reacted with a compound represented by formula (1d) in the presence of a base with or without a solvent to obtain a compound represented by formula (1e). The amount of compound (1d) to be used is generally 1 to 5 equivalents, preferably 1 to 3 equivalents of the compound represented by formula (1c). Examples of a base include alkali metal salts (e.g., Na$_2$CO$_3$, K$_2$CO$_3$, CS$_2$CO$_3$, NaHCO$_3$, KHCO$_3$, NaOH, dimsyl sodium, NaH, NaNH$_2$, t-BuOK, t-BuONa), amines (e.g., Et$_3$N, iPr$_2$NEt, iPr$_2$NH, pyrrolidine, piperidine), AcONa, and AcOK. The amount of the base to be used is generally 1 to 10 equivalents, preferably 1 to 3 equivalents of the compound represented by formula (1c). The reaction temperature ranges from 0° C. to 300° C., and the reaction may be accomplished, e.g., under normal pressure, under elevated pressure or under microwave irradiation. Examples of a reaction solvent available for use include ethers (e.g., dioxane, THF, Et$_2$O), DMF, DMA, NMP, DMPU, HMPA, DMSO, or mixtures thereof. If necessary, an additive is added. Examples of an additive include metal salts (e.g., CuI, CuCl), or copper powder. Although the reaction time will vary depending on the reaction temperature and/or starting compound, it is generally 1 to 12 hours.

Step 1A-4: The compound represented by formula (1e) may be reacted with a base in a solvent and then reacted with a compound represented by formula (1f) to obtain a compound represented by formula (1g). The amount of compound (1f) to be used is generally 1 to 5 equivalents, preferably 1 to 2 equivalents of the compound represented by formula (1e). Examples of a base include n-BuLi and LDA. The amount of the base to be used is generally 1 to 5 equivalents, preferably 1 to 1.2 equivalents of the compound represented by formula (1e). The reaction temperature ranges from −78° C. to the solvent reflux temperature, preferably −78° C. to room temperature. Examples of a reaction solvent available for use include ethers (e.g., dioxane, THF, Et$_2$O), DMF, DMA, DMPU, HMPA, DMSO, or mixtures thereof. Although the reaction time will vary depending on the reaction temperature and/or starting compound, it is generally 30 minutes to 12 hours.

Step 1A-5: The compound represented by formula (1g) may be reacted with a reducing agent in a solvent to obtain a compound represented by formula (1h). Examples of a reducing agent include NaBH$_4$, KBH$_4$, LiB(sec-Bu)$_3$H, (1-Bu)$_2$AlH, and LiAlH$_4$. The amount of the reducing agent is 0.5 to 5 equivalents, preferably 0.5 to 1.2 equivalents of the compound represented by formula (1g). Examples of a solvent include ethers (e.g., dioxane, THF, Et$_2$O), and alcohols (e.g., MeOH, EtOH). The reaction temperature ranges from −78° C. to the solvent reflux temperature, preferably 0° C. to room temperature. Although the reaction time will vary depending on the reaction temperature and/or starting compound, it is generally 30 minutes to 2 hours.

Step 1A-6: The compound represented by formula (1h) may be reacted with methanesulfonyl chloride, p-toluenesulfonyl chloride, anhydrous triflate or the like in a solvent and, if necessary, in the presence of a base such as pyridine or triethylamine, followed by reaction with an azidating agent (e.g., NaN$_3$, LiN$_3$, Zn(N$_3$)$_2$), or alternatively, may be directly treated with diethyl azodicarboxylate (DEAD)/PPh$_3$/HN$_3$, diphenylphosphorylazide (DPPA)/1,8-diazabicyclo[5.4.0]undec-7-ene (DBU), Zn(N$_3$)$_2$/2 pyridine or the like to obtain a compound represented by formula (1i). Examples of a solvent include ethers (e.g., dioxane, THF), halogenated solvents (e.g., CH$_3$CN, CCl$_4$, CHCl$_3$, CH$_2$Cl$_2$), benzene, and toluene.

Step 1A-7: The compound represented by formula (1i) may be reacted with a reducing agent in a solvent and, if necessary, in the presence of a catalyst (e.g., Pd/C, Pd(OH)$_2$/C, PtO$_2$) to obtain a compound represented by formula (1j). Examples of a reducing agent include hydrogen, ammonium formate, hydrazine, PPh$_3$, and Mg. Examples of a solvent available for use include ethers (e.g., dioxane, THF, Et$_2$O), alcohols (e.g., MeOH, EtOH), water, AcOEt, or mixtures thereof.

Step 1A-8: The compound represented by formula (1j) may be reacted with a compound represented by formula (1k) in the presence of a base with or without a solvent, followed by salt formation as needed to obtain a compound represented by formula (1l) or a pharmaceutically acceptable salt thereof. The amount of the compound represented by formula (1k) to be used is generally 1 to 5 equivalents, preferably 1 to 1.2 equivalents of the compound represented by formula (1j). Examples of a base available for use include alkali metal hydroxides (e.g., NaOH, KOH), alkali metal salts (e.g., NaHCO$_3$, K$_2$CO$_3$), and amines (e.g., Et$_3$N, iPr$_2$NEt, iPr$_2$NH). The amount of the base is generally 1 to 10 equivalents, preferably 1.0 to 3.0 equivalents of the compound represented by formula (1j). The reaction temperature ranges from 0° C. to the solvent reflux temperature, preferably 0° C. to room temperature. When a solvent is required, any solvent may be used as long as it is inert to the reaction, including halogenated hydrocarbons (e.g., CHCl$_3$, CH$_2$Cl$_2$), ethers (e.g., dioxane, THF, Et$_2$O), or mixtures thereof. Although the reaction time will vary depending on the reaction temperature and/or starting compound, it is generally 30 minutes to 24 hours.

Step 1A-9: The compound represented by formula (1l) may be reacted with a compound represented by formula (1m) in the presence of a base with or without a solvent, followed by salt formation as needed to obtain a compound represented by formula (1n) or a pharmaceutically acceptable salt thereof. The amount of the compound represented by formula (1m) to be used is 1 to 10 equivalents, preferably 1.1 to 1.5 equivalents of the compound represented by formula (1l). Examples of a base available for use include alkali metal hydroxides (e.g., NaOH, KOH), alkali metal salts (e.g., NaHCO$_3$, K$_2$CO$_3$), and amines (e.g., Et$_3$N, iPr$_2$NEt, iPr$_2$NH). The amount of the base is generally 1 to 10 equivalents, preferably 1.0 to 3.0 equivalents of the compound represented by formula (1l). The reaction temperature ranges from 0° C. to the solvent reflux temperature, preferably 0° C. to room temperature. When a solvent is required, any solvent may be used as long as it is inert to the reaction, including water, ethers (e.g., dioxane, THF, Et$_2$O), DMF, DMA, NMP, DMPU, HMPA, DMSO, or mixtures thereof. Although the reaction time will vary depending on the reaction temperature and/or starting compound, it is generally 30 minutes to 24 hours.

Further, starting from a compound represented by formula (1ga) which is obtained through halogenation of the compound represented by formula (1g), the procedures shown in Steps 1A-5 to 1A-9 of Scheme 1 may be repeated to obtain a halogen-substituted compound represented by formula (1nb).

Furthermore, the compound represented by formula (1ga) may be reacted with a compound represented by formula (1gb) to obtain a compound represented by formula (1gc). Starting from the resulting compound represented by formula (1gc), the procedures shown in Steps 1A-5 to 1A-9 of Scheme 1 may be repeated to obtain a compound represented by formula (1na) having substituent $R^E$.

Step 1A-5A: The compound represented by formula (1g) may be reacted with a halogenating agent to obtain the compound represented by formula (1ga). Examples of a halogenating agent include $Cl_2$, $Br_2$, $I_2$, NCS, NBS, NIS, 2,4,4,6-tetrabromocyclohexadienone, $PCl_5$, and $SOCl_2$. The amount of the halogenating agent to be used is generally 2 to 10 equivalents, preferably 1.0 to 2.5 equivalents of the compound represented by formula (1g). When a solvent is required, any solvent may be used as long as it is inert to the reaction, including water, ethers (e.g., dioxane, THF), polar aprotic solvents (e.g., DMF, DMA, NMP, DMPU, HMPA, DMSO), alcohols (e.g., MeOH, EtOH), halogenated solvents (e.g., $CCl_4$, $CHCl_3$, $CH_2Cl_2$), $CH_3CN$, acetic acid, or mixtures thereof. If necessary, a base is added. Examples of a base include alkali metal hydroxides (e.g., NaOH, KOH), alkali metal salts (e.g., $NaHCO_3$, $K_2CO_3$, AcONa), and amines (e.g., $Et_3N$, $iPr_2NEt$). The amount of the base to be used is generally 1 to 10 equivalents, preferably 1.0 to 1.2 equivalents of the compound represented by formula (1g). The reaction temperature ranges from −78° C. to the solvent reflux temperature, preferably −78° C. to room temperature. Although the reaction time will vary depending on the reaction temperature and/or starting compound, it is generally 30 minutes to 24 hours.

Step 1A-5B: The compound represented by formula (1ga) may be reacted with the compound represented by formula (1gb) in the presence of a transition metal and, if necessary, in the presence of a base to obtain the compound represented by formula (1gc). In the compound represented by formula (1gb), Met' represents a typical metal (e.g., Li, Na, B, Mg, Al, Zn, Sn) or a group represented by a complex between such a typical metal and its ligand (wherein the ligand may be a hydroxyl group, a halogen atom, a methoxy group, or a bidentate ligand represented by the formula —$O(CH_2)_3O$—). The amount of the compound represented by formula (1gb) to be used is 1 to 10 equivalents, preferably 1.0 to 1.5 equivalents of the compound represented by formula (1ga). Examples of a transition metal include tetrakis(triphenylphosphine)palladium(0), palladium acetate (II), palladium chloride (II), tris(dibenzylideneacetone)dipalladium(0)chloroform adduct, and bis(acetylacetonato)nickel(0). The amount of such a transition metal to be used is generally 0.01 to 0.5 equivalents of the compound represented by formula (1ga).

Also, it is desirable to add a phosphine, excluding the case where a phosphine is already coordinated. Examples of a phosphine include triethylphosphine, tributylphosphine, triphenylphosphine, bis(diphenylphosphino)ethane, bis(diphenylphosphino)propane, bis(diphenylphosphino)butane, and bis(diphenylphosphino)ferrocene. The amount of such a phosphine to be used is 1 to 2 equivalents of the transition metal. Examples of a base include alkali metal hydroxides (e.g., NaOH, KOH), and alkali metal salts (e.g., $NaHCO_3$, $Na_2CO_3$, $K_2CO_3$, $K_3PO_4$, $Cs_2CO_3$). The amount of the base to be used is generally 1 to 10 equivalents, preferably 1.5 to 3.0 equivalents of the compound represented by formula (1ga). The reaction temperature ranges from 0° C. to the solvent reflux temperature, preferably room temperature to the solvent reflux temperature. Examples of a solvent available for use include water, ethers (e.g., dioxane, THF, $Et_2O$), DMF, DMA, NMP, DMPU, HMPA, DMSO, or mixtures thereof. Although the reaction time will vary depending on the reaction temperature and/or starting compound, it is generally 30 minutes to 24 hours.

Alternatively, as shown in Scheme 1, Procedures B and C, the compound represented by formula (1n) may also be synthesized by changing the order of reactions in the steps of Scheme 1, Procedure A.

Scheme 1, Procedure B

Step 1B-1: The compound represented by formula (1c) which was obtained in Step 1A-2 of Scheme 1 may be reacted with a base and then with DMF for formylation to obtain a compound represented by formula (1o). The amount of DMF to be used is generally 1 to 5 equivalents, preferably 1 to 2 equivalents of the compound represented by formula (1c). Examples of a base include n-BuLi and LDA. The amount of the base to be used is generally 1 to 5 equivalents, preferably 1 to 1.2 equivalents of the compound represented by formula (1c). The reaction temperature ranges from −78° C. to the solvent reflux temperature, preferably −78° C. to room temperature. Examples of a reaction solvent available for use include ethers (e.g., dioxane, THF, $Et_2O$), DMF, DMA, DMPU, HMPA, DMSO, or mixtures thereof. Although the reaction time will vary depending on the reaction temperature and/or starting compound, it is generally 30 minutes to 12 hours.

Step 1B-2: The compound represented by formula (1o) may be reacted with the compound represented by formula (1d) in the same manner as shown in Step 1A-3 of Scheme 1 to obtain a compound represented by formula (1p).

Step 1B-3: The compound represented by formula (1p) may be reacted with a compound represented by formula (1q) to obtain the compound represented by formula (1h). The amount of the compound represented by formula (1q) to be used is 1 to 10 equivalents, preferably 1.1 to 1.5 equivalents of the compound represented by formula (1p). Examples of a solvent available for use include ethers (e.g., dioxane, THF, $Et_2O$) or mixtures thereof. The reaction temperature ranges from −78° C. to room temperature, preferably −30° C. to 0° C. Although the reaction time will vary depending on the reaction temperature and/or starting compound, it is generally 30 minutes to 24 hours.

Starting from the resulting compound represented by formula (1h), the procedures shown in Steps 1A-6 to 1A-9 of Scheme 1 may be repeated to obtain the compound represented by formula (1n).

Further, starting from a compound represented by formula (1pa) which is obtained through halogenation of the compound represented by formula (1p), the procedures shown in Steps 1B-3 and 1A-6 to 1A-9 of Scheme 1 may be repeated to obtain the halogen-substituted compound represented by formula (1nb).

Furthermore, the compound represented by formula (1pa) may be reacted with the compound represented by formula (1gb) to obtain a compound represented by formula (1pb). Starting from the resulting compound represented by formula (1pb), the procedures shown in Steps 1B-3 and 1A-6 to 1A-9 of Scheme 1 may be repeated to obtain the compound represented by formula (1na) having substituent $R^E$.

Step 1B-3A: Starting from the compound represented by (1p), the same procedure as shown in Step 1A-5A of Scheme 1 may be repeated to obtain the compound represented by formula (1pa).

Step 1B-3B: Starting from the compound represented by formula (1pa) and the compound represented by formula (1gb), the same procedure as shown in Step 1A-5B of Scheme 1 may be repeated to obtain the compound represented by formula (1pb).

Scheme 1, Procedure C

Step 1C-1: Starting from the compound represented by formula (1o) obtained from Step 1B-1 of Scheme 1 and the compound represented by formula (1q), the same procedure as shown in Step 1B-3 of Scheme 1 may be repeated to obtain a compound represented by formula (1r).

Step 1C-2: Starting from the compound represented by formula (1r), the same procedure as shown in Step 1A-6 of Scheme 1 may be repeated to obtain a compound represented by formula (1s).

Step 1C-3: Starting from the compound represented by formula (1s), the same procedure as shown in Step 1A-7 of Scheme 1 may be repeated to obtain a compound represented by formula (1t).

Step 1C-4: Starting from the compound represented by formula (1t) and the compound represented by formula (1d), the same procedure as shown in Step 1A-3 of Scheme 1 may be repeated to obtain the compound represented by formula (1j).

Starting from the resulting compound represented by formula (1j), the procedures shown in Steps 1A-8 to 1A-9 of Scheme 1 may be repeated to obtain the compound represented by formula (1n).

Scheme 2

Step 2-1: Starting from the compound represented by formula (1b) and the compound represented by formula (1f), the same procedure as shown in Step 1A-4 of Scheme 1 may be repeated to obtain a compound represented by formula (2a).

Step 2-2: The compound represented by formula (2a) may be reacted with a halogenating agent to obtain a compound represented by formula (2b). Examples of a halogenating agent include $Cl_2$, $Br_2$, $I_2$, NCS, NBS, NIS, 2,4,4,6-tetrabromocyclohexadienone, $PCl_5$, and $SOCl_2$. The amount of the halogenating agent to be used is generally 2 to 10 equivalents, preferably 1.0 to 2.5 equivalents of the compound represented by formula (2a). When a solvent is required, any solvent may be used as long as it is inert to the reaction, including water, ethers (e.g., dioxane, THF), polar aprotic solvents (e.g., DMF, DMA, NMP, DMPU, HMPA, DMSO), alcohols (e.g., MeOH, EtOH), halogenated solvents (e.g., $CCl_4$, $CHCl_3$, $CH_2Cl_2$), $CH_3CN$, acetic acid, or mixtures thereof. If necessary, a base is added. Examples of a base include alkali metal hydroxides (e.g., NaOH, KOH), alkali metal salts (e.g., $NaHCO_3$, $K_2CO_3$, AcONa), and amines (e.g., $Et_3N$, $iPr_2NEt$). The amount of the base to be used is generally 1 to 10 equivalents, preferably 1.0 to 1.2 equivalents of the compound represented by formula (2a). The reaction temperature ranges from $-78°$ C. to the solvent reflux temperature, preferably $-78°$ C. to room temperature. Although the reaction time will vary depending on the reaction temperature and/or starting compound, it is generally 30 minutes to 24 hours.

Step 2-3: Starting from the compound represented by formula (2b) and the compound represented by formula (1d), the same procedure as shown in Step 1A-3 of Scheme 1 may be repeated to obtain a compound represented by formula (2c).

Step 2-4: The compound represented by formula (2c) may be reacted in a solvent in the presence of a catalyst (e.g., Pd/C, $Pd(OH)_2$/C, $PtO_2$) under a hydrogen atmosphere to obtain a compound represented by formula (2d). Examples of a solvent include ethers (e.g., dioxane, THF), alcohols (e.g., MeOH, EtOH), and AcOEt. The amount of the catalyst to be used is generally 0.01 to 1.0 parts by weight of the compound represented by formula (2c).

Step 2-5: Starting from the compound represented by formula (2d), the same procedure as shown in Step 1A-5 of Scheme 1 may be repeated to obtain a compound represented by formula (2e).

Step 2-6: Starting from the compound represented by formula (2e), the same procedure as shown in Step 1A-6 of Scheme 1 may be repeated to obtain a compound represented by formula (2f).

Step 2-7: Starting from the compound represented by formula (2f), the same procedure as shown in Step 1A-7 of Scheme 1 may be repeated to obtain a compound represented by formula (2g).

Step 2-8: Starting from the compound represented by formula (2g) and the compound represented by formula (1k), the same procedure as shown in Step 1A-8 of Scheme 1 may be repeated to obtain a compound represented by formula (2h).

Step 2-9; Starting from the compound represented by formula (2h) and the compound represented by formula (1m), the same procedure as shown in Step 1A-9 of Scheme 1 may be repeated to obtain a compound represented by formula (2l).

Further, starting from the compound represented by formula (2c), the procedures shown in Steps 2-5 to 2-9 of Scheme 2 may be repeated to obtain a halogen-substituted compound represented by formula (2lb).

Furthermore, the compound represented by formula (2c) may be reacted with the compound represented by formula (1gb) to obtain a compound represented by formula (2ca). Starting from the resulting compound represented by formula (2ca), the procedures shown in Steps 2-5 to 2-9 of Scheme 2 may be repeated to obtain a compound represented by formula (2la) having substituent $R^E$.

Step 2-4A: Starting from the compound represented by (2c), the same procedure as shown in Step 1A-5B of Scheme 1 may be repeated to obtain the compound represented by formula (2ca).

Scheme 3

Step 3-1: Diethyl oxalacetate sodium salt and a compound represented by formula (3a) may be reacted in the presence of acetic acid to obtain a compound represented by formula (3b).

Step 3-2: The compound represented by formula (3b) may be reacted with a halogenating agent (e.g., $POCl_3$) in DMF to obtain a compound represented by formula (3c).

Step 3-3: Starting from the compound represented by formula (3c) and the compound represented by formula (1d), the same procedure as shown in Step 1A-3 of Scheme 1 may be repeated to obtain a compound represented by formula (3d).

Step 3-4: The compound represented by formula (3d) may be reacted with a compound represented by formula (3e) to obtain a compound represented by formula (3f). The amount of the compound represented by formula (3e) to be used is 1 to 10 equivalents, preferably 1.1 to 1.5 equivalents of the compound represented by formula (3d). Examples of a solvent available for use include ethers (e.g., dioxane, THF, $Et_2O$) or mixtures thereof. The reaction temperature ranges from $-78°$ C. to room temperature, preferably $-30°$ C. to $0°$ C. Although the reaction time will vary depending on the reaction temperature and/or starting compound, it is generally 30 minutes to 24 hours.

Step 3-5: The compound represented by formula (3f) may be reacted with a reducing agent in the presence of a Lewis acid to obtain a compound represented by formula (3g). Examples of a Lewis acid include trifluoroacetic acid (TFA), $TiCl_4$, $SnCl_4$, and $AlCl_3$. The amount of the Lewis acid is 1 to 20 equivalents, preferably 5 to 10 equivalents of the compound represented by formula (3f). Examples of a reducing agent include Et₃SiH, Bu₃SnH, and NaBH₄. The amount of the reducing agent is 1 to 5 equivalents, preferably 1 to 3 equivalents of the compound represented by formula (3f). When a solvent is required, any solvent may be used as long as it is inert to the reaction, including halogenated solvents (e.g., CCl₄, CHCl₃, CH₂Cl₂) or mixtures thereof. The reaction temperature ranges from −78° C. to the solvent reflux temperature, preferably 0° C. to room temperature.

Step 3-6: The compound represented by formula (3g) may be reacted with a reducing agent to obtain a compound represented by formula (3h). Examples of a reducing agent include NaBH₄, KBH₄, LiB(H)Et₃, LiB(sec-Bu)₃H, (i-Bu)₂ AlH Al H (O-t-Bu)₃, LiAlH₄, LiHAl(O-t-Bu)₃, and NaH₂Al (OCH₂CH₂OCH₃). The amount of the reducing agent is 0.5 to 5 equivalents, preferably 0.5 to 1.2 equivalents of the compound represented by formula (3g). Examples of a solvent available for use include ethers (e.g., dioxane, THF, diethyl ether), hexane, benzene, toluene, or mixtures thereof. The reaction temperature ranges from −78° C. to room temperature, preferably −78° C. to 0° C. Although the reaction time will vary depending on the reaction temperature and/or starting compound, it is generally 30 minutes to 4 hours.

Step 3-7: The compound represented by formula (3h) may be reacted with the compound represented by formula (1q) in the same manner as shown in Step 1B-3 of Scheme 1 to obtain a compound represented by formula (3i). The amount of the compound represented by formula (1q) to be used is 1 to 10 equivalents, preferably 1.1 to 1.5 equivalents of the compound represented by formula (3h). Examples of a solvent available for use include ethers (e.g., dioxane, THF, Et₂O) or mixtures thereof. The reaction temperature ranges from −78° C. to room temperature, preferably −30° C. to 0° C. Although the reaction time will vary depending on the reaction temperature and/or starting compound, it is generally 30 minutes to 24 hours.

Steps 3-8 and 3-9; Starting from the compound represented by formula (3i), the same procedures as shown in Steps 1A-6 and 1A-7 of Scheme 1 may be repeated to obtain a compound represented by formula (3j).

Step 3-10: Starting from the compound represented by formula (3j) and the compound represented by formula (1k), the same procedure as shown in Step 1A-8 of Scheme 1 may be repeated to obtain a compound represented by formula (3k).

Step 3-11: Starting from the compound represented by formula (3k) and the compound represented by formula (1m), the same procedure as shown in Step 1A-9 of Scheme 1 may be repeated to obtain a compound represented by formula (3l).

Step 3-12: The compound represented by formula (3l) may be reacted with an acid to obtain a compound represented by formula (3m). Examples of an acid include hydrochloric acid/pyridine, and BBr₃. The amount of the acid to be used is 1 to 20 equivalents, preferably 10 to 20 equivalents of the compound represented by formula (3l). When a solvent is required, any solvent may be used as long as it is inert to the reaction, including halogenated solvents (e.g., CCl₄, CHCl₃, CH₂Cl₂) or mixtures thereof. The reaction temperature ranges from room temperature to 200° C., preferably room temperature to 180° C.

For use as pharmaceutical preparations, the compounds of the present invention may be supplemented with commonly used excipients, extenders, pH regulators, solubilizers and so on, and then formulated using standard techniques into tablets, granules, pills, capsules, powders, solutions, suspensions, injections, etc. The pharmaceutical preparations thus obtained can be administered as oral or parenteral formulations.

The compounds of the present invention may be given to adult patients at 1 to 1000 mg per day as a single dose or in divided doses. This dosage may be increased or decreased as appropriate for the type of disease, the age, body weight and symptom of a patient, etc.

Advantages of the Invention

The compounds of the present invention were found to be strong Edg-1(S1P₁) ligands, as is apparent from the test example described later.

BEST MODE FOR CARRYING OUT THE INVENTION

The present invention will be further described in more detail by way of the following examples and test example.

Example 1

3,4-Dichloro-N-[1-(3-ethyl-2(4-methylphenoxy)-3H-imidazol-4-yl)-ethyl]-benzenesulfonamide (Compound 74)

[Formula 18]

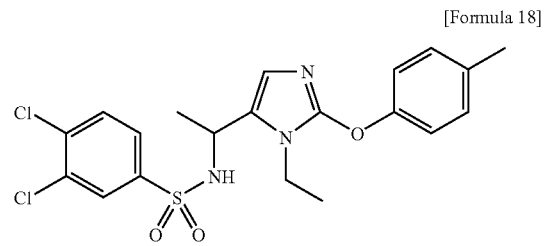

1-Ethyl-2-iodo-1H-imidazole

[Formula 19]

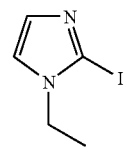

(1) To a solution of 1-ethyl-1H-imidazole (2.844 g) in THF (60 ml), n-BuLi (11.6 ml, 2.59 N in hexane) was added dropwise at −78° C. under an argon atmosphere. After stirring at the same temperature for 30 minutes, a solution of I₂ (7.614 g) in THF (25 ml) was added dropwise. The reaction mixture was warmed to room temperature, diluted with saturated aqueous sodium bicarbonate, and extracted with AcOEt. After washing with saturated aqueous Na₂S₂O₃, the organic layer was dried over MgSO₄, filtered and then evaporated to remove the solvent, thereby giving the titled compound (6.492 g) as a light-yellow solid.

$^1$H NMR (200 MHz, CDCl$_3$) δ ppm: 1.40 (t, J=7.4 Hz, 3H), 3.95 (q, J=7.4 Hz, 2H), 7.02-7.06 (m, 1H), 7.07-7.11 (m, 1H)

1-Ethyl-2(4-methylphenoxy)-1H-imidazole

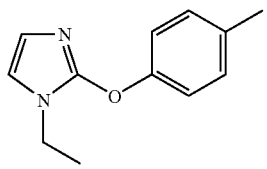

[Formula 20]

(2) A mixture of the compound obtained in Example 1-(1) (30.27 g), 4-cresol (17.69 g), Cs$_2$CO$_3$ (53.43 g) and N,N'-dimethylpropyleneurea (DMPU) (136 ml) was stirred at 200° C. for 3 hours. The mixture was cooled to room temperature, diluted with water, and extracted with AcOEt. After washing with brine, the organic layer was dried over MgSO$_4$, filtered and evaporated under reduced pressure to remove the solvent. The resulting crude product was purified by column chromatography (neutral OH-type SiO$_2$, hexane/AcOEt=10% to 40%) to give the titled compound (8.54 g, yellow oil).

$^1$H NMR (200 MHz, CDCl$_3$) δ ppm: 1.39 (t, J=7.3 Hz, 3H), 2.32 (s, 3H), 3.89 (q, J=7.3 Hz, 3H), 6.65 (d, J=1.8 Hz, 1H), 6.70 (d, J=1.8 Hz, 1H), 7.03-7.320 (m, 4H)

1-(3-Ethyl-2(4-methylphenoxy)-3H-imidazol-4-yl)-ethanol

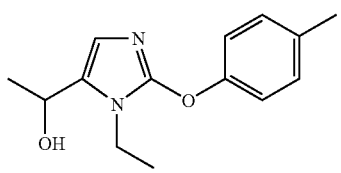

[Formula 21]

(3) To a solution of the compound obtained in Example 1-(2) (2.493 g) in THF (123 ml), n-BuLi (4.8 ml, 2.59 N in hexane) was added dropwise at −78° C. under an argon atmosphere and stirred at the same temperature for 3.5 hours. The reaction mixture was cooled to −100° C., mixed with Ac$_2$O (2.3 ml), warmed to −65° C. over 50 minutes, diluted with saturated aqueous sodium bicarbonate, and extracted with AcOEt. After washing with brine, the organic layer was dried over MgSO$_4$, filtered and then evaporated to remove the solvent. The resulting crude product was purified by column chromatography (NH-type silica gel, AcOEt/hexane=10% to 30%) to give a mixture of 1-(3-ethyl-2(4-methylphenoxy)-3H-imidazol-4-yl)-ethanone and 1-ethyl-2(4-methylphenoxy)-1H-imidazole (1.509 g, colorless oil). To a solution of the resulting compounds (1.508 g) in MeOH (13 ml), NaBH$_4$ (243 mg) was added at 0° C. and stirred at the same temperature for 15 minutes and then at room temperature for 15 minutes. The reaction mixture was concentrated, diluted with water, and extracted with AcOEt. After washing with brine, the organic layer was dried over MgSO$_4$, filtered and then evaporated to remove the solvent. The resulting crude product was purified by column chromatography (NH-type silica gel, AcOEt/hexane=20% to 99%) to give the titled compound (1.131 g, colorless oil).

$^1$H NMR (200 Hz, CDCl$_3$) δ ppm: 1.38 (t, J=7.3 Hz, 3H), 1.62 (d, J=6.6 Hz, 3H), 2.33 (s, 3H), 3.86-4.20 (m, 2H), 4.70-4.88 (m, 1H), 6.60 (d, J=0.9 Hz, 1H), 7.04-7.21 (m, 4H)

5-(1-Azidoethyl)-1-ethyl-2(4-methylphenoxy)-1H-imidazole

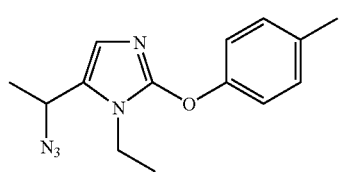

[Formula 22]

(4) To a solution of the compound obtained in Example 1-(3) (1.130 g) in toluene (46 ml), diphenylphosphorylazide (DPPA) (1.48 ml) and 1,8-diazabicyclo[5,4,0]undec-7-ene (DBU) were added at 0° C. and stirred at room temperature for 11.5 hours. The reaction mixture was diluted with water and extracted with AcOEt. After washing with brine, the organic layer was dried over MgSO$_4$, filtered and then evaporated to remove the solvent. The resulting crude product was purified by column chromatography (NH-type silica gel, AcOEt/hexane=0% to 10%) to give the titled compound (983 mg, colorless oil).

$^1$H NMR (200 Hz, CDCl$_3$) δ ppm: 1.38 (t, J=7.1 Hz, 3H), 1.67 (d, J=6.8 Hz, 3H), 2.33 (s, 3H), 3.90-4.07 (m, 2H), 4.25-4.40 (m, 1H), 6.68 (d, J=0.9 Hz, 1H), 7.02-7.30 (m, 4H)

1-(3-Ethyl-2(4-methylphenoxy)-3H-imidazol-4-yl)-ethylamine

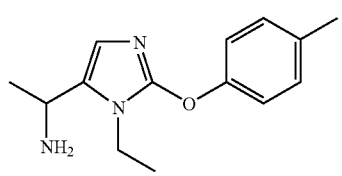

[Formula 23]

(5) A mixture of the compound obtained in Example 1-(4) (983 mg) and palladium-activated carbon (197 mg, Pd 10 wt. %) in toluene (46 ml) was stirred under a hydrogen atmosphere (about 1 atm) at room temperature for 4 hours. The reaction mixture was filtered through celite, and the filtrate was concentrated. The resulting crude product was purified by column chromatography (NH-type silica gel, AcOEt/hexane=10% to 99%) to give the titled compound (754 mg, colorless oil).

$^1$H NMR (200 Hz, CDCl$_3$) δ ppm: 1.37 (t, J=7.1 Hz, 3H), 1.49 (d, J=6.6 Hz, 3H), 2.32 (s, 3H), 3.82-4.12 (m, 3H), 6.53 (d, J=0.9 Hz, 1H), 7.04-7.20 (m, 4H)

3,4-Dichloro-N-[1-(3-ethyl-2(4-methylphenoxy)-3H-imidazol-4-yl)-ethyl]-benzenesulfonamide (Compound 74)

[Formula 24]

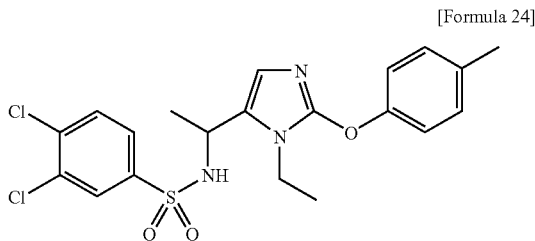

(6) To a solution of the compound obtained in Example 1-(5) (24 mg) in THF (2.0 mL), Et₃N (0.041 mL) and 3,4-dichlorobenzenesulfonyl chloride (48 mg) were added at room temperature and stirred at room temperature for 12 hours. After addition of AcOEt, the organic layer was washed sequentially with 1 N aqueous hydrochloric acid and brine, dried over anhydrous magnesium sulfate, filtered and then evaporated under reduced pressure to remove the solvent. The resulting crude product was purified by NH-type silica gel column chromatography (elution solvent: AcOEt), followed by recrystallization (AcOEt-hexane) to give the titled compound (Compound 74) (25 mg, colorless powder).

$^1$H NMR (200 MHz, DMSO-d6) δ ppm: 1.18 (t, J=7.1 Hz, 3H), 1.26 (d, J=6.8 Hz, 3H), 2.29 (s, 3H), 3.65-3.91 (m, 2H), 4.41-4.62 (m, 1H), 6.42 (s, 1H), 6.97-7.07 (m, 2H), 7.13-7.24 (m, 2H), 7.71 (dd, J=8.4, 2.1 Hz, 1H), 7.87 (d, J=8.4 Hz, 1H), 7.93 (d, J=2.1 Hz, 1H), 8.28-8.43 (m, 1H)

Melting point: 142.5-143.5° C.

Example 2

3,4-Dichloro-N-[1-(1-ethyl-5-(4-methylphenoxy)-1H-imidazol-2-yl)-ethyl]-benzenesulfonamide (Compound 179)

[Formula 25]

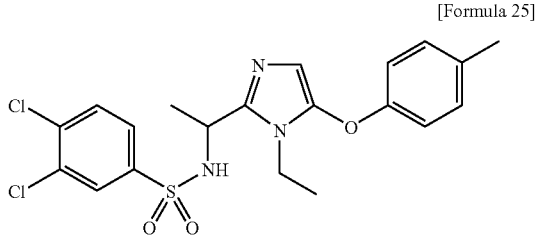

1-(1-Ethyl-1H-imidazol-2-yl)-ethanone

[Formula 26]

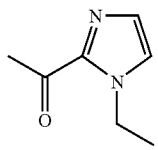

(1) To a solution of 1-ethyl-1H-imidazole (1.923 g) in THF (40 ml), n-BuLi (7.7 ml, 2.59 N in hexane) was added dropwise at −78° C. under an argon atmosphere. After stirring at the same temperature for 30 minutes, the reaction mixture was added dropwise at −78° C. through a cannula to a solution of AcCl (1.56 ml) in THF (40 ml). The reaction mixture was warmed to room temperature over 2 hours, diluted with saturated aqueous sodium bicarbonate, and extracted with AcOEt. After washing with brine, the organic layer was dried over MgSO₄, filtered and then evaporated to remove the solvent. The resulting crude product was purified by silica gel column chromatography (NH-type silica gel, AcOEt/hexane=0% to 10%) to give the titled compound (335 mg, colorless oil).

$^1$H NMR (200 Hz, CDCl₃) δ ppm: 1.42 (t, J=7.3 Hz, 3H), 2.67 (s, 3H), 4.43 (q, J=7.3 Hz, 2H), 7.09 (s, 1H), 7.15 (d, J=0.7 Hz, 1H)

1-(4,5-Dibromo-1-ethyl-1H-imidazol-2-yl)-ethanone

[Formula 27]

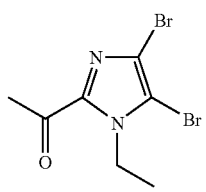

(2) To a solution of the compound obtained in Example 2-(1) (1.08 g) in CH₃CN (78 ml), N-bromosuccinimide (NBS) (2.782 g) was added at 0° C., heated under reflux for 3 hours, and then stirred overnight at room temperature. After distilling off the solvent, the resulting residue was purified by silica gel column chromatography (OH-type neutral silica gel, AcOEt/hexane=5% to 20%) to give the titled compound (1.865 g, colorless oil).

$^1$H NMR (200 Hz, CDCl₃) δ ppm: 1.35 (t, J=7.1 Hz, 3H), 2.63 (s, 3H), 4.51 (q, J=7.1 Hz, 2H)

1-(4-Bromo-1-ethyl-5-(4-methylphenoxy)-1H-imidazol-2-yl)-ethanone

[Formula 28]

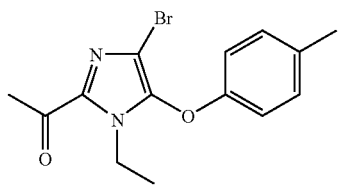

(3) A mixture of the compound obtained in Example 2-(2) (833 mg), 4-cresol (883 μl), Cs₂CO₃ (2.979 g) and DMPU (2.8 ml) was stirred at 100° C. for 30 minutes and then at 150° C. for 1 hour. The reaction mixture was cooled to room temperature, diluted with aqueous NaOH (2.0 N), and extracted with AcOEt/hexane (1/4). After washing with brine, the organic layer was dried over MgSO₄, filtered and evaporated under reduced pressure to remove the solvent. The resulting crude product was purified by column chromatography (NH-type SiO₂, AcOEt/hexane=2% to 5%) to give the titled compound (235 mg, colorless solid).

¹H NMR (200 Hz, CDCl₃) δ ppm: 1.27 (t, J=7.2 Hz, 3H), 2.33 (s, 3H), 2.63 (s, 3H), 4.31 (q, J=7.2 Hz, 2H), 6.76-6.88 (m, 2H), 7.08-7.20 (m, 2H)

1-(1-Ethyl-5(4-methylphenoxy)-1H-imidazol-2-yl)-ethanone

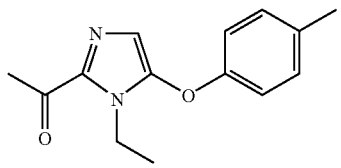

[Formula 29]

(4) A mixture of the compound obtained in Example 2-(3) (154 mg), palladium-activated carbon (31 mg, Pd 10 wt. %) and AcONa (47 mg) in MeOH (4.0 ml) was stirred under a hydrogen atmosphere (about 1 atm) at room temperature for 2 hours. The reaction mixture was filtered through celite, and the filtrate was concentrated, diluted with water and extracted with AcOEt.

The organic layer was washed with brine, dried over MgSO₄, filtered and then evaporated under reduced pressure to remove the solvent, thereby giving the titled compound (113 mg, colorless oil).

¹H NMR (200 Hz, CDCl₃) δ ppm: 1.35 (t, J=7.1 Hz, 3H), 2.35 (s, 3H), 2.61 (s, 3H), 4.40 (q, J=7.1 Hz, 2H), 6.53 (s, 1H), 6.94-7.06 (m, 2H), 7.12-7.22 (m, 2H)

1-(1-Ethyl-5-(4-methylphenoxy)-1H-imidazol-2-yl)-ethanol

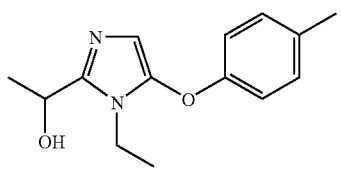

[Formula 30]

(5) To a solution of the compound obtained in Example 2-(4) (171 mg) in MeOH (7.0 ml), NaBH₄ (26 mg) was added at 0° C. and stirred at the same temperature for 15 minutes. The reaction mixture was diluted with water and extracted with AcOEt. After washing with brine, the organic layer was dried over MgSO₄, filtered and then evaporated to remove the solvent, thereby giving the titled compound (158 mg, colorless solid).

¹H NMR (200 Hz, CDCl₃) δ ppm: 1.33 (t, J=7.3 Hz, 3H), 1.67 (d, J=5.9 Hz, 3H), 2.32 (s, 3H), 3.92-4.07 (m, 2H), 4.76-4.98 (m, 1H), 6.35-6.53 (m, 1H), 6.90-7.02 (m, 2H), 7.07-7.18 (m, 2H)

2-(1-Azido-ethyl)-1-ethyl-5-(4-methylphenoxy)-1H-imidazole

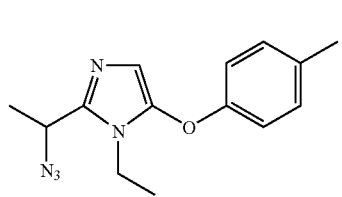

[Formula 31]

(6) Starting from the compound obtained in Example 2-(5), the same procedure as used in Example 1-(4) was repeated to give the titled compound (colorless oil, yield 40%).

¹H NMR (200 Hz, CDCl₃) δ ppm: 1.34 (t, J=7.3 Hz, 3H), 1.79 (d, J=6.8 Hz, 3H), 2.33 (s, 3H), 3.81-4.05 (m, 2H), 4.38-4.53 (m, 1H), 6.47 (s, 1H), 6.91-7.01 (m, 2H), 7.08-7.18 (m, 2H)

1-(1-Ethyl-5-(4-methylphenoxy)-1H-imidazol-2-yl)-ethylamine

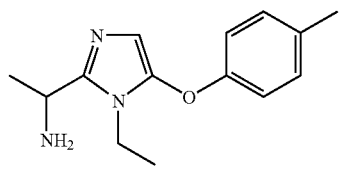

[Formula 32]

(7) Starting from the compound obtained in Example 2-(6), the same procedure as used in Example 1-(5) was repeated to give the titled compound (colorless oil) in quantitative yield.

¹H NMR (200 Hz, CDCl₃) δ ppm: 1.30 (t, J=7.3 Hz, 3H), 1.53 (d, J=6.8 Hz, 3H), 2.32 (s, 3H), 3.77-4.16 (m, 3H), 6.44 (s, 1H), 6.90-7.00 (m, 2H), 7.06-7.16 (m, 2H)

3,4-Dichloro-N-[1-(1-ethyl-5-(4-methylphenoxy)-1H-imidazol-2-yl)-ethyl]-benzenesulfonamide (Compound 179)

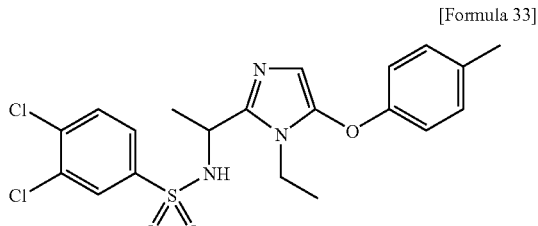

[Formula 33]

(8) Starting from the compound obtained in Example 2-(7), the same procedure as used in Example 1-(6) was repeated to give the titled compound (Compound 179) (colorless powder, yield 73%).

¹H NMR (200 MHz, DMSO-d6) δ ppm: 1.12 (t, J=7.1 Hz, 3H), 1.30 (d, J=6.8 Hz, 3H), 2.28 (s, 3H), 3.67-3.88 (m, 2H), 4.53-4.70 (m, 1H), 6.25 (s, 1H), 6.84-6.95 (m, 2H), 7.12-7.25 (m, 2H), 7.69 (dd, J=8.5, 2.1 Hz, 1H), 7.84 (d, J=8.5 Hz, 1H), 7.90 (d, J=2.1 Hz, 1H), 8.47-8.64 (m, 1H)

Melting point: 133.0-134.5° C.

Example 3

N-[1-(3-Ethyl-2-p-toluoyloxy-3H-imidazol-4-yl)-ethyl]-4-methoxybenzenesulfonamide (Compound 23)

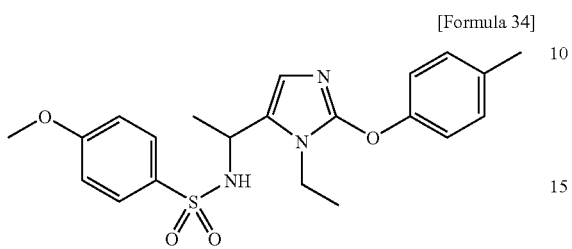

[Formula 34]

To a solution of the compound obtained in Example 1-(5) (12.3 mg) in THF (0.3 ml), Et$_3$N (25 μl) and a solution of 4-methoxybenzenesulfonyl chloride (15.5 mg) in THF (0.3 ml) were sequentially added and stirred at room temperature for 2 hours. After addition of PSA (polymer supported amine, VARIAN, 1.4 meq/g) (75 μl), the reaction mixture was stirred at room temperature for 12 hours and filtered to remove insoluble materials. After distilling off the solvent, the resulting crude product was purified by silica gel column chromatography (acidic OH-type SiO$_2$, AcOEt/hexane=50% to 100%, MeOH/CHCl$_3$=10%) to give the titled compound (Compound 23, 14.3 mg) as a colorless powder.

APCI MS (M−H)$^-$: 414, APCI MS (M+H)$^+$: 416

Example 4

3,4-Dichloro-N-[1-(4-chloro-1-ethyl-5-p-tolyloxy-1H-imidazol-2-yl)-ethyl]-benzenesulfonamide (Compound 183)

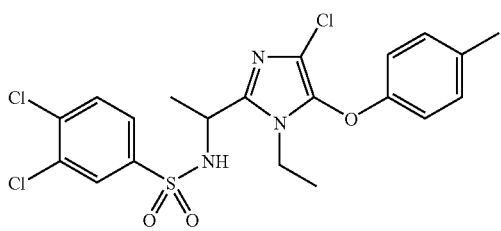

[Formula 35]

1-(4,5-Dichloro-1-ethyl-1H-imidazol-2-yl)-ethanone

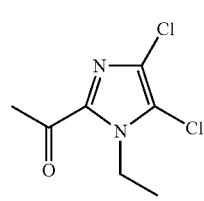

[Formula 36]

(1) The same procedure as used in Example 2-(2) was repeated to give the titled compound (colorless oil, yield 47%), except that N-bromosuccinimide (NBS) was replaced with N-chlorosuccinimide (NCS).

$^1$H NMR (600 MHz, CDCl$_3$) δ ppm: 1.36 (t, J=7.2 Hz, 3H), 2.61 (s, 3H), 4.48 (q, J=7.2 Hz, 2H)

1-(4-Chloro-1-ethyl-5-p-tolyloxy-1H-imidazol-2-yl)-ethanone

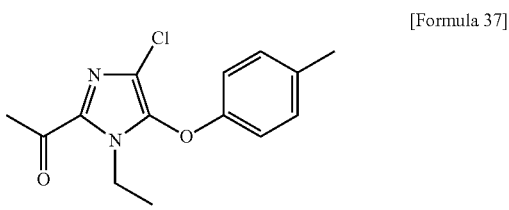

[Formula 37]

(2) Starting from the compound obtained in Example 4-(1), the same procedure as used in Example 2-(3) was repeated to give the titled compound (colorless solid, yield 47%).

$^1$H NMR (600 MHz, CDCl$_3$) δ ppm: 1.28 (t, J=7.2 Hz, 3H), 2.33 (s, 3H), 2.62 (s, 3H), 4.32 (q, J=7.2 Hz, 2H), 6.81-6.86 (m, 2H), 7.12-7.16 (m, 2H)

1-(4-Chloro-1-ethyl-5-p-toluoyloxy-1H-imidazol-2-yl)-ethanol

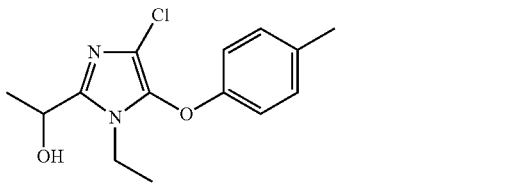

[Formula 38]

(3) Starting from the compound obtained in Example 4-(2), the same procedure as used in Example 2-(5) was repeated to give the titled compound (light-yellow oil, yield 87%).

$^1$H NMR (600 MHz, CDCl$_3$) δ ppm: 1.28 (t, J=7.3 Hz, 3H), 1.66 (d, J=6.4 Hz, 3H), 2.32 (s, 3H), 3.83-3.98 (m, 2H), 4.81-4.88 (m, 1H), 6.81-6.87 (m, 2H), 7.09-7.14 (m, 2H)

2-(1-Azidoethyl)-4-chloro-1-ethyl-5-p-tolyloxy-1H-imidazole

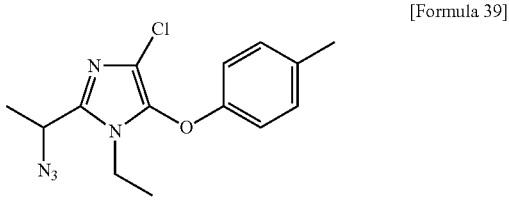

[Formula 39]

(4) Starting from the compound obtained in Example 4-(3), the same procedure as used in Example 1-(4) was repeated to give the titled compound (light-yellow oil, yield 87%).

$^1$H NMR (600 MHz, CDCl$_3$) δ ppm: 1.28 (t, J=7.1 Hz, 3H), 1.78 (d, J=6.4 Hz, 3H), 2.32 (s, 3H), 3.82-3.94 (m, 2H), 4.40-4.45 (m, 1H), 6.81-6.86 (m, 2H), 7.10-7.15 (m, 2H)

1-(4-Chloro-1-ethyl-5-p-tolyloxy-1H-imidazol-2-yl)-ethylamine

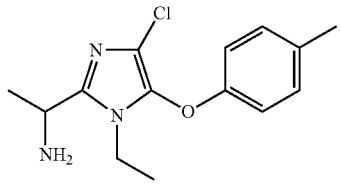

[Formula 40]

(5) To a solution of the compound obtained in Example 4-(4) (460 mg) and PPh$_3$ (790 mg) in THF (50 ml), H$_2$O (0.6 ml) was added and heated under reflux for 15 hours. After H$_2$O (0.6 ml) was further added, the reaction mixture was heated under reflux for an additional 4 hours, cooled to room temperature, and evaporated to remove the solvent. The resulting crude product was purified by silica gel column chromatography (OH-type, neutral SiO$_2$, MeOH/CHCl$_3$=0% to 10%) to give the titled compound (372 mg, colorless oil).

$^1$H NMR (600 MHz, CDCl$_3$) δ ppm: 1.26 (t, J=7.3 Hz, 3H), 1.52 (d, J=6.9 Hz, 3H), 2.31 (s, 3H), 3.79-3.96 (m, 2H), 4.03-4.10 (m, 1H), 6.82-6.88 (m, 2H), 7.08-7.15 (m, 2H)

3,4-Dichloro-N-[1-(4-chloro-1-ethyl-5-p-toluoyloxy-1H-imidazol-2-yl)-ethyl]-benzenesulfonamide (Compound 183)

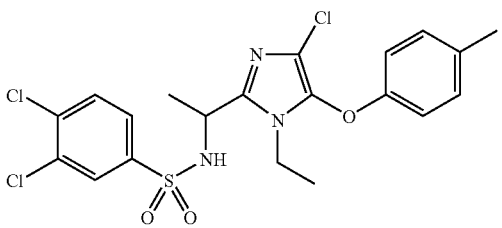

[Formula 41]

(6) Starting from the compound obtained in Example 4-(5), the same procedure as used in Example 1-(6) was repeated to give the titled compound (Compound 183) (colorless powder, yield 66%).

$^1$H NMR (600 MHz, CDCl$_3$) δ ppm: 1.17 (t, J=7.3 Hz, 3H), 1.49 (d, J=6.9 Hz, 3H), 2.32 (s, 3H), 3.68-3.89 (m, 2H), 4.52-4.65 (m, 1H), 5.55-5.72 (m, 1H), 6.72-6.77 (m, 2H), 7.10-7.16 (m, 2H), 7.52-7.61 (m, 2H) 7.84 (d, J=2.3 Hz, 1H)

Melting point: 122.5-123.5° C.

Example 5

3,4-Dichloro-N-{1-[3-ethyl-2-(4-fluorophenoxy)-5-methyl-3H-imidazol-4-yl]-ethyl}-benzenesulfonamide (Compound 188)

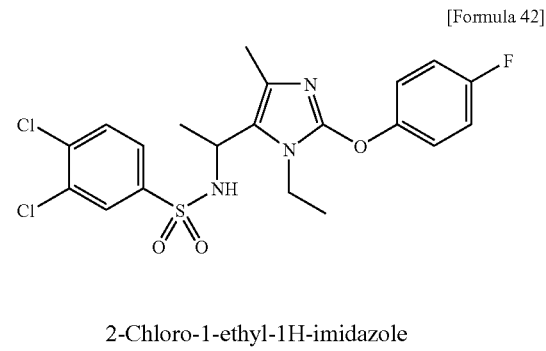

[Formula 42]

2-Chloro-1-ethyl-1H-imidazole

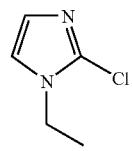

[Formula 43]

(1) To a solution of 1-ethyl-1H-imidazole (2.2 g) in THF (12 ml), n-BuLi (9.1 ml, 2.64 N in hexane) was added dropwise at −78° C. under an argon atmosphere. After stirring at the same temperature for 30 minutes, a solution of hexachloroethane (5.7 g) in THF (12 ml) was added dropwise and stirred at the same temperature for 1 hour. The reaction mixture was diluted with saturated aqueous ammonium chloride, warmed to room temperature, and extracted with AcOEt. After washing with water and saturated aqueous sodium chloride, the organic layer was dried over MgSO$_4$, filtered and then evaporated under reduced pressure to remove the solvent. The resulting crude product was purified by column chromatography (OH-type SiO$_2$, AcOEt/hexane=0% to 20%) to give the titled compound (2.74 g, colorless oil).

$^1$H NMR (600 MHz, CDCl$_3$) δ ppm: 1.40 (t, J=7.3 Hz, 3H), 3.96 (q, J=7.3 Hz, 2H), 6.88-6.98 (m, 2H)

1-(2-Chloro-3-ethyl-3H-imidazol-4-yl)-ethanone

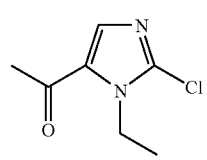

[Formula 44]

(2) To a solution of the compound obtained in Example 5-(1) (2.74 g) in THF (40 ml), n-BuLi (8.35 ml, 2.64 N in hexane) was added dropwise at −78° C. under an argon atmosphere and stirred at the same temperature for 30 minutes. The resulting reaction mixture was added at −78° C. to a solution of Ac$_2$O (2.1 ml) in THF (40 ml) and warmed to 0° C. over 2.5 hours. The reaction mixture was diluted with saturated aqueous sodium bicarbonate and extracted with AcOEt. After washing with saturated aqueous sodium chloride, the organic layer was dried over MgSO₄, filtered and then evaporated to remove the solvent. The resulting crude product was purified by column chromatography (NH-type SiO$_2$, AcOEt/hexane=10%) to give the titled compound (2.57 g, light-yellow oil).

¹H NMR (600 MHz, CDCl$_3$) δ ppm: 1.33 (t, J=7.2 Hz, 3H), 2.46 (s, 3H) 4.42 (q, J=7.2 Hz, 2H) 7.69 (s, 1H)

1-[3-Ethyl-2-(4-fluorophenoxy)-3H-imidazol-4-yl]-ethanone

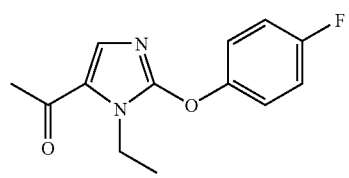

[Formula 45]

(3) A mixture of the compound obtained in Example 5-(2) (13.20 g), 4-fluorophenol (12.86 g), Cs$_2$CO$_3$ (49.9 g) and DMPU (15 ml) was stirred at 200° C. for 2 hours. After cooling to room temperature, MeOH/CHCl$_3$ (MeOH/CHCl$_3$=20%) was added and insoluble materials were filtered off. The filtrate was concentrated, and the resulting crude product was purified by column chromatography (OH-type neutral SiO$_2$, AcOEt/hexane=0% to 30%) to give the titled compound (22.37 g, light-yellow oil).

¹H NMR (600 MHz, CDCl$_3$) δ ppm: 1.38 (t, J=7.2 Hz, 3H), 2.42 (s, 3H), 4.38 (q, J=7.2 Hz, 2H), 7.04-7.12 (m, 2H), 7.19-7.23 (m, 2H), 7.47 (s, 1H)

1-[5-Bromo-3-ethyl-2-(4-fluorophenoxy)-3H-imidazol-4-yl]-ethanone

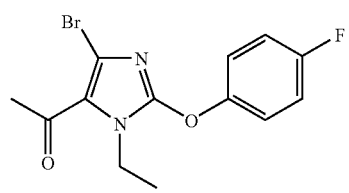

[Formula 46]

(4) To a solution of the compound obtained in Example 5-(3) (5.0 g) in DMF (50 ml), N-bromosuccinimide (NBS) (7.15 g) was added and stirred at room temperature for 6 hours. After NBS (1.83 g) was further added and stirred for an additional 4 hours, the reaction mixture was concentrated. The resulting residue was purified by silica gel column chromatography (OH-type neutral SiO$_2$, AcOEt/hexane=0% to 10%) to give the titled compound (4.916 g, yellow oil).

¹H NMR (600 MHz, CDCl$_3$) δ ppm: 1.35 (t, J=7.1 Hz, 3H), 2.64 (s, 3H), 4.37 (q, J=7.1 Hz, 2H), 7.06-7.11 (m, 2H), 7.20-7.24 (m, 2H)

1-[3-Ethyl-2-(4-fluorophenoxy)-5-methyl-3H-imidazol-4-yl]-ethanone

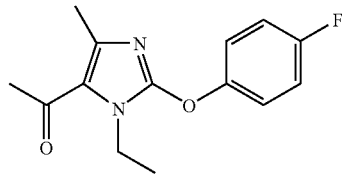

[Formula 47]

(5) A mixture of the compound obtained in Example 5-(4) (3.66 g), trimethylboroxin (1.57 ml), Pd(PPh$_3$)$_4$ (1.29 g) and K$_2$CO$_3$ (4.64 g) in dioxane (25 ml) was stirred under an argon atmosphere at 115° C. for 6 hours. To this mixture, trimethylboroxin (0.52 ml) was further added and stirred at the same temperature for an additional 4 hours. The reaction mixture was cooled to room temperature and filtered to remove insoluble materials. The filtrate was concentrated, and the resulting residue was purified by column chromatography (OH-type neutral SiO$_2$, AcOEt/hexane=0% to 50%) to give the titled compound (627 mg, yellow oil).

¹H NMR (600 MHz, CDCl$_3$) δ ppm: 1.33 (t, J=7.0 Hz, 3H), 2.46 (2 s, 6H), 4.32 (q, J=7.0 Hz, 2H) 7.05-7.10 (m, 2H) 7.19-7.22 (m, 2H)

1-[3-Ethyl-2-(4-fluorophenoxy)-5-methyl-3H-imidazol-4-yl]-ethanol

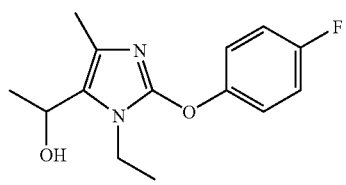

[Formula 48]

(6) Starting from the compound obtained in Example 5-(5), the same procedure as used in Example 2-(5) was repeated to give the titled compound (light-yellow oil, yield 42%).

¹H NMR (600 MHz, CDCl$_3$) δ ppm: 1.35 (t, J=7.1 Hz, 3H), 1.58 (dd, J=6.9, 1.8 Hz, 3H), 2.13 (s, 3H), 3.93-4.09 (m, 2H), 4.94-5.01 (m, 1H), 6.99-7.06 (m, 2H), 7.15-7.20 (m, 2H)

1-[3-Ethyl-2-(4-fluorophenoxy)-5-methyl-3H-imidazol-4-yl]-ethylazide

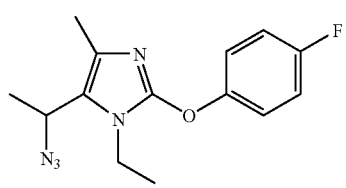

[Formula 49]

(7) Starting from the compound obtained in Example 5-(6), the same procedure as used in Example 1-(4) was repeated to give the titled compound (yellow oil, yield 44%).

¹H NMR (600 MHz, CDCl₃) δ ppm: 1.36 (t, J=7.3 Hz, 3H), 1.60 (d, J=7.3 Hz, 3H), 2.19 (s, 3H), 3.88-4.00 (m, 2H), 4.70-4.76 (m, 1H), 7.00-7.08 (m, 2H), 7.17-7.22 (m, 2H)

5-(1-Aminoethyl)-1-ethyl-2-(4-fluorophenoxy)-4-methyl-1H-imidazole

[Formula 50]

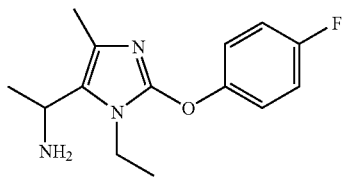

(8) A mixture of the compound obtained in Example 5-(7) (120 mg) and palladium-activated carbon (24 mg, Pd 10 wt. %) in MeOH (3.0 ml) was stirred under a hydrogen atmosphere (about 1 atm) at room temperature for 4 hours. The reaction mixture was filtered through celite, and the filtrate was concentrated to give the titled compound (120 mg, colorless oil).

¹H NMR (600 MHz, CDCl₃) δ ppm: 1.33 (t, J=7.1 Hz, 3H), 1.48 (d, J=6.9 Hz, 3H), 2.16 (s, 3H), 3.92-4.14 (m, 2H), 4.27 (q, J=6.9 Hz, 1H), 6.99-7.05 (m, 2H), 7.14-7.21 (m, 2H)

3,4-Dichloro-N-{1-[3-ethyl-2-(4-fluorophenoxy)-5-methyl-3H-imidazol-4-yl]-ethyl}-benzenesulfonamide (Compound 188)

[Formula 51]

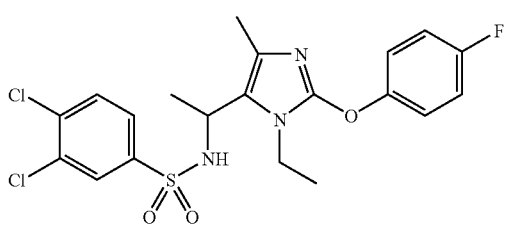

(9) Starting from the compound obtained in Example 5-(8), the same procedure as used in Example 1-(6) was repeated to give the titled compound (Compound 188) (colorless powder, yield 73%).

¹H NMR (600 MHz, CDCl₃) δ ppm: 1.25 (t, J=7.1 Hz, 3H), 1.55 (d, J=6.9 Hz, 3H), 2.00 (s, 3H), 3.60-3.73 (m, 1H), 3.77-3.89 (m, 1H), 4.63-4.74 (m, 1H), 4.95-5.03 (m, 1H), 7.00-7.08 (m, 2H), 7.11-7.18 (m, 2H), 7.43-7.52 (m, 2H), 7.75 (d, J=1.8 Hz, 1H)

Melting point: 119.5-120.0° C.

Example 6

3,4-Dichloro-N-[1-(4-ethyl-1-methyl-5-p-tolyloxy-1H-pyrazol-3-yl)-ethyl]-benzenesulfonamide (Compound 180)

[Formula 52]

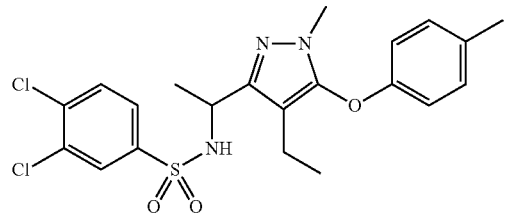

5-Hydroxy-1-methyl-1H-pyrazole-3-carboxylic acid ethyl ester

[Formula 53]

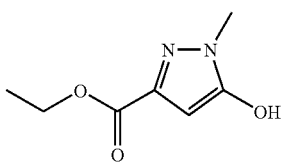

(1) To a solution of diethyl oxalacetate sodium salt (30.0 g) in toluene (200 ml), acetic acid (200 ml) and methylhydrazine (15 ml) were added and stirred at 100° C. for 8.5 hours. The reaction mixture was concentrated, and the resulting residue was diluted with saturated aqueous sodium chloride and extracted with AcOEt. The resulting organic layer was dried over MgSO₄, filtered and evaporated under reduced pressure to remove the solvent. The resulting solid was washed with Et₂O/hexane (Et₂O/hexane=2/1) and dried to give the titled compound (18.8 g, brown powder).

¹H NMR (600 MHz, DMSO-D6) δ ppm: 1.25 (t, J=7.1 Hz, 3H), 3.59 (s, 3H), 4.16-4.25 (m, 2H), 5.77 (s, 1H)

5-Chloro-4-formyl-1-methyl-1H-pyrazole-3-carboxylic acid ethyl ester

[Formula 54]

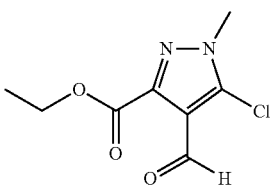

(2) To 1,2-dichloroethane (75 ml), DMF (13.7 ml) and POCl₃ (82.5 ml) were sequentially added dropwise at 0° C. under a nitrogen atmosphere. To this mixture, a solution of the compound obtained in Example 6-(1) (10.0 g) in 1,2-dichloroethane (75 ml) was added dropwise and warmed to room temperature. After stirring at 110° C. for 4.5 hours, the reaction mixture was cooled to room temperature and evaporated to remove the solvent. The resulting residue was added to saturated aqueous sodium bicarbonate and stirred for 2 hours. After extraction with AcOEt, the resulting organic layer was dried over MgSO₄, filtered and evaporated under reduced pressure to remove the solvent. The resulting crude product was recrystallized (AcOEt/hexane) to give the titled compound (14.7 g, yellow solid).

¹H NMR (600 MHz, DMSO-D6) δ ppm: 1.32 (t, J=7.0 Hz, 3H), 3.92 (s, 3H), 4.36 (q, J=7.0 Hz, 2H), 10.24 (s, 1H)

4-Formyl-1-methyl-5-p-toluoyloxy-1H-pyrazole-3-carboxylic acid ethyl ester

[Formula 55]

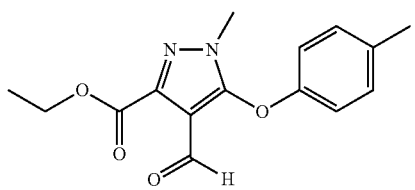

(3) To a solution of 4-cresol (3.62 ml) in DMF (80 ml), NaH (1.38 g, 60% in mineral oil) was added at room temperature and stirred at room temperature for 15 minutes, followed by addition of the compound obtained in Example 6-(2) (5.00 g). After stirring at 110° C. for 1.5 hours, the reaction mixture was cooled to room temperature and evaporated to remove the solvent. The resulting residue was purified by column chromatography (OH-type SiO₂, AcOEt/hexane=0% to 50%) to give the titled compound (3.54 g, colorless solid).

¹H NMR (600 MHz, DMSO-D6) δ ppm: 1.27-1.38 (m, 3H), 2.27 (s, 3H), 3.74 (s, 3H), 4.32-4.42 (m, 2H), 6.84-6.94 (m, 2H), 7.10-7.20 (m, 2H), 10.08 (s, 1H)

4-(1-Hydroxyethyl)-1-methyl-5-p-toluoyloxy-1H-pyrazole-3-carboxylic acid ethyl ester

[Formula 56]

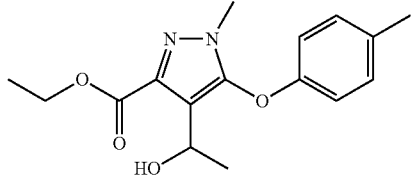

(4) To a solution of the compound obtained in Example 6-(3) (3.50 g) in THF (20 ml)/Et₂O (120 ml), MeMgBr (5.26 ml, 3.0 mmol in Et₂O) was added at −30° C. under a nitrogen atmosphere. After warming to 0° C., the reaction mixture was stirred for 2.5 hours, diluted with saturated aqueous ammonium chloride and saturated aqueous sodium chloride, and then extracted with AcOEt. The organic layer was dried over Na₂SO₄, filtered and evaporated under reduced pressure to remove the solvent. The resulting crude product was purified by column chromatography (OH-type SiO₂, AcOEt/hexane=0% to 50%) to give the titled compound (2.17 g, light-yellow oil).

¹H NMR (600 MHz, DMSO-D6) δ ppm: 1.22 (d, J=6.4 Hz, 3H), 1.28-1.32 (m, 3H), 2.26 (s, 3H), 3.56 (s, 3H), 4.28 (q, J=6.9 Hz, 2H), 4.75 (d, J=4.6 Hz, 1H), 5.03-5.11 (m, 1H), 6.79-6.84 (m, 2H), 7.13-7.19 (m, 2H)

4-Ethyl-1-methyl-5-p-tolyloxy-1H-pyrazole-3-carboxylic acid ethyl ester

[Formula 57]

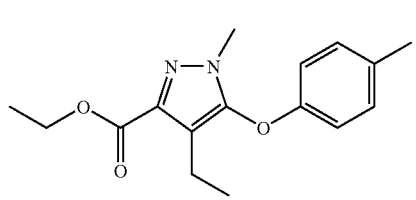

(5) To a solution of the compound obtained in Example 6-(4) (2.14 g) in CHCl₃ (40 ml), CF₃COOH (5.4 ml) and Et₃SiH (2.3 ml) were added at −20° C. and stirred at room temperature for 3.5 hours. The resulting reaction mixture was purified by column chromatography (OH-type SiO₂, AcOEt/hexane=0% to 50%) to give the titled compound (1.36 g, colorless oil).

¹H NMR (600 MHz, DMSO-D6) δ ppm: 0.93 (t, J=7.5 Hz, 3H), 1.29 (t, J=7.0 Hz, 3H), 2.27 (s, 3H), 2.42 (q, J=7.5 Hz, H), 3.63 (s, 3H), 4.27 (q, J=7.0 Hz, 2H), 6.78-6.87 (m, H), 7.16-7.22 (m, 2H)

4-Ethyl-1-methyl-5-p-tolyloxy-1H-pyrazole-3-carbaldehyde

[Formula 58]

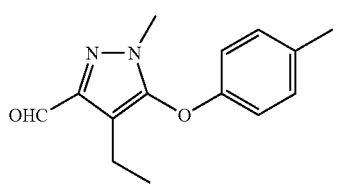

(6) To a solution of the compound obtained in Example 6-(5) (1.36 g) in THF (30 ml), LiB(C₂H₅)₃H (9.9 ml, 1.0 M in THF) was added at −20° C. and stirred for 2 hours. The reaction mixture was then warmed to 0° C. and stirred for 2 hours, followed by addition of AcOH (10% in EtOH). After stirring at room temperature for 0.5 hours, the reaction mixture was evaporated to remove the solvent, diluted with aqueous HCl (1.0 M) and extracted with AcOEt. The organic layer was dried over MgSO₄, filtered and evaporated under reduced pressure to remove the solvent. The resulting crude product was purified by column chromatography (OH-type SiO₂, AcOEt/hexane=0% to 99%) to give the titled compound (72 mg, colorless oil) and 4-ethyl-1-methyl-5-p-tolyloxy-1H-pyrazol-3-yl)-methanol (554 mg, colorless oil).

4-Ethyl-1-methyl-5-p-tolyloxy-1H-pyrazole-3-carbaldehyde

¹H NMR (600 MHz, DMSO-D6) δ ppm: 0.94 (t, J=7.5 Hz, 3H), 2.27 (s, 3H), 2.42 (q, J=7.5 Hz, 2H), 3.71 (s, 3H), 6.84-6.89 (m, 2H), 7.18-7.22 (m, 2H), 9.81 (s, 1H)

4-Ethyl-1-methyl-5-p-toluoyloxy-1H-pyrazol-3-yl)-methanol

¹H NMR (600 MHz, DMSO-D6) δ ppm: 0.94 (t, J=7.8 Hz, 3H), 2.23 (q, J=7.8 Hz, 2H), 2.26 (s, 3H), 3.48 (s, 3H), 4.34 (d, J=5.5 Hz, 2H), 4.90 (t, J=5.5 Hz, 1H), 6.76-6.83 (m, 2H), 7.12-7.22 (m, 2H)

1-(4-Ethyl-1-methyl-5-p-toluoyloxy-1H-pyrazol-3-yl)-ethanol

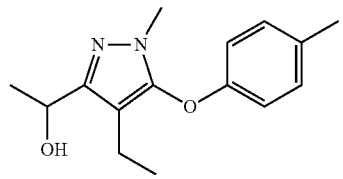

[Formula 59]

(7) To a solution of 4-ethyl-1-methyl-5-p-tolyloxy-1H-pyrazole-3-carbaldehyde obtained in Example 6-(6) (470 mg) in Et₂O (10 ml), MeMgBr (0.71 ml, 3.0 mmol in Et₂O) was added at −30° C. under a nitrogen atmosphere. After stirring at 0° C. for 4 hours, the reaction mixture was diluted with saturated aqueous ammonium chloride and extracted with AcOEt. The organic layer was dried over Na₂SO₄, filtered and evaporated under reduced pressure to remove the solvent. The resulting crude product was purified by column chromatography (OH-type SiO₂, AcOEt/hexane=0% to 50%) to give the titled compound (406 mg, colorless oil).

¹H NMR (600 MHz, DMSO-D6) δ ppm: 0.93 (m, 3H), 1.39 (d, J=6.4 Hz, 3H), 2.22-2.32 (m, 5H), 3.47 (s, 3H), 4.64-4.72 (m, 1H), 4.92 (d, J=5.0 Hz, 1H), 6.75-6.81 (m, 2H), 7.14-7.20 (m, 2H)

3-(1-Azidoethyl)-4-ethyl-1-methyl-5-p-toluoyloxy-1H-pyrazole

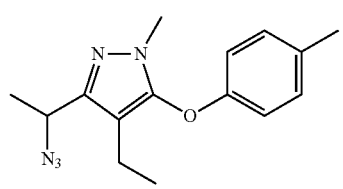

[Formula 60]

(8) Starting from the compound obtained in Example 6-(7), the same procedure as used in Example 1-(4) was repeated to give the titled compound (colorless oil, yield 70%).

¹H NMR (600 MHz, DMSO-D6) δ ppm: 0.92 (t, J=7.8 Hz, 3H), 1.53 (d, J=6.9 Hz, 3H), 2.23 (q, J=7.8 Hz, 2H), 2.27 (s, 3H), 3.54 (s, 3H), 4.69 (q, J=6.9 Hz, 1H), 6.75-6.83 (m, 2H), 7.14-7.22 (m, 2H)

1-(4-Ethyl-1-methyl-5-p-toluoyloxy-1H-pyrazol-3-yl)-ethylamine

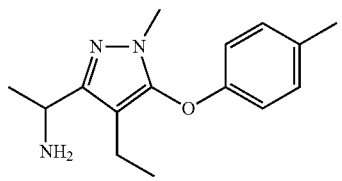

[Formula 61]

(9) Starting from the compound obtained in Example 6-(8), the same procedure as used in Example 1-(5) was repeated to give the titled compound (colorless oil, yield 89%).

¹H NMR (600 MHz, DMSO-D6) δ ppm: 0.92 (m, 3H), 1.29 (d, J=6.9 Hz, 3H), 2.18-2.29 (m, 5H), 3.46 (s, 3H), 3.94 (q, J=6.9 Hz, 1H), 6.75-6.82 (m, 2H), 7.14-7.20 (m, 2H)

3,4-Dichloro-N-[1-(4-ethyl-1-methyl-5-p-tolyloxy-1H-pyrazol-3-yl)-ethyl]-benzenesulfonamide (Compound 180)

[Formula 62]

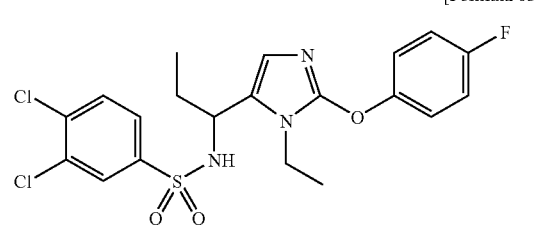

(10) Starting from the compound obtained in Example 6-(9), the same procedure as used in Example 1-(6) was repeated to give the titled compound (Compound 180) (colorless powder, yield 48%).

¹H NMR (600 MHz, DMSO-d6) δ ppm: 0.78 (t, J=7.6 Hz, 3H), 1.33 (d, J=6.9 Hz, 3H), 1.95-2.12 (m, 2H), 2.26 (s, 3H), 3.37 (s, 3H), 4.37-4.51 (m, 1H), 6.60-6.70 (m, 2H), 7.12-7.22 (m, 2H), 7.64 (dd, J=8.5, 2.1 Hz, 1H), 7.77-7.89 (m, 2H), 8.41 (brs, 1H)

Melting point: 114.0-115.0° C.

Example 7

3,4-Dichloro-N-{1-[3-ethyl-2-(4-fluorophenoxy)-3H-imidazol-4-yl]-propyl}-benzenesulfonamide (Compound 191)

[Formula 63]

2-Chloro-3-ethyl-3H-imidazole-4-carbaldehyde

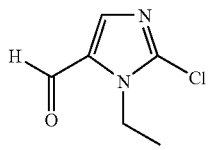
[Formula 64]

(1) To a solution of 2-chloro-1-ethyl-1H-imidazole obtained in Example 5-(1) (15.0 g) in THF (570 ml), n-BuLi (2.64 M in hexane, 45.5 ml) was added dropwise at −78° C. over 1 hour and stirred at the same temperature for 30 minutes. Dimethylformamide (8.9 ml) was added dropwise at the same temperature over 15 minutes, and the reaction mixture was warmed to 0° C. over 5 hours. The reaction mixture was diluted with saturated ammonium chloride solution, and the aqueous layer was extracted with ethyl acetate. The organic layer was washed with saturated aqueous sodium chloride, dried over magnesium sulfate, filtered and concentrated. The resulting residue was purified by silica gel column chromatography (OH-type $SiO_2$, AcOEt/hexane 0% to 60%) to give the titled compound (14.1 g) as a colorless crystal.

$^1$H NMR (600 MHz, $CDCl_3$) δ ppm: 1.37 (t, J=7.1 Hz, 3H), 4.27-4.50 (m, 2H), 7.69 (s, 1H), 9.64 (s, 1H)

3-Ethyl-2-(4-fluorophenoxy)-3H-imidazole-4-carbaldehyde

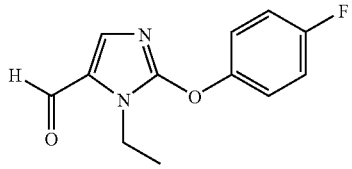
[Formula 65]

(2) A suspension of the compound obtained in Example 7-(1) (5.0 g), 4-fluorophenol (2.87 g) and $Cs_2CO_3$ (10.4 g) in DMPU (10 ml) was stirred at 200° C. for 1 hour. After cooling to room temperature, the reaction mixture was diluted with methanol/chloroform (1/4) and filtered. The filtrate was concentrated, and the resulting residue was purified by column chromatography (OH-type $SiO_2$, AcOEt/hexane=0% to 30%) to give the titled compound (4.16 g) as a light-pink liquid.

$^1$H NMR (600 MHz, $CDCl_3$) δ ppm: 1.44 (t, J=7.3 Hz, 3H), 4.37 (q, J=7.3 Hz, 2H), 7.10-7.17 (m, 2H), 7.36-7.40 (m, 2H)

1-[3-Ethyl-2-(4-fluorophenoxy)-3H-imidazol-4-yl]-propan-1-ol

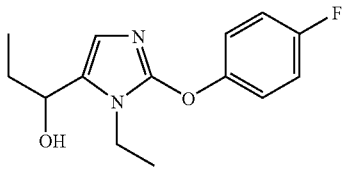
[Formula 66]

(3) To a solution of the compound obtained in Example 7-(2) (468 mg) in $Et_2O$ (4.0 ml), EtMgBr (1.0 M in THF, 4.0 ml) was added at 0° C. and stirred at the same temperature to room temperature for 2 hours. The reaction mixture was diluted with saturated ammonium chloride solution, and the aqueous layer was extracted with ethyl acetate. After washing with saturated aqueous sodium chloride, the organic layer was dried over magnesium sulfate and filtered. The filtrate was concentrated, and the resulting residue was purified by silica gel column chromatography (OH-type $SiO_2$, AcOEt/hexane=0% to 50%) to give the titled compound (1.1 g) as a colorless solid.

$^1$H NMR (600 MHz, $CDCl_3$) δ ppm: 1.06 (t, J=7.3 Hz, 3H), 1.39 (t, J=7.1 Hz, 3H), 1.83-2.02 (m, 2H), 3.95-4.10 (m, 2H), 4.43-4.51 (m, 1H), 6.53-6.60 (m, 1H), 7.02-7.10 (m, 2H), 7.17-7.25 (m, 2H)

5-(1-Azidopropyl)-1-ethyl-2-(4-fluorophenoxy)-1H-imidazole

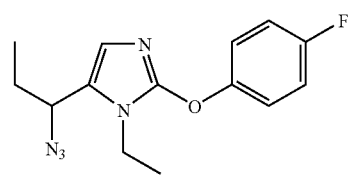
[Formula 67]

(4) Starting from the compound obtained in Example 7-(3) (550 mg), the same procedure as used in Example 1-(4) was repeated to give the titled compound (606 mg) as a colorless oil.

$^1$H NMR (600 MHz, $CDCl_3$) δ ppm; 1.02-1.11 (m, 3H), 1.39 (t, J=7.1 Hz, 3H), 1.96-2.06 (m, 2H), 3.89-4.02 (m, 2H), 4.02-4.08 (m, 1H), 6.64-6.71 (m, 1H), 7.02-7.41 (m, 4H)

1-[3-Ethyl-2-(4-fluorophenoxy)-3H-imidazol-4-yl]-propylamine

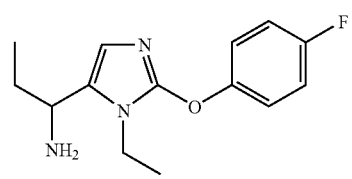
[Formula 68]

(5) Starting from the compound obtained in Example 7-(4) (606 mg), the same procedure as used in Example 1-(5) was repeated to give the titled compound (214 mg) as a colorless powder.

$^1$H NMR (600 MHz, $CDCl_3$) δ ppm: 1.00 (t, J=7.3 Hz, 3H), 1.37 (t, J=7.1 Hz, 3H), 1.63-1.73 (m, 1H), 1.84-1.94 (m, 1H), 3.70 (t, J=6.9 Hz, 1H), 3.93-4.10 (m, 2H), 6.50 (s, 1H), 7.01-7.07 (m, 2H), 7.17-7.24 (m, 2H)

3,4-Dichloro-N-{1-[3-ethyl-2-(4-fluorophenoxy)-3H-imidazol-4-yl]-propyl}-benzenesulfonamide (Compound 191)

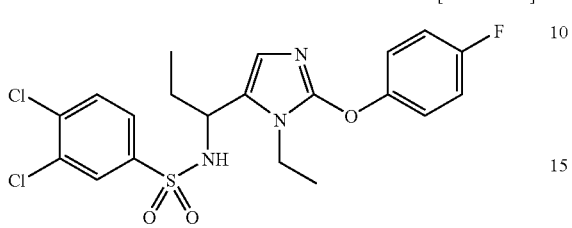

[Formula 69]

(6) Starting from the compound obtained in Example 7-(5) (107 mg), the same procedure as used in Example 1-(6) was repeated to give the titled compound (Compound 191) (144 mg) as a colorless powder.

$^1$H NMR (600 MHz, CDCl$_3$) δ ppm: 0.92 (t, J=7.3 Hz, 3H), 1.30 (t, J=7.1 Hz, 3H), 1.68-1.87 (m, 2H), 3.77-3.93 (m, 2H), 4.30-4.40 (m, 1H), 4.80-4.92 (m, 1H), 6.43 (s, 1H), 7.02-7.11 (m, 2H), 7.14-7.22 (m, 2H), 7.52-7.56 (m, 1H), 7.56-7.62 (m, 1H), 7.86 (d, J=1.8 Hz, 1H)

Melting point: 137.5-138.5° C.

Example 8

*3,4-Dichloro-N-{1-[3-ethyl-2-(4-fluorophenoxy)-3H-imidazol-4-yl]-propyl}-benzenesulfonamide (Compounds 253 and 254)

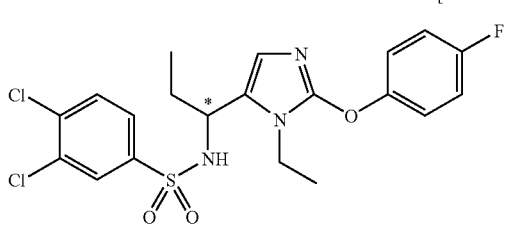

[Formula 70]

The compound obtained in Example 7 (80 mg) was optically resolved on an optical resolution column (column: CHIRALPAK AD [Daicel Chemical Industries, Ltd., Japan], 2 cmφ×25 cmL; eluent: i-PrOH/hexane=50%, flow rate: 6.0 ml/min) to give the titled compound (Compound 253) [(R)-(+)-form, 31 mg, colorless powder, whose configuration was determined by X-ray structural analysis] and another titled compound (Compound 254) [(S)-(−)-form, 28 mg, colorless powder, whose configuration was determined by X-ray structural analysis].

(R)-(+)-3,4-Dichloro-N-{1-[3-ethyl-2-(4-fluorophenoxy)-3H-imidazol-4-yl]-propyl}-benzenesulfonamide (Compound 253)

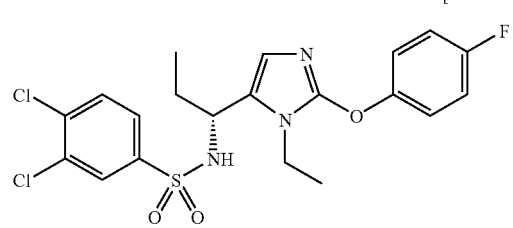

[Formula 71]

$[α]_D^{26}$ +19.7° (c 0.436, CHCl$_3$)

Retention time: 7.6 min (column: CHIRALPAK AD [Daicel Chemical Industries, Ltd., Japan], 4.6 mmφ×250 mL; eluent: i-PrOH/hexane=60%; flow rate: 0.5 ml/min)

(S)-(−)-3,4-Dichloro-N-{1-[3-ethyl-2-(4-fluorophenoxy)-3H-imidazol-4-yl]-propyl}-benzenesulfonamide (Compound 254)

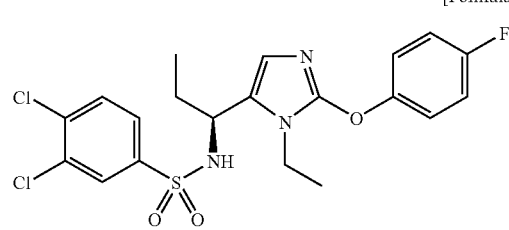

[Formula 72]

$[α]_D^{25}$ -17.3° (c 0.557, CHCl$_3$)

Retention time: 14.7 min (column: CHIRALPAK AD [Daicel Chemical Industries, Ltd., Japan], 4.6 mmφ×250 mL; eluent: i-PrOH/hexane=60%; flow rate: 0.5 ml/min)

Example 9

3,4-Dichloro-N-{1-[3-ethyl-2-(4-chlorophenoxy)-3H-imidazol-4-yl]-ethyl}-benzenesulfonamide (Compound 189)

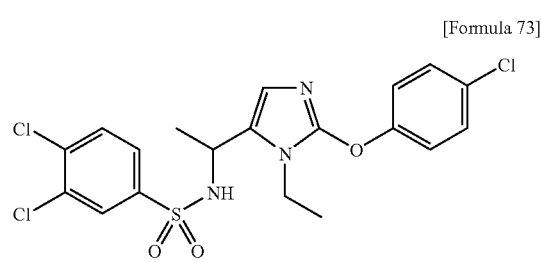

[Formula 73]

1-(2-Chloro-3-ethyl-3H-imidazol-4-yl)-ethanol

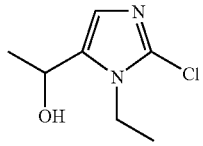

[Formula 74]

(1) To a solution of 2-chloro-3-ethyl-3H-imidazole-4-carbaldehyde obtained in Example 7-(1) (13.60 g) in Et$_2$O (429 ml), MeMgBr (37.2 ml, 3.0 M in Et$_2$O) was added at −30° C. under an argon atmosphere. After warming to 0° C., the reaction mixture was diluted with saturated aqueous NH$_4$Cl and extracted with AcOEt. The organic layer was washed with saturated aqueous sodium chloride, dried over MgSO$_4$, filtered and concentrated. The resulting crude product (brown solid) was washed with hexane and then dried to give the titled compound (13.01 g) as a light-brown solid.

$^1$H NMR (200 MHz, CDCl$_3$) δ ppm: 1.37 (t, J=7.3 Hz, 3H), 1.62 (d, J=6.6 Hz, 3H), 3.89-4.30 (m, 2H), 4.80 (q, J=6.6 Hz, 1H), 6.80 (s, 1H)

5-(1-Azidoethyl)-2-chloro-1-ethyl-1H-imidazole

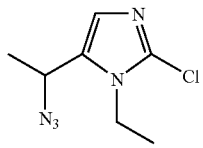

[Formula 75]

(2) Starting from the compound obtained in Example 9-(1) (11.95 g), the same procedure as used in Example 1-(4) was repeated to give the titled compound (light-yellow oil, 13.67 g).

$^1$H NMR (200 MHz, CDCl$_3$) δ ppm: 1.37 (t, J=7.3 Hz, 3H), 1.69 (d, J=6.6 Hz, 3H), 3.90-4.15 (m, 2H), 4.26-4.40 (m, 1H), 6.95 (d, J=0.9 Hz, 1H)

1-(2-Chloro-3-ethyl-3H-imidazol-4-yl)-ethylamine

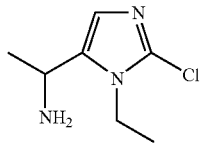

[Formula 76]

(3) To a solution of the compound obtained in Example 9-(2) (5.99 g) and PPh$_3$ (7.869 g) in THF (300 ml), H$_2$O (10 ml) was added and heated under reflux for 15.5 hours. After cooling to room temperature, the solvent was distilled off, and the resulting crude product was dissolved in CHCl$_3$ (200 ml). Hydrochloric acid (1.0 N, 100 ml) was added to separate the organic layer, and CHCl$_3$ (200 ml) was added to the aqueous layer to further separate the organic layer. The aqueous layer was adjusted to a basic pH with NaOH (5.0 g), salted out with NaCl and extracted with CHCl$_3$ (200 ml×2). The combined organic layers were dried over Na$_2$SO$_4$, filtered and concentrated to give the titled compound (colorless oil, 4.588 g).

$^1$H NMR (200 MHz, CDCl$_3$) δ ppm: 1.36 (t, J=7.3 Hz, 3H), 1.49 (d, J=6.6 Hz, 3H), 3.90-4.29 (m, 3H), 6.80 (s, 1H)

1-[2-(4-Chlorophenoxy)-3-ethyl-3H-imidazol-4-yl]-ethylamine

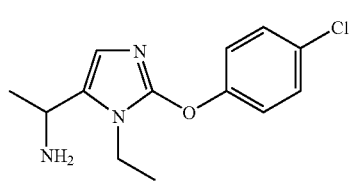

[Formula 77]

(4) Into a pressure-resistant screw-capped test tube, the compound obtained in Example 9-(3) (120 mg), 4-chlorophenol (133 mg), Cs$_2$CO$_3$ (563 mg) and DMPU (0.69 ml) were introduced and stirred at 200° C. for 3 hours and then at 250° C. for 1.5 hours. After cooling to room temperature, MeOH/CHCl$_3$ (MeOH/CHCl$_3$=20%, 5 ml) was added and the reaction mixture was purified (NH-type SiO$_2$, MeOH/CHCl$_3$=1/4, 5 ml) to give a brown oil, which was then purified by column chromatography (neutral OH-type SiO$_2$, AcOEt, MeOH/CHCl$_3$=0% to 20%) to give the titled compound (58 mg, brown oil).

$^1$H NMR (200 MHz, CDCl$_3$) δ ppm: 1.36 (t, J=7.0 Hz, 3H), 1.50 (d, J=6.6 Hz, 3H), 3.79-4.12 (m, 3H), 6.55 (d, J=0.9 Hz, 1H), 7.12-7.36 (m, 4H)

3,4-Dichloro-N-{1-[3-ethyl-2-(4-chlorophenoxy)-3H-imidazol-4-yl]-ethyl}-benzenesulfonamide (Compound 189)

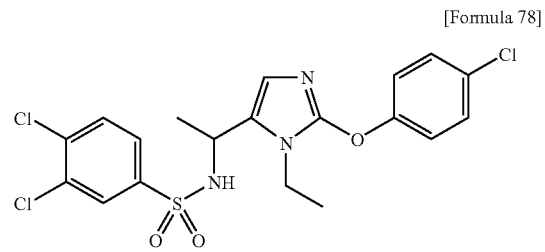

[Formula 78]

(5) Starting from the compound obtained in Example 9-(4) (55 mg), the same procedure as used in Example 1-(6) was repeated to give the titled compound (Compound 189) (53 mg) as a colorless powder.

$^1$H NMR (600 MHz, CDCl$_3$) δ ppm: 1.35 (t, J=7.1 Hz, 3H), 1.37 (d, J=6.9 Hz, 3H), 3.87-4.05 (m, 2H), 4.58-4.70 (m, 1H), 4.81 (brs, 1H), 6.55 (s, 1H), 7.14-7.22 (m, 2H), 7.34 (d, J=8.7 Hz, 2H), 7.61 (d, J=8.7 Hz, 1H), 7.67-7.75 (m, 1H), 7.94-8.01 (m, 1H)

Melting point: 153.0-157.0° C.

Example 10

3,4-Dichloro-N-{1-[2-(4-chlorophenoxy)-3-ethyl-3H-imidazol-4-yl]-ethyl}-N-methyl-benzenesulfonamide (Compound 248)

[Formula 79]

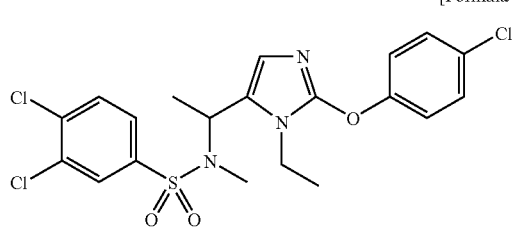

To a solution of the compound obtained in Example 9-(5) (36 mg) in DMF (2.0 ml), $K_2CO_3$ (21 mg) and MeI (5 μl) were added and stirred at room temperature for 7 hours. Insoluble materials were filtered off, and the filtrate was concentrated. The resulting crude product was purified by column chromatography (NH-type $SiO_2$, MeOH/$CHCl_3$=0% to 2%), followed by recrystallization (AcOEt-hexane) to give the titled compound (Compound 248) (30 mg, colorless powder).

$^1$H NMR (200 MHz, $CDCl_3$) δ ppm: 1.15 (d, J=7.0 Hz, 3H), 1.39 (t, J=7.3 Hz, 3H), 2.63 (s, 3H), 4.04-4.16 (m, 2H), 5.29 (q, J=7.0 Hz, 1H), 6.59 (s, 1H), 7.16-7.24 (m, 2H), 7.30-7.36 (m, 2H), 7.64 (d, J=8.4 Hz, 1H), 7.69 (dd, J=8.4, 1.8 Hz, 1H), 7.96 (d, J=1.8 Hz, 1H)

Melting point: 142.0-144.0° C.

Example 11

N-{1-[2-(3-Aminophenoxy)-3-ethyl-3H-imidazol-4-yl]-ethyl}-3,4-dichlorobenzenesulfonamide (Compound 233)

[Formula 80]

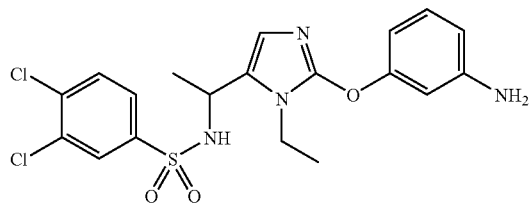

1-(2-Chloro-3-ethyl-3H-imidazol-4-yl)-ethylamine 1.5 trifluoroacetate salt

[Formula 81]

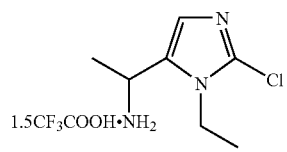

(1) The compound obtained in Example 9-(3) (4.20 g) was dissolved in $CHCl_3$ (48 ml), followed by addition of trifluoroacetic acid (2.8 ml) at 0° C. After warming to room temperature, the reaction mixture was stirred for 1 hour, and then concentrated to give the titled compound (8.262 g, colorless powder).

$^1$H NMR (200 MHz, DMSO-D6) δ ppm: 1.23 (t, J=7.3 Hz, 3H), 1.53 (d, J=6.6 Hz, 3H), 3.77-4.23 (m, 2H), 4.45-4.59 (m, 1H), 7.08 (s, 1H), 8.25 (brs, 3H)

Elementary analysis: calcd (C, 34.85%; H, 3.95%; N, 12.19%). found (C, 34.58%; H, 3.85%; N, 12.11%).

3-[5-(1-Aminoethyl)-1-ethyl-1H-imidazol-2-yloxy]-phenylamine

[Formula 82]

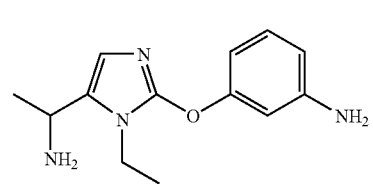

(2) Into a pressure-resistant screw-capped test tube, the compound obtained in Example 11-(1) (1.00 g), 3-aminophenol (633 mg), $Cs_2CO_3$ (2.83 g) and DMPU (4.0 ml) were introduced and stirred at 250° C. for 2 hours. After cooling to room temperature, $CHCl_3$ and water were added, and the mixture was concentrated. The resulting crude product was purified by column chromatography (neutral OH-type $SiO_2$, MeOH/$CHCl_3$=10% to 20%) to give the titled compound (103 mg, brown oil).

$^1$H NMR (600 MHz, DMSO-D6) δ ppm: 1.19-1.24 (m, 3H), 1.35 (d, J=6.4 Hz, 3H), 3.80-4.00 (m, 3H), 5.19-5.24 (m, 2H), 6.19-6.22 (m, 1H), 6.29-6.33 (m, 2H), 6.43 (d, J=0.9 Hz, 1H), 6.93-6.98 (m, 1H)

N-{1-[2-(3-Aminophenoxy)-3-ethyl-3H-imidazol-4-yl]-ethyl}-3,4-dichlorobenzenesulfonamide (Compound 233)

[Formula 83]

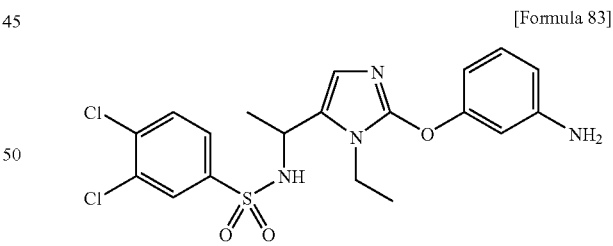

(3) To a solution of the compound obtained in Example 11-(2) (97 mg) and $Et_3N$ (0.11 mL) in THF (1.0 mL), a solution of 3,4-dichlorobenzenesulfonyl chloride (96.7 mg) in THF (1.0 mL) was added at −78° C. and stirred overnight at room temperature. The reaction mixture was concentrated, and the resulting crude product was purified by silica gel column chromatography (NH-type $SiO_2$, MeOH/$CHCl_3$=2%) to give the titled compound (Compound 233) (150 mg, light-brown amorphous substance).

$^1$H NMR (600 MHz, $CDCl_3$) δ ppm: 1.31 (t, J=7.1 Hz, 3H), 1.36 (d, J=6.9 Hz, 3H), 3.73 (brs, 2H), 3.84-3.95 (m, 2H), 4.59-4.65 (m, 1H), 5.03 (d, J=8.3 Hz, 1H), 6.45-6.49 (m, 1H), 6.49 (s, 1H), 6.51-6.56 (m, 2H), 7.09-7.14 (m, 1H), 7.57 (d, J=8.3 Hz, 1H), 7.63-7.66 (m, 1H), 7.96 (d, J=2.3 Hz, 1H)

Example 12

3,4-Dichloro-N-{1-[3-ethyl-2-(3-methanesulfonylaminophenoxy)-3H-imidazol-4-yl]-ethyl}-benzenesulfonamide (Compound 234)

[Formula 84]

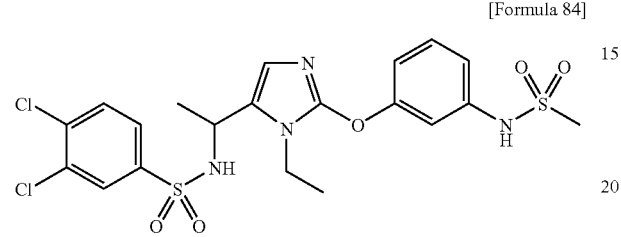

To a solution of the compound obtained in Example 11-(3) (37 mg) in pyridine (0.37 ml), methanesulfonyl chloride (0.01 ml) was added at room temperature and stirred at room temperature for 5 hours. After addition of water, the reaction mixture was concentrated, and the resulting crude product was purified by column chromatography (NH-type $SiO_2$, MeOH/$CHCl_3$=5% to 10%) to give the titled compound (33 mg, colorless amorphous substance).

$^1$H NMR (600 MHz, $CDCl_3$) δ ppm: 1.31-1.39 (m, 6H), 2.97 (s, 3H), 3.90-3.97 (m, 2H), 4.59-4.67 (m, 1H), 5.06 (d, J=8.3 Hz, 1H), 6.56 (s, 1H), 6.91-6.97 (m, 2H), 7.04 (s, 1H), 7.24-7.29 (m, 1H), 7.62 (d, J=8.3 Hz, 1H), 7.70 (d, J=8.7 Hz, 1H), 7.87 (s, 1H), 7.97 (d, J=1.4 Hz, 1H)

Example 13

3,4-Dichloro-N-{1-[3-ethyl-2-(3-pyrrol-1-yl-phenoxy)-3H-imidazol-4-yl]-ethyl}-benzenesulfonamide (Compound 249)

[Formula 85]

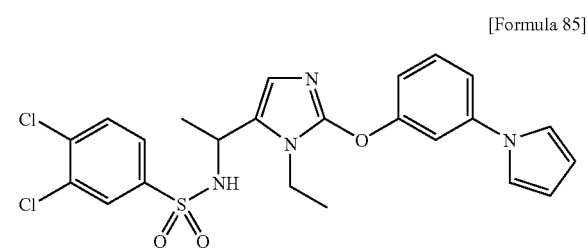

To a solution of the compound obtained in Example 11-(3) (40 mg) in AcOH (300 μl), 2,5-dimethoxy-tetrahydrofuran (20.3 μl) was added and stirred at 130° C. for 1 hour. The reaction mixture was cooled to room temperature and concentrated under reduced pressure. The resulting crude product was purified by column chromatography (neutral OH-type $SiO_2$, MeOH/$CHCl_3$=0% to 2%) and further purified by column chromatography (NH-type $SiO_2$, AcOEt) to give the titled compound (Compound 249) (19 mg, colorless powdery compound).

$^1$H NMR (600 MHz, $CDCl_3$) δ ppm: 1.36 (t, J=7.3 Hz, 3H), 1.40 (d, J=6.9 Hz, 3H), 3.91-4.00 (m, 2H), 4.52-4.57 (m, 1H), 4.63-4.69 (m, 1H), 6.32-6.34 (m, 1H), 6.57 (s, 1H), 7.04-7.73 (m, 9H), 7.95-7.99 (m, 1H)

Example 14

3,4-Dichloro-N-[1-(3-ethyl-2-p-tolylsulfanyl-3H-imidazol-4-yl)-ethyl]-benzenesulfonamide (Compound 241)

[Formula 86]

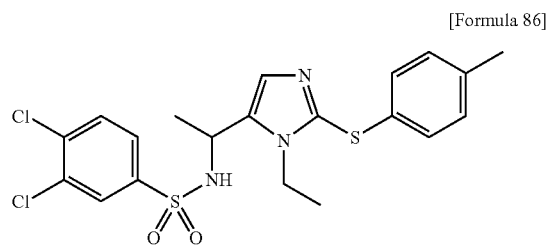

3-Ethyl-2-p-tolylsulfanyl-3H-imidazole-4-carbaldehyde

[Formula 87]

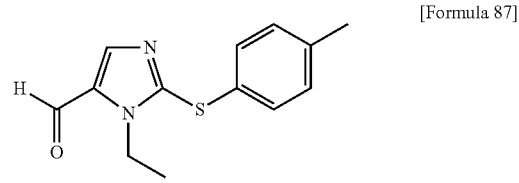

(1) Into a pressure-resistant screw-capped test tube, the compound obtained in Example 7-(1) (500 mg), DMF (2.0 ml), 4-methylbenzenethiol (803 mg) and $Cs_2CO_3$ (3.08 g) were introduced and stirred at 150° C. for 2 hours and then at 170° C. for 2 hours. After cooling to room temperature, the reaction mixture was diluted with saturated aqueous $NH_4Cl$ and extracted with AcOEt. The organic layer was washed with saturated aqueous sodium chloride, dried over $MgSO_4$, filtered and concentrated. The resulting crude product was purified by column chromatography (OH-type acidic $SiO_2$, AcOEt/hexane=0% to 20%) to give the titled compound (571 mg, yellow solid).

$^1$H NMR (600 MHz, $CDCl_3$) δ ppm: 1.31 (t, J=7.1 Hz, 3H), 2.35 (s, 3H), 4.39-4.48 (m, 2H), 7.06-7.29 (m, 2H), 7.36-7.43 (m, 2H), 7.75 (s, 1H), 9.62 (s, 1H)

1-(3-Ethyl-2-p-tolylsulfanyl-3H-imidazol-4-yl)-ethanol

[Formula 88]

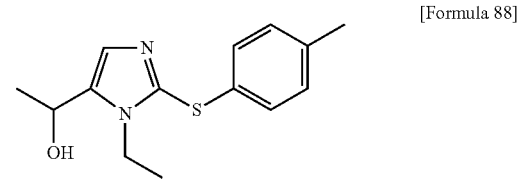

(2) To a solution of the compound obtained in Example 14-(1) (571 mg) in THF (5.0 ml), MeMgBr (1.55 ml, 3.0 M in $Et_2O$) was added at room temperature under an argon atmosphere and stirred for 5 hours. The reaction mixture was diluted with saturated aqueous NH₄Cl, extracted with AcOEt, dried over MgSO₄, filtered and concentrated. The resulting crude product was purified by column chromatography (OH-type neutral SiO₂, AcOEt/hexane=20% to 99%) to give the titled compound (490 mg, colorless oil).

¹H NMR (600 MHz, CDCl₃) δ ppm: 1.25 (t, J=7.8 Hz, 3H), 1.65 (d, J=6.9 Hz, 3H), 2.29 (s, 3H), 4.07-4.28 (m, 2H), 4.79-4.89 (m, 1H), 7.05-7.12 (m, 3H), 7.14-7.21 (m, 2H)

5-(1-Azidoethyl)-1-ethyl-2-p-tolylsulfanyl-1H-imidazole

[Formula 89]

(3) Starting from the compound obtained in Example 14-(2) (490 mg), the same procedure as used in Example 1-(4) was repeated to give the titled compound (colorless oil, 360 mg).

¹H NMR (600 MHz, CDCl₃) δ ppm: 1.25 (t, J=7.3 Hz, 3H), 1.70 (d, J=6.9 Hz, 3H), 2.29 (s, 3H), 4.02-4.18 (m, 2H), 4.32-4.40 (m, 1H), 7.08 (d, J=8.7 Hz, 2H), 7.13-7.20 (m, 3H)

3,4-Dichloro-N-[1-(3-ethyl-2-p-tolylsulfanyl-3H-imidazol-4-yl)-ethyl]-benzenesulfonamide (Compound 241)

[Formula 90]

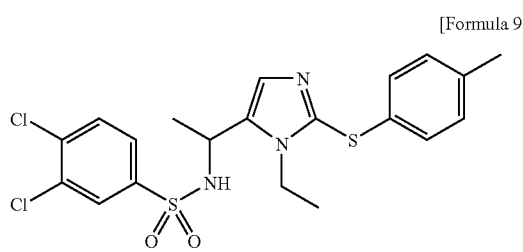

(4) To a solution of the compound obtained in Example 14-(3) (360 mg) and PPh₃ (657 mg) in THF (4.0 ml), H₂O (0.44 ml) was added and heated under reflux for 4.5 hours. After cooling to room temperature, the solvent was distilled off and the resulting crude product was purified by column chromatography (OH-type neutral SiO₂, AcOEt/hexane=0% to 60%) to give a colorless oil (284 mg), which was then dissolved in THF (2.0 ml). To this solution, Et₃N (0.30 ml) and 3,4-dichlorobenzenesulfonyl chloride (316 mg) were added at room temperature and stirred at room temperature for 12 hours. After addition of AcOEt, the organic layer was washed sequentially with 1 N aqueous hydrochloric acid and brine, dried over anhydrous magnesium sulfate, filtered and evaporated under reduced pressure to remove the solvent. The resulting crude product was purified by NH-type silica gel column chromatography (elution solvent: AcOEt), followed by recrystallization (AcOEt-hexane) to give the titled compound (Compound 241) (267 mg, colorless powder).

¹H NMR (600 MHz, CDCl₃) δ ppm: 1.20 (t, J=7.3 Hz, 2H), 1.37 (d, J=6.9 Hz, 3H), 2.30 (s, 3H), 4.00-4.20 (m, 2H), 4.59-4.71 (m, 1H), 5.27 (d, J=8.3 Hz, 1H), 6.89 (s, 1H), 7.07-7.12 (m, 2H), 7.16-7.21 (m, 2H), 7.53 (d, J=8.3 Hz, 1H), 7.64 (dd, J=8.3, 2.3 Hz, 1H), 7.95 (d, J=2.3 Hz, 1H)

Melting point: 173.0-174.0° C.

Example 15

3,4-Dichloro-N-{1-[3-ethyl-2-(toluene-4-sulfonyl)-3H-imidazol-4-yl]-ethyl}-benzenesulfonamide (Compound 252)

[Formula 91]

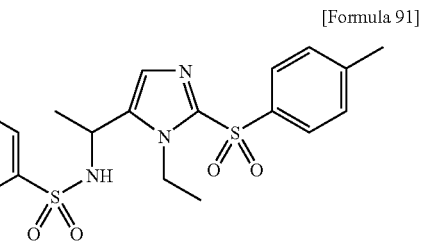

To a solution of the compound obtained in Example 14-(4) (100 mg) in chloroform (2.0 ml), m-chloroperbenzoic acid (611 mg) was added and stirred overnight at room temperature. M-Chloroperbenzoic acid (410 mg) was further added and stirred at room temperature for an additional 3 hours. After addition of AcOEt, the organic layer was washed sequentially with 5% aqueous Na₂S₂O₃ and saturated aqueous sodium bicarbonate, dried over MgSO₄, filtered and evaporated to remove the solvent. The resulting crude product was purified by column chromatography (neutral OH-type SiO₂, AcOEt/hexane=0% to 30%) and further purified by column chromatography (NH-type SiO₂, AcOEt/hexane=0% to 99%), followed by recrystallization (AcOEt/hexane) to give the titled compound (Compound 252) (13 mg, colorless powdery compound).

¹H NMR (600 MHz, CDCl₃) δ ppm: 1.38-1.43 (m, 6H), 2.45 (s, 3H), 4.32-4.53 (m, 2H), 4.62-4.70 (m, 1H), 6.84 (s, 1H), 7.35-7.39 (m, 2H), 7.52-7.56 (m, 1H), 7.59-7.63 (m, 1H), 7.89-7.94 (m, 3H)

Melting point: 180.0-183.0° C.

Example 16

3,4-Dichloro-N-{1-[3-ethyl-2-(1H-indol-6-yloxy)-3H-imidazol-4-yl]-ethyl}-benzenesulfonamide (Compound 250)

[Formula 92]

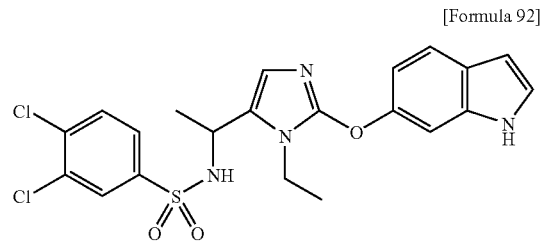

1-[3-Ethyl-2-(1H-indol-6-yloxy)-3H-imidazol-4-yl]-ethylamine

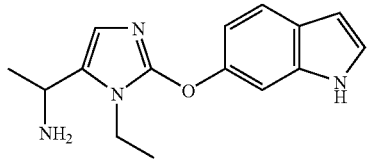

[Formula 93]

(1) Into a pressure-resistant screw-capped test tube, the compound obtained in Example 11-(1) (500 mg), 1H-indol-6-ol (405 mg), $Cs_2CO_3$ (1.42 g) and DMPU (2.0 ml) were introduced and stirred at 250° C. for 2.5 hours. After cooling to room temperature, MeOH/CHCl$_3$ (MeOH/CHCl$_3$=1/4) was added and insoluble materials were filtered off. The filtrate was concentrated, and the resulting crude product was purified by column chromatography (NH-type SiO$_2$, MeOH/CHCl$_3$=0% to 2%) and further purified by column chromatography (neutral OH-type SiO$_2$, MeOH/CHCl$_3$=20% to 50%) to give the titled compound (146 mg, brown oil).

$^1$H NMR (600 MHz, CDCl$_3$) δ ppm: 1.40 (t, J=7.1 Hz, 3H), 1.49 (d, J=6.4 Hz, 3H), 3.97-4.12 (m, 3H), 6.46-6.49 (m, 1H), 6.54 (s, 1H), 6.96 (dd, J=8.5, 2.1 Hz, 1H), 7.11-7.14 (m, 1H), 7.30-7.34 (m, 1H), 7.56 (d, J=8.7 Hz, 1H), 8.42 (brs, 1H)

3,4-Dichloro-N-{1-[3-ethyl-2-(1H-indol-6-yloxy)-3H-imidazol-4-yl]-ethyl}-benzenesulfonamide (Compound 250)

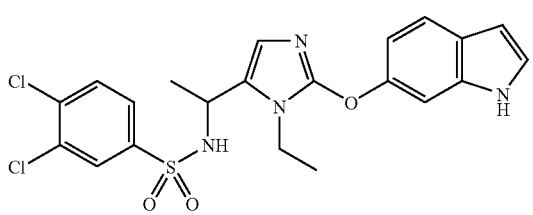

[Formula 94]

(2) To a solution of the compound obtained in Example 16-(1) (36 mg) and Et$_3$N (37.1 μl) in THF (0.5 ml), a solution of 3,4-dichlorobenzenesulfonyl chloride (20.8 μl) in THF (0.5 ml) was added at −78° C. The reaction mixture was warmed to room temperature and stirred overnight. The reaction mixture was concentrated, and the resulting crude product was purified by column chromatography (NH-type SiO$_2$, MeOH/CHCl$_3$=2% to 5%), followed by recrystallization (AcOEt-hexane) to give the titled compound (Compound 250) (19 mg, colorless powder).

$^1$H NMR (600 MHz, CDCl$_3$) δ ppm: 1.33-1.40 (m, 6H), 3.90-4.01 (m, 2H), 4.61-4.72 (m, 2H), 6.49 (s, 1H), 6.51-6.53 (m, 1H), 6.95 (dd, J=8.5, 2.1 Hz, 1H), 7.16-7.19 (m, 1H), 7.32 (d, J=2.3 Hz, 1H), 7.57-7.61 (m, 2H), 7.65-7.69 (m, 1H), 7.97 (d, J=2.3 Hz, 1H), 8.28 (brs, 1H)

Melting point: 150.5-153.5° C.

Example 17

3,4-Dichloro-N-(1-{3-ethyl-2-[3-(4-methylpiperazin-1-yl)-phenoxy]-3H-imidazol-4-yl}-ethyl)-benzenesulfonamide (Compound 184)

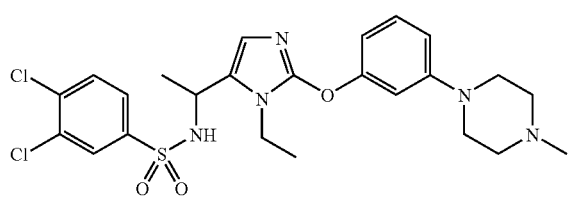

[Formula 95]

1-{3-Ethyl-2-[3-(4-methylpiperazin-1-yl)-phenoxy]-3H-imidazol-4-yl}-ethanone

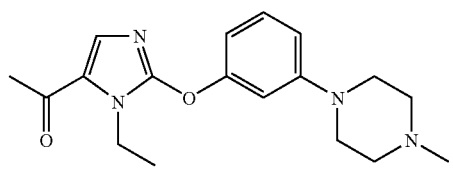

[Formula 96]

(1) A mixture of 2-chloro-1-ethyl-1H-imidazole obtained in Example 5-(2) (1.0 g), 3-(4-methylpiperazin-1-yl)-phenol (1.67 g), Cs$_2$CO$_3$ (3.78 g) and DMPU (3.0 ml) was stirred at 200° C. for 1 hour. After cooling to room temperature, AcOEt was added and insoluble materials were filtered off. The filtrate was concentrated, and the resulting crude product was purified by column chromatography (OH-type neutral SiO$_2$, AcOEt/hexane=0% to 99%) to give the titled compound (1.88 g, yellow oil).

$^1$H NMR (600 MHz, CDCl$_3$) δ ppm: 1.36 (t, J=7.1 Hz, 3H), 2.35 (s, 3H), 2.41 (s, 3H), 2.53-2.58 (m, 4H), 3.19-3.28 (m, 4H), 4.31-4.40 (m, 2H), 6.63-6.71 (m, 1H), 6.74-6.81 (m, 2H), 7.21-7.31 (m, 1H), 7.49 (s, 1H)

1-{3-Ethyl-2-[3-(4-methylpiperazin-1-yl)-phenoxy]-3H-imidazol-4-yl}-ethanol

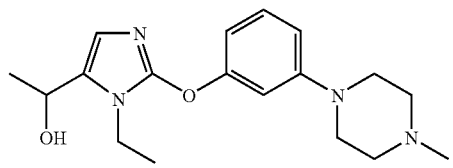

[Formula 97]

(2) To a solution of the compound obtained in Example 17-(1) (1.87 g) in MeOH (10.0 ml), NaBH$_4$ (325 mg) was added at 0° C. and stirred at the same temperature for 2 hours. The reaction mixture was diluted with saturated aqueous NH$_4$Cl and extracted with AcOEt. After washing with brine, the organic layer was dried over MgSO$_4$, filtered and then evaporated to remove the solvent. The resulting crude product was purified by column chromatography (OH-type neutral SiO₂, AcOEt/hexane=0% to 99%, MeOH/CHCl₃=0% to 3%) to give the titled compound (1.40 g, yellow oil).

$^1$H NMR (600 MHz, CDCl₃) δ ppm: 1.37 (t, J=7.3 Hz, 3H), 1.62 (d, J=6.4 Hz, 3H), 2.34 (s, 3H), 2.52-2.59 (m, 4H), 3.18-3.24 (m, 4H), 3.92-4.11 (m, 2H), 4.77-4.85 (m, 1H), 6.61-6.67 (m, 2H), 6.69-6.73 (m, 1H), 6.76-6.79 (m, 1H), 7.18-7.23 (m, 1H)

1-{3-[5-(1-Azidoethyl)-1-ethyl-1H-imidazol-2-yloxy]-phenyl}-4-methylpiperazine

[Formula 98]

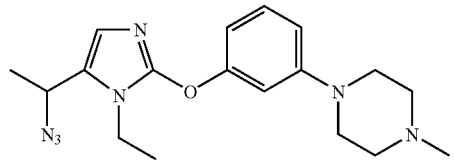

(3) To a solution of the compound obtained in Example 17-(2) (408 mg) in toluene (6.0 ml), DPPA (1.48 ml) and DBU (368 µl) were added at 0° C. and stirred at room temperature for 16 hours. After addition of CHCl₃, the reaction mixture was purified by column chromatography (OH-type neutral SiO₂, MeOH/CHCl₃=5% to 10%) to give the titled compound (332 mg, light-brown oil).

$^1$H NMR (600 MHz, CDCl₃) δ ppm: 1.37 (t, J=7. Hz, 3H), 1.68 (d, J=6.9 Hz, 3H), 2.34 (s, 3H), 2.52-2.61 (m, 4H), 3.18-3.25 (m, 4H), 3.86-4.04 (m, 2H), 4.30-4.37 (m, 1H), 6.64-6.67 (m, 1H), 6.70-6.73 (m, 2H), 6.74-6.76 (m, 1H), 7.19-7.24 (m, 1H)

1-(3-Ethyl-2-[3-(4-methylpiperazin-1-yl)-phenoxy]-3H-imidazol-4-yl)-ethylamine

[Formula 99]

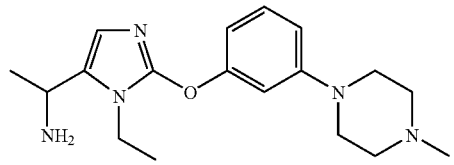

(4) A mixture of the compound obtained in Example 17-(3) (322 mg) and palladium-activated carbon (32 mg, Pd 10 wt. %) in MeOH (6.5 ml) was stirred under a hydrogen atmosphere (about 1 atm) at room temperature for 14 hours. The reaction mixture was filtered through celite, and the filtrate was concentrated. The resulting crude product was purified by column chromatography (NH-type silica gel, MeOH/CHCl₃=0% to 2%) to give the titled compound (190 mg, colorless oil).

$^1$H NMR (600 MHz, CDCl₃) δ ppm: 1.36 (t, J=7.1 Hz, 3H), 1.49 (d, J=6.4 Hz, 3H), 2.35 (s, 3H), 2.53-2.60 (m, 4H), 3.19-3.25 (m, 4H), 3.90-4.11 (m, 3H), 6.55-6.56 (m, 1H), 6.63-6.71 (m, 2H), 6.76-6.79 (m, 1H), 7.15-7.25 (m, 1H)

3,4-Dichloro-N-(1-{3-ethyl-2-[3-(4-methylpiperazin-1-yl)-phenoxy]-3H-imidazol-4-yl}-ethyl)-benzenesulfonamide (Compound 184)

[Formula 100]

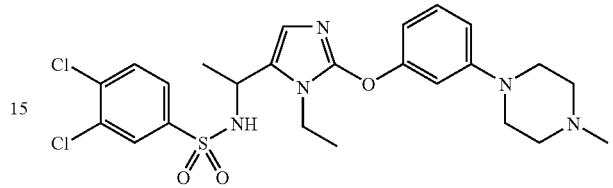

(5) To a solution of the compound obtained in Example 17-(4) (60 mg) in THF (3.0 ml), Et₃N (50 µl) and 3,4-dichlorobenzenesulfonyl chloride (30 mg) were added at room temperature and stirred at room temperature for 3 hours. The reaction mixture was concentrated, and the resulting crude product was purified by column chromatography (neutral OH-type SiO₂, AcOEt/hexane=50% to 99%, MeOH/CHCl₃=0% to 5%) and further purified by column chromatography (NH-type SiO₂, AcOEt/hexane=50% to 99%, MeOH/CHCl₃=0% to 2%), followed by recrystallization (AcOEt-hexane) to give the titled compound (Compound 184) (65 mg, colorless powder).

$^1$H NMR (600 MHz, CDCl₃) δ ppm: 1.33 (t, J=7.1 Hz, 3H), 1.37 (d, J=6.9 Hz, 3H), 2.36 (s, 3H), 2.50-2.65 (m, 4H), 3.18-3.30 (m, 4H), 3.83-4.00 (m, 2H), 4.58-4.69 (m, 1H), (m, 1H), 6.48-6.55 (m, 1H), 6.60-6.66 (m, 1H), (m, 2H), 7.18-7.25 (m, 1H), 7.56-7.62 (m, 1H), (m, 1H), 7.97 (s, 1H)

Melting point: 164.5-165.5° C.

Starting from corresponding starting materials, the same procedures as shown in Examples 1 to 17 were repeated, followed by salt formation as needed to obtain the compounds shown in Table 1 below.

The compounds obtained in the above examples are also shown in Table 1, along with other compounds.

In Table 1, some compounds have two data values for each of APCI MS (M−H)− and APCI MS (M+H)+. This is because two peaks were detected due to the presence of chlorine or bromine isotopes.

Test Example 1

S1P₁ Binding Inhibition Test

Using a human Edg-1 (S1P₁) gene transferred HEK-293 cell strain membrane fraction, the Edg-1 (S1P₁) binding inhibiting action of the compounds of the present invention was determined in accordance with the method described in the literature (Science. 2002, 296: 346) (showing a binding of Kd=0.15 nM, Bmax=2.5 fmol/µg to [$^{33}$P]-S1P). The membrane fraction was obtained by treating the cells with a solubilizing buffer (1 mM Tris/HCl, pH 7.2) for 10 minutes on ice, centrifuging at 1000×g for 5 minutes to remove insoluble fractions, and then centrifuging at 40000×g for 30 minutes at 4° C. The resulting membrane fraction was dissolved in a binding buffer (20 mM Tris-HCl, pH 7.4, 100 mM NaCl, 15 mM NaF, 2 mM deoxypyridoxine, 4 mg/mL fatty acid-free BSA), and then [$^{33}$P]-S1P (manufactured by ARC, final concentration 0.1 nM) and a DMSO solution (final concentration of the compound 10$^{-5}$ M, final concentration of DMSO 0.1%) of the test compound were added. Thereafter, the mixture was stirred and then treated for one hour at 30° C. Using a harvester, the membrane fraction was harvested onto unifilter-96 GF/C filter (manufactured by Perkin Elmer), washing was carried out four times with the binding buffer, and the filter was dried. Twenty five μL Microscint 0 (manufactured by Perkin Elmer) was added, and radioactivity was measured using Top Count NXT (manufactured by Packard) to calculate the amount (A) of [$^{33}$P]-S1P bound to the membrane fraction at the time when the compound was added.

The same procedure was carried out in the absence of the test compound, and the amount (B) of [$^{33}$P]-S1P bound was calculated. Further, the same procedure was carried out in the absence of the test compound by use of HEK-293 cells to which no Edg-1 (S1P$_1$) gene was introduced, and the background amount (C) of [$^{33}$P]-S1P bound was calculated.

The Edg-1 (S1P$_1$) binding inhibition rates of the compound calculated using the following equation are shown in Table 1.

$$\text{Inhibition rate (\%)} = [1 - (A-C)/(B-C)] \times 100.$$

Moreover, the concentration required for a test compound to produce 50% inhibition of the binding caused in the absence of the test compound was also calculated (IC$_{50}$). The above membrane system binding test was performed in the presence of a test compound at various concentrations to calculate the inhibition rate of Edg-1(S1P$_1$) binding at each concentration according to the above equation, followed by calculating an IC$_{50}$ value for each compound with data analysis software, Origin (Lightstone Corp., Japan).

The results indicated that the compounds listed below had IC$_{50}$ values of 70 nM or less and showed particularly strong activity:

Compounds 186, 189, 194, 214, 229 and 236.

Moreover, the compounds listed below had IC$_{50}$ values of 35 nM or less and showed stronger activity:

Compounds 187 and 234.

The compounds listed below had IC$_{50}$ values of 15 nM or less and showed much stronger activity:

Compounds 208, 246 and 247.

Detailed IC$_{50}$ data are shown below for individual compounds (unit: nM):

Compound 184: 14.3; Compound 185: 3.7; Compound 190: 10.9; Compound 192: 23.0: Compound 195: 20.0; Compound 198: 10.3; Compound 200: 17.0; Compound 203: 23.5; Compound 207: 18.2; Compound 209: 42.0; Compound 213: 49.0; Compound 235: 58.5; Compound 244: 32.5; Compound 250: 20.5; and Compound 253: 27.5.

TABLE 1-1

| Compound No. | Chemical structure | APCI MS (M − H)$^-$ | APCI MS (M + H)+ | Binding test (membrane) % inhibition (10 μM) |
|---|---|---|---|---|
| Compound 1 | 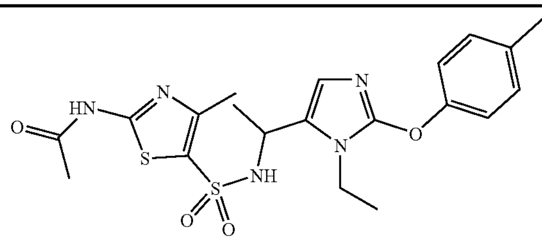 | 462 | 464 | |
| Compound 2 | 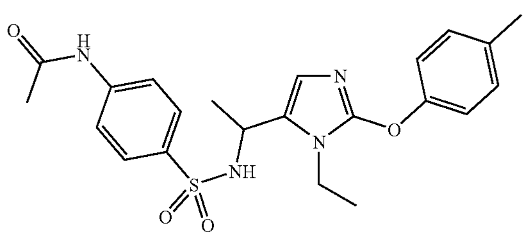 | 441 | 443 | |
| Compound 3 | 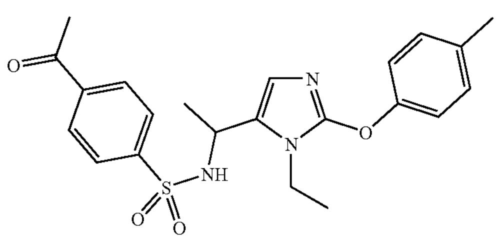 | 426 | 428 | 96.7 |
| Compound 4 | 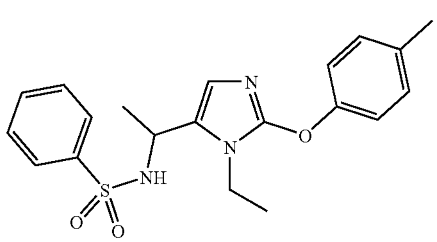 | 384 | 386 | 72.8 |

TABLE 1-1-continued

| Compound No. | Chemical structure | APCI MS (M − H)⁻ | APCI MS (M + H)+ | Binding test (membrane) % inhibition (10 μM) |
|---|---|---|---|---|
| Compound 5 | 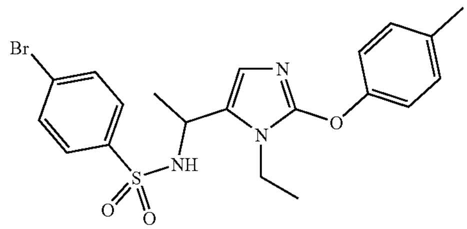 | 462, 464 | 464, 466 | 105.8 |
| Compound 6 | 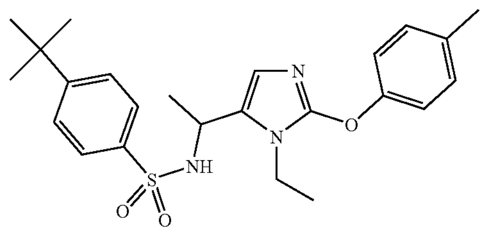 | 440 | 442 | 54.7 |
| Compound 7 | 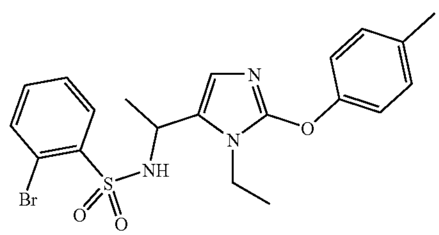 | 462, 464 | 464, 466 | 63.3 |

TABLE 1-2

| Compound No. | Chemical structure | APCI MS (M − H)⁻ | APCI MS (M + H)+ | Binding test (membrane) % inhibition (10 μM) |
|---|---|---|---|---|
| Compound 8 | 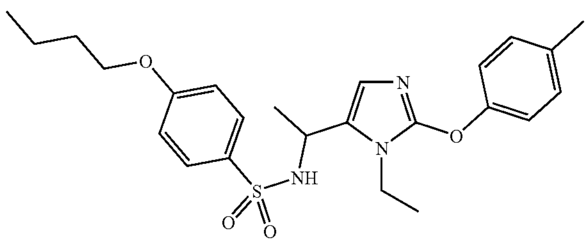 | 456 | 458 | |
| Compound 9 | 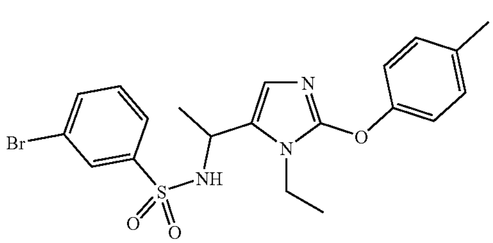 | 462, 464 | 464, 466 | 112.7 |

TABLE 1-2-continued

| Compound No. | Chemical structure | APCI MS (M − H)⁻ | APCI MS (M + H)+ | Binding test (membrane) % inhibition (10 μM) |
| --- | --- | --- | --- | --- |
| Compound 10 | 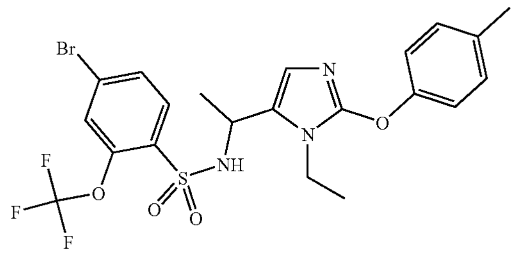 | 546, 548 | 548, 550 | 68.6 |
| Compound 11 | 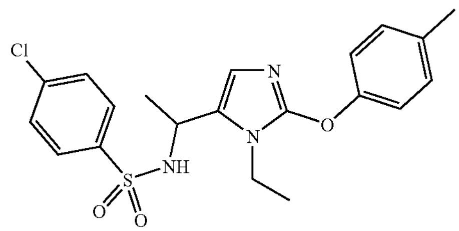 | 418 | 420 | 102.7 |
| Compound 12 | 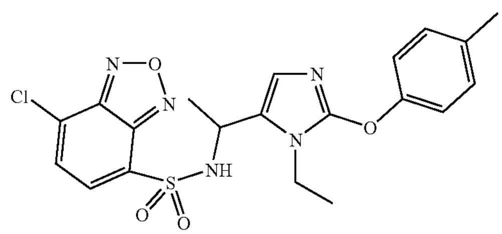 | 460 | 462 | 68.1 |
| Compound 13 | 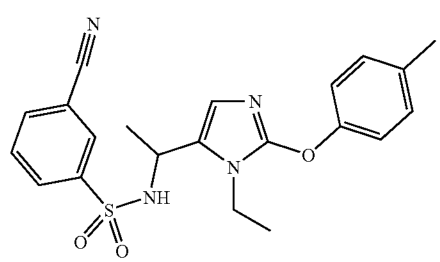 | 409 | 411 | 64.4 |
| Compound 14 | 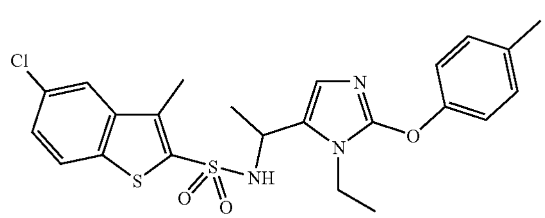 | 488 | 490 | 76.5 |

TABLE 1-3

| Compound No. | Chemical structure | APCI MS (M − H)⁻ | APCI MS (M + H)+ | Binding test (membrane) % inhibition (10 μM) |
|---|---|---|---|---|
| Compound 15 | 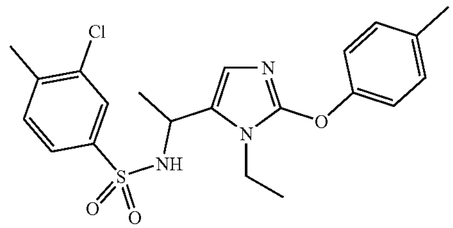 | 432 | 434 | 108.2 |
| Compound 16 | 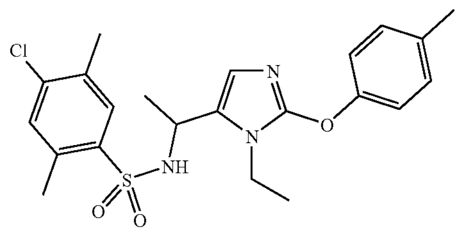 | 446 | 448 | 109.1 |
| Compound 17 | 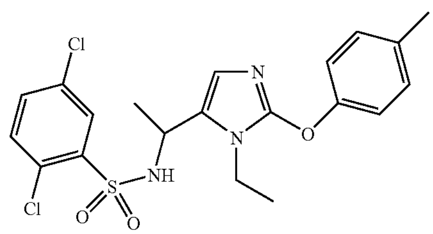 | 452 | 454 | 80.0 |
| Compound 18 | 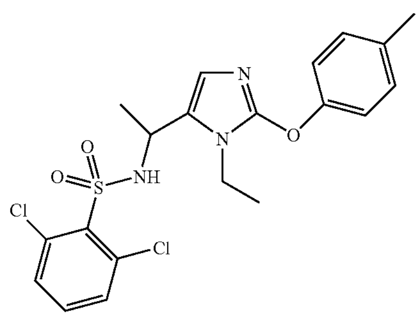 | 452 | 454 | 72.8 |
| Compound 19 | 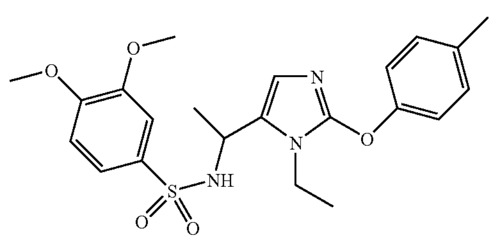 | 444 | 446 | 87.3 |
| Compound 20 | 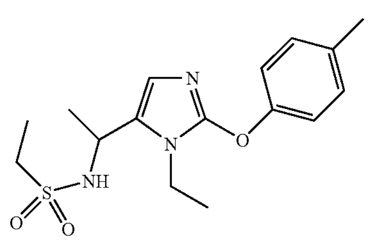 | 336 | 338 | |

TABLE 1-3-continued

| Compound No. | Chemical structure | APCI MS (M − H)− | APCI MS (M + H)+ | Binding test (membrane) % inhibition (10 μM) |
|---|---|---|---|---|
| Compound 21 | 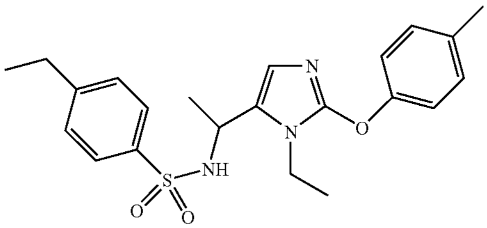 | 412 | 414 | 66.8 |

TABLE 1-4

| Compound No. | Chemical structure | APCI MS (M − H)− | APCI MS (M + H)+ | Binding test (membrane) % inhibition (10 μM) |
|---|---|---|---|---|
| Compound 22 | 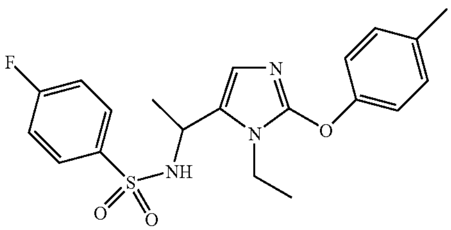 | 402 | 404 | 92.1 |
| Compound 23 | 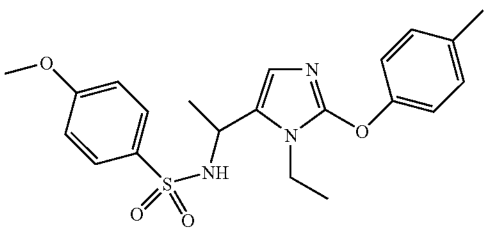 | 414 | 416 | 98.6 |
| Compound 24 | 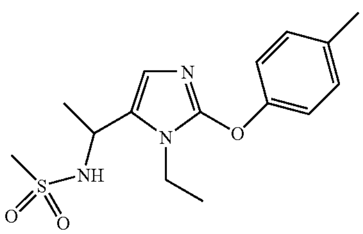 | 322 | 324 | |
| Compound 25 | 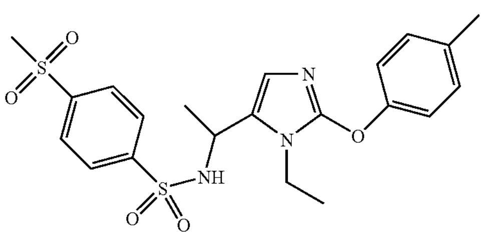 | 462 | 464 | 62.0 |
| Compound 26 | 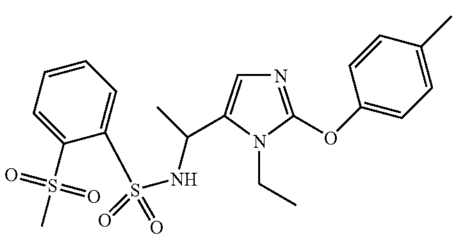 | 462 | 464 | |

TABLE 1-4-continued

| Compound No. | Chemical structure | APCI MS (M − H)− | APCI MS (M + H)+ | Binding test (membrane) % inhibition (10 μM) |
|---|---|---|---|---|
| Compound 27 | 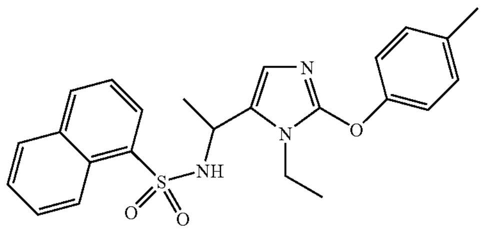 | 434 | 436 | 68.5 |
| Compound 28 | 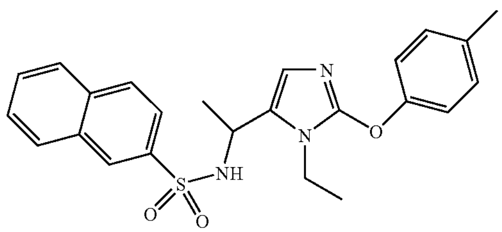 | 434 | 436 | 114.1 |

TABLE 1-5

| Compound No. | Chemical structure | APCI MS (M − H)− | APCI MS (M + H)+ | Binding test (membrane) % inhibition (10 μM) |
|---|---|---|---|---|
| Compound 29 | 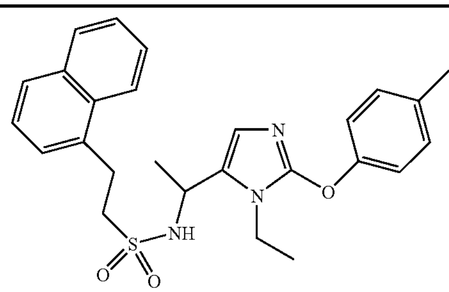 | 462 | 464 | 52.5 |
| Compound 30 | 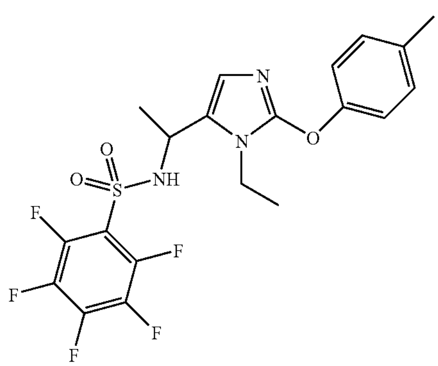 | 474 | 476 | 75.8 |
| Compound 31 | 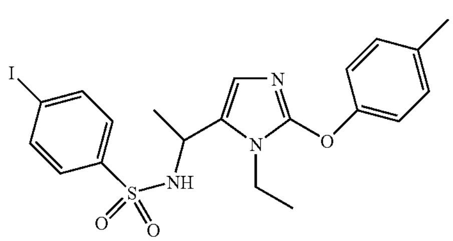 | 510 | 512 | 93.3 |

TABLE 1-5-continued

| Compound No. | Chemical structure | APCI MS (M − H)− | APCI MS (M + H)+ | Binding test (membrane) % inhibition (10 μM) |
|---|---|---|---|---|
| Compound 32 | 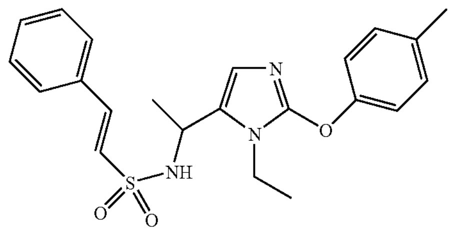 | 410 | 412 | 93.5 |
| Compound 33 | 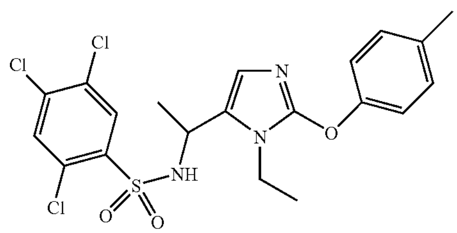 | 486, 488 | 488, 490 | 114.6 |
| Compound 34 | 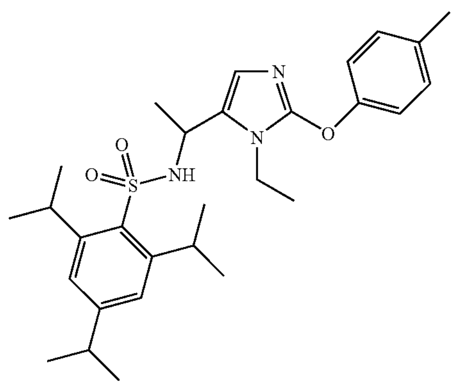 | 510 | 512 | |
| Compound 35 | 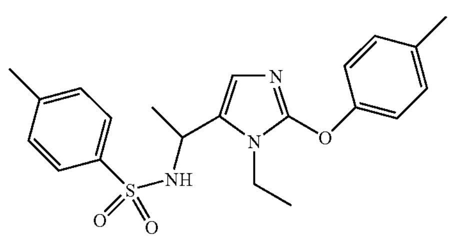 | 398 | 400 | 98.1 |

TABLE 1-6

| Compound No. | Chemical structure | APCI MS (M − H)− | APCI MS (M + H)+ | Binding test (membrane) % inhibition (10 μM) |
|---|---|---|---|---|
| Compound 36 | 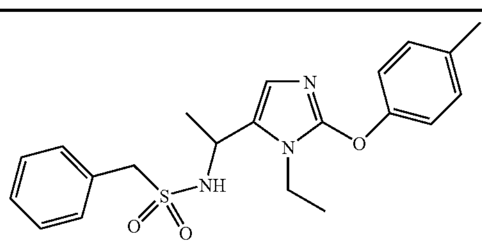 | 398 | 400 | |

TABLE 1-6-continued

| Compound No. | Chemical structure | APCI MS (M − H)− | APCI MS (M + H)+ | Binding test (membrane) % inhibition (10 μM) |
|---|---|---|---|---|
| Compound 37 | 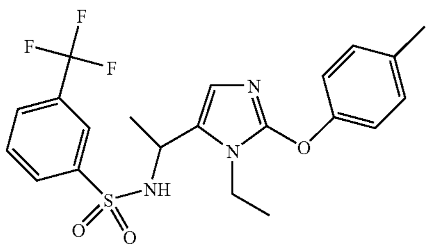 | 452 | 454 | 98.5 |
| Compound 38 | 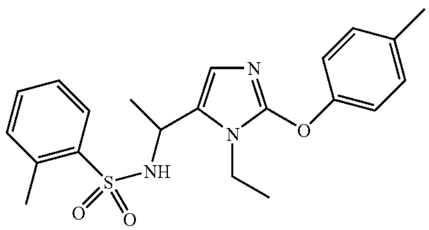 | 398 | 400 | 79.8 |
| Compound 39 | 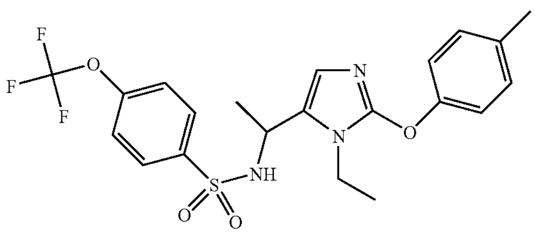 | 468 | 470 | 64.8 |
| Compound 40 | 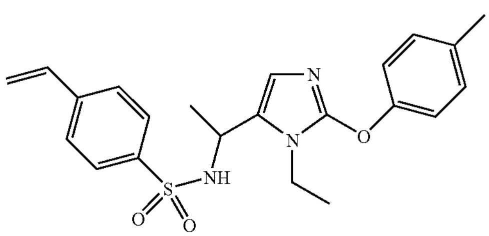 | 410 | 412 | 81.2 |
| Compound 41 | 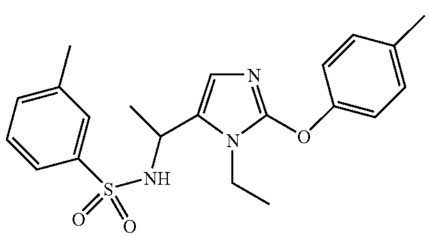 | 398 | 400 | 82.3 |
| Compound 42 | 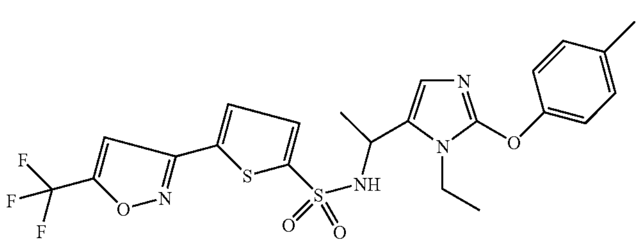 | 525 | 527 | |

TABLE 1-7
| Compound No. | Chemical structure | APCI MS (M − H)− | APCI MS (M + H)+ | Binding test (membrane) % inhibition (10 μM) |
|---|---|---|---|---|
| Compound 43 | 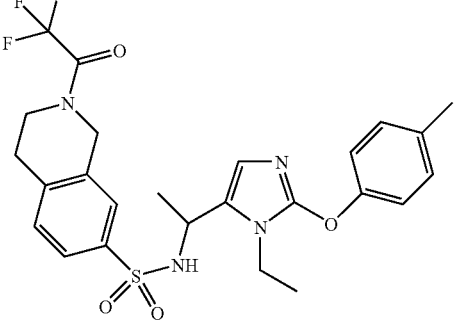 | 535 | 537 | |
| Compound 44 | 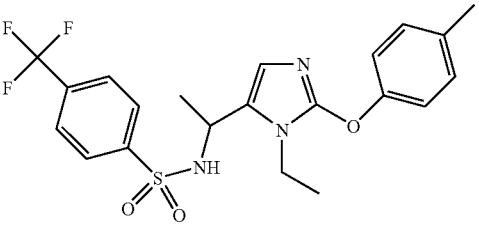 | 452 | 454 | 93.5 |
| Compound 45 | 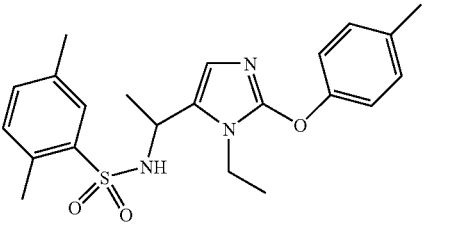 | 412 | 414 | 85.8 |
| Compound 46 | 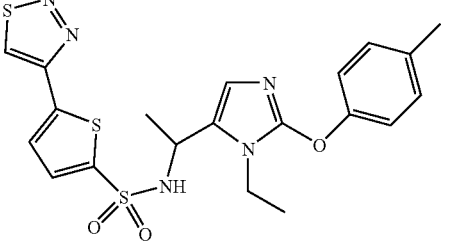 | 474 | 476 | 58.8 |
| Compound 47 | 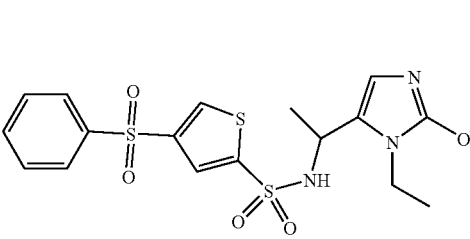 | 530 | 532 | |
| Compound 48 | 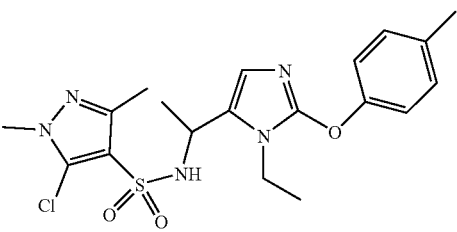 | 436 | 438 | |

TABLE 1-7-continued

| Compound No. | Chemical structure | APCI MS (M − H)− | APCI MS (M + H)+ | Binding test (membrane) % inhibition (10 μM) |
|---|---|---|---|---|
| Compound 49 | 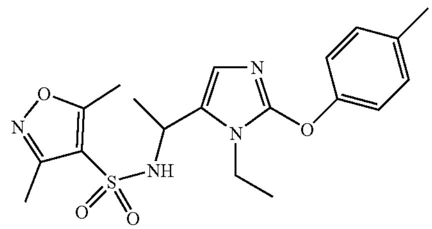 | 403 | 405 | |

TABLE 1-8

| Compound No. | Chemical structure | APCI MS (M − H)− | APCI MS (M + H)+ | Binding test (membrane) % inhibition (10 μM) |
|---|---|---|---|---|
| Compound 50 | 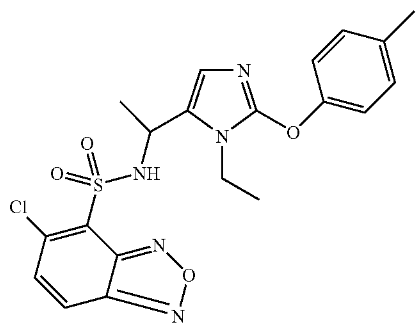 | 460 | 462 | |
| Compound 51 | 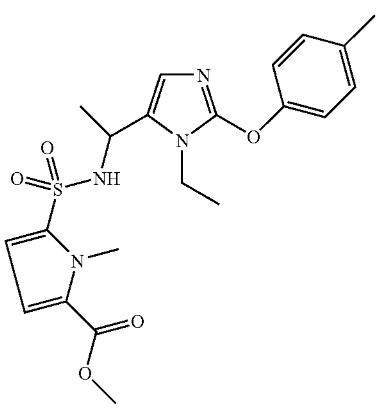 | 445 | 447 | 93.7 |
| Compound 52 | 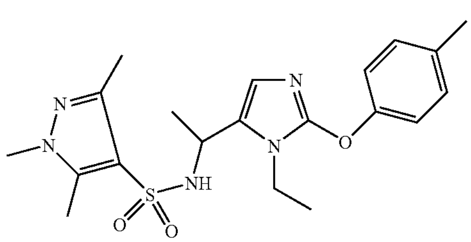 | 416 | 418 | |

TABLE 1-8-continued

| Compound No. | Chemical structure | APCI MS (M − H)− | APCI MS (M + H)+ | Binding test (membrane) % inhibition (10 μM) |
|---|---|---|---|---|
| Compound 53 | 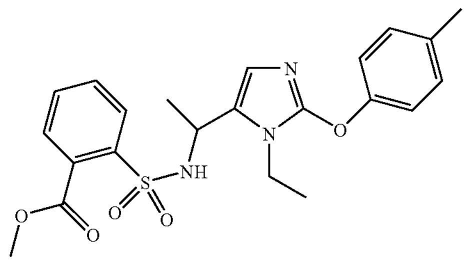 | 442 | 444 | |
| Compound 54 | 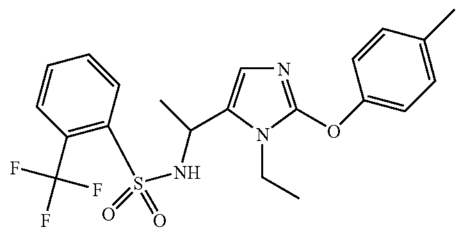 | 452 | 454 | |
| Compound 55 | 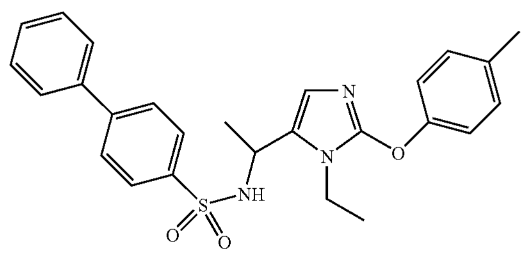 | 460 | 462 | |
| Compound 56 | 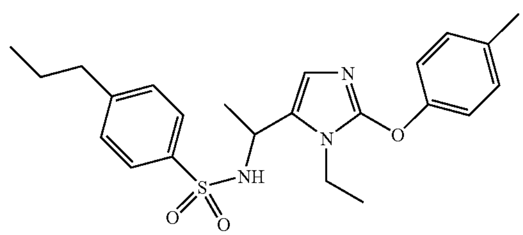 | 426 | 428 | 57.3 |

TABLE 1-9

| Compound No. | Chemical structure | APCI MS (M − H)− | APCI MS (M + H)+ | Binding test (membrane) % inhibition (10 μM) |
|---|---|---|---|---|
| Compound 57 | 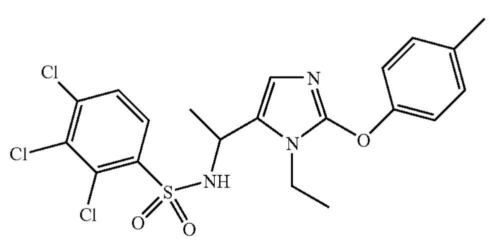 | 486, 488 | 488, 490 | 103.1 |

TABLE 1-9-continued

| Compound No. | Chemical structure | APCI MS (M − H)⁻ | APCI MS (M + H)+ | Binding test (membrane) % inhibition (10 μM) |
| --- | --- | --- | --- | --- |
| Compound 58 | 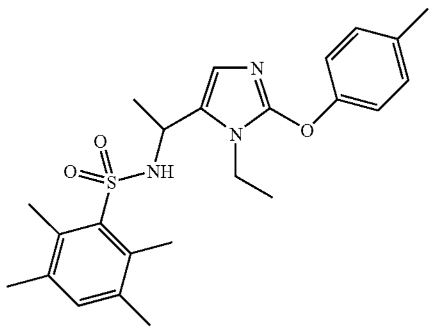 | 440 | 442 | 66.4 |
| Compound 59 | 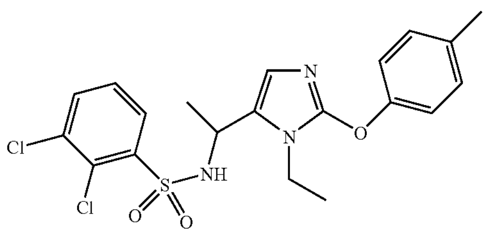 | 452 | 454 | 101.3 |
| Compound 60 | 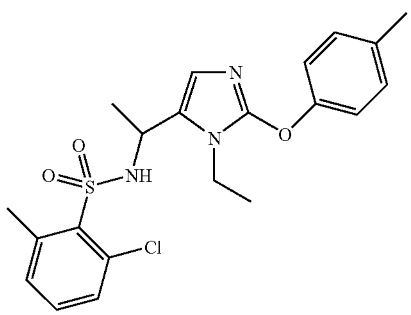 | 432 | 434 | 64.5 |
| Compound 61 | 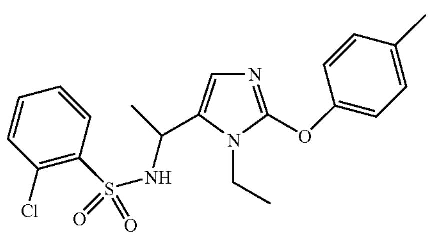 | 418 | 420 | |
| Compound 62 | 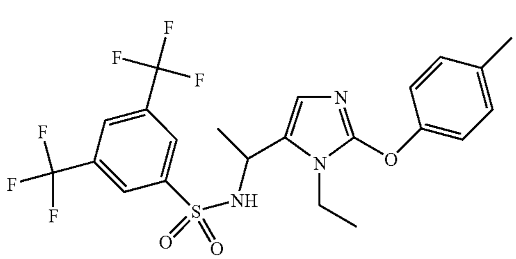 | 520 | 522 | 85.6 |

TABLE 1-9-continued

| Compound No. | Chemical structure | APCI MS (M − H)− | APCI MS (M + H)+ | Binding test (membrane) % inhibition (10 μM) |
|---|---|---|---|---|
| Compound 63 | 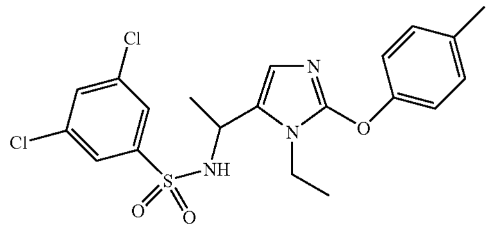 | 452 | 454 | 95.3 |

TABLE 1-10

| Compound No. | Chemical structure | APCI MS (M − H)− | APCI MS (M + H)+ | Binding test (membrane) % inhibition (10 μM) |
|---|---|---|---|---|
| Compound 64 | 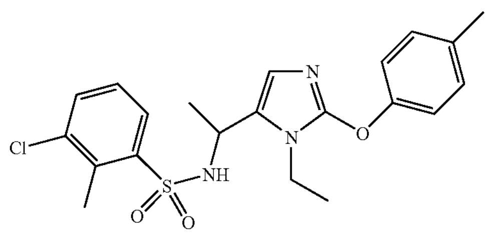 | 432 | 434 | 96.7 |
| Compound 65 | 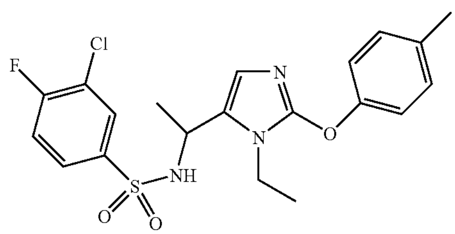 | 436 | 438 | 105.8 |
| Compound 66 | 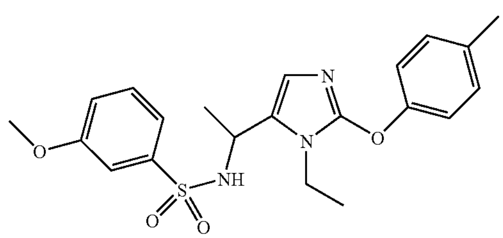 | 414 | 416 | 89.9 |
| Compound 67 | 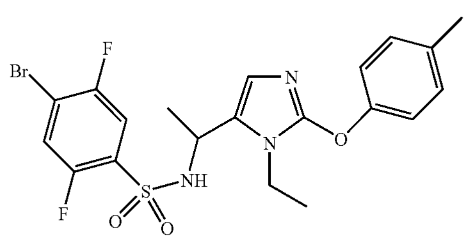 | 498, 500 | 500, 502 | 84.6 |

TABLE 1-10-continued

| Compound No. | Chemical structure | APCI MS (M − H)− | APCI MS (M + H)+ | Binding test (membrane) % inhibition (10 μM) |
|---|---|---|---|---|
| Compound 68 | 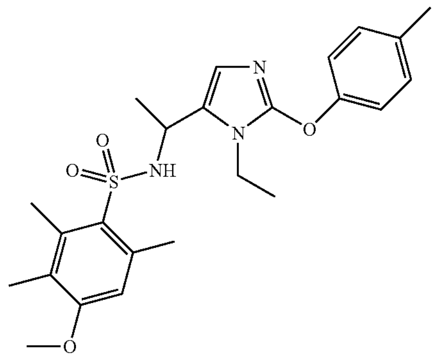 | 456 | 458 | 64.7 |
| Compound 69 | 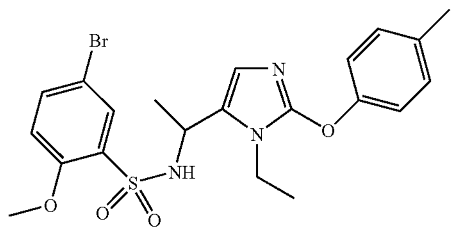 | 492, 494 | 494, 496 | 82.9 |
| Compound 70 | 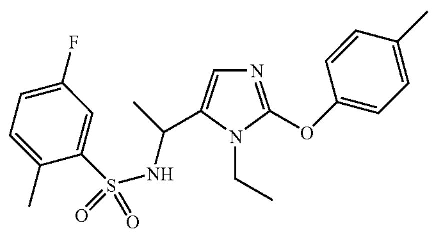 | 416 | 418 | 56.8 |

TABLE 1-11

| Compound No. | Chemical structure | APCI MS (M − H)− | APCI MS (M + H)+ | Binding test (membrane) % inhibition (10 μM) |
|---|---|---|---|---|
| Compound 71 | 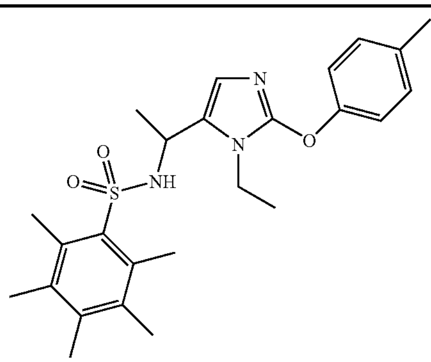 | 454 | 456 | 72.0 |
| Compound 72 | 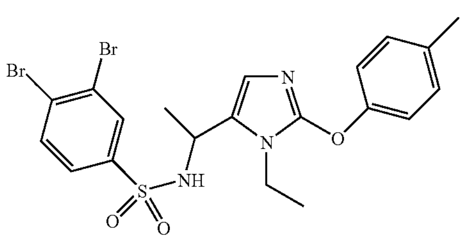 | 540, 542 | 542, 544 | 90.1 |

TABLE 1-11-continued

| Compound No. | Chemical structure | APCI MS (M − H)− | APCI MS (M + H)+ | Binding test (membrane) % inhibition (10 μM) |
|---|---|---|---|---|
| Compound 73 | 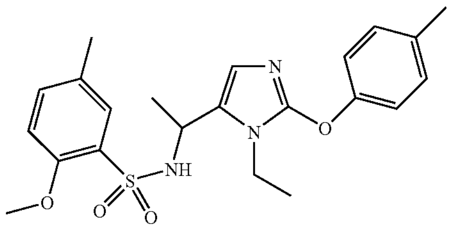 | 428 | 430 | 74.3 |
| Compound 74 | 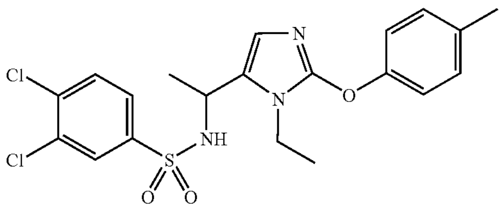 | 452 | 454 | 101.3 |
| Compound 75 | 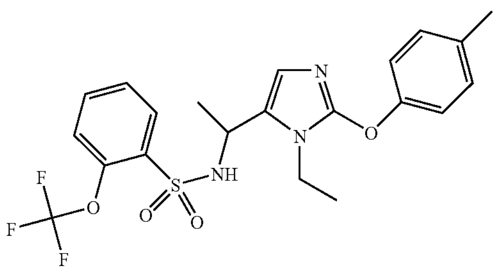 | 468 | 470 | |
| Compound 76 | 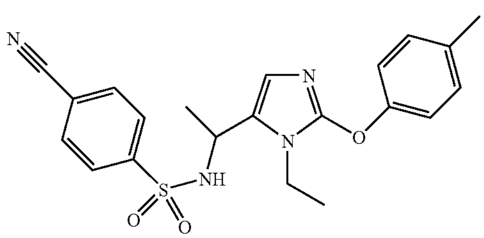 | 409 | 411 | 89.3 |
| Compound 77 | 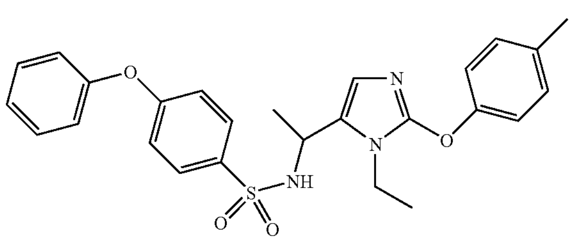 | 476 | 478 | |

TABLE 1-12
| Compound No. | Chemical structure | APCI MS (M − H)⁻ | APCI MS (M + H)+ | Binding test (membrane) % inhibition (10 μM) |
|---|---|---|---|---|
| Compound 78 | 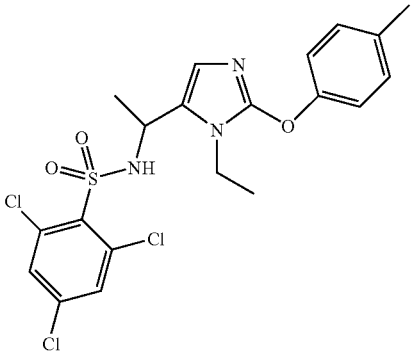 | 486, 488 | 488, 490 | 66.7 |
| Compound 79 | 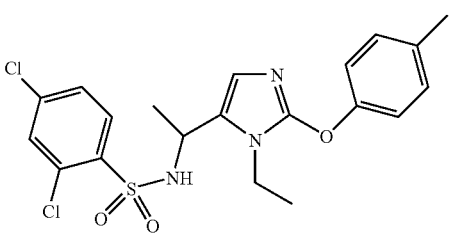 | 452 | 454 | 90.1 |
| Compound 80 | 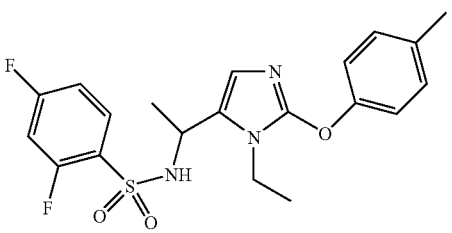 | 420 | 422 | 61.2 |
| Compound 81 | 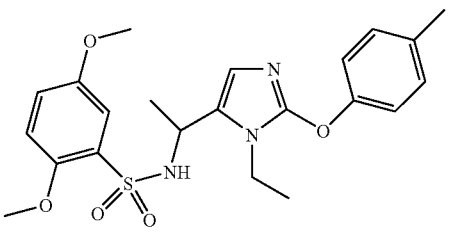 | 444 | 446 | 83.1 |
| Compound 82 | 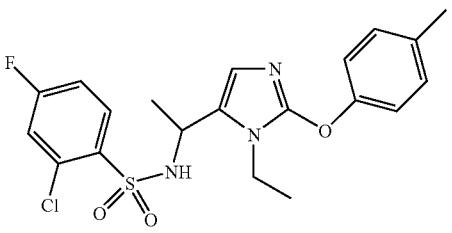 | 436 | 438 | 64.2 |
| Compound 83 | 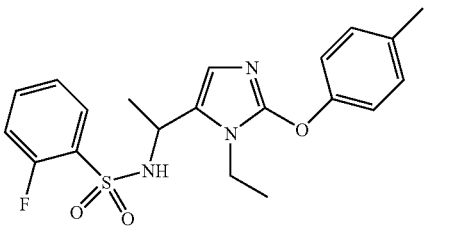 | 402 | 404 | |

TABLE 1-12-continued

| Compound No. | Chemical structure | APCI MS (M − H)⁻ | APCI MS (M + H)+ | Binding test (membrane) % inhibition (10 μM) |
|---|---|---|---|---|
| Compound 84 | 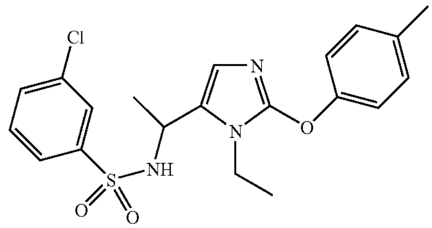 | 418 | 420 | 72.4 |

TABLE 1-13

| Compound No. | Chemical structure | APCI MS (M − H)⁻ | APCI MS (M + H)+ | Binding test (membrane) % inhibition (10 μM) |
|---|---|---|---|---|
| Compound 85 | 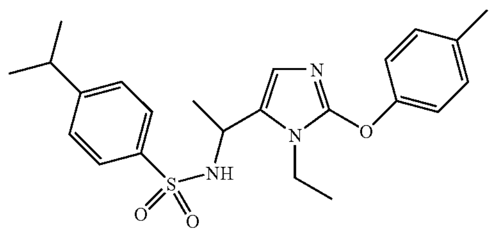 | 426 | 428 | |
| Compound 86 | 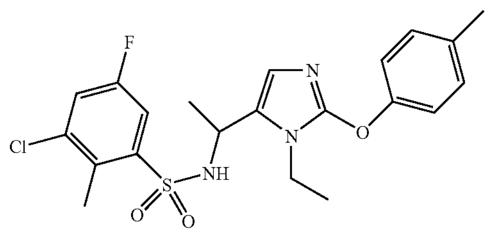 | 450 | 452 | 74.4 |
| Compound 87 | 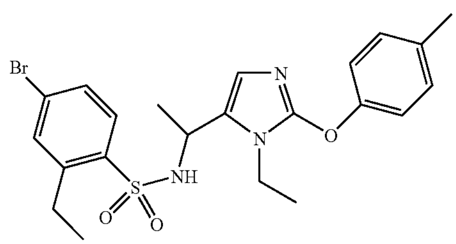 | 490, 492 | 492, 494 | 65.6 |
| Compound 88 | 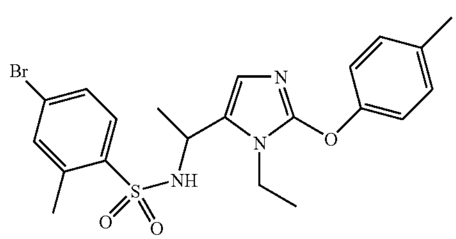 | 476, 478 | 478, 480 | 74.2 |
| Compound 89 | 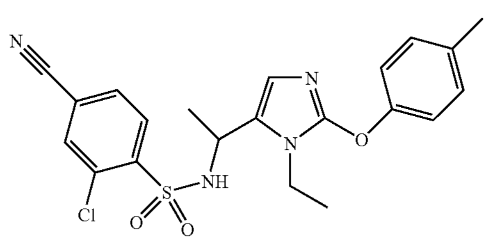 | 443 | 445 | 71.8 |

TABLE 1-13-continued

| Compound No. | Chemical structure | APCI MS (M − H)− | APCI MS (M + H)+ | Binding test (membrane) % inhibition (10 μM) |
|---|---|---|---|---|
| Compound 90 | 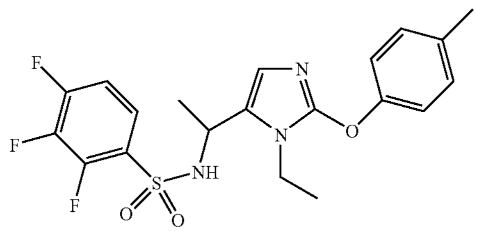 | 438 | 440 | 78.6 |
| Compound 91 | 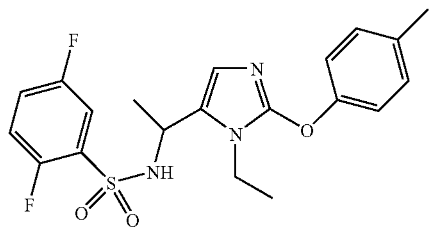 | 420 | 422 | |

TABLE 1-14

| Compound No. | Chemical structure | APCI MS (M − H)− | APCI MS (M + H)+ | Binding test (membrane) % inhibition (10 μM) |
|---|---|---|---|---|
| Compound 92 | 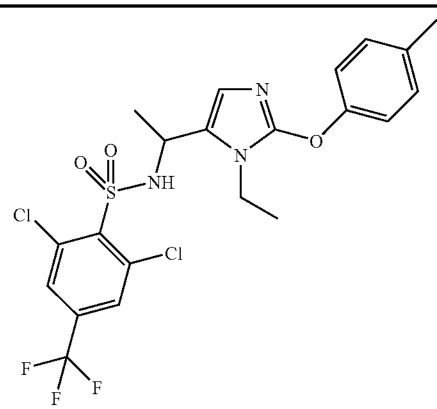 | 520 | 522 | |
| Compound 93 | 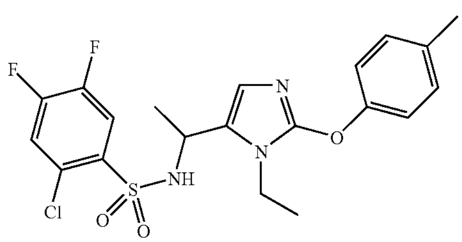 | 454 | 456 | 75.2 |
| Compound 94 | 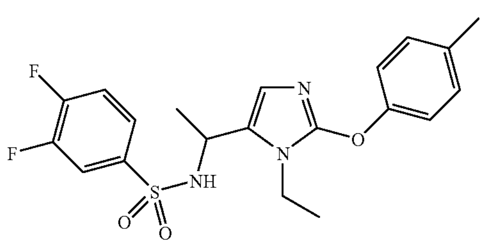 | 420 | 422 | 86.5 |

TABLE 1-14-continued

| Compound No. | Chemical structure | APCI MS (M − H)⁻ | APCI MS (M + H)+ | Binding test (membrane) % inhibition (10 μM) |
|---|---|---|---|---|
| Compound 95 | 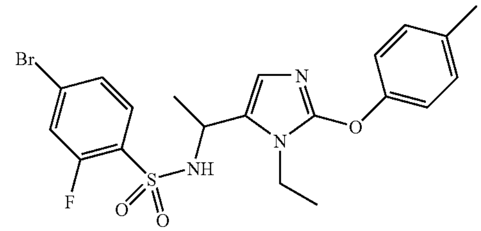 | 480, 482 | 482, 484 | 80.1 |
| Compound 96 | 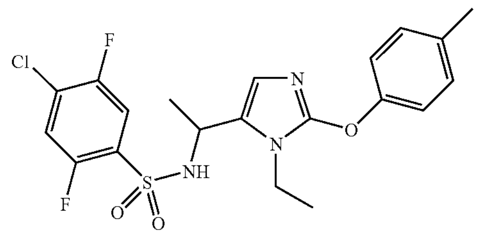 | 454 | 456 | 80.4 |
| Compound 97 | 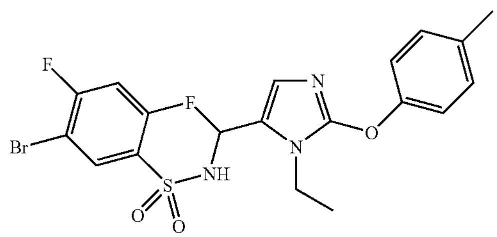 | 498, 500 | 500, 502 | 90.8 |
| Compound 98 | 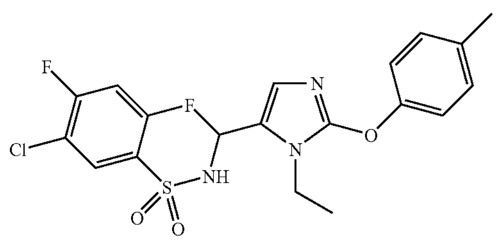 | 454 | 456 | 88.7 |

TABLE 1-15

| Compound No. | Chemical structure | APCI MS (M − H)⁻ | APCI MS (M + H)+ | Binding test (membrane) % inhibition (10 μM) |
|---|---|---|---|---|
| Compound 99 | 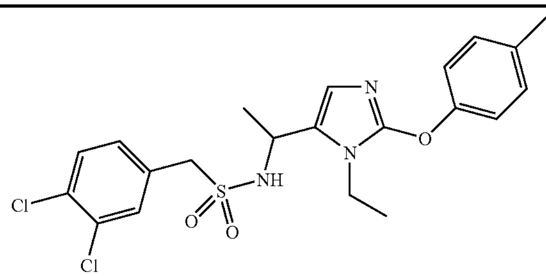 | 466 | 468 | |

TABLE 1-15-continued

| Compound 100 | | 488 | 490 | |
|---|---|---|---|---|
| Compound 101 | | 466 | 468 | 106.9 |
| Compound 102 | | 576, 578 | 578, 580 | 78.2 |
| Compound 103 | | 420 | 422 | 53.0 |
| Compound 104 | | 486 | 488 | 70.9 |

TABLE 1-15-continued

| Compound | | APCI MS (M − H)⁻ | APCI MS (M + H)+ | Binding test (membrane) % inhibition (10 μM) |
|---|---|---|---|---|
| Compound 105 | *3-fluorophenylsulfonamide linked to 1-ethyl-2-(p-tolyloxy)imidazole via CH(CH₃)* | 402 | 404 | 84.2 |

TABLE 1-16

| Compound No. | Chemical structure | APCI MS (M − H)⁻ | APCI MS (M + H)+ | Binding test (membrane) % inhibition (10 μM) |
|---|---|---|---|---|
| Compound 106 | *4-acetamido-3-chlorophenylsulfonamide linked to 1-ethyl-2-(p-tolyloxy)imidazole via CH(CH₃)* | 475 | 477 | |
| Compound 107 | *5-chloro-2-methoxyphenylsulfonamide linked to 1-ethyl-2-(p-tolyloxy)imidazole via CH(CH₃)* | 448 | 450 | 79.8 |
| Compound 108 | *2,4-dichloro-6-methylphenylsulfonamide linked to 1-ethyl-2-(p-tolyloxy)imidazole via CH(CH₃)* | 466 | 468 | 81.3 |
| Compound 109 | *2,4,5-trifluorophenylsulfonamide linked to 1-ethyl-2-(p-tolyloxy)imidazole via CH(CH₃)* | 438 | 440 | 81.3 |

TABLE 1-16-continued

| Compound No. | Chemical structure | APCI MS (M − H)− | APCI MS (M + H)+ | Binding test (membrane) % inhibition (10 μM) |
| --- | --- | --- | --- | --- |
| Compound 110 | [2,5-dibromophenyl-SO2-NH-CH(CH3)-imidazole(N-ethyl, 2-O-p-tolyl)] | 540, 542 | 542, 544 | 86.4 |
| Compound 111 | [isoxazol-5-yl-thiophene-2-SO2-NH-CH(CH3)-imidazole(N-ethyl, 2-O-p-tolyl)] | 457 | 459 | 59.6 |
| Compound 112 | [3-chlorobenzyl-SO2-NH-CH(CH3)-imidazole(N-ethyl, 2-O-p-tolyl)] | 432 | 434 | |

TABLE 1-17

| Compound No. | Chemical structure | APCI MS (M − H)− | APCI MS (M + H)+ | Binding test (membrane) % inhibition (10 μM) |
| --- | --- | --- | --- | --- |
| Compound 113 | [2,4-dibromophenyl-SO2-NH-CH(CH3)-imidazole(N-ethyl, 2-O-p-tolyl)] | 540, 542 | 542, 544 | 77.8 |
| Compound 114 | [3-cyano-4-fluorophenyl-SO2-NH-CH(CH3)-imidazole(N-ethyl, 2-O-p-tolyl)] | 427 | 429 | 96.8 |
| Compound 115 | [3,5-dimethylphenyl-SO2-NH-CH(CH3)-imidazole(N-ethyl, 2-O-p-tolyl)] | 412 | 414 | 92.9 |

TABLE 1-17-continued

| Compound | Chemical structure | APCI MS (M − H)⁻ | APCI MS (M + H)+ | Binding test (membrane) % inhibition (10 μM) |
|---|---|---|---|---|
| Compound 116 | 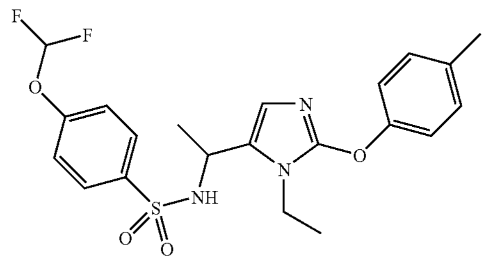 | 450 | 452 | 78.2 |
| Compound 117 | 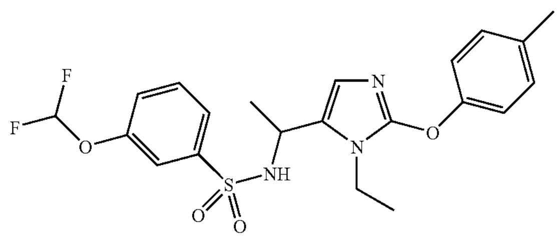 | 450 | 452 | 87.3 |
| Compound 118 | 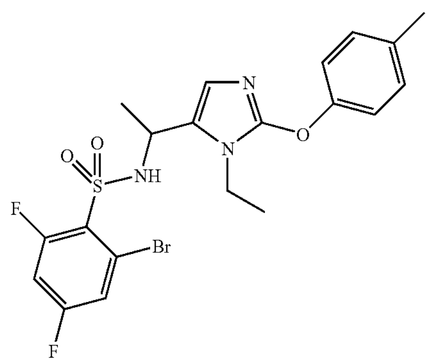 | 498, 500 | 500, 502 | 62.5 |
| Compound 119 | 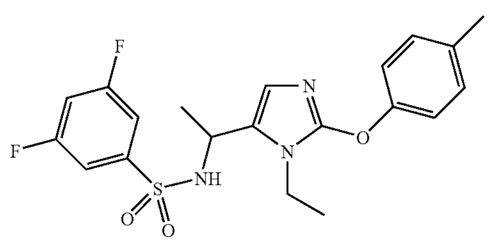 | 420 | 422 | 91.1 |

TABLE 1-18

| Compound No. | Chemical structure | APCI MS (M − H)⁻ | APCI MS (M + H)+ | Binding test (membrane) % inhibition (10 μM) |
|---|---|---|---|---|
| Compound 120 | 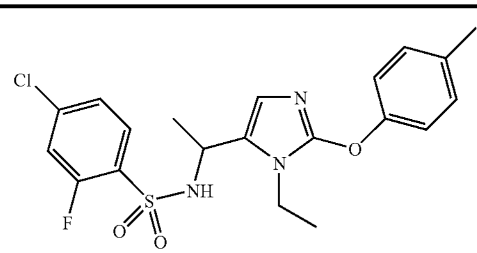 | 436 | 438 | 81.2 |

TABLE 1-18-continued

| Compound 121 | [structure] | 438 | 440 | 101.0 |
| Compound 122 | [structure] | 476, 478 | 478, 480 | 100.5 |
| Compound 123 | [structure] | 480, 482 | 482, 484 | 70.6 |
| Compound 124 | [structure] | 530, 532 | 532, 534 | 65.6 |
| Compound 125 | [structure] | 530, 532 | 532, 534 | |

TABLE 1-18-continued

| Compound | Chemical structure | APCI MS (M − H)⁻ | APCI MS (M + H)+ | Binding test (membrane) % inhibition (10 μM) |
|---|---|---|---|---|
| Compound 126 | 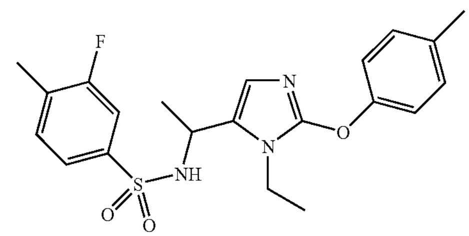 | 416 | 418 | 99.3 |

TABLE 1-19

| Compound No. | Chemical structure | APCI MS (M − H)⁻ | APCI MS (M + H)+ | Binding test (membrane) % inhibition (10 μM) |
|---|---|---|---|---|
| Compound 127 | 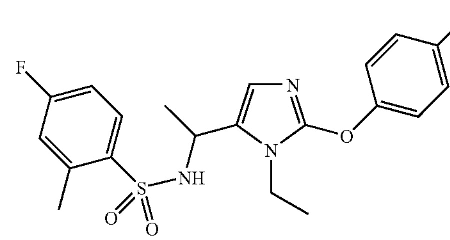 | 416 | 418 | 86.4 |
| Compound 128 | 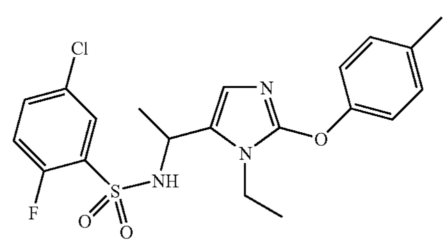 | 436 | 438 | 65.6 |
| Compound 129 | 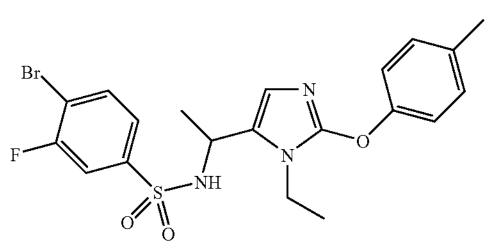 | 480, 482 | 482, 484 | 102.0 |
| Compound 130 | 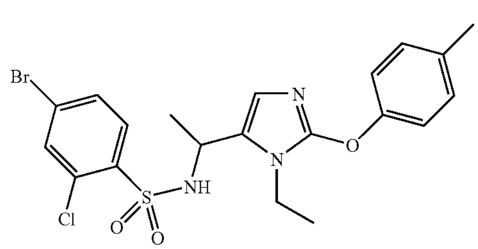 | 496, 498 | 498, 500 | 77.5 |

TABLE 1-19-continued

| Compound | Chemical structure | APCI MS (M − H)⁻ | APCI MS (M + H)+ | Binding test (membrane) % inhibition (10 μM) |
|---|---|---|---|---|
| Compound 131 | 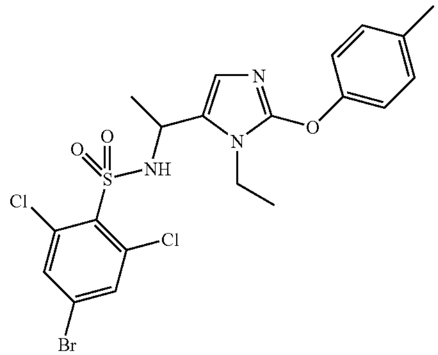 | 530, 532 | 532, 534 | |
| Compound 132 | 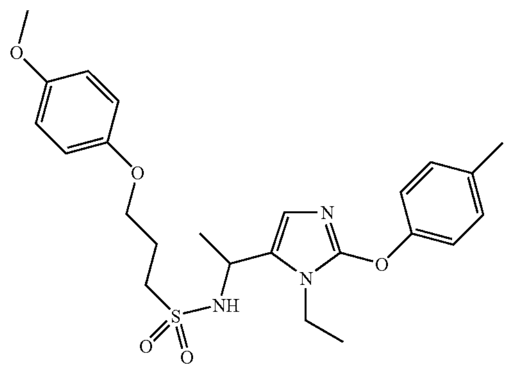 | 472 | 474 | |
| Compound 133 | 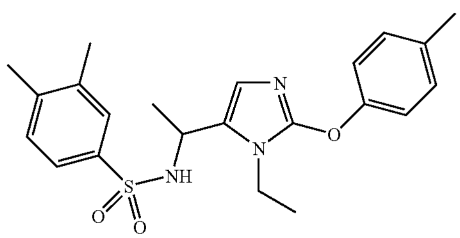 | 412 | 414 | 104.1 |

TABLE 1-20

| Compound No. | Chemical structure | APCI MS (M − H)⁻ | APCI MS (M + H)+ | Binding test (membrane) % inhibition (10 μM) |
|---|---|---|---|---|
| Compound 134 | 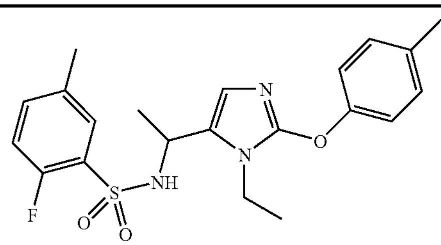 | 416 | 418 | 81.0 |
| Compound 135 | 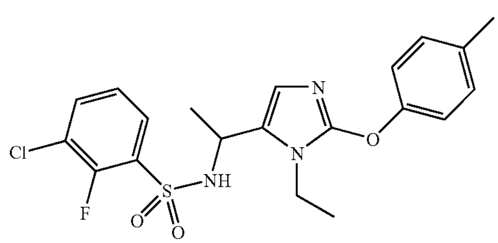 | 436 | 438 | 83.4 |

TABLE 1-20-continued

| Compound 136 | [structure] | 470 | 472 |
| Compound 137 | [structure] | 490 | 492 |
| Compound 138 | [structure] | 477 | 479 |
| Compound 139 | [structure] | 399 | 401 |
| Compound 140 | [structure] | 414 | 416 |

TABLE 1-21

| Compound No. | Chemical structure | APCI MS (M − H)⁻ | APCI MS (M + H)+ | Binding test (membrane) % inhibition (10 μM) |
|---|---|---|---|---|
| Compound 141 | 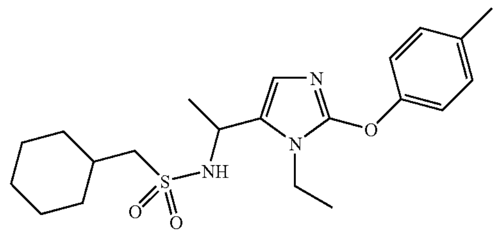 | 404 | 406 | |
| Compound 142 | 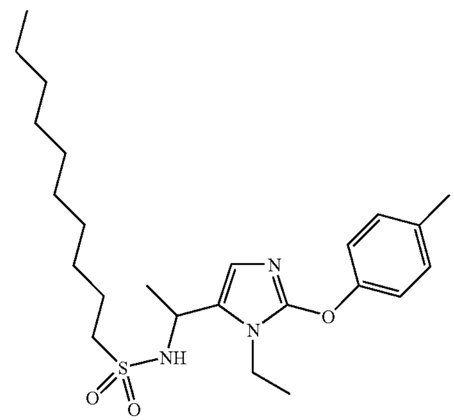 | 448 | 450 | |
| Compound 143 | 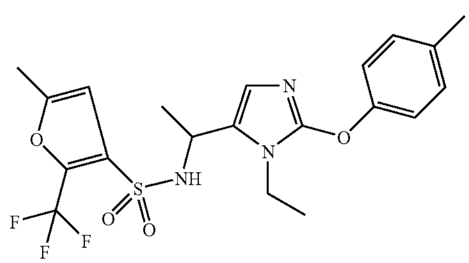 | 456 | 458 | 58.8 |
| Compound 144 | 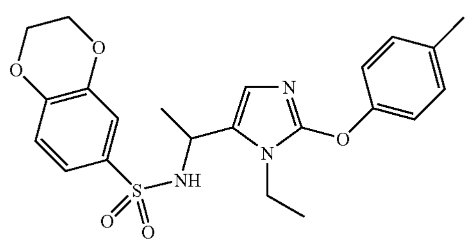 | 442 | 444 | 94.1 |
| Compound 145 | 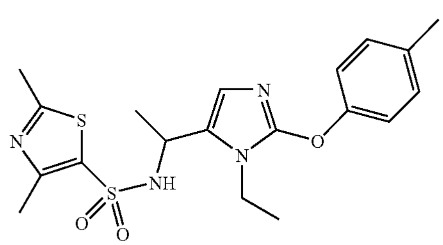 | 419 | 421 | |

TABLE 1-21-continued

| Compound | Chemical structure | APCI MS (M − H)⁻ | APCI MS (M + H)+ | Binding test (membrane) % inhibition (10 μM) |
|---|---|---|---|---|
| Compound 146 | 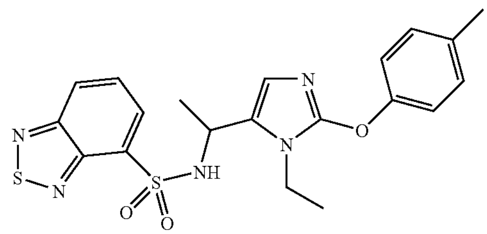 | 442 | 444 | 57.8 |
| Compound 147 | 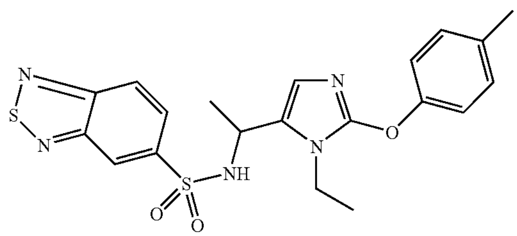 | 442 | 444 | 73.2 |

TABLE 1-22

| Compound No. | Chemical structure | APCI MS (M − H)⁻ | APCI MS (M + H)+ | Binding test (membrane) % inhibition (10 μM) |
|---|---|---|---|---|
| Compound 148 | 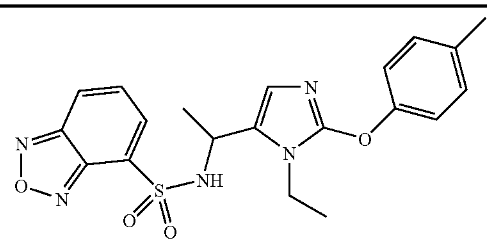 | 426 | 428 | |
| Compound 149 | 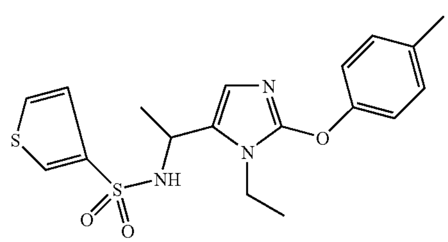 | 390 | 392 | |
| Compound 150 | 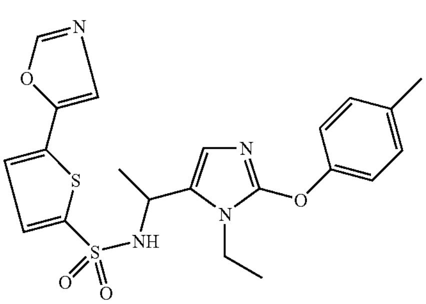 | 457 | 459 | |
| Compound 151 | 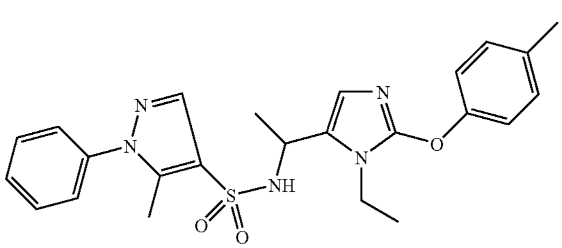 | 464 | 466 | |

TABLE 1-22-continued

| Compound 152 | [structure] | 473 | 475 |
| Compound 153 | [structure] | 538 | 540 |
| Compound 154 | [structure] | 514 | 516 |

TABLE 1-23

| Compound No. | Chemical structure | APCI MS (M − H)⁻ | APCI MS (M + H)+ | Binding test (membrane) % inhibition (10 μM) |
|---|---|---|---|---|
| Compound 155 | [structure] | 418 | 420 | |
| Compound 156 | [structure] | 444 | 446 | |

Note: APCI MS values use $(M-H)^-$ and $(M+H)^+$.

TABLE 1-23-continued

| Compound | Structure | | | |
|---|---|---|---|---|
| Compound 157 | (structure) | 533 | 535 | |
| Compound 158 | (structure) | 486 | 488 | 57.0 |
| Compound 159 | (structure) | 512 | 514 | |
| Compound 160 | (structure) | 556 | 558 | |
| Compound 161 | (structure) | 426 | 428 | 71.2 |

TABLE 1-24

| Compound No. | Chemical structure | APCI MS (M − H)− | APCI MS (M + H)+ | Binding test (membrane) % inhibition (10 μM) |
|---|---|---|---|---|
| Compound 162 | 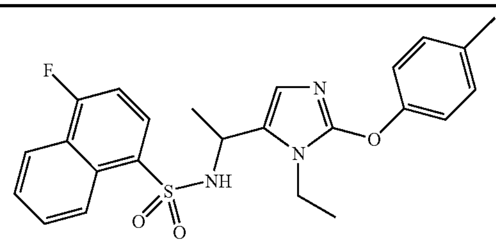 | 452 | 454 | 70.2 |
| Compound 163 | 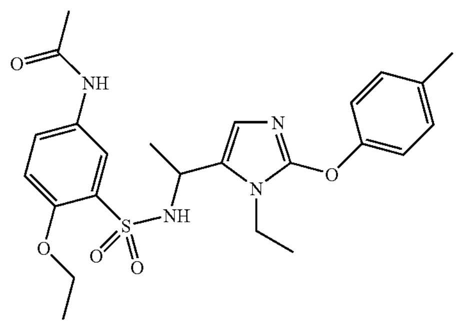 | 485 | 487 | |
| Compound 164 | 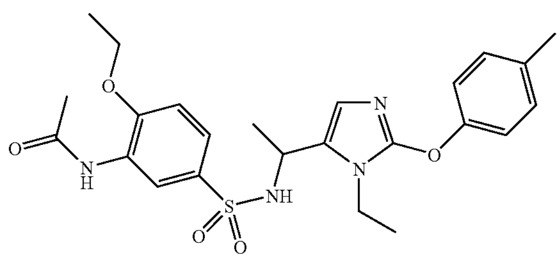 | 485 | 487 | |
| Compound 165 | 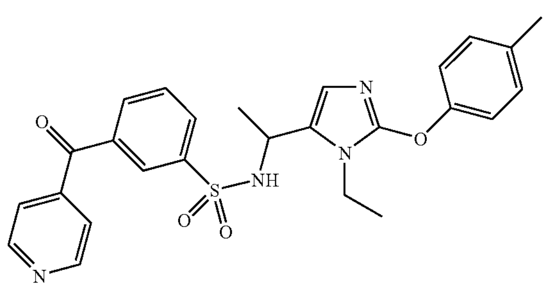 | 489 | 491 | |
| Compound 166 | 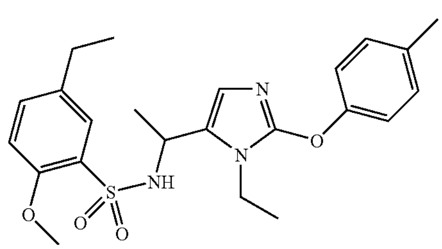 | 442 | 444 | 80.7 |
| Compound 167 | 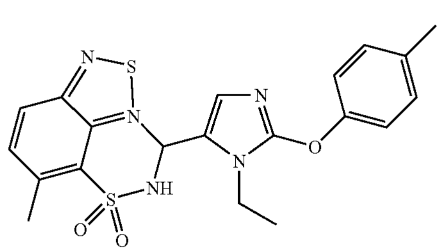 | 456 | 458 | |

TABLE 1-24-continued
| Compound 168 | 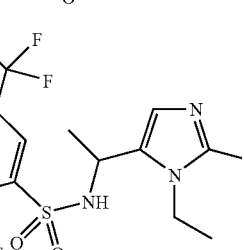 | 432 | 434 | |
TABLE 1-25
| Compound No. | Chemical structure | APCI MS (M − H)⁻ | APCI MS (M + H)+ | Binding test (membrane) % inhibition (10 μM) |
|---|---|---|---|---|
| Compound 169 | 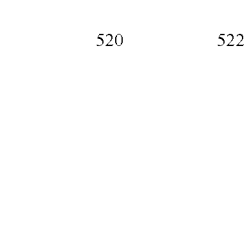 | 435 | 437 | 62.0 |
| Compound 170 | 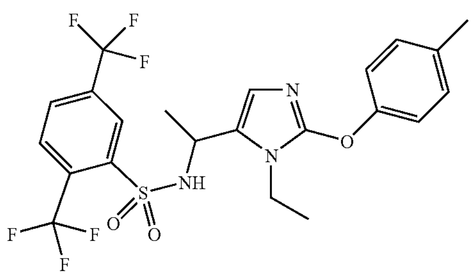 | 520 | 522 | |
| Compound 171 | 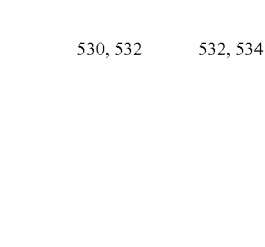 | 530, 532 | 532, 534 | |
| Compound 172 | 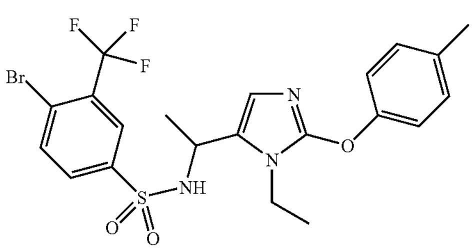 | 530, 532 | 532, 534 | 75.9 |

TABLE 1-25-continued
| Compound | | APCI MS (M − H)⁻ | APCI MS (M + H)+ | Binding test (membrane) % inhibition (10 μM) |
|---|---|---|---|---|
| Compound 173 | 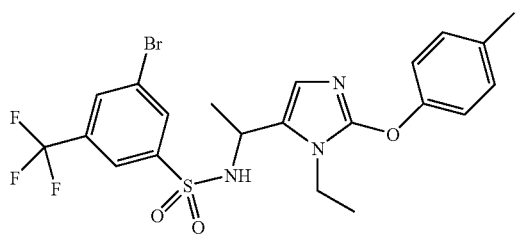 | 530, 532 | 532, 534 | |
| Compound 174 | 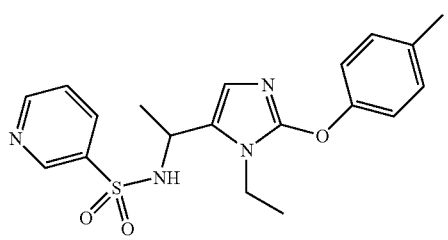 | 385 | 387 | |
| Compound 175 | 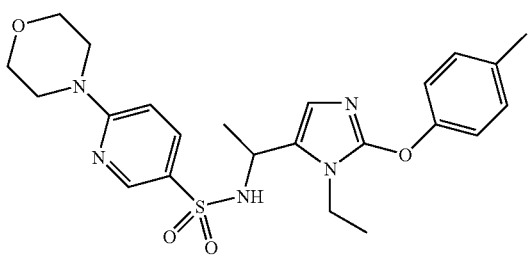 | 470 | 472 | |
TABLE 1-26
| Compound No. | Chemical structure | APCI MS (M − H)⁻ | APCI MS (M + H)+ | Binding test (membrane) % inhibition (10 μM) |
|---|---|---|---|---|
| Compound 176 | 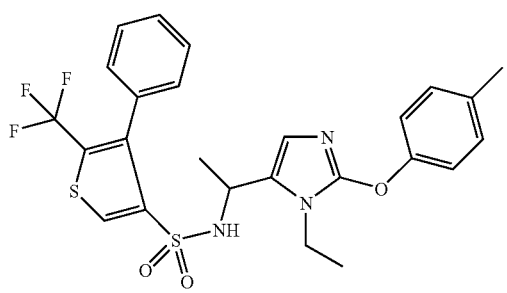 | 534 | 536 | |
| Compound 177 | 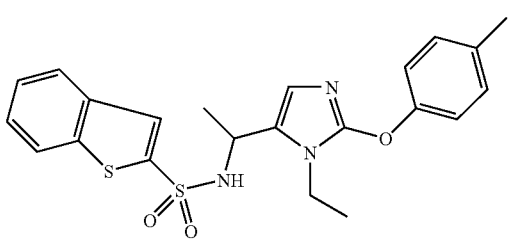 | 440 | 442 | 77.7 |

TABLE 1-26-continued

| Compound No. | Chemical structure | | | |
|---|---|---|---|---|
| Compound 178 | (structure) | 440 | 442 | 64.2 |

TABLE 1-27

| Compound No. | Chemical structure | Melting point (° C.) | Binding test (membrane) % inhibition (10 μM) |
|---|---|---|---|
| Compound 179 | (structure) | 133.0-134.5 | 95.9 |
| Compound 180 | (structure) | 114.0-115.0 | |
| Compound 181 | (structure) | 154.5-155.5 | |
| Compound 182 | (structure) | 137.5-138.5 | |
| Compound 183 | (structure) | 122.5-123.5 | |

TABLE 1-27-continued

| Compound | Chemical structure | Melting point (°C.) | Binding test (membrane) % inhibition (10 μM) |
|---|---|---|---|
| Compound 184 | 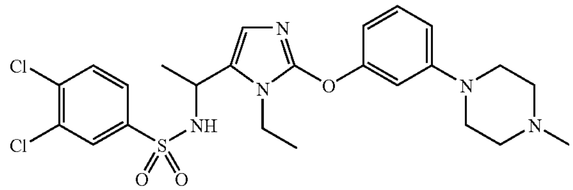 | 164.5-165.5 | 95.3 |
| Compound 185 | 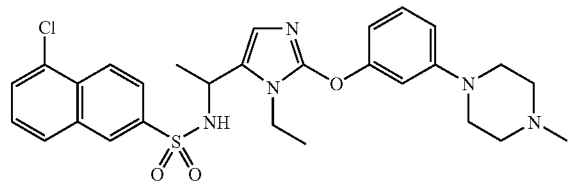 | 205.5-206.0 | 100.3 |

TABLE 1-28

| Compound No. | Chemical structure | Melting point (°C.) | Binding test (membrane) % inhibition (10 μM) |
|---|---|---|---|
| Compound 186 | 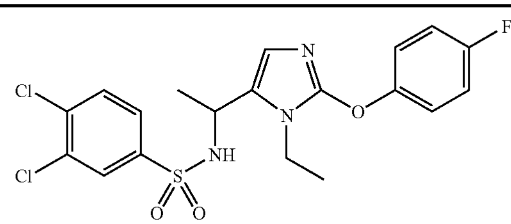 | 156.0-157.0 | 99.8 |
| Compound 187 | 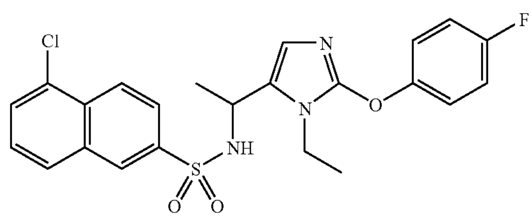 | 138.0-141.0 | 101.3 |
| Compound 188 | 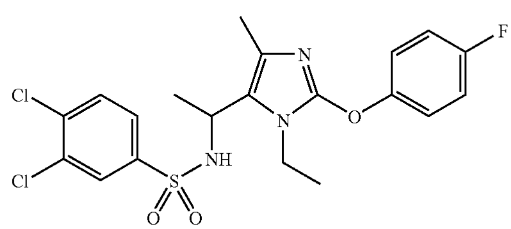 | 119.5-120.5 | 100.0 |
| Compound 189 | 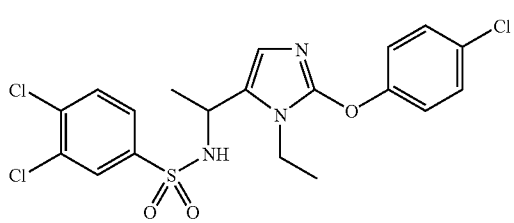 | 153.0-157.0 | 97.2 |
| Compound 190 | 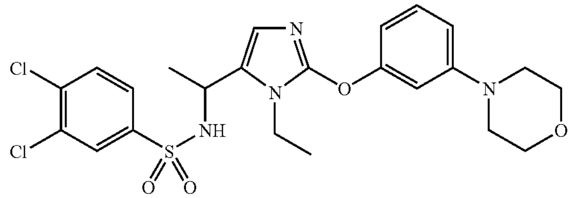 | 167.0-169.0 | 100.6 |

TABLE 1-28-continued
| Compound 191 | 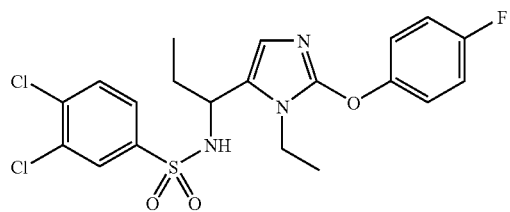 | 137.5-138.5 | 100.5 |
| Compound 192 | 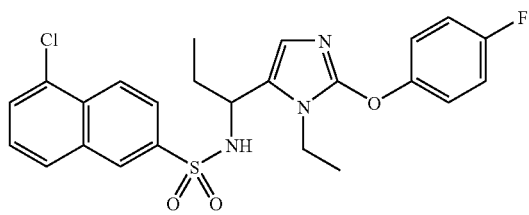 | 118.0-120.0 | 101.2 |
TABLE 1-29
| Compound No. | Chemical structure | Melting point (° C.) | Binding test (membrane) % inhibition (10 μM) |
|---|---|---|---|
| Compound 193 | 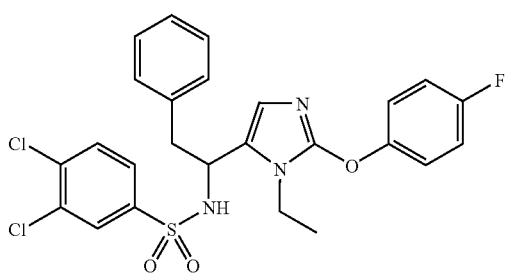 | 114.5-115.5 | 98.6 |
| Compound 194 | 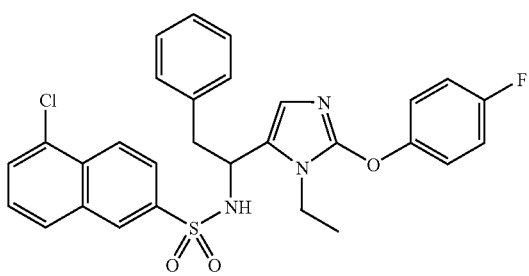 | 172.5-174.0 | 93.0 |
| Compound 195 | 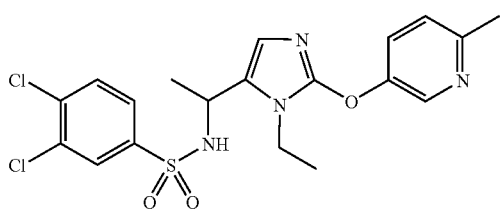 | 174.0-175.0 | 96.1 |

TABLE 1-29-continued

| Compound No. | Chemical structure | Melting point (° C.) | Binding test (membrane) % inhibition (10 μM) |
|---|---|---|---|
| Compound 196 | 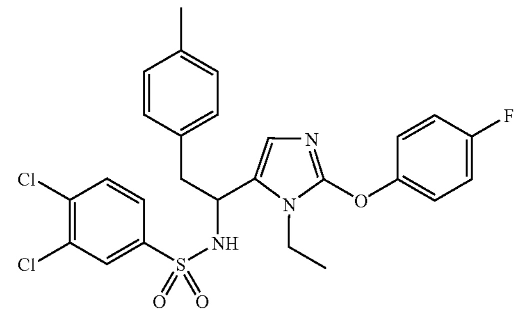 | 123.5-124.0 | 88.9 |
| Compound 197 | 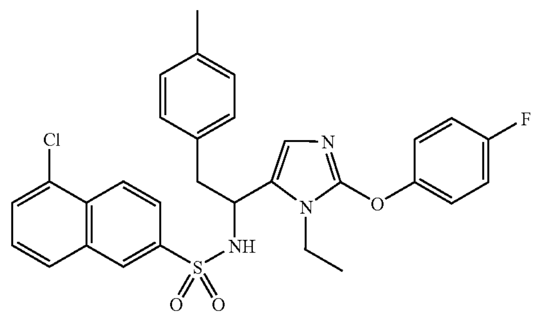 | 166.0-167.0 | 95.3 |
| Compound 198 | 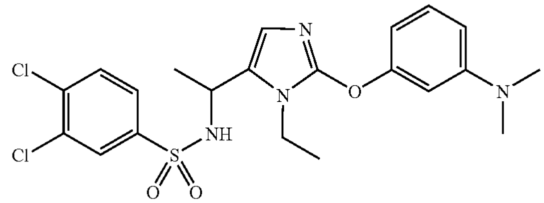 | 171.0-172.0 | 97.8 |
| Compound 199 | 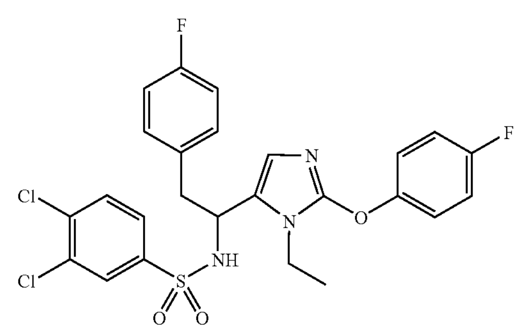 | 145.5-146.5 | 97.3 |

TABLE 1-30

| Compound No. | Chemical structure | Melting point (° C.) | Binding test (membrane) % inhibition (10 μM) |
| --- | --- | --- | --- |
| Compound 200 | 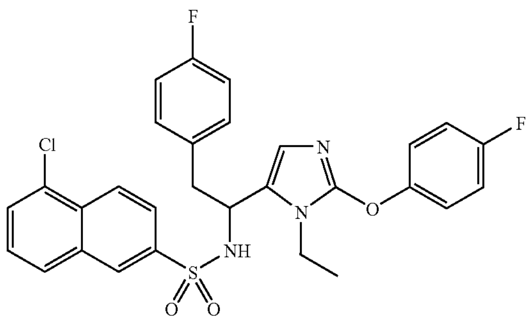 | 175.0-176.0 | 97.1 |
| Compound 201 | 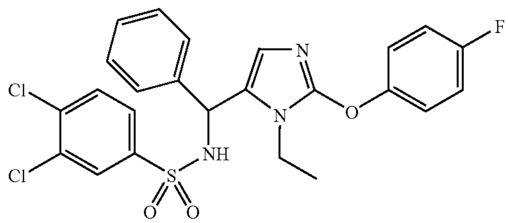 | 157.5-158.0 | |
| Compound 202 | 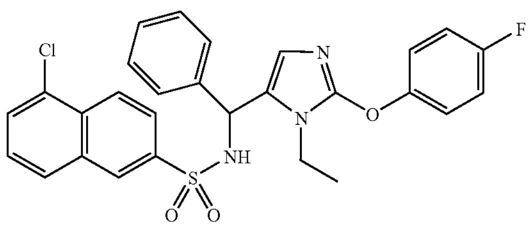 | 171.5-172.5 | 69.3 |
| Compound 203 | 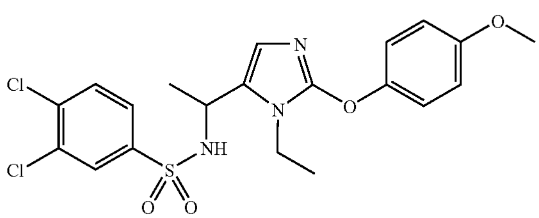 | 146.5-148.0 | 102.1 |
| Compound 204 | 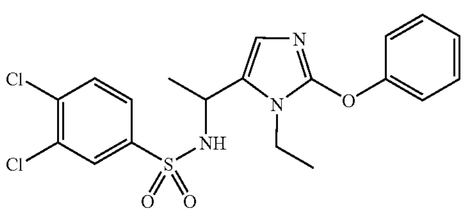 | 166.5-167.5 | 95.7 |
| Compound 205 | 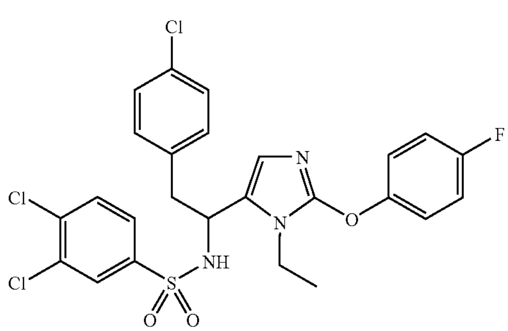 | 155.5-156.5 | 94.4 |

TABLE 1-30-continued

| Compound No. | Chemical structure | Melting point (° C.) | Binding test (membrane) % inhibition (10 μM) |
|---|---|---|---|
| Compound 206 | 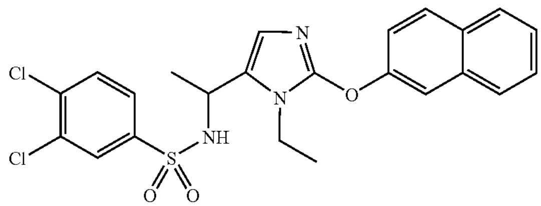 | 172.0-173.0 | 98.5 |

TABLE 1-31

| Compound No. | Chemical structure | Melting point (° C.) | Binding test (membrane) % inhibition (10 μM) |
|---|---|---|---|
| Compound 207 | 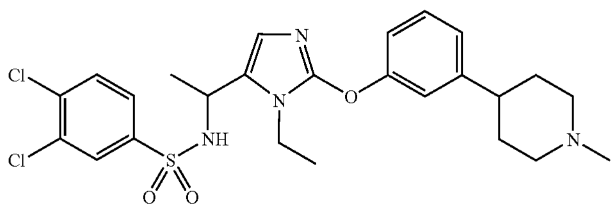 | 161.0-163.5 | 100.6 |
| Compound 208 | 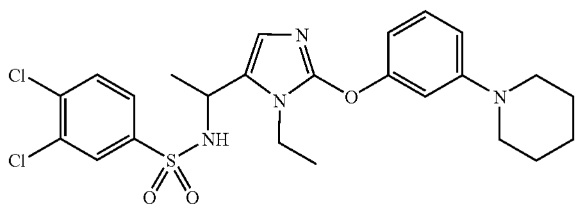 | 169.5-170.5 | 99.6 |
| Compound 209 | 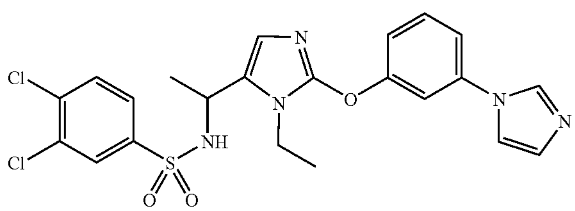 | 170.0-171.0 | 98.9 |
| Compound 210 | 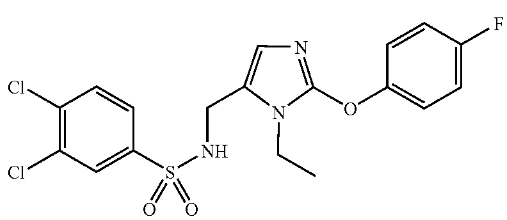 | 154.0-155.0 | 90.6 |
| Compound 211 | 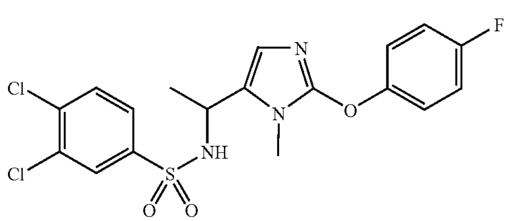 | 179.5-180.5 | 92.2 |

TABLE 1-31-continued

| Compound No. | Chemical structure | Melting point (° C.) | Binding test (membrane) % inhibition (10 μM) |
|---|---|---|---|
| Compound 212 | 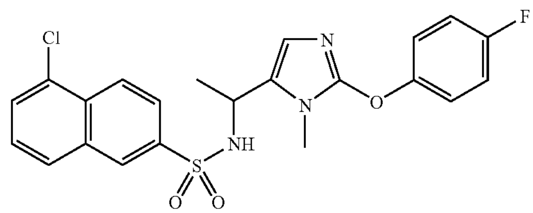 | 134.0-135.0 | 92.0 |
| Compound 213 | 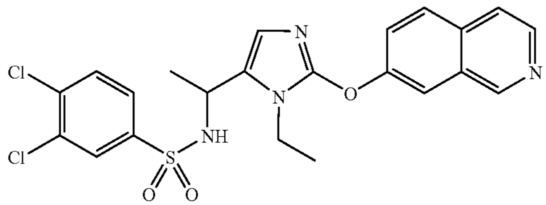 | 185.5-187.5 | 99.6 |

TABLE 1-32

| Compound No. | Chemical structure | Melting point (° C.) | Binding test (membrane) % inhibition (10 μM) |
|---|---|---|---|
| Compound 214 | 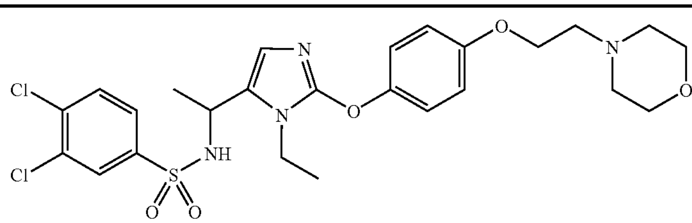 | 167.0-168.0 | 101.9 |
| Compound 215 | 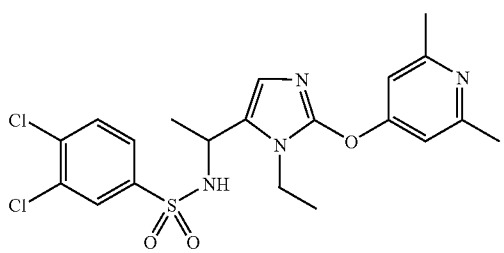 | 179.0-180.0 | 100.4 |
| Compound 216 | 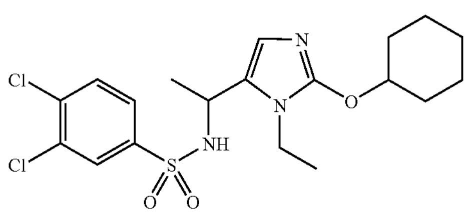 | 180.0-181.0 | 92.0 |
| Compound 217 | 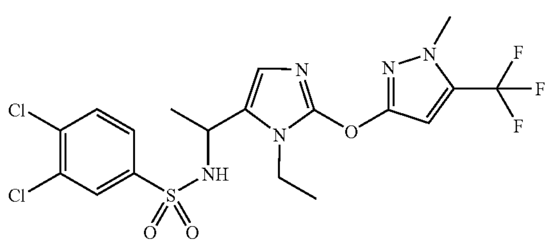 | 146.0-148.0 | 96.3 |

TABLE 1-32-continued

| Compound No. | Chemical structure | Melting point (° C.) | Binding test (membrane) % inhibition (10 μM) |
|---|---|---|---|
| Compound 218 | 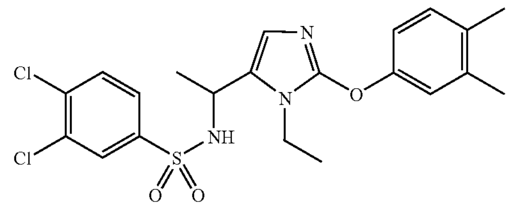 | 102.5-107.5 | 101.4 |
| Compound 219 | 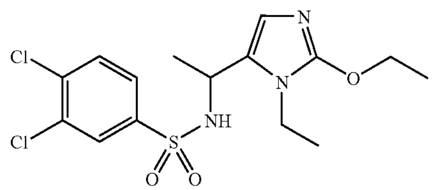 | 195.0-196.0 | 83.2 |
| Compound 220 | 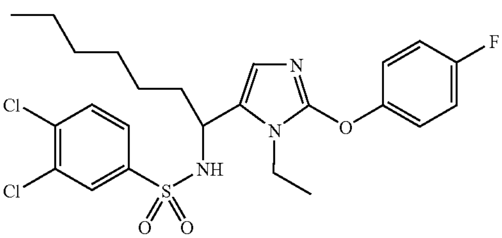 | 79.0-80.0 | 68.3 |

TABLE 1-33

| Compound No. | Chemical structure | Melting point (° C.) | Binding test (membrane) % inhibition (10 μM) |
|---|---|---|---|
| Compound 221 | 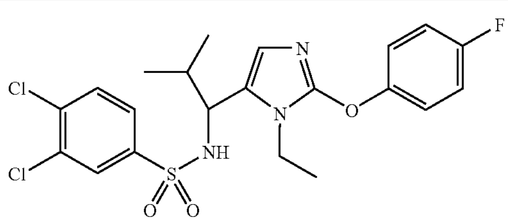 | 101.0-102.0 | 52.6 |
| Compound 222 | 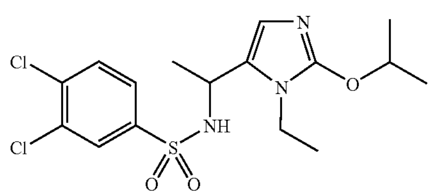 | 178.0-180.0 | 87.6 |
| Compound 223 | 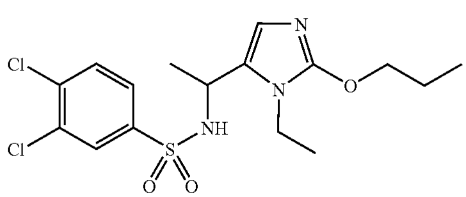 | 181.0-183.0 | 92.1 |

TABLE 1-33-continued

| Compound No. | Chemical structure | Melting point (° C.) | Binding test (membrane) % inhibition (10 μM) |
|---|---|---|---|
| Compound 224 | 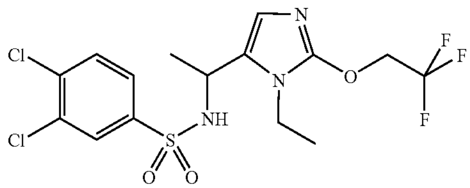 | 133.5-134.5 | 87.0 |
| Compound 225 | 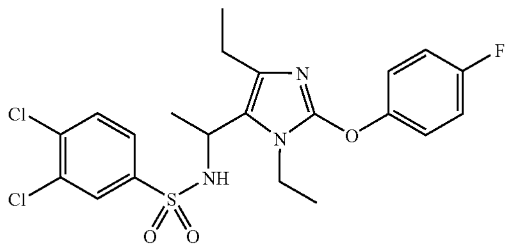 | 122.0-124.0 | 98.9 |
| Compound 226 | 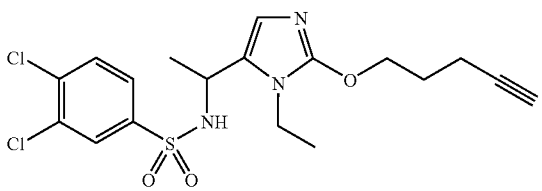 | 172.5-173.5 | 91.5 |
| Compound 227 | 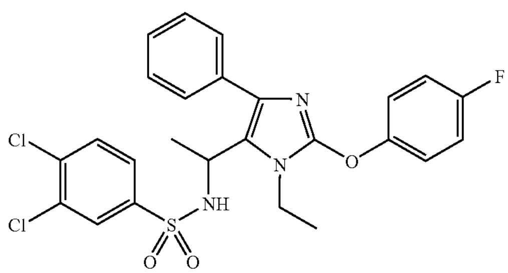 | 216.5-217.5 | |

TABLE 1-34

| Compound No. | Chemical structure | Melting point (° C.) | Binding test (membrane) % inhibition (10 μM) |
|---|---|---|---|
| Compound 228 | 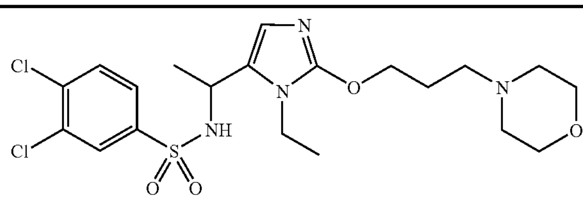 | 160.5-162.5 | 96.0 |
| Compound 229 | 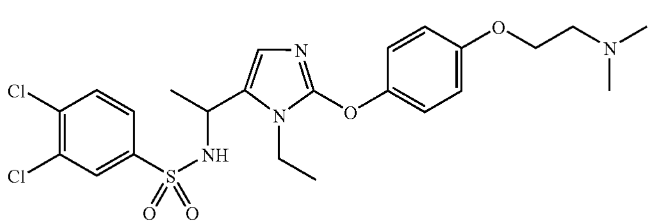 | 106.0-107.0 | 99.0 |

TABLE 1-34-continued

| Compound No. | Chemical structure | Melting point (°C.) | Binding test (membrane) % inhibition (10 μM) |
|---|---|---|---|
| Compound 230 | 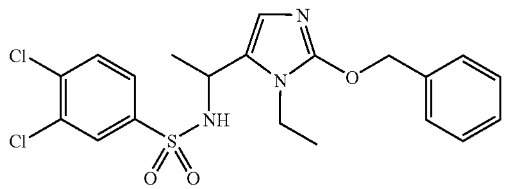 | 102.0-103.0 | 90.7 |
| Compound 231 | 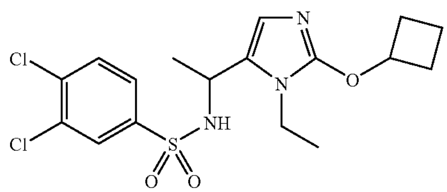 | 162.0-163.0 | 97.4 |
| Compound 232 | 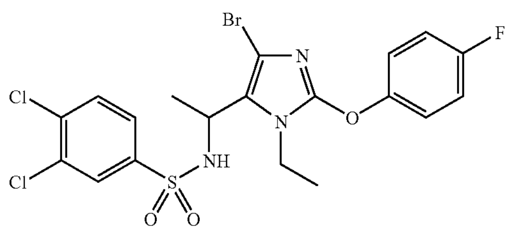 | 128.5-129.5 | 92.3 |
| Compound 233 | 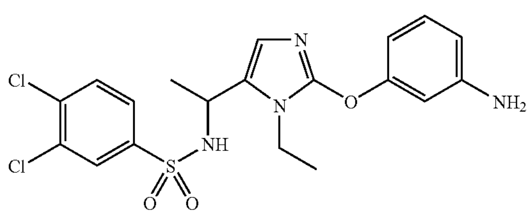 | | |
| Compound 234 | 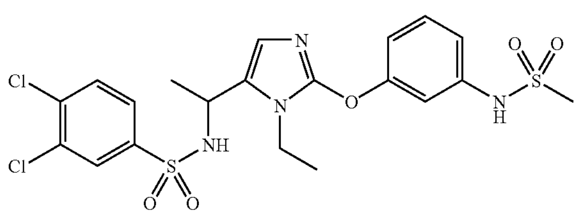 | | 98.1 |

TABLE 1-35

| Compound No. | Chemical structure | Melting point (°C.) | Binding test (membrane) % inhibition (10 μM) |
|---|---|---|---|
| Compound 235 | 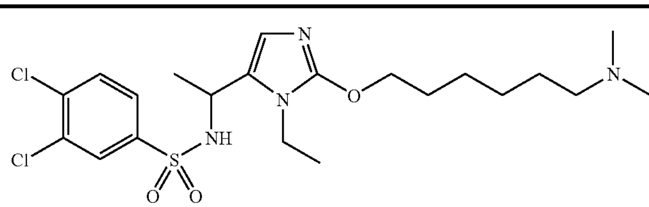 | 137.5-142.5 | 94.0 |

TABLE 1-35-continued

| Compound No. | Chemical structure | Melting point (° C.) | Binding test (membrane) % inhibition (10 μM) |
|---|---|---|---|
| Compound 236 | 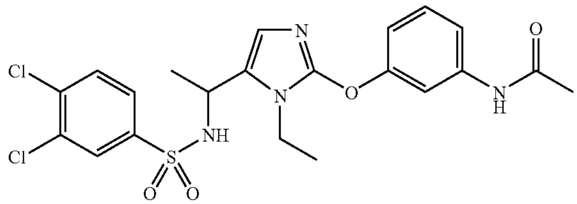 | 213.5-215.5 | 96.8 |
| Compound 237 | 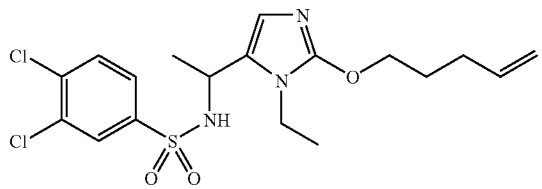 | 152.5-152.5 | 93.1 |
| Compound 238 | 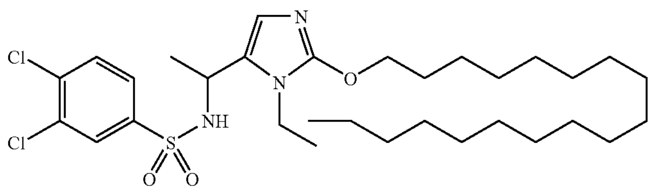 | 117.0-118.0 | |
| Compound 239 | 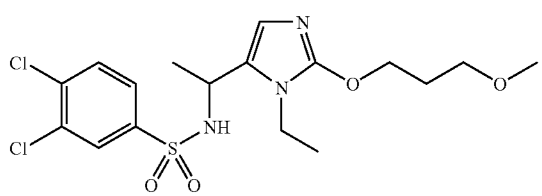 | 151.5-152.5 | 95.9 |
| Compound 240 | 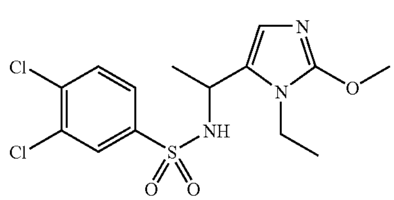 | 199.0-200.0 | |
| Compound 241 | 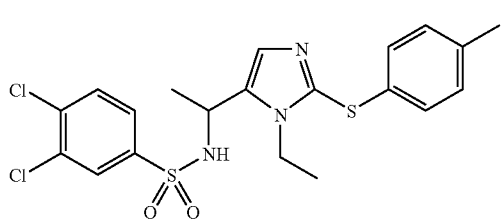 | 173.0-174.0 | 82.6 |

TABLE 1-36

| Compound No. | Chemical structure | Melting point (° C.) | Binding test (membrane) % inhibition (10 μM) |
|---|---|---|---|
| Compound 242 | 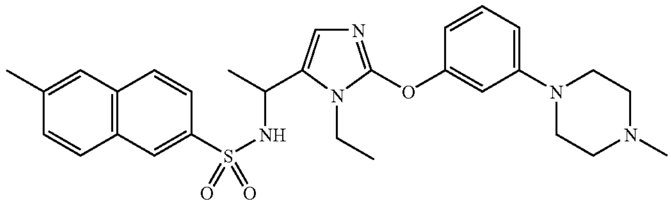 | 175.0-177.0 | 94.5 |
| Compound 243 | 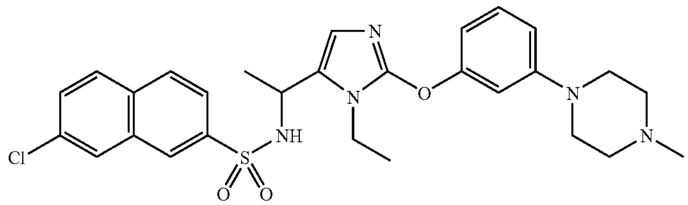 | 135.0-136.0 | 97.4 |
| Compound 244 | 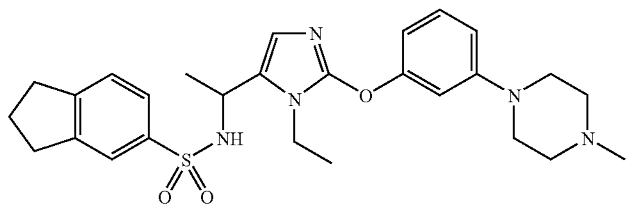 | 160.0-162.0 | 98.3 |
| Compound 245 | 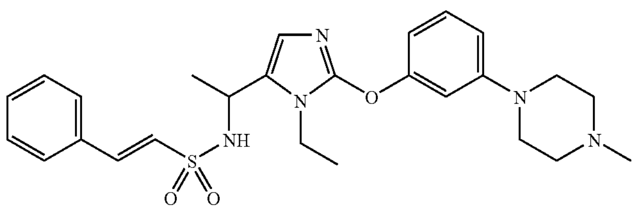 | 141.0-143.0 | 98.9 |
| Compound 246 | 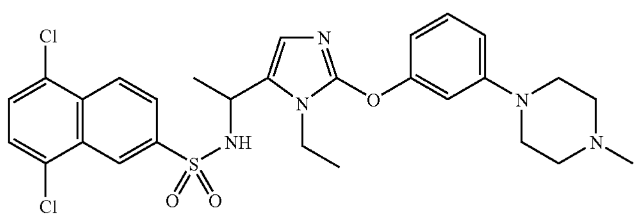 | 220.0-223.0 | 100.6 |
| Compound 247 | 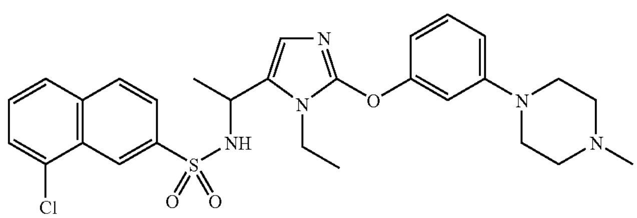 | 196.0-198.0 | 99.9 |
| Compound 248 | 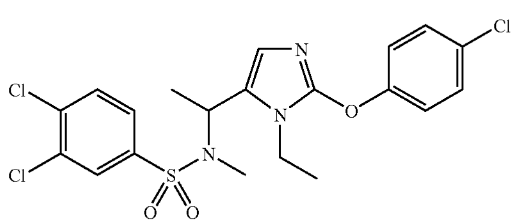 | 142.0-144.0 | 90.2 |

TABLE 1-36-continued

| Compound No. | Chemical structure | Melting point (° C.) | Binding test (membrane) % inhibition (10 μM) |
|---|---|---|---|
| Compound 249 | 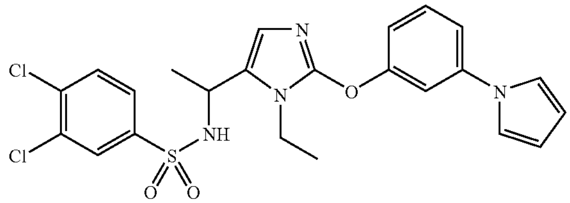 | | 100.1 |

TABLE 1-37

| Compound No. | Chemical structure | Melting point (° C.) | Binding test (membrane) % inhibition (10 μM) |
|---|---|---|---|
| Compound 250 | 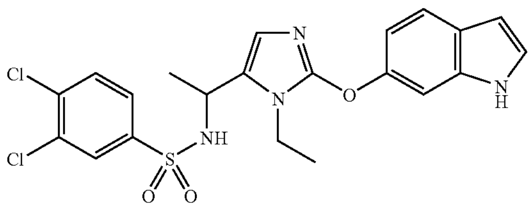 | 150.5-153.5 | 101.4 |
| Compound 251 | 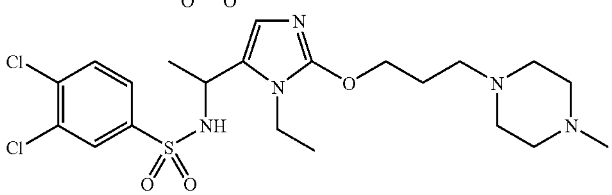 | 187.5-168.5 | 96.3 |
| Compound 252 | 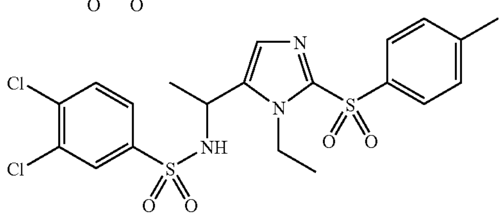 | 180.0-183.0 | 52.5 |
| Compound 253 | ABS | | 100.3 |
| Compound 254 | ABS | | 68.6 |

Preparation examples will be given below for intermediates of formula (II) according to the present invention.

Starting from corresponding starting materials, the same procedures as shown in Example 1-(1) to (5), Example 2-(1) to (7), Example 4-(1) to (5), Example 5-(1) to (8), Example 7-(1) to (8), Example 9-(1) to (4), Example 11-(1) and (2), Example 16-(1) and Example 17-(1) to (4) were repeated, followed by salt formation as needed to obtain intermediate compounds or salts thereof, which are useful in preparing the compounds of formula (I) according to the present invention. The intermediates thus prepared are shown in Table 2, along with the intermediates obtained in the examples shown above.

TABLE 2-1

| Compound No. | Chemical structure | $^1$H-NMR |
| --- | --- | --- |
| Intermediate 1 | 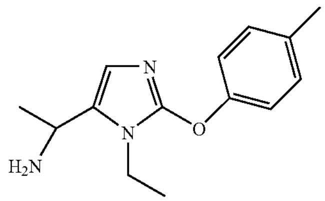 | (200 MHz, CDCl$_3$) δ ppm: 1.37(t, J = 7.1 Hz, 3H), 1.49(d, J = 6.6 Hz, 3H), 2.32(s, 3H), 3.82-4.12(m, 3H), 6.53(d, J = 0.9 Hz, 1H) 7.04-7.20(m, 4H) |
| Intermediate 2 | 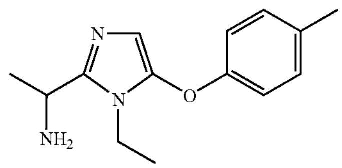 | (200 MHz, CDCl$_3$) δ ppm: 1.30(t, J = 7.3 Hz, 3 H), 1.53(d, J = 6.8 Hz, 3H), 2.32 (s, 3 H), 3.77-4.16(m, 3H), 6.44(s, 1H), 6.90-7.00(m, 2H), 7.06-7.16(m, 2H) |
| Intermediate 3 | 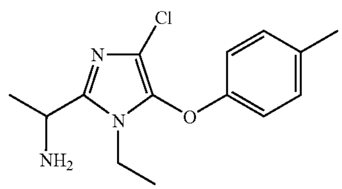 | (600 MHz, CDCl$_3$) δ ppm: 1.26(t, J = 7.3 Hz, 3H), 1.52(d, J = 6.9 Hz, 3H), 2.31(s, 3H), 3.79-3.96(m, 2H), 4.03-4.10(m, 1H), 6.82-6.88(m, 2H), 7.08-7.15(m, 2H) |
| Intermediate 4 | 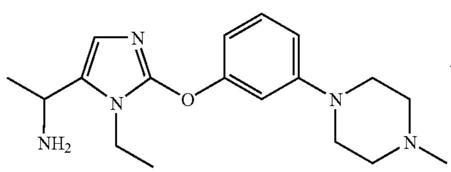 | (600 MHz, CDCl$_3$) δ ppm: 1.36(t, J = 7.1 Hz, 3H), 1.49(d, J = 6.4 Hz, 3H), 2.35(s, 3H), 2.53-2.60(m, 4H), 3.19-3.25(m, 4H), 3.90-4.11(m, 3H), 6.55-6.56(m, 1H), 6.63-6.71(m, 2H), 6.76-6.79(m, 1H), 7.15-7.25(m, 1H) |
| Intermediate 5 | 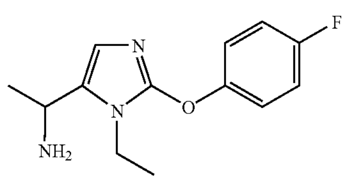 | (600 MHz, CDCl$_3$) δ ppm: 1.38(t, J = 7.1 Hz, 3H), 1.49(d, J = 6.9 Hz, 3H), 3.94-4.12(m, 3H), 6.52(s, 1H), 6.99-7.09(m, 2H). 7.17-7.23(m, 2H) |
| Intermediate 6 | 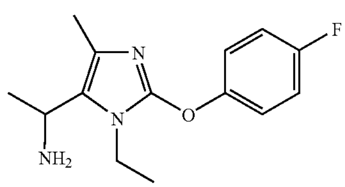 | (600 MHz, CDCl$_3$) δ ppm: 1.33(t, J = 7.1 Hz, 3H), 1.48(d, J = 6.9 Hz, 3 H), 2.16 (s, 3H), 8.92-4.14 (m, 2 H), 4.27 (q, J = 6.9 Hz, 1 H), 6.99-7.05 (m, 2 H), 7.14-7.21 (m, 2 H) |
| Intermediate 7 | 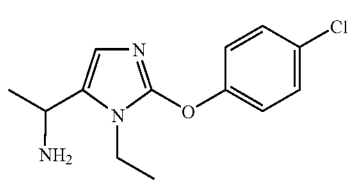 | (200 MHz. CDCl$_3$) δ ppm: 1.36(t, J = 7.0 Hz, 3H), 1.50(d, J = 6.6 Hz, 3H), 3.79-4.12(m, 3H), 6.55(d, J = 0.9 Hz, 1H), 7.12-7.36(m, 4H) |
| Intermediate 8 | 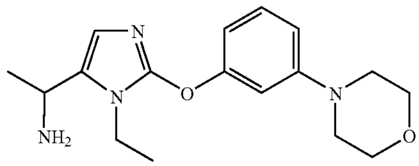 | (600 MHz, CDCl$_3$) δ ppm: 1.36(t, J = 7.1 Hz, 3H), 1.50(d, J = 6.9 Hz, 3H), 3.12-3.20(m, 4H), 3.81-3.88(m, 4H), 3.91-4.08(m, 3H), 6.54-6.60(m, 1H), 6.63-6.73(m, 2H), 6.75-6.79 (m, 1H), 7.19-7.25(m, 1H) |

TABLE 2-1-continued

| Compound No. | Chemical structure | $^1$H-NMR |
|---|---|---|
| Intermediate 9 | 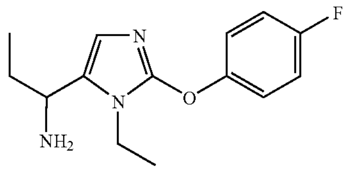 | (600 MHz, CDCl$_3$) δ ppm: 1.00(t, J = 7.3 Hz, 1.37(t, J = 7.1 Hz, 3H), 1.63-1.73(m, 1H), 1.84-1.94(m, 1H), 3.70 (t, J = 6.9 Hz, 1H), 3.93-4.10(m, 2H), 6.50(s, 1H), 7.01-7.07(m, 2H), 7.17-7.24 (m, 2H) |

TABLE 2-2

| Intermediate 10 | | (600 MHz, CDCl$_3$) δ ppm: 1.34(t, J = 7.1 Hz, 3H), 2.85(dd, J = 13.4, 9.4 Hz, 1H), 3.23(dd, J = 13.4, 4.6 Hz, 1H), 3.86-4.09(m, 3H), 6.62(s, 1H), 7.01-7.09 (m, 2H), 7.14-7.41(m, 7H) |
|---|---|---|
| Intermediate 11 | | 600 MHz, CDCl$_3$) δ ppm: 1.39(t, J = 6.9 Hz, 3H), 1.49(d, J = 6.0 Hz, 3H), 2.54(s, 3H), 3.93-4.17(m, 3H), 6.52(s, 1H), 7.11-7.20 (m, 1H), 7.54-7.64(m, 1H), 8.43(s, 1H) |
| Intermediate 12 | | (600 MHz, CDCl$_3$) δ ppm: 1.33(t, J = 7.3 Hz, 3H), 2.34(s, 3H), 2.91(dd, J = 13.6, 9.4 Hz, 1H), 3.23 (dd, J = 13.6, 4.6 Hz, 1H), 3.83-3.92(m, 1H), 3.98-4.05(m, 2H), 6.66(s, 1H), 6.78-6.81(m, 1H), 7.01-7.08(m, 2H), 7.11-7.25 (m, 5H) |
| Intermediate 13 | | (600 MHz, CDCl$_3$) δ ppm: 1.36(t, J = 7.3 Hz, 3H), 1.48(d, J = 6.4 Hz, 3H), 2.93(s, 6H), 3.90-4.07(m, 2H), 4.12-4.21(m, 1H), 6.45-6.53(m, 2H), 6.52-6.57 (m, 2H), 7.12-7.21(m, 1H) |
| Intermediate 14 | | (600 MHz, CDC$_3$) δ ppm: 1.24(t, J = 6.9 Hz, 3H), 2.87-3.31(m, 2H), 3.67-4.04(m, 3H), 6.65-7.40(m, 9H) |
| Intermediate 15 | | (600 MHz, CDCl$_3$) δ ppm: 1.04(t, J = 7.1 Hz, 3H), 3.68-3.86(m, 2H), 3.89(s, 1H), 6.57(s, 1H), 6.99-7.42 (m, 9H) |

TABLE 2-2-continued

| Intermediate 16 | 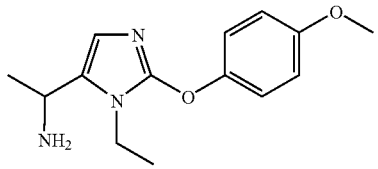 | (600 MHz, CDCl₃) δ ppm: 1.36(t, J = 7.1 Hz, 3H), 1.49(d, J = 6.9 Hz, 3H), 3.79(s, 3H), 3.93-4.10(m, 2H), 4.13-4.21(m, 1H), 6.50(s, 1H), 6.86-6.93(m, 2H), 7.12-7.18(m, 2H) |
|---|---|---|
| Intermediate 17 | 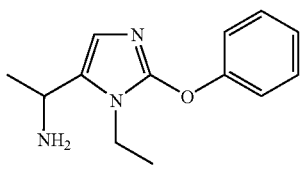 | (600 MHz, CDCl₃) δ ppm: 1.35-1.39(m, 3H), 1.47-1.50(m, 3H), 3.94-4.20(m, 3H), 6.55(d, J = 0.9 Hz, 1H), 7.13-7.16(m, 1H), 7.20-7.23(m, 2H), 7.33-7.38(m, 2H) |
| Intermediate 18 | 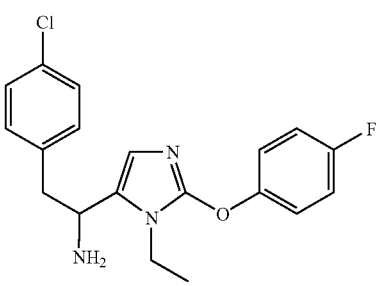 | (600 MHz, CDCl₃) δ ppm: 1.31(t, J = 7.3 Hz, 3H), 2.88(dd, J = 13.4, 8.7 Hz, 1H), 3.18(dd, J = 13.4, 5.3 Hz, 1H), 3.85-3.93(m, 1H), 3.96-4.04(m, 2H) 6.64(s, 1H), 7.02-7.31(m, 8H) |

TABLE 2-3

| Intermediate 19 | 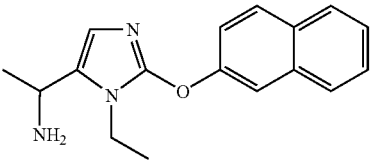 | (600 MHz, CDCl₃) δ ppm: 1.40(t, J = 7.1 Hz, 3H), 1.51(d, J = 6.4 Hz, 3H), 3.98-4.20(m, 3H), 6.59(d, J = 0.9 Hz, 1H), 7.37-7.48(m, 3H), 7.65(d, J = 2.8 Hz, 1H), 7.75-7.86(m, 3H) |
|---|---|---|
| Intermediate 20 | 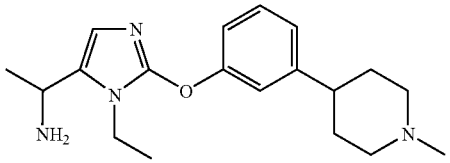 | (600 MHz, CDCl₃) δ ppm: 1.34-1.38(m, 3H), 1.48-1.51(m, 3H), 1.76-1.86(m, 4H), 1.99-2.05(m, 2H), 2.31(s, 3H), 2.44-2.50(m, 1H), 2.93-2.99(m, 2H), 3.92-4.20(m, 3H), 6.55 (s, 1H), 6.95-7.07(m, 3H) 7.25-7.30(m, 1H) |
| Intermediate 21 | 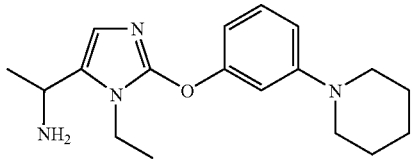 | (600 MHz, CDCl₃) δ ppm: 1.36(t, J = 7.1 Hz, 3H), 1.49(d, J = 6.9 Hz, 3H), 1.53-1.71(m, 6H), 3.11-3.18(m, 4H), 3.91-4.07(m, 3H), 6.56(s, 1H), 6.58-6.61(m, 1H), 6.68-6.72(m, 1H), 6.74-6.77(m, 1H), 7.15-7.20(m, 1H) |
| Intermediate 22 | 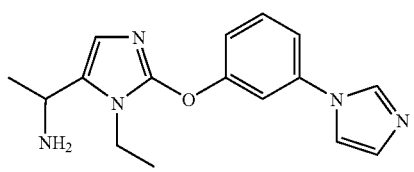 | (600 MHz, CDCl₃) δ ppm: 1.35-1.42(m, 3H), 1.48-1.52(m, 3H),3.97-4.06(m, 2H), 4.08-4.21 (m, 1H), 6.58(s, 1H), 7.18-7.36 (m, 5H), 7.45-7.48(m, 1H), 7.86 (s, 1H) |
| Intermediate 23 | 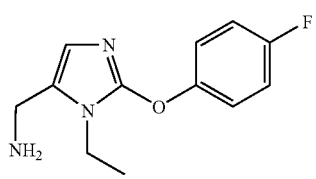 | (600 MHz, CDCl₃) δ ppm: 1.29(t, J = 7.3 Hz, 3H), 3.89(brs, 2H), 3.95(q, J = 7.3 Hz, 2H), 6.73(s, 1H), 7.00-7.04(m, 2H), 7.14-7.18(m, 2H) |

TABLE 2-3-continued

| Intermediate 24 | 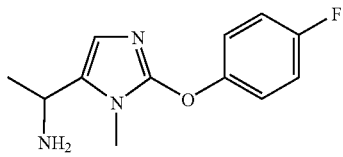 | (600 MHz, CDCl₃) δ ppm: 1.48(d, J = 6.9 Hz, 3H), 3.58(s, 3H), 3.98-4.05(m, 1H), 6.50-6.54 (m, 1H), 7.01-7.09(m, 2H), 7.17-7.22(m, 2H) |
|---|---|---|
| Intermediate 25 | 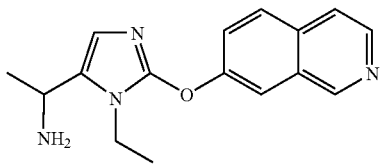 | (600 MHz, CDCl₃) δ ppm: 1.41(t, J = 7.1 Hz, 3H), 1.52(d, J = 6.4 Hz, 3H), 3.99-4.20(m, 3H), 6.60(d, J = 0.9 Hz, 1H), 7.61-7.65(m, 2H), 7.83-7.87(m, 2H), 8.49(d, J = 5.5 Hz, 1H), 9.20(s, 1H) |
| Intermediate 26 | 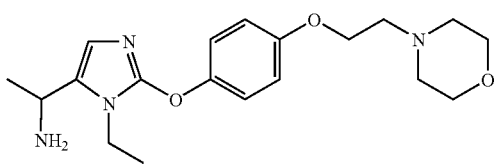 | (600 MHz, CDCl₃) δ ppm: 1.38(t, J = 7.1 Hz, 3H), 1.48(d, J = 6.4 Hz, 3H), 2.55-2.60(m, 4H), 2.79 (t, J = 5.7 Hz, 2H), 3.72-3.75(m, 4H), 3.94-4.10(m, 3H), 4.09(t, J = 5.7 Hz, 2H), 6.49(s, 1H), 6.87-6.91(m, 2H), 7.13-7.16(m, 2H) |
| Intermediate 27 | 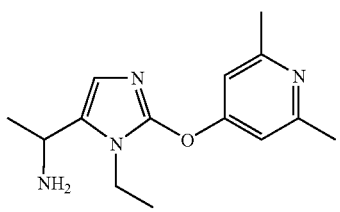 | (600 MHz, CDCl₃) δ ppm: 1.29-1.53(m, 6H), 2.49(s, 6H), 3.89-4.36(m, 3H), 6.60-6.84(m, 3H) |

TABLE 2-4

| Intermediate 28 | 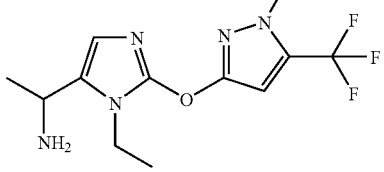 | (600 MHz, CDCl₃) δ ppm: 1.34-1.41(m, 3H), 1.47-1.50(m, 3H), 3.91(s, 3H), 3.98-4.11(m, 3H), 6.53(d, J = 0.9 Hz, 1H), 6.65(s,1H) |
|---|---|---|
| Intermediate 29 | 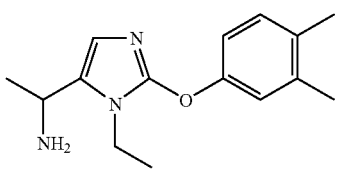 | (600 MHz, CDCl₃) δ ppm: 1.35-1.39(m, 3H), 1.46-1.50(m, 3H), 2.22(s, 3H), 2.24(s, 3H)3.98-4.08(m, 3H), 6.51(d, J = 0.9 Hz, 1H), 6.91-6.95 (m, 1H), 6.97-7.00(m, 1H), 7.10(d, J = 8.3 Hz, 1H) |
| Intermediate 30 | 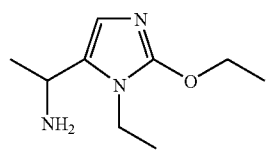 | (600 MHz, CDCl₃) δ ppm: 1.28(t, J = 7.1 Hz, 3H), 1.39(t, J = 7.1 Hz, 3H). 1.44(d, J = 6.4 Hz, 3H), 3.79-3.97(m, 3H), 4.35-4.41(m, 2H), 6.44(s, 1H) |
| Intermediate 31 | 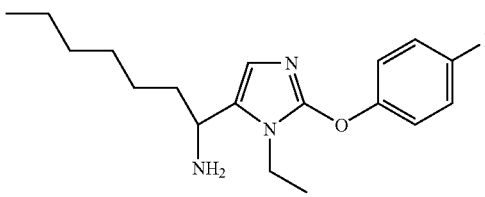 | (600 MHz, CDCl₃) δ ppm: 0.87-0.91(m, 3H), 1.24-1.87(m, 13H), 3.76-3.79(m, 1 H), 3.95-4.07(m, 2H), 6.51(s, 1H), 7.01-7.06(m, 2H), 7.18-7.25 (m, 2H) |

TABLE 2-4-continued

| Intermediate 32 | 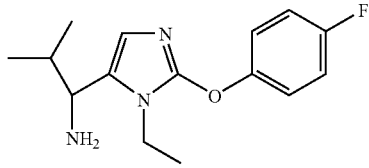 | (600 MHz, CDCl₃) δ ppm: 0.95(d, J = 6.9 Hz, 3H), 1.04(d, J = 6.4 Hz, 3H), 1.36(t, J = 7.1 Hz, 3H), 1.92-1.99(m, 1H), 3.53(d, J = 7.3 Hz, 1H), 3.95-4.03(m, J = 2 H), 6.51(s, 1H), 7.02-7.06(m, 2H), 7.19-7.22(m, 2H) |
|---|---|---|
| Intermediate 33 | 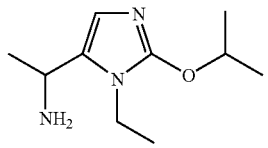 | (600 MHz, CDCl₃) δ ppm: 1.27(t, J = 7.1 Hz, 3H), 1.37(d, J = 6.4 Hz, 6H), 1.45(d, J = 6.9 Hz, 3H), 3.77-3.91(m, 2H), 3.92-3.97(m, 1H), 5.04-5.11(m, 1H), 6.45(s, 1H) |
| Intermediate 34 | 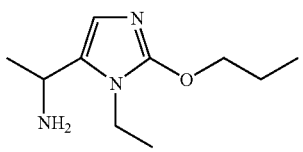 | (600 MHz, CDCl₃) δ ppm: 1.01(t, J = 7.3 Hz, 3H), 1.29(t, J = 7.1 Hz, 3H), 1.45(d, J = 6.4 Hz, 3H), 1.76-1.83(m, 2H), 3.79-3.97(m, 3H), 4.26-4.30(m, 2H), 6.43(d, J = 0.9 Hz, 1H) |
| Intermediate 35 | 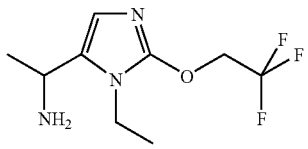 | (600 MHz, CDCl₃) δ ppm: 1.32(t, J = 7.1 Hz, 3H), 1.46(d, J = 6.9 Hz, 3H), 3.82-4.03(m, 3H), 4.69-4.78 (m, 2H), 6.45(s, 1H) |
| Intermediate 36 | 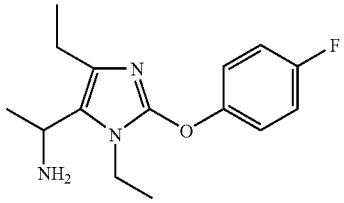 | (600 MHz, CDCl₃) δ ppm: 1.13(t, J = 7.6 Hz, 3H), 1.24-1.29(m, 3H), 1.47(d, J = 6.9 Hz, 3H), 2.43-2.54(m, 2H), 3.87-4.11(m, 2H), 4.24-4.31 (m, 1H), 6.96-7.40 (m, 2 H) |

TABLE 2-5

| Intermediate 37 | 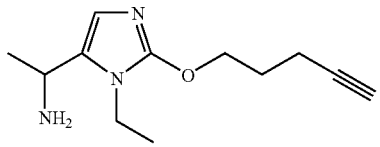 | (600 MHz, CDCl₃) δ ppm: 1.29(t, J = 7.1 Hz, 3H), 1.45(d, J = 6.9 Hz, 3H), 1.97(t, J = 2.8 Hz, 1H), 1.99-2.05(m, 2H), 2.34-2.39(m, 2H), 3.79-3.97(m, 3H), 4.43(t, J = 6.2 Hz, 2H), 6.44(s, 1H) |
|---|---|---|
| Intermediate 38 | 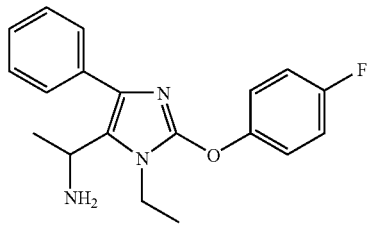 | (600 MHz, CDCl₃) δ ppm: 1.43(t, J = 7.1 Hz, 3H), 1.52(d, J = 6.9 Hz, 3H), 4.11-4.39(m, 2H), 4.62-4.68(m, 1H), 6.97-7.50(m, 9H) |
| Intermediate 39 | 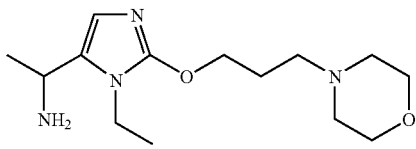 | (600 MHz, CDCl₃) δ ppm: 1.27(t, J = 7.1 Hz, 3H), 1.54(d, J = 6.9 Hz, 3H), 2.01-2.05(m, 2H), 2.52-2.62(m, 6H), 3.74-3.79(m, 4H), 3.80-3.94(m, 2H), 4.03-4.09(m, 1H), 4.39(t, J = 6.4 Hz, 2H), 6.54(s, 1H) |

TABLE 2-5-continued

| | | |
|---|---|---|
| Intermediate 40 | | (600 MHz, CDCl₃) δ ppm: 1.34-1.40(m, 3H), 1.46-1.50(m, 3H), 2.34-2.39(m, 2H), 2.36(s, 6H), 2.72-2.78(m, 2H), 3.95-4.09(m, 2H), 4.13-4.20(m, 1H), 6.50(s, 1H), 6.88-6.91(m, 2H), 7.14-7.16(m, 2H) |
| Intermediate 41 | | (600 MHz, CDCl₃) δ ppm: 1.29(t, J = 7.3 Hz, 3H), 1.46(d, J = 6.4 Hz, 3H), 3.82-3.99(m, 3H), 5.38 (s, 2H), 6.48(s, 1H), 7.31-7.45(m, 5H) |
| Intermediate 42 | | (600 MHz, CDCl₃) δ ppm: 1.28(t, J = 7.1 Hz, 3H), 1.50(d, J = 6.4 Hz, 3H), 1.58-1.68(m, 1H), 1.77-1.86(m, 1H), 2.08-2.19(m, 2H), 2.41-2.51(m, 2H), 3.80-3.91(m, 2H), 3.99-4.05 (m, 1H), 5.07-5.14(m, 1H), 6.52(s, 1H) |
| Intermediate 43 | | (600 MHz, CDCl₃) δ ppm: 1.37(t, J = 7.1 Hz, 3H), 1.50(d, J = 6.9 Hz, 3H), 4.00-4.22 (m, 2H), 4.31 (q, J = 6.9 Hz, 1H), 7.00-7.06(m, 2H), 7.18-7.24 (m, 2H) |
| Intermediate 44 | | (600 MHz, DMSO-D6) δ ppm: 1.19-1.24(m, 3H), 1.35(d, J = 6.4 Hz, 3H), 3.80-4.00(m, 3H), 5.19-5.24 (m, 2H), 6.19-6.22(m, 1H), 6.29-6.33(m, 2H), 6.43 (d, J = 0.9 Hz, 1H), 6.93-6.98(m, 1H) |
| Intermediate 45 | | (600 MHz, CDCl₃) δ ppm: 1.25-1.55(m, 12H), 1.75-1.81(m, 2H), 2.23-2.35(m, 8H), 3.79-3.97(m, 3H), 4.31(t, J = 6.6 Hz, 2H), 6.43(d, J = 0.9 Hz, 1H) |

TABLE 2-6

| | | |
|---|---|---|
| Intermediate 46 | | (600 MHz, CDCl₃) δ ppm: 1.29(t, J = 7.1 Hz, 3H), 1.45(d, J = 6.9 Hz, 3H), 1.85-1.91(m, 2H), 2.18-2.23(m, 2H), 3.80-3.97(m, 3H), 3.80-3.97(m, 3H), 4.34(t, J = 6.4 Hz, 2H), 4.98-5.01(m, 1H), 5.03-5.08 (m, 1H), 5.81-5.89(m, 1H), 6.44(s, 1H) |
| Intermediate 47 | | (600 MHz, CDCl₃) δ ppm: 0.88(t, J = 6.0 Hz, 3H), 1.20-1.36(m, 31H), 1.38-1.44(m, 2H), 1.58(d, J = 6.9 Hz, 3 H), 1.72-1.79(m, 2H), 3.83-3.88(m, 2H), 4.10-4.15(m, 1H), 4.26-4.34(m, 2H), 6.62(s, 1H) |
| Intermediate 48 | | (600 MHz, CDCl₃) δ ppm: 1.27(t, J = 7.1 Hz, 3H), 1.54(d, J = 6.9 Hz, 3H). 2.02-2.07(m, 2H), 3.34 (s, 3H), 3.52(t, J = 6.4 Hz, 2H), 3.81-3.91(m, 2H), 4.05-4.10(m, 1H) 4.38-4.43(m, 2H), 6.56(s, 1H) |

TABLE 2-6-continued

| Intermediate 49 | 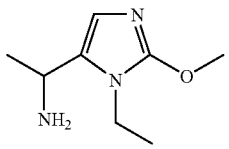 | (600 MHz, CDCl$_3$) δ ppm: 1.27(t, J = 7.1 Hz, 3H), 1.37(d, J = 6.4 Hz, 3H), 3.21(s, 3H), 3.69-3.84 (m, 2H), 3.87-3.93 (m, 1H), 6.00(s, 1H) |
|---|---|---|
| Intermediate 50 | 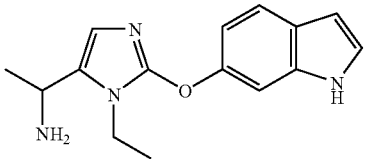 | (600 MHz, CDCl$_3$) δ ppm: 1.40(t, J = 7.1 Hz, 3H), 1.49(d, J = 6.4 Hz, 3H), 3.97-4.12(m, 3H), 6.46-6.49(m, 1H), 6.54(s, 1H), 6.96(dd, J = 8.5, 2.1 Hz, 1H), 7.11-7.14(m, 1H), 7.30-7.34(m, 1H), 7.56 (d, J = 8.7 Hz), 1H), 8.42(brs, 1H) |
| Intermediate 51 | 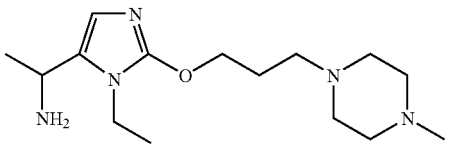 | (600 MHz, CDCl$_3$) δ ppm: 1.28(t, J = 7.1 Hz, 3H), 1.45(d, J = 6.9 Hz, 3H), 1.95-2.02(m, 2H), 2.36-2.85(m, 13H), 3.78-3.98(m, 3H), 4.37(t, J = 6.4 Hz, 2H), 6.44(d, J = 0.9 Hz, 1H) |

INDUSTRIAL APPLICABILITY

Since the compounds of the present invention are excellent Edg-1(S1P$_1$) ligands, they are useful as therapeutic and/or prophylactic agents for autoimmune disease such as Crohn's disease, irritable colitis, Sjogren's syndrome, multiple sclerosis and systemic lupus erythematosus, as well as other diseases such as rheumatoid arthritis, asthma, atopic dermatitis, rejection after organ transplantation, cancer, retinopathy, psoriasis, osteoarthritis, age-related macular degeneration, etc.

The invention claimed is:

1. A compound represented by formula (I) or a pharmaceutically acceptable salt thereof:

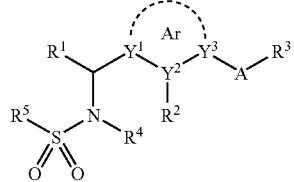

[Formula 1]

{wherein Ar is a substituent represented by the following formula:

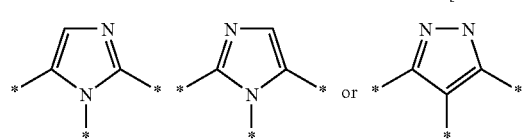

[Formula 6]

which may be substituted with a substituent selected from the group consisting of a C$_1$-C$_6$ alkyl group, a phenyl group and a halogen atom, Y$^1$, Y$^2$ and Y$^3$ each represent a carbon atom or a nitrogen atom, A represents an oxygen atom, a sulfur atom, a group represented by the formula —SO$_2$—, or a group represented by the formula —NR$^6$— (wherein R$^6$ represents a hydrogen atom or a C$_1$-C$_6$ alkyl group), provided that when Ar is a group represented by the following formula:

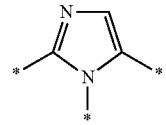

A is not a sulfur atom or a group represented by the formula —SO$_2$—,

R$^1$ represents a hydrogen atom, a C$_1$-C$_6$ alkyl group which may be substituted with a substituent(s) selected from the following group [wherein said group consists of a hydroxyl group, a halogen atom, a C$_1$-C$_6$ alkoxy group (wherein said alkoxy group may be substituted with a phenyl group) and a phenyl group (wherein said phenyl group may be substituted with a substituent(s) selected from the group consisting of a halogen atom and a C$_1$-C$_6$ alkyl group)], a C$_3$-C$_8$ cycloalkyl group, a C$_2$-C$_8$ alkenyl group, a C$_2$-C$_8$ alkynyl group, or a phenyl group, R$^2$ represents a hydrogen atom, a C$_1$-C$_6$ alkyl group, or a C$_3$-C$_8$ cycloalkyl group, R$^3$ represents (i) a hydrogen atom, (ii) a C$_1$-C$_{18}$ alkyl group, (iii) a C$_2$-C$_8$ alkenyl group which may be substituted with a phenyl group or a benzyloxy group, (iv) a C$_2$-C$_8$ alkynyl group which may be substituted with a phenyl group, (v) a C$_3$-C$_8$ cycloalkyl group which may be condensed with a benzene ring, (vi) a C$_1$-C$_6$ alkyl group substituted with a substituent(s) selected from the following group [wherein said group consists of a halogen atom, a phenyl group (wherein said phenyl group may be substituted with 1 to 5 substituents selected from the group consisting of a phenyl group, a cyano group, a halogen atom, a C$_1$-C$_6$ alkyl group, a C$_1$-C$_6$ alkoxy group, a trifluoromethyl group, a methoxycarbonyl group, a C$_1$-C$_6$ alkylthio group, a dimethylamino group, a nitro group and an acetamido group), a C$_3$-C$_8$ cycloalkyl group, a hydroxyl group, a C$_1$-C$_6$ alkylthio group, a C$_1$-C$_6$ alkoxy group, a benzyloxy group, a phenoxy group, a trifluoromethyl group, a difluoromethyl group, a benzenesulfonyl group, a naphthyl group, a $C_7$-$C_{10}$ tricycloalkyl group, a carbomethoxy(phenyl)methyl group, a diphenylmethyl group, a 1-phenylethyl group, an imidazolyl group, an indolyl group, a pyridyl group, an oxetanyl group, an oxolanyl group, a methylpiperidinyl group, a piperazino group which may be substituted with a $C_1$-$C_6$ alkyl group(s), a benzylpiperidinyl group, a morpholino group, a 2-oxopyrrolidin-1-yl group, a 2-oxoimidazolidin-1-yl group, a group represented by the formula:

(wherein $R^{11}$ represents a hydrogen atom or a $C_1$-$C_6$ alkyl group), a group represented by the formula:

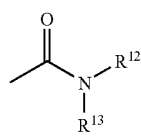

[Formula 2]

(wherein $R^{12}$ and $R^{13}$ each represent a hydrogen atom or a $C_1$-$C_6$ alkyl group), a group represented by the formula:

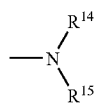

[Formula 3]

(wherein $R^{14}$ and $R^{15}$ each represent a hydrogen atom, a $C_1$-$C_6$ alkyl group, a phenyl group or a 4-pyridylcarbonyl group), and the formula:

(wherein $R^{16}$ represents a $C_1$-$C_6$ alkyl group or a phenyl group)], (vii) an oxolanyl group, a methylpiperidinyl group, or a group represented by the formula:

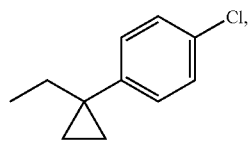

[Formula 4]

or (viii) an optionally substituted aryl group,
$R^4$ represents a hydrogen atom, or a $C_1$-$C_6$ alkyl group which may be substituted with a carboxyl group, and
$R^5$ represents (i) a $C_1$-$C_{10}$ alkyl group, (ii) a $C_1$-$C_{10}$ alkyl group which is substituted with one or two substituents selected from the following group (wherein said group consists of a $C_3$-$C_8$ cycloalkyl group, a pyridyl group, and a phenyl, phenoxy or naphthyl group which may be substituted with one or two substituents selected from the group consisting of a halogen atom and a $C_1$-$C_6$ alkoxy group) (iii) a $C_3$-$C_8$ cycloalkyl group, (iv) a $C_2$-$C_8$ alkenyl group, (v) a $C_2$-$C_8$ alkenyl group substituted with a phenyl group, (vi) a $C_2$-$C_8$ alkynyl group, (vii) a $C_2$-$C_8$ alkynyl group substituted with a phenyl group, or (viii) an optionally substituted aryl group, provided that when Ar is a group represented by the following formula:

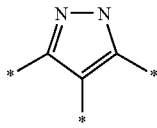

[Formula 5]

which may be substituted with a $C_1$-$C_6$ alkyl group, $R^5$ is not a $C_1$-$C_{10}$ alkyl group}.

2. The compound or pharmaceutically acceptable salt thereof according to claim 1, wherein in formula (I),
  A represents an oxygen atom, a sulfur atom, or a group represented by the formula —$NR^6$— (wherein $R^6$ represents a hydrogen atom or a $C_1$-$C_6$ alkyl group),
  $R^1$ represents a hydrogen atom, a $C_1$-$C_6$ alkyl group, or a $C_1$-$C_6$ alkyl group substituted with a phenyl group,
  $R^2$ represents a $C_1$-$C_6$ alkyl group, or a $C_3$-$C_8$ cycloalkyl group,
  $R^3$ represents a $C_1$-$C_6$ alkyl group, or an optionally substituted aryl group,
  $R^4$ represents a hydrogen atom, or a $C_1$-$C_6$ alkyl group, and
  $R^5$ represents (i) a $C_1$-$C_{10}$ alkyl group, (ii) a $C_1$-$C_{10}$ alkyl group which is substituted with one or two substituents selected from the following group (wherein said group consists of a $C_3$-$C_8$ cycloalkyl group, a phenyl group, a naphthyl group, a pyridyl group, and a phenyl group substituted with one or two substituents selected from the group consisting of a halogen atom and a $C_1$-$C_6$ alkoxy group) (iii) a $C_3$-$C_8$ cycloalkyl group, (iv) a $C_2$-$C_8$ alkenyl group, (v) a $C_2$-$C_8$ alkenyl group substituted with a phenyl group, (vi) a $C_2$-$C_8$ alkynyl group, (vii) a $C_2$-$C_8$ alkynyl group substituted with a phenyl group, or (viii) an optionally substituted aryl group.

3. The compound or pharmaceutically acceptable salt thereof according to claim 1, wherein Ar is a substituent represented by the following formula:

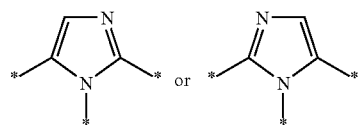

[Formula 7]

which may be substituted with a substituent selected from the group consisting of a $C_1$-$C_6$ alkyl group, a phenyl group and a halogen atom.

4. The compound or pharmaceutically acceptable salt thereof according to claim 1, wherein Ar is a substituent represented by the following formula:

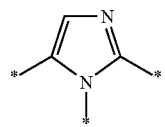

[Formula 8]

which may be substituted with a substituent selected from the group consisting of a $C_1$-$C_6$ alkyl group, a phenyl group and a halogen atom.

5. The compound or pharmaceutically acceptable salt thereof according to claim 1, wherein A is an oxygen atom.

6. The compound or pharmaceutically acceptable salt thereof according to claim 1, wherein $R^1$ is a $C_1$-$C_6$ alkyl group which may be substituted with a halogen atom(s), or a benzyl group which may be substituted with a substituent(s) selected from the group consisting of a halogen atom and a $C_1$-$C_6$ alkyl group.

7. The compound or pharmaceutically acceptable salt thereof according to claim 1, wherein $R^1$ is a methyl group, an ethyl group or a benzyl group which may be substituted with a halogen atom(s).

8. The compound or pharmaceutically acceptable salt thereof according to claim 1, wherein $R^1$ is a methyl group or an ethyl group.

9. The compound or pharmaceutically acceptable salt thereof according to claim 1, wherein $R^4$ is a hydrogen atom.

10. The compound or pharmaceutically acceptable salt thereof according to claim 1, wherein $R^2$ is a $C_1$-$C_6$ alkyl group or a $C_3$-$C_6$ cycloalkyl group.

11. The compound or pharmaceutically acceptable salt thereof according to claim 1, wherein $R^2$ is an ethyl group or a cyclopropyl group.

12. The compound or pharmaceutically acceptable salt thereof according to claim 1, wherein $R^5$ is (i) a $C_1$-$C_{10}$ alkyl group, (ii) a $C_1$-$C_{10}$ alkyl group which is substituted with one or two substituents selected from the following group (wherein said group consists of a $C_3$-$C_8$ cycloalkyl group, a pyridyl group, and a phenyl, phenoxy or naphthyl group which may be substituted with one or two substituents selected from the group consisting of a halogen atom and a $C_1$-$C_6$ alkoxy group), (iii) a $C_2$-$C_8$ alkenyl group which may be substituted with a phenyl group, or (iv) a phenyl group, a naphthyl group, a thienyl group, a pyrrolyl group, a pyrazolyl group, a pyridyl group, a furanyl group, a benzothienyl group, an isoquinolinyl group, an isoxazolyl group, a thiazolyl group, a benzothiadiazolyl group, a benzoxadiazolyl group, a phenyl group condensed with a 5- to 7-membered saturated hydrocarbon ring which may contain one or two oxygen atoms as ring members, a uracil group, a coumaryl group, a dihydroindolyl group, or a tetrahydroisoquinolinyl group, wherein these groups may each be substituted with 1 to 5 substituents selected from the following group

[wherein said group consists of a $C_1$-$C_6$ alkyl group which may be substituted with a fluorine atom(s), a $C_2$-$C_8$ alkenyl group, a halogen atom, a $C_1$-$C_6$ alkoxy group which may be substituted with a fluorine atom(s), a pyrazolyl, oxazolyl, isoxazolyl, thiadiazolyl or pyrimidinyl group, which may be substituted with a substituent(s) selected from the group Y (wherein the group Y consists of a methyl group, a trifluoromethyl group, a halogen atom and a methylsulfanyl group), a $C_1$-$C_6$ alkylthio group, a $C_1$-$C_6$ alkylsulfonyl group, a benzenesulfonyl group, a morpholinosulfonyl group, a morpholinocarbonylamino group, an aminosulfonyl group, a $C_2$-$C_{10}$ alkoxycarbonyl group, a morpholino group which may be substituted with a $C_1$-$C_6$ alkyl group(s), a phenyl group which may be substituted with a $C_1$-$C_6$ alkoxy group(s), a phenoxy group, a pyridinecarbonyl group, a pyridineoxy group, a cyano group, a $C_2$-$C_7$ alkanoyl group which may be substituted with a fluorine atom(s) and a $C_2$-$C_7$ alkanoylamino group].

13. The compound or pharmaceutically acceptable salt thereof according to claim 1, wherein $R^5$ is a $C_1$-$C_{10}$ alkyl group substituted with a $C_3$-$C_8$ cycloalkyl group, a $C_1$-$C_{10}$ alkyl group substituted with a naphthyl group, a $C_2$-$C_8$ alkenyl group substituted with a phenyl group, a phenyl or naphthyl group which may be substituted with 1 to 5 substituents selected from the following group (wherein said group consists of a $C_1$-$C_6$ alkyl group, a halogen atom, a $C_1$-$C_6$ alkoxy group, a trifluoromethoxy group, a difluoromethoxy group, a trifluoromethyl group, a $C_1$-$C_6$ alkenyl group, a $C_1$-$C_6$ alkylsulfonyl group, a $C_2$-$C_7$ alkanoyl group, a $C_2$-$C_7$ alkoxycarbonyl group and a cyano group), a pyrrolyl group which may be substituted with a substituent(s) selected from the group consisting of a $C_1$-$C_6$ alkyl group and a methoxycarbonyl group, a furanyl group which may be substituted with a substituent(s) selected from the following group (wherein said group consists of a $C_1$-$C_6$ alkyl group, a trifluoromethyl group and a halogen atom), a thienyl group which may be substituted with a substituent(s) selected from the following group (wherein said group consists of a $C_1$-$C_6$ alkyl group, a trifluoromethyl group, a thiadiazolyl group, an oxazolyl group and a halogen atom), or a benzothienyl, dihydrobenzodioxepinyl, benzodioxolyl, dihydrobenzodioxinyl, dihydrobenzofuranyl, tetrahydronaphthyl, indanyl, thiadiazolyl, benzoxadiazolyl or benzothiadiazolyl group which may be substituted with a substituent(s) selected from the group consisting of a $C_1$-$C_6$ alkyl group and a halogen atom.

14. The compound or pharmaceutically acceptable salt thereof according to claim 1, wherein $R^5$ is a $C_1$-$C_6$ alkyl group substituted with a naphthyl group, a $C_2$-$C_6$ alkenyl group substituted with a phenyl group, an unsubstituted phenyl group, a phenyl group substituted with 1 to 5 substituents selected from the following group (wherein said group consists of a methyl group, a methoxy group and a halogen atom), a phenyl group which is substituted with 1 to 3 substituents selected from the following group and at least one of whose 3- and 4-positions is substituted (wherein said group consists of a $C_1$-$C_6$ alkyl group, a halogen atom, a methoxy group, a trifluoromethoxy group, a difluoromethoxy group, a trifluoromethyl group, a $C_1$-$C_6$ alkenyl group, a methylsulfonyl group, an acetyl group, a methoxycarbonyl group and a cyano group), a naphthyl group which may be substituted with a substituent(s) selected from the following group (wherein said group consists of a halogen atom, a $C_1$-$C_6$ alkyl group, a cyano group and a $C_1$-$C_6$ alkylsulfonyl group), a furanyl group which may be substituted with a substituent(s) selected from the group consisting of a trifluoromethyl group and a halogen atom, or a benzothienyl, benzoxadiazolyl, benzodioxolyl, dihydrobenzodioxinyl, dihydrobenzofuranyl, indanyl or benzothiadiazolyl group which may be substituted with a substituent(s) selected from the group consisting of a $C_1$-$C_6$ alkyl group and a halogen atom.

15. The compound or pharmaceutically acceptable salt thereof according to claim 1, wherein $R^5$ is a phenyl group whose 3- and 4-positions are each substituted with a halogen atom, or a naphthyl group which may be substituted with a substituent(s) selected from the group consisting of a halogen atom, a $C_1$-$C_6$ alkyl group and a cyano group.

16. The compound or pharmaceutically acceptable salt thereof according to claim 1, wherein $R^3$ is a phenyl group, a naphthyl group, a pyrazolyl group, a pyridyl group, an indolyl group, a benzothiazolyl group, a benzothiadiazolyl group, a pyrazolopyrimidinyl group, a quinolinyl group, an isoquinolinyl group, a benzothienyl group or a dihydroquinolinonyl group, wherein these groups may each be substituted with 1 to 3 substituents selected from the following group [wherein said group consists of substituents listed below: a $C_1$-$C_6$ alkyl group which may be substituted with a fluorine atom(s), a $C_3$-$C_8$ cycloalkyl group, a halogen atom, a $C_1$-$C_6$ alkoxy group (wherein said alkoxy group may be substituted with a substituent(s) selected from the group consisting of a fluorine atom, a phenyl group, an amino group substituted with two $C_1$-$C_4$ alkyl groups and a morpholino group), a phenoxy group, a phenyl group, a carboxyl group, a $C_2$-$C_{10}$ alkoxycarbonyl group, a hydroxyl group, a $C_2$-$C_7$ monocyclic saturated hydrocarbon group containing a nitrogen atom(s) as a ring member(s) (wherein said saturated hydrocarbon group may be substituted with a $C_1$-$C_6$ alkyl group(s)), a nitrogen-containing monocyclic unsaturated hydrocarbon group, a morpholinyl group which may be substituted with a $C_1$-$C_6$ alkyl group(s), a piperazino group which may be substituted with a substituent(s) selected from the following group (wherein said group consists of a $C_1$-$C_6$ alkyl group (wherein said alkyl group may be substituted with an amino group which may be substituted with one or two $C_1$-$C_6$ alkyl groups, a morpholino group, a hydroxyl group, or a $C_1$-$C_6$ alkoxy group), a formyl group, a $C_2$-$C_7$ alkanoyl group, a carbamoyl group which may be substituted with one or two $C_1$-$C_4$ alkyl groups, an aminosulfonyl group which may be substituted with one or two $C_1$-$C_6$ alkyl groups, and a $C_1$-$C_6$ alkylsulfonyl group), and the formula:

$$-NR^7R^8$$

wherein $R^7$ and $R^8$ each represent a hydrogen atom, a $C_1$-$C_6$ alkyl group (wherein said alkyl group may be substituted with an amino group which may be substituted with one or two $C_1$-$C_6$ alkyl groups, a hydroxyl group, or a $C_1$-$C_6$ alkoxy group), a $C_1$-$C_6$ alkanoyl group, a carbamoyl group which may be substituted with one or two $C_1$-$C_4$ alkyl groups, a morpholinocarbonyl group, an aminosulfonyl group which may be substituted with one or two $C_1$-$C_6$ alkyl groups, or a $C_1$-$C_6$ alkylsulfonyl group, or alternatively, $R^7$ and $R^8$ optionally form, together with the nitrogen atom to which $R^7$ and $R^8$ are attached, a 3- to 8-membered saturated hydrocarbon ring, wherein said ring may be substituted with a substituent(s) selected from the group consisting of a dimethylenedioxy group, an oxo group and a hydroxyl group].

17. The compound or pharmaceutically acceptable salt thereof according to claim 1, wherein $R^3$ is a 2-naphthyl group (wherein said naphthyl group may be substituted with a substituent(s) selected from the group consisting of a halogen atom and a $C_1$-$C_6$ alkyl group), a 3-pyrazolyl group (wherein said pyrazolyl group may be substituted with a substituent(s) selected from the group consisting of a $C_1$-$C_6$ alkyl group, a trifluoromethyl group and a halogen atom), or a 5-benzothiazolyl, 5-benzothiadiazolyl, 7-dihydroquinolinonyl, 7-isoquinolinyl, 7-quinolinyl, 3-pyridyl or indolyl group which may be substituted with a $C_1$-$C_6$ alkyl group(s), an unsubstituted phenyl group, or a substituted phenyl group shown in (A) to (C) below:
  (A) a phenyl group whose 4-position is substituted with a substituent selected from the group consisting of a $C_1$-$C_6$ alkyl group, a $C_3$-$C_8$ cycloalkyl group, a $C_1$-$C_6$ alkoxy group (wherein said alkoxy group may be substituted with a substituent(s) selected from the group consisting of an amino group substituted with two $C_1$-$C_4$ alkyl groups, a morpholino group and a phenyl group), a halogen atom, a trifluoromethoxy group, a phenoxy group, a phenyl group, a 1-pyrrolyl group, and —$NR^AR^B$ (wherein $R^A$ and $R^B$ are each a $C_1$-$C_6$ alkyl group, or $R^A$ and $R^B$ optionally form, together with the nitrogen atom to which $R^A$ and $R^B$ are attached, a 3- to 5-membered saturated hydrocarbon ring), and further whose 3-position may be substituted with a substituent selected from the group consisting of a $C_1$-$C_6$ alkyl group, a halogen atom and a $C_1$-$C_6$ alkoxy group,
  (B) a phenyl group whose 3-position is substituted with a substituent selected from the group consisting of a hydroxyl group, a $C_1$-$C_6$ alkyl group and a $C_1$-$C_6$ alkoxy group (wherein said alkoxy group may be substituted with a substituent(s) selected from the group consisting of an amino group substituted with two $C_1$-$C_4$ alkyl groups, a morpholino group and a phenyl group), and further which may be substituted with one or two $C_1$-$C_6$ alkyl groups or whose 4-position may be substituted with a halogen atom, and
  (C) a phenyl group whose 3-position is substituted with a substituent selected from the group consisting of nitrogen-containing groups shown in (i) to (v) below, and further whose 4-position may be substituted with a halogen atom:
  (i) a $C_2$-$C_7$ monocyclic saturated hydrocarbon group containing a nitrogen atom(s) as a ring member(s) (wherein said saturated hydrocarbon group may be substituted with a $C_1$-$C_6$ alkyl group(s)),
  (ii) a nitrogen-containing monocyclic unsaturated hydrocarbon group,
  (iii) a morpholinyl group which may be substituted with a $C_1$-$C_6$ alkyl group(s),
  (iv) a piperazino group [wherein said piperazino group may be substituted with a $C_1$-$C_6$ alkyl group which may be substituted with a substituent(s) selected from the following group (wherein said group consists of an amino group substituted with two $C_1$-$C_4$ alkyl groups and a morpholino group) or a $C_2$-$C_7$ alkanoyl group], and
  (v) the formula —$NR^7R^8$
  wherein $R^7$ and $R^8$ each represent a hydrogen atom, a $C_1$-$C_6$ alkyl group (wherein said alkyl group may be substituted with an amino group which may be substituted with one or two $C_1$-$C_6$ alkyl groups, a hydroxyl group, or a $C_1$-$C_6$ alkoxy group), a $C_1$-$C_6$ alkanoyl group, a carbamoyl group which may be substituted with one or two $C_1$-$C_4$ alkyl groups, a morpholinocarbonyl group, an aminosulfonyl group which may be substituted with one or two $C_1$-$C_6$ alkyl groups, or a $C_1$-$C_6$ alkylsulfonyl group, or alternatively, $R^7$ and $R^8$ optionally form, together with the nitrogen atom to which $R^7$ and $R^8$ are attached, a 3- to 8-membered saturated hydrocarbon ring, wherein said ring may be substituted with a substituent(s) selected from the group consisting of a dimethylenedioxy group, an oxo group and a hydroxyl group.

18. The compound or pharmaceutically acceptable salt thereof according to claim 1, wherein $R^3$ is a phenyl group whose 3-position is substituted with a substituent selected from the group consisting of nitrogen-containing groups shown in (i) to (v) below, and further whose 4-position may be substituted with a halogen atom:
  (i) a $C_2$-$C_7$ monocyclic saturated hydrocarbon group containing a nitrogen atom(s) as a ring member(s) (wherein said saturated hydrocarbon group may be substituted with a $C_1$-$C_6$ alkyl group(s)),
  (ii) a nitrogen-containing monocyclic unsaturated hydrocarbon group,
  (iii) a morpholinyl group which may be substituted with a $C_1$-$C_6$ alkyl group(s),
  (iv) a piperazino group [wherein said piperazino group may be substituted with a $C_1$-$C_6$ alkyl group which may be substituted with a substituent(s) selected from the following group (wherein said group consists of an amino group substituted with two $C_1$-$C_4$ alkyl groups and a morpholino group) or a $C_2$-$C_7$ alkanoyl group], and
  (v) the formula —$NR^7R^8$
  wherein $R^7$ and $R^8$ each represent a hydrogen atom, a $C_1$-$C_6$ alkyl group (wherein said alkyl group may be substituted with an amino group which may be substituted with one or two $C_1$-$C_6$ alkyl groups, a hydroxyl group, or a $C_1$-$C_6$ alkoxy group), a $C_1$-$C_6$ alkanoyl group, a carbamoyl group which may be substituted with one or two $C_1$-$C_4$ alkyl groups, a morpholinocarbonyl group, an aminosulfonyl group which may be substituted with one or two $C_1$-$C_6$ alkyl groups, or a $C_1$-$C_6$ alkylsulfonyl group, or alternatively, $R^7$ and $R^8$ optionally form, together with the nitrogen atom to which $R^7$ and $R^8$ are attached, a 3- to 8-membered saturated hydrocarbon ring, wherein said ring may be substituted with a substituent(s) selected from the group consisting of a dimethylenedioxy group, an oxo group and a hydroxyl group.

19. The compound or pharmaceutically acceptable salt thereof according to claim 1, wherein $R^3$ is a phenyl group whose 4-position is substituted with a fluorine atom or a chlorine atom.

20. The compound or pharmaceutically acceptable salt thereof according to claim 1, wherein $R^3$ is a 6-indolyl group.

21. The compound or pharmaceutically acceptable salt thereof according to claim 1, wherein $R^3$ is a $C_1$-$C_{18}$ alkyl group which may be substituted with a substituent(s) selected from the following group (wherein said group consists of a halogen atom, an amino group which may be substituted with one or two $C_1$-$C_6$ alkyl groups, a $C_1$-$C_6$ alkoxy group, a piperazino group which may be substituted with a $C_1$-$C_6$ alkyl group(s), a phenyl group and a morpholino group), a $C_2$-$C_8$ alkenyl group, a $C_2$-$C_8$ alkynyl group, or a $C_3$-$C_8$ cycloalkyl group.

22. The compound or pharmaceutically acceptable salt thereof according to claim 1, wherein $R^3$ is a $C_1$-$C_6$ alkyl group substituted with a substituent(s) selected from the following group (wherein said group consists of an amino group which may be substituted with one or two $C_1$-$C_6$ alkyl groups, and a $C_1$-$C_6$ alkoxy group), or a $C_3$-$C_5$ cycloalkyl group.

23. A pharmaceutical preparation comprising the compound or pharmaceutically acceptable salt thereof according to any one of claims 1 to 22.

24. A method of treating an autoimmune disease selected from the group consisting of Crohn's disease, irritable colitis, Sjogren's syndrome, multiple sclerosis and systemic lupus erythematosus, or a disease selected from the group consisting of rheumatoid arthritis, asthma, atopic dermatitis, rejection after organ transplantation, cancer, retinopathy, psoriasis, osteoarthritis or age-related macular degeneration, which comprises applying the pharmaceutical preparation according to claim 23 to a subject in need thereof.

25. A compound represented by formula (II) or a salt thereof:

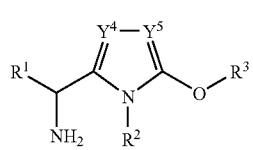

[Formula 9]

(wherein $R^1$ represents a hydrogen atom, a $C_1$-$C_6$ alkyl group which may be substituted with a substituent(s) selected from the following group [wherein said group consists of a hydroxyl group, a halogen atom, a $C_1$-$C_6$ alkoxy group (wherein said alkoxy group may be substituted with a phenyl group) and a phenyl group (wherein said phenyl group may be substituted with a substituent(s) selected from the group consisting of a halogen atom and a $C_1$-$C_6$ alkyl group)], a $C_3$-$C_8$ cycloalkyl group, a $C_1$-$C_8$ alkenyl group, a $C_9$-$C_8$ alkynyl group, or a phenyl group, $R^2$ represents a hydrogen atom, a $C_1$-$C_6$ alkyl group, or a $C_3$-$C_8$ cycloalkyl group, $R^3$ represents (ii) a $C_1$-$C_{18}$ alkyl group, (iii) a $C_2$-$C_8$ alkenyl group which may be substituted with a phenyl group or a benzyloxy group, (iv) a $C_2$-$C_8$ alkynyl group which may be substituted with a phenyl group, (v) a $C_3$-$C_8$ cycloalkyl group which may be condensed with a benzene ring, (vi) a $C_1$-$C_6$ alkyl group substituted with a substituent(s) selected from the following group [wherein said group consists of a halogen atom, a phenyl group (wherein said phenyl group may be substituted with 1 to 5 substituents selected from the group consisting of a phenyl group, a cyano group, a halogen atom, a $C_1$-$C_6$ alkyl group, a $C_1$-$C_6$ alkoxy group, a trifluoromethyl group, a methoxycarbonyl group, a $C_1$-$C_6$ alkylthio group, a dimethylamino group, a nitro group and an acetamido group), a $C_3$-$C_8$ cycloalkyl group, a hydroxyl group, a $C_1$-$C_6$ alkylthio group, a $C_1$-$C_6$ alkoxy group, a benzyloxy group, a phenoxy group, a trifluoromethyl group, a difluoromethyl group, a benzenesulfonyl group, a naphthyl group, a $C_7$-$C_{10}$ tricycloalkyl group, a carbomethoxy(phenyl)methyl group, a diphenylmethyl group, a 1-phenylethyl group, an imidazolyl group, an indolyl group, a pyridyl group, an oxetanyl group, an oxolanyl group, a methylpiperidinyl group, a piperazino group which may be substituted with a $C_1$-$C_6$ alkyl group(s), a benzylpiperidinyl group, a morpholino group, a 2-oxopyrrolidin-1-yl group, a 2-oxoimidazolidin-1-yl group, a group represented by the formula:

—$CO_2R^{11}$ (wherein $R^{11}$ represents a hydrogen atom or a $C_1$-$C_6$ alkyl group), a group represented by the formula:

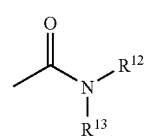

[Formula 2]

(wherein $R^{12}$ and $R^{13}$ each represent a hydrogen atom or a $C_1$-$C_6$ alkyl group), a group represented by the formula:

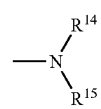

[Formula 3]

(wherein $R^{14}$ and $R^{15}$ each represent a hydrogen atom, a $C_1$-$C_6$ alkyl group, a phenyl group or a 4-pyridylcarbonyl group), and the formula:

—$COR^{16}$ (wherein $R^{16}$ represents a $C_1$-$C_6$ alkyl group or a phenyl group)], (vii) an oxolanyl group, a methylpiperidinyl group, or a group represented by the formula:

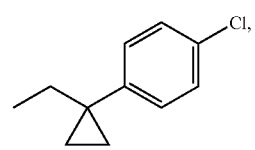

[Formula 4]

or (viii) an optionally substituted aryl group, and $Y^4$ and $Y^5$ each represent a nitrogen atom or the formula $CR^{17}$ (wherein $R^{17}$ represents a hydrogen atom, a $C_1$-$C_6$ alkyl group, a phenyl group, or a halogen atom), provided that only one of $Y^4$ and $Y^5$ is a nitrogen atom and the other is $CR^{17}$).

26. The compound or salt thereof according to claim 25, wherein in formula (II), $Y^4$ is CH, and $Y^5$ is a nitrogen atom.

27. The compound or salt thereof according to claim 25, wherein $R^1$ is a $C_1$-$C_6$ alkyl group which may be substituted with a halogen atom(s), or a benzyl group which may be substituted with a substituent(s) selected from the group consisting of a halogen atom and a $C_1$-$C_6$ alkyl group.

28. The compound or salt thereof according to claim 25, wherein $R^1$ is a methyl group, an ethyl group or a benzyl group which may be substituted with a halogen atom(s).

29. The compound or salt thereof according to claim 25, wherein $R^1$ is a methyl group or an ethyl group.

30. The compound or salt thereof according to claim 25, wherein $R^2$ is a $C_1$-$C_6$ alkyl group or a $C_3$-$C_8$ cycloalkyl group.

31. The compound or salt thereof according to claim 25, wherein $R^2$ is an ethyl group or a cyclopropyl group.

32. The compound or salt thereof according to claim 25, wherein $R^3$ is a phenyl group, a naphthyl group, a pyrazolyl group, a pyridyl group, an indolyl group, a benzothiazolyl group, a benzothiadiazolyl group, a pyrazolopyrimidinyl group, a quinolinyl group, an isoquinolinyl group, a benzothienyl group or a dihydroquinolinonyl group, wherein these groups may each be substituted with 1 to 3 substituents selected from the following group [wherein said group consists of substituents listed below: a $C_1$-$C_6$ alkyl group which may be substituted with a fluorine atom(s), a $C_3$-$C_8$ cycloalkyl group, a halogen atom, a $C_1$-$C_6$ alkoxy group (wherein said alkoxy group may be substituted with a substituent(s) selected from the group consisting of a fluorine atom, a phenyl group, an amino group substituted with two $C_1$-$C_4$ alkyl groups and a morpholino group), a phenoxy group, a phenyl group, a carboxyl group, a $C_2$-$C_{10}$ alkoxycarbonyl group, a hydroxyl group, a $C_2$-$C_7$ monocyclic saturated hydrocarbon group containing a nitrogen atom(s) as a ring member(s) (wherein said saturated hydrocarbon group may be substituted with a $C_1$-$C_6$ alkyl group(s)), a nitrogen-containing monocyclic unsaturated hydrocarbon group, a morpholinyl group which may be substituted with a $C_1$-$C_6$ alkyl group(s), a piperazino group which may be substituted with a substituent(s) selected from the following group [wherein said group consists of a $C_1$-$C_6$ alkyl group (wherein said alkyl group may be substituted with an amino group which may be substituted with one or two $C_1$-$C_6$ alkyl groups, a morpholino group, a hydroxyl group, or a $C_1$-$C_6$ alkoxy group), a formyl group, a $C_2$-$C_7$ alkanoyl group, a carbamoyl group which may be substituted with one or two $C_1$-$C_4$ alkyl groups, an aminosulfonyl group which may be substituted with one or two $C_1$-$C_6$ alkyl groups, and a $C_1$-$C_6$ alkylsulfonyl group], and the formula:

—$NR^7R^8$ wherein $R^7$ and $R^8$ each represent a hydrogen atom, a $C_1$-$C_6$ alkyl group (wherein said alkyl group may be substituted with an amino group which may be substituted with one or two $C_1$-$C_6$ alkyl groups, a hydroxyl group, or a $C_1$-$C_6$ alkoxy group), a $C_1$-$C_6$ alkanoyl group, a carbamoyl group which may be substituted with one or two $C_1$-$C_4$ alkyl groups, a morpholinocarbonyl group, an aminosulfonyl group which may be substituted with one or two $C_1$-$C_6$ alkyl groups, or a $C_1$-$C_6$ alkylsulfonyl group, or alternatively, $R^7$ and $R^8$ optionally form, together with the nitrogen atom to which $R^7$ and $R^8$ are attached, a 3- to 8-membered saturated hydrocarbon ring, wherein said ring may be substituted with a substituent(s) selected from the group consisting of a dimethylenedioxy group, an oxo group and a hydroxyl group].

33. The compound or salt thereof according to claim 25, wherein $R^3$ is a 2-naphthyl group (wherein said naphthyl group may be substituted with a substituent(s) selected from the group consisting of a halogen atom and a $C_1$-$C_6$ alkyl group), a 3-pyrazolyl group (wherein said pyrazolyl group may be substituted with a substituent(s) selected from the group consisting of a $C_1$-$C_6$ alkyl group, a trifluoromethyl group and a halogen atom), or a 5-benzothiazolyl, 5-benzothiadiazolyl, 7-dihydroquinolinonyl, 7-isoquinolinyl, 7-quinolinyl, 3-pyridyl or indolyl group which may be substituted with a $C_1$-$C_6$ alkyl group(s), an unsubstituted phenyl group, or a substituted phenyl group shown in (A) to (C) below:

(A) a phenyl group whose 4-position is substituted with a substituent selected from the group consisting of a $C_1$-$C_6$ alkyl group, a $C_3$-$C_8$ cycloalkyl group, a $C_1$-$C_6$ alkoxy group (wherein said alkoxy group may be substituted with a substituent(s) selected from the group consisting of an amino group substituted with two $C_1$-$C_4$ alkyl groups, a morpholino group and a phenyl group), a halogen atom, a trifluoromethoxy group, a phenoxy group, a phenyl group, a 1-pyrrolyl group, and —$NR^AR^B$ (wherein $R^A$ and $R^B$ are each a $C_1$-$C_6$ alkyl group, or $R^A$ and $R^B$ optionally form, together with the nitrogen atom to which $R^A$ and $R^B$ are attached, a 3- to 5-membered saturated hydrocarbon ring), and further whose 3-position may be substituted with a substituent selected from the group consisting of a $C_1$-$C_6$ alkyl group, a halogen atom and a $C_1$-$C_6$ alkoxy group, (B) a phenyl group whose 3-position is substituted with a substituent selected from the group consisting of a hydroxyl group, a $C_1$-$C_6$ alkyl group and a $C_1$-$C_6$ alkoxy group (wherein said alkoxy group may be substituted with a substituent(s) selected from the group consisting of an amino group substituted with two $C_1$-$C_4$ alkyl groups, a morpholino group and a phenyl group), and further which may be substituted with one or two $C_1$-$C_6$ alkyl groups or whose 4-position may be substituted with a halogen atom, and (C) a phenyl group whose 3-position is substituted with a substituent selected from the group consisting of nitrogen-containing groups shown in (i) to (v) below, and further whose 4-position may be substituted with a halogen atom:

(i) a $C_2$-$C_7$ monocyclic saturated hydrocarbon group containing a nitrogen atom(s) as a ring member(s) (wherein said saturated hydrocarbon group may be substituted with a $C_1$-$C_6$ alkyl group(s)), (ii) a nitrogen-containing monocyclic unsaturated hydrocarbon group, (iii) a morpholinyl group which may be substituted with a $C_1$-$C_6$ alkyl group(s), (iv) a piperazino group [wherein said piperazino group may be substituted with a $C_1$-$C_6$ alkyl group which may be substituted with a substituent(s) selected from the following group (wherein said group consists of an amino group substituted with two $C_1$-$C_4$ alkyl groups and a morpholino group) or a $C_2$-$C_7$ alkanoyl group], and (v) the formula —$NR^7R^8$ wherein $R^7$ and $R^8$ each represent a hydrogen atom, a $C_1$-$C_6$ alkyl group (wherein said alkyl group may be substituted with an amino group which may be substituted with one or two $C_1$-$C_6$ alkyl groups, a morpholino group, a hydroxyl group, or a $C_1$-$C_6$ alkoxy group), a $C_1$-$C_6$ alkanoyl group, a carbamoyl group which may be substituted with one or two $C_1$-$C_4$ alkyl groups, a morpholinocarbonyl group, an aminosulfonyl group which may be substituted with one or two $C_1$-$C_6$ alkyl groups, or a $C_1$-$C_6$ alkylsulfonyl group, or alternatively, $R^7$ and $R^8$ optionally form, together with the nitrogen atom to which $R^7$ and $R^8$ are attached, a 3- to 8-membered saturated hydrocarbon ring, wherein said ring may be substituted with a substituent(s) selected from the group consisting of a dimethylenedioxy group, an oxo group and a hydroxyl group.

34. The compound or salt thereof according to claim 25, wherein $R^3$ is a $C_1$-$C_{18}$ alkyl group which may be substituted with a substituent(s) selected from the following group (wherein said group consists of a halogen atom, an amino group which may be substituted with one or two $C_1$-$C_6$ alkyl groups, a $C_1$-$C_6$ alkoxy group, a piperazino group which may be substituted with a $C_1$-$C_6$ alkyl group(s), a phenyl group and a morpholino group), a $C_2$-$C_8$ alkenyl group, a $C_2$-$C_8$ alkynyl group, or a $C_3$-$C_8$ cycloalkyl group.

\* \* \* \* \*